(12) United States Patent
Shin et al.

(10) Patent No.: US 12,171,493 B2
(45) Date of Patent: Dec. 24, 2024

(54) SCANNING PATIENT INTERFACE SYSTEMS AND METHODS

(71) Applicant: Intelon Optics, Inc., Lexington, MA (US)

(72) Inventors: Andrew Shin, Chestnut Hill, MA (US); Jonathan Drewes, Oviedo, FL (US); Maxwell Kotlarchyk, Arlington, MA (US); Yen-Wei Lin, Natick, MA (US)

(73) Assignee: Intelon Optics, Inc., Lexington, MA (US)

( * ) Notice: Subject to any disclaimer, the term of this patent is extended or adjusted under 35 U.S.C. 154(b) by 657 days.

(21) Appl. No.: 17/029,589

(22) Filed: Sep. 23, 2020

(65) Prior Publication Data

US 2021/0085178 A1 Mar. 25, 2021

Related U.S. Application Data

(60) Provisional application No. 62/904,209, filed on Sep. 23, 2019.

(51) Int. Cl.
*A61B 3/14* (2006.01)
*A61B 3/12* (2006.01)
(Continued)

(52) U.S. Cl.
CPC ............ *A61B 3/14* (2013.01); *A61B 3/1225* (2013.01); *A61B 3/13* (2013.01); *A61B 3/113* (2013.01)

(58) Field of Classification Search
CPC ........... A61B 3/14; A61B 3/1225; A61B 3/13; A61B 3/113; A61B 3/10; A61B 3/12; G02B 26/101; G02B 26/108
See application file for complete search history.

(56) References Cited

U.S. PATENT DOCUMENTS 5,054,885 A * 10/1991 Melby .................. F21V 7/00
359/638
7,280,206 B2 * 10/2007 Wildnauer ............ G02B 27/58
356/334
(Continued)

FOREIGN PATENT DOCUMENTS

CN 103940799 A * 7/2014
CN 103954602 A * 7/2014
(Continued)

OTHER PUBLICATIONS

Paul Davidovits et al., Scanning Laser Microscope, 223 Nature 831 (1969). (Year: 1969).*

(Continued)

*Primary Examiner* — Cara E Rakowski
*Assistant Examiner* — Wesley Scott Ashton
(74) *Attorney, Agent, or Firm* — Acuity IP, LLC; Nathan S. Cassell

(57) ABSTRACT

Systems and methods are disclosed for generating an elastic stiffness map for a volume of an ophthalmic tissue of an eye of a patient. Exemplary systems and methods involve a laser assembly, an optical scanning assembly, an objective lens assembly, a beam control assembly, an eye camera assembly, and a Brillouin spectrometer assembly. Systems and methods can operate to transmit x,y coordinate scan control signals to the optical scanning assembly, transmit z coordinate scan control signals to the objective lens assembly, and generate the elastic stiffness map for the volume of the ophthalmic tissue of the eye based on Brillouin signals generated by a Brillouin spectrometer of the Brillouin spectrometer assembly.

8 Claims, 18 Drawing Sheets

(51) Int. Cl.
*A61B 3/13* (2006.01)
*A61B 3/113* (2006.01)

(56) References Cited

U.S. PATENT DOCUMENTS

| | | | |
|---|---|---|---|
| 7,898,656 | B2 | 3/2011 | Yun et al. |
| 8,115,919 | B2 | 2/2012 | Yun et al. |
| 9,020,580 | B2 * | 4/2015 | Friedman ............... A61B 3/145 |
| | | | 600/431 |
| 9,410,880 | B2 * | 8/2016 | Zhao ..................... G01N 21/47 |
| 9,498,114 | B2 * | 11/2016 | Friedman ............. A61B 3/1025 |
| 9,498,122 | B2 * | 11/2016 | Friedman ............... G01J 3/0213 |
| 9,777,053 | B2 | 10/2017 | Yun |
| 10,351,616 | B2 | 7/2019 | Yun |
| 10,800,831 | B2 | 10/2020 | Yun |
| 2003/0153825 | A1 * | 8/2003 | Mooradian ........... A61B 5/0059 |
| | | | 600/407 |
| 2007/0233056 | A1 | 10/2007 | Yun |
| 2009/0273777 | A1 | 11/2009 | Yun et al. |
| 2009/0323056 | A1 | 12/2009 | Yun et al. |
| 2012/0302862 | A1 | 11/2012 | Yun et al. |
| 2015/0055078 | A1 * | 2/2015 | Johnstone ............. G02B 3/0081 |
| | | | 349/200 |
| 2015/0148654 | A1 | 5/2015 | Whanwook et al. |
| 2016/0139390 | A1 * | 5/2016 | Bukshtab ............. G02B 17/006 |
| | | | 359/577 |
| 2016/0151202 | A1 | 6/2016 | Scarcelli et al. |
| 2016/0220110 | A1 * | 8/2016 | Vogler ...................... A61B 3/10 |
| 2017/0176338 | A1 * | 6/2017 | Wu ........................ G02B 21/367 |
| 2017/0254749 | A1 | 9/2017 | Yun |
| 2017/0360297 | A1 | 12/2017 | Yun et al. |
| 2018/0002398 | A1 | 1/2018 | Yun |
| 2018/0160898 | A1 * | 6/2018 | Yoo ......................... A61B 3/103 |
| 2019/0038766 | A1 * | 2/2019 | Mohanty ................ A61K 41/00 |
| 2019/0124320 | A1 * | 4/2019 | Taubin ................. G01N 21/8806 |
| 2019/0309045 | A1 | 10/2019 | Yun |
| 2019/0335994 | A1 | 11/2019 | Yun et al. |
| 2020/0182694 | A1 * | 6/2020 | Scarcelli ................ G01J 3/2803 |
| 2020/0187771 | A1 * | 6/2020 | Yun ....................... A61B 3/1173 |
| 2020/0256726 | A1 * | 8/2020 | Scarcelli ............ G01N 21/6458 |

FOREIGN PATENT DOCUMENTS

| | | | | |
|---|---|---|---|---|
| CN | 109187438 | A | * | 1/2019 |
| CN | 109211875 | A | * | 1/2019 |
| EP | 3118608 | B1 | * | 2/2020 ............ G01J 3/0208 |
| JP | 2007298365 | A | * | 11/2007 |
| WO | WO-2007073848 | A2 | * | 7/2007 ............... A61B 3/12 |
| WO | 2007/092911 | A2 | | 8/2007 |
| WO | WO-2009111370 | A2 | * | 9/2009 ........... G01N 21/643 |
| WO | 2009/134719 | A2 | | 11/2009 |
| WO | 2012/149570 | A1 | | 11/2012 |
| WO | 2015/010119 | A2 | | 1/2015 |
| WO | WO-2015135415 | A1 | * | 9/2015 ............ G01J 3/0208 |
| WO | WO-2016081731 | A1 | * | 5/2016 ............ A61B 3/102 |
| WO | WO-2019036714 | A1 | * | 2/2019 ............ A61B 3/00 |
| WO | WO-2020247473 | A1 | * | 12/2020 ............ G01J 3/4412 |

OTHER PUBLICATIONS

David A. Marcus, High-Performance Optical Filters for Fluorescence Analysis, 10 Cell Motility and the Cytoskeleton 62-70 (1988). (Year: 1988).*
Ugur ilingiroglu et al., Range Sensing with a Scheimpflug Camera and a CMOS Sensor/Processor Chip, 4 IEEE Sensors Journal 36-44 (2004). (Year: 2004).*
Rüdiger Paschotta, Etalons, 2006, pp. 1-7 [online], [retrieved Jan. 10, 2023], retrieved from the Internet <URL: https://www.rp-photonics.com/etalons.html>. (Year: 2006).*
How to Parfocal Microscope Objectives, 2015, pp. 1-4 [online], [retrieved on Jan. 4, 2023], retrieved from the Internet <URL: https://www/.microscopeworld.com/t-parafocal_objectives.aspx>. (Year: 2015).*
Thomas Sebastian et al., Micro-focused Brillouin Light Scattering: Imaging Spin Waves at the Nanoscale, 3 Frontiers in Physics 1-23 (2015). (Year: 2015).*
Daniel R. Opel et al., Light-emitting Diodes A Brief Review and Clinical Experience, 8 J Clin Aesthet Dermatol. 36-44 (2015). (Year: 2015).*
Joshua Vasquez, Up-Close and Personal with Laser Cuts, 2016, pp. 1-26 [online], [retrieved 2022-01-09], retrieved from the Internet <URL: https://hackaday.com/2016/04/28/up-close-and-personal-with-laser-cuts/>. (Year: 2016).*
High Power Motorised Beam Expanders, 2018, pp. 1-20 [Online], [retrieved on Jan. 10, 2023], retrieved from the Internet <URL: https://www.optogama.com/storage/app/media/Items/22064/MEX-HPv2.1.pdf>. (Year: 2018).*
Jim Brown, Why are Microscopes Parfocal and Parcentric?, Nov. 3, 2019, pp. 1-4 [online], [retrieved on Jan. 4, 2023], retrieved from the Internet <URL: https://knowledgeburrow.com/why-are-microscopes-parfocal-and-parcentric/>. (Year: 2019).*
Peng Shao et al., Spatially-resolved Brillouin Spectroscopy Reveals Biomechanical Changes in Early Ectatic Corneal Disease and Post-crosslinking in vivo, 2018, pp. 1-39 [online], [retrieved Nov. 27, 2023], retrieved from the Internet <URL: https://arxiv.org/ftp/arxiv/papers/1802/1802.01055.pdf>. (Year: 2018).*
Seok Hyun Yun et al., Brillouin Microscopy: Assessing Ocular Tissue Biomechanics, 29 Curr Opin Ophthalmol 299-305 (2018). (Year: 2018).*
Ivan Moreno et al., Thin-film Spatial Filters, 30 Optics Letters 914-916 (2005). (Year: 2005).*
Moonseok Kim et al., Shear Brillouin Light Scattering Microscope, 24 Optics Express 319-328 (2016). (Year: 2016).*
Zachary Coker et al., Assessing Performance of Modern Brillouin Spectrometers, 26 Optics Express 2400-2409 (2018). (Year: 2018).*
Eitan Edrei et al., Sensor-less Adaptive Optics for Brillouin Micro-spectroscopy, 2018, pp. 1-9 [online], [retrieved May 13, 2024], retrieved from the Internet <URL: https://arxiv.org/pdf/1802.03007>. (Year: 2018).*
Frequency Domain Filters and its Types, 2019, pp. 1-6 [online], [retrieved May 9, 2024], retrieved from the Internet <URL: https://www.geeksforgeeks.org/frequency-domain-filters-and-its-types/>. (Year: 2019).*
Giuliano Scarcelli et al., In Vivo Measurement of Age-Related Stiffening in the Crystalline Lens by Brillouin Optical Microscopy, 101 Biophysical Journal 1539-1545 (2011). (Year: 2011).*
Guillaume Lepert et al., Assessing Corneal Biomechanics with Brillouin Spectro-microscopy, 187 Faraday Discussions 415-428 (2016). (Year: 2016).*
Robert Prevedel et al., Brillouin Microscopy—a Revolutionary Tool for Mechanobiology?, 2019, pp. 1-19 [online], [retrieved Aug. 12, 2024], retrieved from the Internet <URL: https://arxiv.org/pdf/1901.02006>. (Year: 2019).*
Scarcelli "Confocal Brillouin microscopy for three-dimensional mechanical imaging" Nat Photonics. 2: 39-43, Dec. 9, 2007.
Scarcelli "Brillouin Optical Microscopy for Corneal Biomechanics" Investigative Ophthalmology & Visual Science, vol. 53, 185-190, Jan. 2012.
Scarcelli "In vivo Brillouin optical microscopy of the human eye" Optics Express vol. 20, Issue 8, pp. 9197-9202, Apr. 2012.
Scarcelli "Biomechanical Characterization of Keratoconus Corneas Ex Vivo With Brillouin Microscopy" Investigative Ophthalmology & Visual Science vol. 55, 4490-4495, Jul. 2014.
Hillen "The Hubble Telescope of the Eye" The Opthalmologist, pp. 19-29, Mar. 2017.
Yun "Brillouin microscopy: assessing ocular tissue biomechanics" Curr Opin Ophthalmol. 29(4): 299-305, Jul. 2018.
Shao "Spatially-resolved Brillouin spectroscopy reveals biomechanical abnormalities in mild to advanced keratoconus in vivo" Scientific Reports vol. 9, Article No. 7467 (May 2019).
Giuseppe Antonacci "Brillouin Scattering Microscopy for Mechanical Imaging" Imperial College of London, Department of Physics, Apr. 14, 2015.

* cited by examiner

SCANNING PATIENT INTERFACE SYSTEMS AND METHODS

CROSS-REFERENCE TO RELATED APPLICATIONS

This application claims the benefit of U.S. Provisional Patent Application No. 62/904,209 filed Sep. 23, 2019, the disclosure of which is incorporated herein by reference.

BACKGROUND

Embodiments of the present invention related generally to the field of biological tissue imaging, and in particular to ophthalmic Brillouin optical spectroscopy scanning techniques for measuring multiple locations in ocular tissues.

Brillouin spectroscopy has been used for the in vivo imaging and characterization of biological tissues, such as the cornea of the eye. This technique can be used to obtain biomechanical and physiological properties of ocular components, including various ocular tissues and/or structures, such as the cornea, sclera, crystalline lens, vitreous, and retina, in the eye of a patient or a living animal. These techniques can be used to perform procedures for diagnosis of, treatment of, and/or surgical planning for ocular disorders, as well as basic study and longitudinal clinical studies. The information is obtained from the spectral analysis of Brillouin light scattering that is associated with the hypersonic acoustic properties in the ocular components. To facilitate Brillouin imaging, the focused light can be scanned over the interrogated sample (e.g. eye).

The techniques enable noninvasive interrogation of the biomechanical information that is relevant to and useful in diagnosing ocular disorders, such as corneal ectasia and presbyopia, as well as treating these problems. Thus, a quantitative approach is provided for screening refractive surgery patients, identifying candidates at risk, and optimizing ablation patterns.

By using Brillouin scattering spectroscopy to monitor a visco-elastic modulus of an ocular tissue during a procedure, that procedure can be guided in pre-treatment phases, post-treatment phases, and/or in real time using feedback from the monitored visco-elastic modulus. The monitored visco-elastic modulus can provide a measurement of biomechanical changes caused by cellular processes associated with procedures such as surgical procedures or other types of treatment procedures. Biomechanical changes to an ocular component (or other biological tissue) may include changes that affect their structures at a cellular spatial scale (e.g., extracellular matrix, collagen fibers, astrocytes, keratocytes, and the like.).

Brillouin scattering spectroscopy enables the direct mapping of visco-elastic modulus in the context of many material characteristics, including intraocular pressure (TOP), without the need to simulate mechanical models based on normative statistical populations, such as inverse modeling. Various scan types have been implemented for facilitating Brillouin imaging.

Although existing Brillouin scattering spectroscopy scanning techniques can be effective in providing valuable information regarding the biomechanical properties of the eye, still further improvements are desired. Embodiments of the present invention provide solutions for at least some of these outstanding needs.

BRIEF SUMMARY

Embodiments of the present invention encompass scanning systems and methods for ophthalmic Brillouin optical spectroscopy systems that enable the measurement of multiple locations in ocular tissues without the need to reposition the system instrument during the scanning operation. Such systems and methods can be used to collect volumetric biomechanical data from ocular tissues, for example the cornea and crystalline lens. In some cases, systems and methods can be used to build or generate one or more maps of longitudinal elastic modulus distribution in an ocular tissue in a short amount of time and with consistency from one exam to another. Exemplary embodiments can exhibit diffraction limited optical performance over the confocal volume.

Embodiments of the present invention allow for the achievement of Brillouin spectroscopy scanning in many instances where manual scanning has proved difficult or impossible, such as scanning with a non-coaxial eye camera and fixation target in a clinical setting. Advantageously, embodiments of the present invention provide systems having a small form factor, and synergy between the scan repositioning time and axial scan duration can allow subjects to blink between consecutive scan positions while the system targets the next location.

In addition to applications for Brillouin spectroscopy scanning of ocular tissues, embodiments of the present invention may be used when tissue scans in vivo or ex vivo may benefit from having registration between values of longitudinal elastic modulus and position. Embodiments of the present invention may be used when it is difficult, impractical, or undesirable to move the sample relative to the measurement apparatus.

Exemplary embodiments may employ beam scanning modalities for diagnostic and treatment, and for tracking the position and/or orientation of the eye. In some embodiments, patient interface Brillouin scanning modalities as disclosed herein may involve using large numerical apertures, maintaining a close to diffraction limited probe beam, using optical elements with minimal back-reflections, employing confocal imaging, using desired working distances, probing corneal, aqueous humor, and/or crystalline lens tissues, using different wavelengths for an eye tracking camera and/or a fixation target, having a probing beam that is optically coaxial, or any combination of the features described above. Often, scanning systems will include or involve the use of software code that controls the beam position. Desirably, the system operates with little or no aberrations of the probing beam or deviation of the focused spot from its diffraction limit in order to maximize light efficiency and volumetric specificity.

Some previously reported scanning techniques involve the use of a coaxial beam that is focused confocally, and the entire patient interface is translated manually, from point to point, relative to the person's eye, for each x,y capture on the person's eye. Such systems can involve focusing the light on the person's eye, translating the entire patient interface in z to build up a characteristic profile (i.e. for the depth) that would be at one x,y point in the map, in the person's eye. Then manually repositioning the entire patient interface so that the beam is directed to another x,y position on the person's eye, capturing another point, repeating for a number of points, and then stitching together all those individual points, so as to create a map. The map is then co-registered onto person's eye, giving that extra dimension of spatially resolved elasticity information. This can be a cumbersome and lengthy process with patient scanning times lasting several minutes or more for each eye.

Embodiments of the present invention encompass the use of a single capture approach with an automated scanning system. In some cases, a user, operator, or physician can initially align the instrument to the patient using features of the patient's eye as a target, and thereafter the patient interface system proceeds with the full automated scanning procedure. In related aspects, procedures can be automated based on image processing analysis and motion can be controlled by motors.

In a first aspect, embodiments of the present invention encompass systems and methods for generating an elastic stiffness map for a volume of an ophthalmic tissue of an eye of a patient. An exemplary system can include a laser assembly that generates a collimated illumination laser beam, an optical scanning assembly that redirects a beam path of the portion of the collimated illumination laser beam, an objective lens assembly that focuses the redirected portion of the collimated illumination laser beam to produce a focused illumination laser beam having focused spot, and that adjusts a scan position of the focused spot, a beam control assembly, an eye camera assembly that receives imaging light from the eye and generates electrical signals in response to the received imaging light, and a Brillouin spectrometer assembly having a Brillouin spectrometer and a spatial filter that is parfocal with the focused spot. The Brillouin spectrometer can be configured to generate Brillouin signals as the focused spot is scanned to discrete locations throughout the volume of the ophthalmic tissue and Brillouin scattered light from the focused spot at the discrete locations is returned to the spatial filter. The imaging light can travel from the eye through the beam control assembly and to the eye camera assembly. The focused illumination laser beam produced by the objective lens assembly can travel through the beam control assembly and toward the eye. The system can also include a processing assembly in operative association with the optical scanning assembly, the objective lens assembly, the eye camera assembly, and the Brillouin spectrometer assembly. The processing assembly can have a processor, an electronic storage location operatively coupled with the processor, and processor executable code stored on the electronic storage location and embodied in a tangible non-transitory computer readable medium. The processor executable code can include machine-readable instructions that, when executed by the processor, cause the processor to transmit x,y coordinate scan control signals to the optical scanning assembly, transmit z coordinate scan control signals to the objective lens assembly, and generate the elastic stiffness map for the volume of the ophthalmic tissue of the eye based on the Brillouin signals.

In some cases, the imaging light and the focused illumination laser beam between the eye and the beam control assembly are co-linear. In some cases, a system may further include a polarizing beam splitter that reflects a portion of the collimated illumination laser beam that is generated by the laser assembly. In some cases, the beam control assembly includes a dichroic filter assembly. In some cases, the dichroic filter assembly can include a shortpass dichroic filter and a longpass dichroic filter. In some cases, the imaging light travels from the eye through the shortpass dichroic filter and the longpass dichroic filter and to the eye camera assembly. In some cases, the focused illumination laser beam produced by the objective lens assembly is reflected by the shortpass dichroic filter toward the eye. In some cases, the machine-readable instructions, when executed by the processor, cause the processor to generate the elastic stiffness map for the volume of the ophthalmic tissue of the eye based on the electrical signals generated by the eye camera assembly. In some cases, the electrical signals generated by the eye camera assembly comprise information regarding a location of a reference coordinate of the eye. In some cases, the machine-readable instructions, when executed by the processor, cause the processor to generate the x,y coordinate scan control signals based on the electrical signals generated by the eye camera assembly. In some cases, the machine-readable instructions, when executed by the processor, cause the processor to generate the z coordinate scan control signals based on the electrical signals generated by the eye camera assembly. In some cases, a system may include a quarter-wave plate assembly that converts the focused illumination laser beam from a first polarization orientation to a second polarization orientation.

In another aspect, embodiments of the present invention encompass systems and methods for scanning a focused spot of a diagnostic beam to discrete locations within a volume of an ophthalmic tissue of an eye of a patient. Exemplary systems may include a beam expansion assembly that expands a collimated diagnostic beam from a first diameter to a second diameter that is larger than the first diameter, an optical scanning assembly that redirects an x,y beam path of the expanded collimated (or uncollimated) diagnostic beam, an objective lens assembly that focuses the redirected expanded collimated (or uncollimated) diagnostic beam to produce a focused diagnostic beam, and that controls a z depth location of a focused spot of the focused diagnostic beam, an eye camera assembly, a beam control assembly, where the focused diagnostic beam is directed by the beam control assembly toward the eye, and where imaging light travels from the eye through the beam control assembly and to the eye camera assembly, a Brillouin spectrometer assembly having a Brillouin spectrometer and a spatial filter that is parfocal with the focused spot, where the Brillouin spectrometer generates Brillouin signals as the focused spot is scanned to discrete locations throughout the volume of the ophthalmic tissue and Brillouin scattered light from the focused spot at the discrete locations is returned to the spatial filter, a processing assembly in operative association with the optical scanning assembly, the objective lens assembly, the eye camera assembly, and the Brillouin spectrometer assembly. The processing assembly can include a processor, an electronic storage location operatively coupled with the processor, and processor executable code stored on the electronic storage location and embodied in a tangible non-transitory computer readable medium. The processor executable code can include machine-readable instructions that, when executed by the processor, cause the processor to detect movement of a reference coordinate of the eye based on the imaging light, and generate an elastic stiffness map for the volume of the ophthalmic tissue of the eye based on the Brillouin signals and the detected movement of the reference coordinate.

In some cases, a system can include a fixation assembly that provides the eye with a gaze target. In some cases, the processor executable code includes machine-readable instructions that, when executed by the processor, cause the processor to generate x,y scanning control signals for the optical scanning assembly based on the detected movement of the reference coordinate. In some cases, the processor executable code includes machine-readable instructions that, when executed by the processor, cause the processor to generate z scanning control signals for the objective lens assembly based on the detected movement of the reference coordinate. In some cases, the beam control assembly includes a dichroic filter assembly. In some cases, the dichroic filter assembly includes a shortpass dichroic filter and a longpass dichroic filter. In some cases, the imaging light travels from the eye through the shortpass dichroic filter and the longpass dichroic filter and to the eye camera assembly. In some cases, the focused illumination laser beam produced by the objective lens assembly is reflected by the shortpass dichroic filter toward the eye.

DETAILED DESCRIPTION

Figure 1:
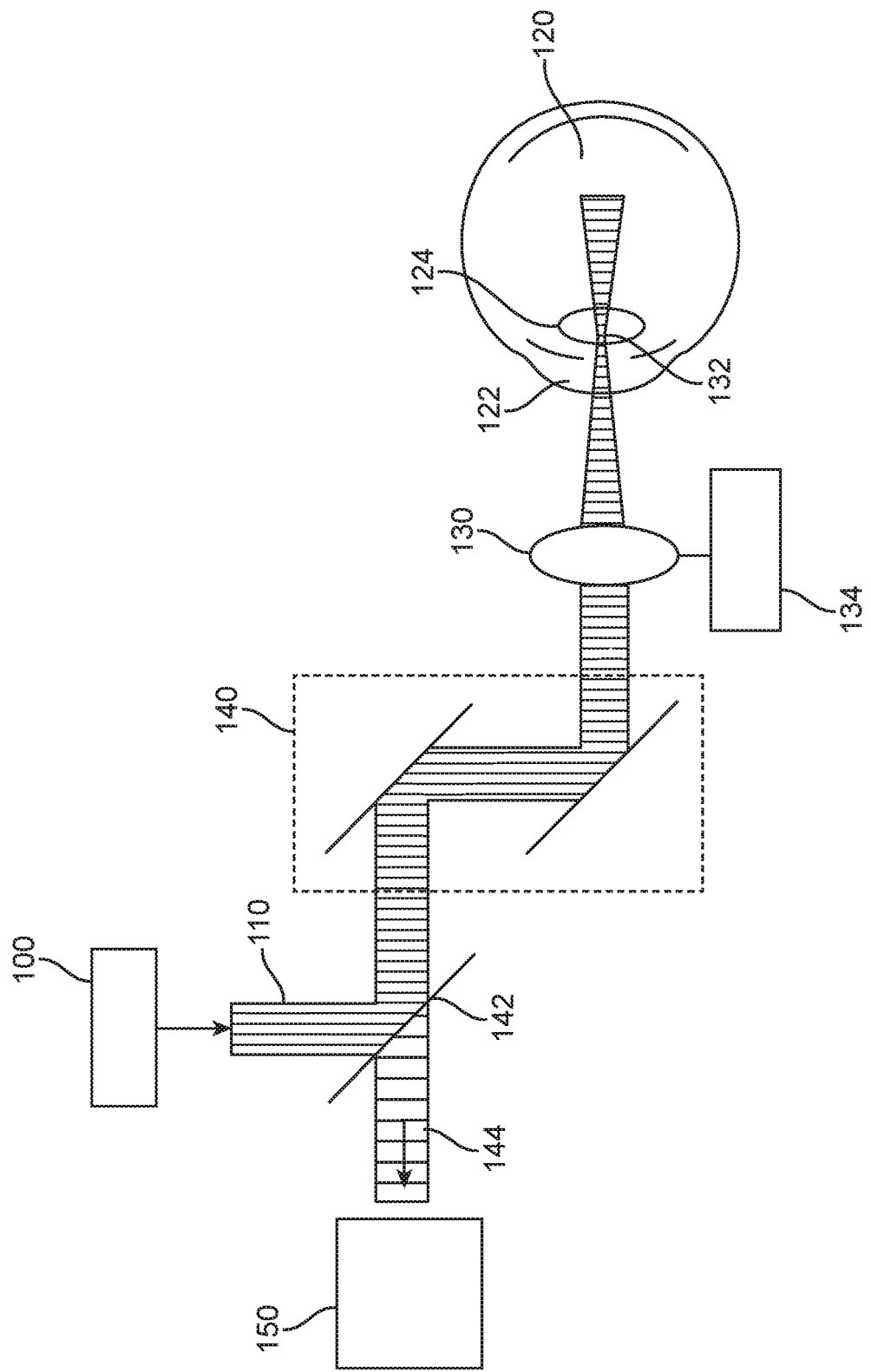
FIG. 1 depicts aspects of a system for generating an elastic stiffness map for a volume of an ophthalmic tissue of an eye of a patient, according to embodiments of the present invention.

Imaging and scanning interface systems and related techniques such as ophthalmic Brillouin spectroscopy are disclosed herein. Embodiments of the present invention encompass patient interface systems and methods that involve the use of laser source and spectrometer modules (including reference arm sub-modules) for evaluating biomechanical properties of physiological tissues, such as ocular tissues. In some embodiments, the system provides an ophthalmic diffraction limited approach, with z (depth) scanning, for Brillion spectrometry, that includes eye tracking. Exemplary scanning techniques enable the system to effectively collect data from the corneal area, without having to manually reposition the beam to different locations.

It has long been known that the lens of the eye tends to stiffen with age. As the lens hardens, the muscle holding the lens cannot alter its shape easily, and the person has increasing difficulty focusing on close objects or loss of accommodation ability, a condition called presbyopia. Presbyopia affects almost every person over the age of 45. Nevertheless, clinicians have limited tools to characterize the biomechanical alterations in the lens. Furthermore, no drugs are currently commercially available that can prevent, slow, or reverse the progressive nature of this condition.

Cataract, opacity of the lens, is the leading cause of blindness in the world. Age-related nuclear cataract is the most common form, affecting more than 50% of U.S. residents 65 and older. Despite its prevalence, the only standard of care for cataract patients today is surgery, an invasive procedure, which is usually performed after patients have suffered from deteriorating vision for many years before they are eligible for the procedure. About 1.5 million people in the U.S. (of the 87 million with cataracts) receive cataract surgery annually, leaving more than 85 million people untreated for this condition. A drug that can treat or prevent the damage of the lens proteins is being actively sought for. However, our limited understanding of the mechanisms of cataracts and the dearth of techniques capable of monitoring the genesis of cataracts had impeded the drug development. Although the detailed mechanisms underlying the cataract formation remain to be further elucidated, it has been known that the opacity of the lens can result from the denaturation of lens proteins. This structural and physiological modification can alter the lens's elastic properties. Therefore, the ability to measure lens elasticity in patients may be useful for early diagnosis and development of non-surgical interventions for cataracts.

In the cornea, the mechanical balance between corneal stiffness and intraocular pressure is critical in maintaining the appropriate shape and normal function of cornea. An abnormal change in the mechanical properties of the cornea can therefore degrade visual acuity and threaten vision. Corneal ectasia refers to a bulging of the cornea, occurring when it is not strong enough mechanically to withstand the intraocular pressure. Ectasia may result from a degenerative disease called Keratoconus. Keratoconus and Keratoectasia occur in 1 out of 1000 people among the general population, and may be present in patients before they undergo LASIK surgery. The corneal biomechanic weakening of undiagnosed/undetected early stage keratoconus may be the reason behind many ectasia cases that occur after performing LASIK, which further weakens the cornea. All of these conditions and procedures are intrinsically linked to ocular mechanical properties, and from a diagnostic standpoint are expected to alter, at a very early stage, the mechanical properties of ocular tissues.

Ectasia is also one of the rare but serious adverse outcomes after LASIK (laser-assisted in situ keratomileusis) surgery. Currently about 1.5 million LASIK operations are performed annually in the U.S. As LASIK becomes increasingly popular, the incidence of post-LASIK ectasia has continued to increase. A promising therapeutic approach to corneal ectasia is increasing the stiffness of the stroma by crosslinking the naturally present collagen fibers in the cornea, a procedure known as corneal collagen crosslinking (CXL). The viscoelastic properties of the cornea are also known to affect the tonometry measurement of intraocular pressure.

As a consequence, the biomechanical properties may be an appropriate target for diagnosis and monitoring of onset and progression of cataract and refractive disorders such as myopia, hyperopia, astigmatism, and presbyopia as well as corneal pathologies and treatments and other vision conditions that involve the retina, macular degeneration, and glaucoma. For this reason, there has been a great deal of interest in measuring the mechanical properties of the lens, retina, vitreous, scleral, and corneal tissues for diagnosis and for monitoring of treatments.

Conventional techniques, from the traditional slit-lamp microscopy to newer imaging technologies (computer videokeratography, OCT, confocal microscopy, ultrasound, Scheimpflug photography) are excellent in imaging the structure of cornea, sclera, conjunctiva, and crystalline lens but may fail on their own to provide their physiological and biomechanical information. Current clinical instruments, such as pachymetry (measuring thickness) and topography (mapping surface curvature), have been limited in screening patients at high risk of post-LASIK ectasia; patients with normal appearing corneas have developed the complication.

Several techniques have been used to characterize the mechanical properties of the cornea, sclera, and lens ex vivo and in vivo. For example, comprehensive but destructive analysis has been performed by spinning cup, mechanical stretchers, stress-strain equipment or by inflation tests. Other mechanical testing methods include laser induced optical breakdown based on bubble creation and the ocular response analyze measuring corneal hysteresis on the surface without spatial information. Ultrasound is an attractive tool as it allows noninvasive methods such as elastography. Of particular note is ultrasound pulse-echo techniques and ultrasound spectroscopy, where pulsed or continuous-wave acoustic waves are launched onto the cornea, and the propagation speed to and attenuation are measured to compute the viscoelastic moduli of the tissue. However, the ultrasound-based techniques have drawbacks of relatively low spatial resolution and measurement sensitivity. Other techniques involve analyzing the deformation wave of the cornea under an air puff and cross-sectional imaging, using curve fitting of the surface deformation to extract mechanical properties. Laser speckle imaging has been used to analyze biomechanical properties of tissues as well.

Brillouin light scattering in a tissue or any other medium arises due to the interaction between an incident light and acoustic waves within the matter. Consider a probe light with a frequency v and a wavelength k, which is illuminated to the sample. In spontaneous Brillouin process, the acoustic waves or acoustic phonons are naturally present due to thermal fluctuations. Such fluctuations propagate through the medium in the form of acoustic waves. These acoustic waves generate periodic modulations of the refractive index. Brillouin scattering can be generated by at least one or many acoustic waves or acoustic phonons, which form phase-matched index modulation.

Hence, it is possible to evaluate or monitor properties of a tissue or ocular component of an eye by providing projected electromagnetic radiation (e.g. light) to the tissue or ocular component so as to interact with an acoustic wave in the tissue or ocular component, such that returning electromagnetic radiation is produced based on the interaction. The returning radiation can be analyzed so as to evaluate a viscoelastic modulus of the tissue or ocular component. By scanning the projected electromagnetic radiation through a plane or volume of the tissue or ocular component and analyzing the returning electromagnetic radiation, it is possible to construct a multi-dimensional (e.g. two, three, or four dimensional) elasticity map for the tissue or ocular component. Embodiments of the present invention encompass systems and methods for monitoring properties of a biological tissue, for example by generating an elasticity or elastic stiffness map for a plane, thickness, or volume of the tissue, using certain scanning techniques. In some embodiments, the terms "electromagnetic radiation" and "light" or "laser light" maybe used interchangeably.

Embodiments of the present invention encompass systems and methods for collecting axial Brillouin scans from a patient eye without the need to reposition the instrument's optical head or for the patient to move or change gaze direction. In exemplary embodiments, a confocal scan system is created by conjugate alignment of a focused laser spot in the eye tissue with the input of an optical fiber. Some embodiments encompass a multimode design that captures more light over a larger area for the return path only. The core of the fiber effectively replicates the conjugate aperture of a traditional confocal imaging system. It is understood, however, that some embodiments may not require the use of fiber. For example, the entire system could be constructed in a confocal manner with a spatial pin hole. However in many embodiments, fiber suites the design well, since it can assist with modularization.

In some instances, the fiber can operate to provide a spatial filter (e.g. at or corresponding to the conjugate image plane). For example, the input or core of the fiber can operate as a spatial filter. The fiber can be a single mode fiber or a multimode fiber. In some instances, a spatial filter can be referred to as a pinhole spatial filter, a spatial aperture, or a circular (radial) aperture. With confocal microscopy, it is possible to control the depth of field, and eliminate or reduce background information away from the focal plane (e.g. which would otherwise lead to image degradation). Exemplary confocal techniques use spatial filtering to eliminate out-of-focus light. In some cases, confocal techniques use spatial filtering to eliminate high frequencies of light. In some cases, the spatial filter can operate to remove emission that does not originate from the focal plane. In some cases, the spatial filter can operate to filter the depth of focus and to block extrafocal signal.

The axial scanning of the beam focus can be achieved by translating the objective along the z-axis, effectively moving the focal point of the beam axially into the tissue. In some embodiments, the minimum numerical aperture (NA) of the objective is 0.1, where higher NAs correspond to tighter spatial resolution of the focus. In some embodiments, higher NAs can improve spatial localization and Rayleigh range of the Gaussian beam. In some cases, calculated maps can be interpolated, so that spatial resolution greater than 1 mm is not required. However, lower NA objectives can degrade both the spatial resolution and Rayleigh range of the beam, contributing to strong back reflections from the eye surface over the scan depth. In some cases, a quarter waveplate can be positioned between the scan objective and the eye to optically isolate back-reflections from any incoming light that may contaminate the spectrometer signal. In some cases, a quarter waveplate can be placed anywhere between the beam splitter and the eye, and can operate to isolate back reflections from optical elements between it and the beam splitter. In some cases, only the light scattered or back reflected after the quarter wave plate will make it past the polarizing beam splitter before the scanning system and ultimately coupled into the single mode fiber input of the spectrometer.

In some cases, a dichroic filter can be positioned between the objective and the eye. In some cases, an eye tracking camera can be aligned to be co-axial with the laser beam path, and can detect images of the eye from near-infrared (NIR) illumination projected onto the eye. In some cases, the dichroic can be designed to have superior flatness, a minimum thickness to fit in the space, and can operate to achieve a minimum working distance of 30 mm (50 mm nominal). In the co-axial configuration, the laser and eye camera focus can be parfocal. In some instances, the scan pattern is inherently registered with the eye surface without geometric distortion, removing complications from accurate data analysis. By positioning the dichroic between the scan objective and the eye, and between the eye camera and the eye, the eye camera can be registered to the laser scan path without being optically dependent on the on the objective design. This allows for enhanced flexibility in the target eye camera field of view (FOV) and spacing of elements. In some instances, the laser source is reflected at 90 degrees to minimize optical aberrations and astigmatism that would be caused by transmitting the converging laser beam through the filter (i.e. to maintain the diffraction limited spot). In some cases, a dichroic operates to combine the scanning diagnostic laser beam and eye illumination into a co-linear light path.

The dichroic filters can be further configured to pass or reflect the visible fixation light for controlling the patient's gaze direction. A separate dichroic can be used to combine and split the fixation wavelength and the eye camera illumination wavelength. In some cases, this dichroic can also be used to fold in alternative modalities, such as OCT. Alternatively, fixation light can be optically decoupled from shared laser scan and eye camera path to allow for larger fixation angles for the eye. This may be desirable to address angle-dependent back reflections from the surface of the eye. According to some embodiments, if the incident angle of scan laser on the eye is approximately 10 degrees or less, the power of the back reflected signal of the original laser wavelength overwhelms the shifted Brillouin signal, making it undetectable. By incorporating a matrix of light-emitting diode (LEDs) that may be switched over the course of the scan procedure, the patients gaze may be directed to increase the relative incident angle addressing any issues with the back reflection. This approach could involve a couple of independent points or a full matrix. It could also involve a more detailed image as in some other conventional eye exams. In some instances, the FOV of the camera is designed to be large enough to capture the full FOV of the cornea at different gaze angles.

According to some embodiments, pointing or redirecting of the scan beam can be achieved using a pair of Risley prisms in conjunction with an axially scanning objective. An afocal magnification relay can increase the beam size to the desired size before entering the scanning system. Lenses can be spaced in a Galilean configuration (negative lens followed by positive lens) to shorten the path length of the system. The beam angle of collimated rays entering the scan objective can be controlled by rotating the wedged prism pair relative to one another about the optical axis. The system can be designed so that 180 degrees relative rotation of the prisms corresponds to the full scan FOV of the eye at the target working distance. The prisms can be separate optical elements (glass or plastics with an angular wedge) or a tunable fluid filled prismatic element. In some cases, the large aperture of the prism pair allows for beam magnification to occur prior to entering the scan system, reducing complexity and length of the scan setup. Optical performance of this system can be optimized by minimizing the distance between the prism pair and the back aperture of the objective. Additionally, beam wobble over the scan range is minimized by minimizing the distance between the prism pair. Rotation of the prisms can be achieved using a motorized rotational mount, which may be stepper, servo, piezo, or DC motors to control the actuation of the rotation. The telecentricity of the scan over the eye FOV can either be almost telecentric, completely telecentric, or designed to become normal to the typical curvature of the eye. Although matching the eye curvature may be ideal to reduce astigmatism at the wider field points, assumptions may need to be made about the nominal profile. In some cases, designing for normal corneal incidence can make alignment and calibration more complex.

In other embodiments of the prism scanning system, the laser path and the eye camera path share the same objective using a dichroic in the collimated space between the scanning elements and the focusing objective. In such configurations, scanning laser light can be transmitted through the dichroic allowing for direct illumination of the scan pattern on the eye without being reflected at 90 degrees. In such configurations, the eye camera performance and FOV can be dependent on the design of the scan objective. Additionally, the scan path optical performance can be degraded since adding the dichroic into path can necessitate increasing the distance between the scan prisms and the entrance pupil of the objective. Additional aberrations can be compensated in this configuration by adding lens surfaces to the objective design to maintain diffraction limited performance over the scan FOV.

In other embodiments, scanning is achieved by galvanometer mirrors (galvos). Galvo scanners may be separate motorized mirrors or a pair may be integrated into a single housing with a threaded adapter for lens assemblies to be attached to either the input or output. X and Y galvos may be combined into a single assembly or physically separated. In some cases, physically separated galvos have the advantage of less pupil wobble over the scan. In some cases, intermediate optics may be desired to effectively relay the pupil from one axis to another maintaining wobble-free ideal performance. Following the galvo scanner, afocal optics can relay the collimated scan pupil of the galvos to the collimated entrance pupil of the scan objective. Beam magnification to fill the entrance pupil of the objective can be achieved by an afocal relay. Magnifying the beam prior to the galvos may be desirable, although this may necessitate larger clear apertures for the paddle mirrors. In some cases, the larger the paddle mirrors, the more separation there is and more beam wobble over the scan area.

Instead of using galvanometers for the angular beam scanning, a larger aperture multi-axis motorized mirror may also be used. This may be piezo or another type of motorized drive. If the aperture is large enough, similar to the scanning prism pair, the beam can be magnified prior to scanning, keep the length and complexity of the system relatively short. Since the mirror is single element and multi-axis, it can angularly point the beam without any wobble. In some cases, a tip-tilt mirror may be used.

In other embodiments, there is only magnification of the beam to fill the entrance pupil of the objective. X and Y scanning of the beam can be achieved by moving the optical head using linear motorized stages internal to the instrument, and therefore, the entire base of the instrument remains stationary.

According to some embodiments, scanning systems can be constructed by assembling optomechanical hardware onto a mechanical base allowing for translation and aligned to a sample or biological tissue. XY or XYZ motion may be accomplished by mechanical handles, knobs, or joysticks which may be manually or electromechanically controlled with motors. A scanning interface may be on a lift table and the patient may have an adjustable chin or forehead rest to accommodate for ergonomics. In some cases, a system can be accompanied by software algorithms that allow for the definition of a scan pattern for each eye. In some cases, one or more aspects of a system can be used in an ophthalmological diagnostic device to assess a longitudinal elastic modulus distribution in ocular tissues.

In some cases, components such as a central processing unit (CPU), electronics, software, and/or peripherals can be mounted into a lift table enabling a patient's height adjustment to find a comfortable position. In some cases, a patient interface can be placed on a table, while one or more other modules can be mounted below the table with a grommet for cable connections.

In certain embodiments, an input laser source (e.g. 780 nm) is locked and filtered to achieve a minimum of 10 MHz spectral stability and low levels of ASE noise. Laser locking can be achieved using an etalon element either in the laser source prior to fiber coupling or in the scanning interface at the collimated fiber input. The laser source is often coupled and connected to the patient interface via single mode polarization-maintaining (PM) fiber to allow for both modularity and serviceability of the system, as well as an ideal Gaussian beam input into the scanner interface. PM fiber can be used to maintain the polarization of the beam between system submodules, as the light will be later divided by a polarizing beam splitter (PBS). An adjustable lens or fixed fiber collimator on a kinematic mount can allow for alignment of a nicely collimated and parallel input beam. Irises can be used throughout the assembly and optomechanical alignment process and can be used ensure that the addition of optical elements does not impose any unwanted angular deviation of the light path. In some cases, the focal length of the input collimator can be chosen to keep the initial keep the beam less than 5 mm to limit aperture sizes through optical elements. In some cases, a scanning technique can involve using a converging focused narrow laser beam to raster across a tissue. The focused beam can be focused on a plane on or in the tissue as the beam rasters across the tissue. In some cases, this focal plane can be adjusted incrementally to create a three-dimensional image. The three-dimensional image can be stored. In some cases, the three-dimensional image can be viewed and analyzed across any plane in the specimen. In some cases, the image elements can be identified by three coordinates and elements can be called voxels, or volume elements. In some cases, a planar image can include elements having two coordinates, where the elements are referred to as pixels, or picture elements.

It is understood that in some embodiments, other wavelengths of laser light can be used. In some cases, a continuous wave (CW) laser format may be used. In some cases, a pulsed laser format may be used.

In some cases, if the initial polarization quality of the laser source was insufficient, a high extinction (e.g. 100,000:1) polarizer may be added to further purify the polarization of the beam. The linear polarization axis of the beam can be rotated using a half wave plate or liquid crystal element to adjust the relative amounts of light split by a PBS. One path of the light can be directed to the eye scanning system, while the other path can be directed to a reference calibration material. The PBS can be mounted in a stationary mount. It may be oriented perpendicular to incident light or at a small angle to eliminate possible reflections from entering the scanning interface output fiber to the spectrometer. In some embodiments, the light going to the scanning interface can be either the path reflected in the PBS or transmitted through depending on the design.

In the scanning path, light can pass through or be directed by scanning elements as described elsewhere herein (e.g. using a wedged prism pair, galvos, mirrors, and/or or tunable optics). The scan objective can be aligned at its nominal on axis position and with minimal angular deviation imposed by the prism wedges. The light may be reflected back using an externally mounted mirror to ensure proper alignment of the optical elements and beam collimation over a distance of several meters. Ensuring the beam collimation over a long distance can be important for high efficiency (e.g. a minimum of 70%) of the confocal coupling of the reflected laser beam into the single mode output fiber connected to the spectrometer.

The laser scan path can be reflected off the dichroic at 90 degrees onto a target, and it can be located at the focal working distance of the laser beam. At the same time, the eye camera can image the target through the dichroic. The imaging lens of the eye camera can be adjusted so the target and the laser spot are also in focus. The f-number of the eye camera pinhole can be adjusted to improve the camera resolution and achieve the desired depth of field for the eye for an in-focus image and easier alignment to the parfocal image plane.

In some embodiments, the Brillouin scanner system is designed to be used as an ophthalmological diagnostic device to assess longitudinal elastic modulus distribution in ocular tissues. The system and eye camera can be aligned to the patient using a joystick that is either manual or motorized (linear stepper, servo, or other motors). Once the device is aligned the patient, the operator can initiate the laser scan. A pattern of points can be acquired on the patient's eye. For each lateral location, Brillouin signal can be captured in depth over the full range of the ocular tissue being measured. In some cases, the scanning system relocates the beam over the FOV of the eye to achieve signal capture over the designated range of field points. Signals can be analyzed and interpolated to generate elastic stiffness maps of the tissue.

The scanning modalities disclosed herein enable the generation or building of one or more maps of longitudinal elastic modulus distribution in ocular tissues, in a short amount of time, and with consistency from one exam to another. Currently available manual positioning modalities (e.g. manual positioning of an objective lens) used in ophthalmic clinical research and similar studies can be slow and may not allow for the precise positioning of a scan, relative to the eye, in the presence of eye movements. Relatedly, patients and system operators alike can experience fatigue during a long exam acquisition cycle. Inconsistent maps can make it more difficult to compare data between different exams or control the volume of the measurement. These issues can be problematic for users, physicians, operators, patients, and other individuals.

Still further, currently available manual positioning techniques can involve lengthy examination times, as well as inconsistent tissue map coverage, which can lead to less accurate positional information obtained from the scans due to the complex geometry of a fixation target, an eye tracking camera, and a measurement objective. With galvanometer scanners, which likely can include a large opto-mechanical configuration, there may be beam wobbling from larger paddle mirrors.

Using embodiments of the present invention, it is possible to create consistent maps (e.g. with accurate positional registration), provide faster data acquisition, require less operator involvement, and/or maintain a more compact opto-mechanical setup. In some cases, system and method embodiments disclosed herein involve the use of hardware and/or software to enable the precise positioning of axial scans.

Turning now to the drawings, FIG. 1 illustrates an exemplary embodiment for Brillouin imaging. A first arrangement 100 provides a first electromagnetic radiation 110, which is delivered to an eye 120. A most appropriate form of the electromagnetic radiation 110 is light in the visible or near infrared range. The first arrangement includes a light source, which is typically a single-frequency laser, a filtered Mercury lamp, or other types of light emitters known in the art. The light source can have a wavelength between 530 nm and 1350 nm, but other wavelengths and light powers that are known to be safe for use in the eye can be used. The linewidth of the light is typically less than 1 GHz or in some embodiments less than 100 MHz, but light sources with broader linewidth or multiple spectral lines may be used in conjunction with appropriate arrangements.

The electromagnetic radiation 110 is directed to the eye 120 to probe various portions of ocular tissues, including but not limited to the cornea 122 and the crystalline lens 124. In general, an imaging lens 130 is used to focus the electromagnetic radiation 110 onto a small spot. The imaging lens 130 can be a spherical convex lens, aspheric lens, objective lens, theta lens, or cylindrical lens for line focusing. A focus 132 can be scanned over the eye 120 to obtain biomechanical information at multiple locations in ocular tissues and thereby to obtain Brillouin images.

To scan the axial position of the focus 132 within the ocular tissues, the imagining lens 130 may be mounted on a translation stage 134. Alternatively, a tunable element that changes the convergence angle of the probe light may be employed. To scan the transverse position of the focus, a one- or two-axis beam scanner 140 is employed. The scanner 140 can be a galvanometer-mounted mirror, MEMS mirror, translation stages, or spatial light modulator. In some cases, the scanner 140 can be a prism scanner. In some cases, a scanner 140 can be a tip-tilt mirror.

The acousto-optic interaction in the tissue gives rise to light scattering, generating second electromagnetic radiation. Several mechanisms for light scattering are known in the art, which includes Rayleigh and Mie scattering, Raman scattering, and Brillouin scattering. While in general biological tissues support all of these scattering mechanisms, Brillouin scattering is directly associated with the acoustic waves in the medium. A portion of the at least one second electromagnetic radiation can be collected by the imaging lens 130. In an epi-detection configuration, the interacting probe and Brillouin-scattered lights travel in the nearly opposite directions. Alternatively, a dual-axis configuration can be employed, where the probe and scattered light for a finite angle.

The system may employ a beam splitter 142 to reflect and transmit the first and second electromagnetic radiations. The beam splitter 142 may have an equal 50/50 splitting ratio or unequal splitting ratios for optimization of the efficiencies of signal generation and collection. The beam splitter 142 may be a neutral splitter with broad spectral bandwidth or a dichroic splitter based on multilayer coating, interference, or diffraction. The portion of the second electromagnetic radiation 144 is sent to a second arrangement 150, which is configured to receive the at least one portion 144 of the at least one second electro-magnetic radiation.

In some embodiments, the second arrangement 150 employs at least one spectral analysis unit, such as a spectrometer, a monochromator, fixed or scanning spectral filters, or other devices known in the art. The second arrangement 150 is configured to measure various properties of the second electromagnetic radiation 144, including but not limited to the center frequency and width of its spectrum, as well as the intensity and polarization of the electrical field. In particular, the frequency difference between the at least one first electromagnetic radiation 110 entering the tissues and the at least one portion of the second electromagnetic radiation 144, which includes the Brillouin scattered light, is of importance.

The frequency shift $V_B$ of the Brillouin scattered light with respect to the probe light 110 is given by $$V_B = \pm \frac{2nV}{\lambda} \sin\left(\frac{\theta}{2}\right)$$

where n is the local refractive index in the interrogated tissue, V is the speed of the acoustic wave in the sample, and θ is the scattering angle, i.e. the angle between the incident and the scattered light, such as in the dual-axis geometry. In an epi-backward detection configuration, θ=π is a reasonably good approximation. In typical soft tissues, the speed of the acoustic wave ranges from 1000 to 3000 m/s, and the Brillouin frequency shifts are typically between 2 and 20 GHz, depending on the wavelength.

The intrinsic spectral width or linewidth of the Brillouin scattered light is given by:

$$\Delta V_B = \frac{\alpha V}{\pi}$$

where α is the attenuation coefficient of the acoustic wave in the sample.

The longitudinal complex elastic modulus, M=M'+iM", where the real part M' refers to the elastic modulus and the imaginary part M" is the viscous modulus is given by:

$$M'=\rho V^2$$

$$M''=2\rho V^3 \alpha/V_B$$

Therefore, the measurement of the spectral characteristics of the Brillouin scattered light provides the information about the biomechanical properties of the ocular tissue. The useful information obtained by the Brillouin measurement includes but is not limited to the acoustic speed, acoustic attenuation coefficient, Brillouin elastic modulus, Brillouin viscous modulus, and electrostriction coefficient. As is further described below, by scanning the focus within the tissue different spatial locations can be probed, which provides the information in a spatially resolved manner. This spatial information can in turn be useful to evaluate for the diagnosis of the mechanical integrity or health of the ocular tissue.

The index of refraction and acoustic speed of a given material are generally dependent on the local temperature and pressure. This dependence may be harnessed for the analysis of inflammatory or pathologic states in the eye via the measurement of the temperature or pH-value in the aqueous and vitreous humors. The magnitude of the Brillouin scattered radiation is related to the coupling of acoustic and optical energy inside the sample, which is related to the material properties, such as the electrostriction coefficient.

The Brillouin viscoelastic moduli defined in the two equations above represent the tissue properties at the hypersonic GHz frequencies. Most soft tissues, including the corneal tissues and crystalline lens, exhibit viscoelastic properties characterized by frequency-dependent moduli. Slower relaxation processes have little time to respond to fast mechanical or acoustic modulation, such as GHz acoustic phonons, and thus hardly contribute to the "softness" of the material. As a consequence, modulus tends to increase with frequency. In addition, the propagation of acoustic phonons is governed by the longitudinal modulus, which is typically much higher than the Young's or shear modulus owing to the incompressibility (i.e. Poisson's ratio≈0.5) of water. The two effects, finite relaxation time and low compressibility, provide qualitative explanation for the observed large difference in modulus between the Brillouin and standard mechanical tests.

Figure 2:
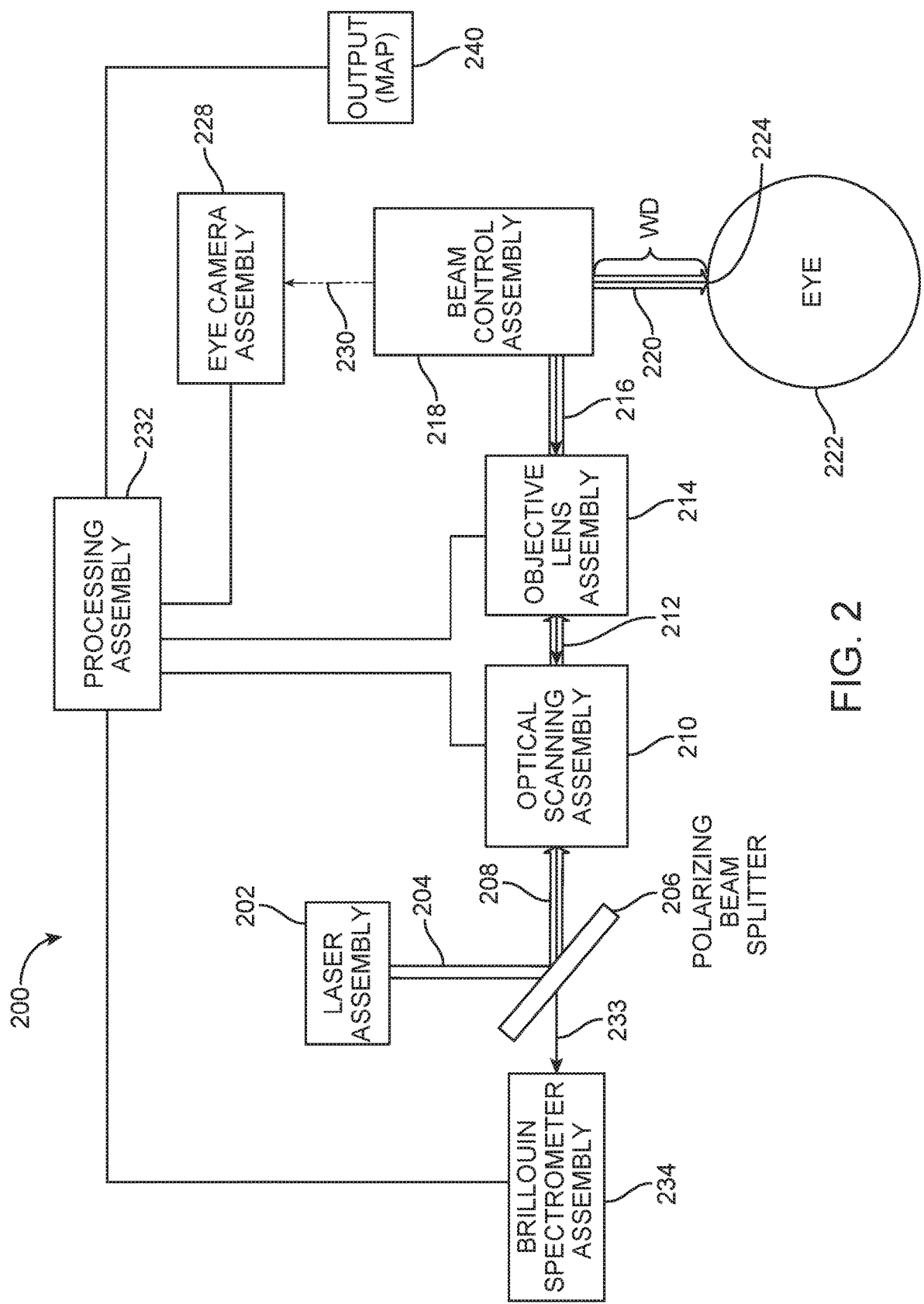
FIG. 2 depicts aspects of a system for generating an elastic stiffness map for a volume of an ophthalmic tissue of an eye of a patient, according to embodiments of the present invention.

FIG. 2 depicts aspects of a patient interface system 200 according to embodiments of the present invention. As discussed elsewhere herein, system 200 can be used to generate an elastic stiffness map 240 for a volume of an ophthalmic tissue of an eye of a patient. As shown here, system 200 includes a laser assembly 202 that generates a collimated scanning diagnostic laser beam 204, a polarizing beam splitter 206 that reflects a portion 208 of the collimated scanning diagnostic laser beam 204, and the reflected portion 208 is then transmitted to an optical scanning assembly 210. In some cases, the patient interface system 200 may not include the polarizing beam splitter 206. The optical scanning assembly 210 operates to redirect a beam path of the reflected portion 208 of the collimated scanning diagnostic laser beam. For example, the optical scanning assembly 210 can change the angular direction of the beam path of the reflected portion 208 of the collimated scanning diagnostic laser beam. The redirected reflected portion 212 of the collimated scanning diagnostic laser beam is then transmitted to an objective lens assembly 214, which operates to focus the redirected portion 212 of the collimated scanning diagnostic laser beam to produce a focused scanning diagnostic laser beam 216. In turn, the focused scanning diagnostic laser beam 216 is reflected by a beam control assembly 218, and the reflected focused portion 220 is transmitted toward an eye 222 of the patient. As shown here, diagnostic scanning light and imaging light between the beam control assembly 218 and the eye 222 can be co-linear, and involve integrated returning light paths.

Figure 5:
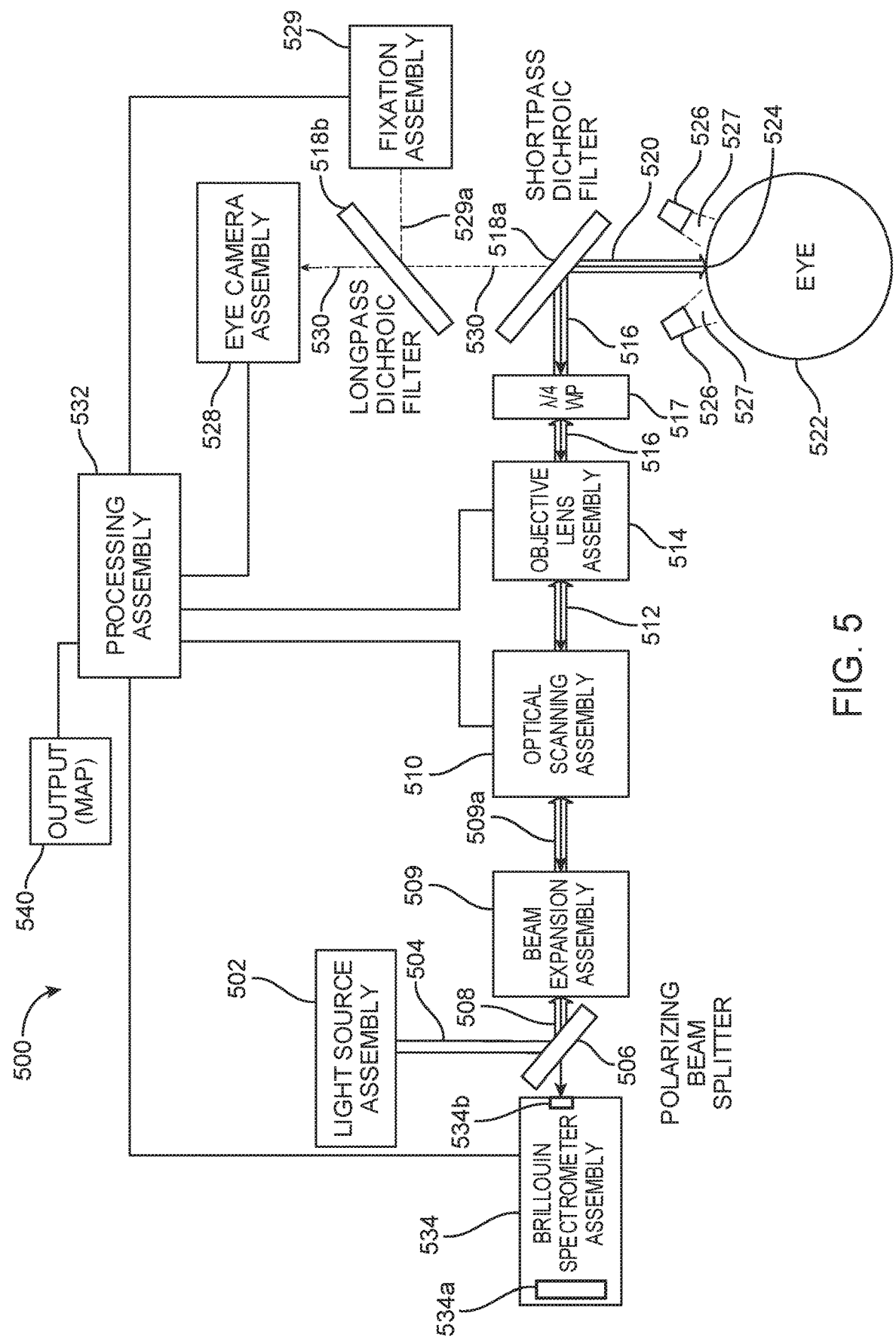
FIG. 5 depicts aspects of a system for generating an elastic stiffness map for a volume of an ophthalmic tissue of an eye of a patient, according to embodiments of the present invention.

As discussed elsewhere herein, for example with reference to FIG. 5, a beam control assembly 218 may include one or more dichroic filters. In some cases, a beam control assembly can be referred to as a beam combining assembly. In some cases, a beam control assembly can operate to combine together light of different wavelengths together. In some cases, a beam control assembly can be referred to as a beam splitter/combiner assembly. In some cases, a beam control assembly can operate to transmit and/or reflect light.

With returning reference to FIG. 2, the reflected focused scanning diagnostic laser beam 220 has focused spot 224, and operation of the optical scanning assembly 210 or the objective lens assembly 214, or the combined operation of the optical scanning assembly 210 and the objective lens assembly 214, can adjust a scan position of the focused spot 224 to various locations in one or more tissues of the eye 222. The optical scanning assembly 210 and/or the objective lens assembly 214 can include motorized elements, which can provide for an internal scanning technique, whereby the diagnostic beam can be scanned as desired or instructed, without moving the entire patient interface.

According to some embodiments, operation of the objective lens assembly 214 can involve moving or translating an objective lens of the assembly, such that the focused spot 224 moves along a z depth axis in the eye. Operation of the optical scanning assembly 210 can involve redirecting the focused spot within an xy plane that is perpendicular to the z axis (e.g. the axis of light propagation). In this way, an image on an eye camera assembly 228 can be used to provide a reference point, for the beam scanning and tracking, but the overall field of view and fixed focus of the eye would remain generally unchanged, over the duration of a scan procedure. In this way, it is possible to establish a start point for the scanning process, and then going forward track the relative motion of the eye to the previously scanned points. In contrast, with previously known systems, the entire system was moved in order to reposition the scan points, and as such the field of view on the eye camera changed as well, which could introduce some undesirable effects. According to some embodiments, the patient interface system 200 has a minimum ±5 mm diffraction limited scanning field of view. According to some embodiments, the patient interface system 200 has a minimum ±6 mm diffraction limited scanning field of view. In some cases, the minimum may be smaller. For example, some embodiments may involve mostly only axially scanning the beam for the crystalline lens, and not over the full wide field of view, due to aberrations. In some cases, it is possible to measure spots at target field points using a beam profiler over the field of view. In some instances, the patient interface system 200 has a ±5 mm scan depth. In some cases, it is possible to measure a spot with a beam profiler axially over depth.

The objective lens assembly 214 can include an objective lens having a relatively large numerical aperture (NA). For example, the NA can have a value of 0.1, or higher. In some cases, the NA can be 0.125. In some cases, the NA can be 0.4. In some cases, the NA can be greater than 0.4. In cases where the NA is greater, the objective may larger as well. In some cases, the NA may be lower than 0.1. If the NA is excessively low, the spatial resolution may also be excessively low, and there may be a greater likelihood of reflections contaminating the signal. The system 200 can also have a working distance (WD) which can be defined as the distance between the beam control assembly 218 and the patient eye 222. In some cases, the working distance can be about 50 mm. In some cases, the working distance can have a value between about 20 and 30 mm. In some cases, the working distance can be greater than 50 mm. In exemplary embodiments, the working distance is not critical for the operation of the instrument, but rather is an ergonomic design choice. Typically, the working distance is sufficiently large to prevent components of the system 200 from contacting the patient eye, which may introduce unwanted contamination onto the eye, hurt the patient, and/or contaminate the optics. In some cases, the design of the lens objective may involve balancing factors such as the size of the lens objective, the NA of the lens objective, and the working distance of the system. In some cases, a larger numerical aperture may be desired to achieve sufficiently tight focal spot within the tissue, so that a good Brillouin signal is obtained.

It is often desirable to perform the scanning in a time efficient and light efficient manner. Embodiments of the present invention are well suited for providing diagnostic methods using a minimal scan time. Embodiments are also well suited for use with Brillouin imaging, which typically involves very low light levels. In this way, it is possible to complete a scan quickly while also obtaining a usable signal. Such approaches can provide for the improved accuracy of measured data, and also for improving the patient experience, as they do not need to keep their eyes open for an excessively lengthy period of time.

The patient interface system 200 also includes an eye camera assembly 228 that receives imaging light 230 from the eye (which optionally may have passed through beam control assembly 218) and that generates electrical signals in response to the received imaging light 230. In some cases, the eye camera assembly has a working distance of 200 mm. In some cases, the eye camera assembly has a focal length of 50 mm.

The patient interface system 200 can further include a Brillouin spectrometer assembly 234 having a Brillouin spectrometer and a spatial filter that is parfocal with the focused spot (e.g. in a conjugate focal plane). The Brillouin spectrometer can generate Brillouin signals as the focused spot 224 is scanned to discrete locations throughout a volume or plane thickness of ophthalmic tissue of the eye 222. Brillouin scattered light from the focused spot at the discrete locations is returned to the spatial filter. As shown here, a carrier wave 233 is received by the Brillouin spectrometer assembly 234.

Figure 3B:
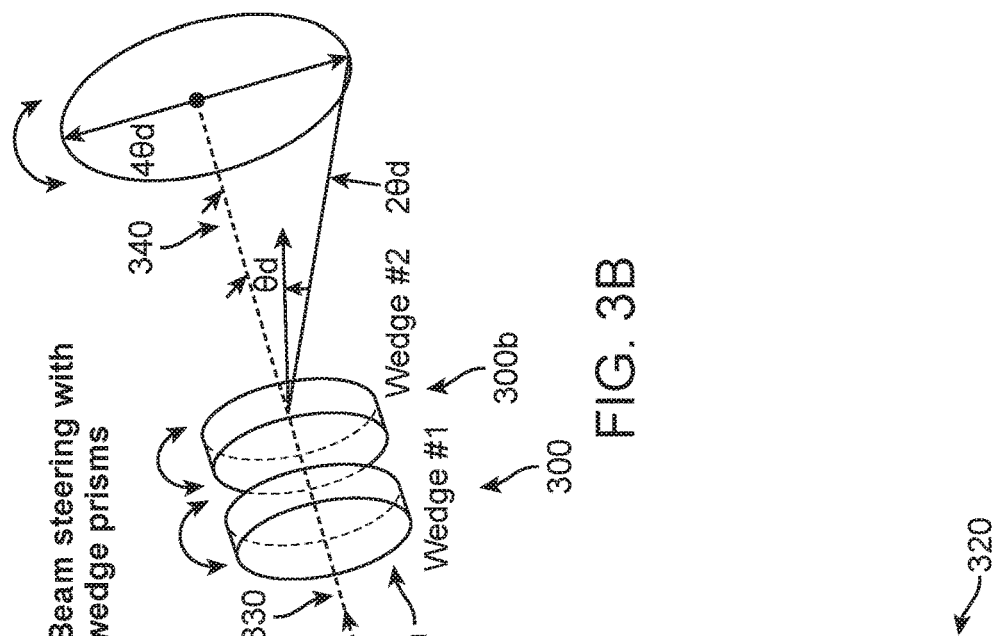
FIG. 3 depicts aspects of an optical scanning assembly for use in an imaging, scanning, or mapping system, according to embodiments of the present invention.
Figure 3C:
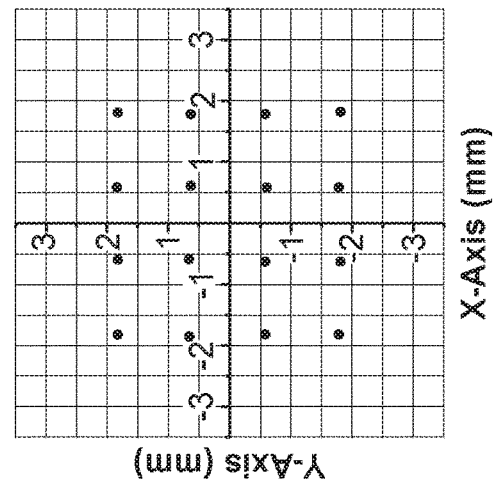
Figure 3A:
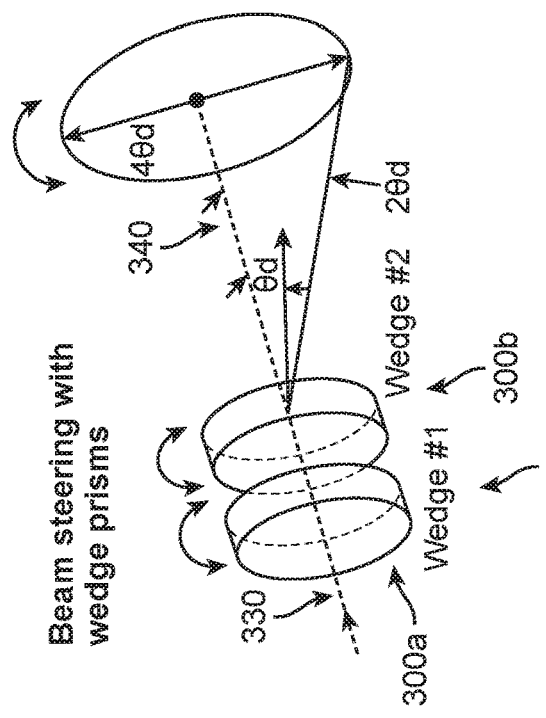

Additionally, the patient interface system 200 includes a processing assembly 232 in operative association with the optical scanning assembly 210, the objective lens assembly 214, the eye camera assembly 228, and the Brillouin spectrometer assembly 234. The processing assembly 232 can include a processor, an electronic storage location operatively coupled with the processor, and processor executable code stored on the electronic storage location and embodied in a tangible non-transitory computer readable medium. The processor executable code can include machine-readable instructions that, when executed by the processor, cause the processor to generate x,y coordinate scan control signals for the optical scanning assembly 210. In some cases, x,y coordinate scan control signals for the optical scanning assembly 210 can be generated based on the electrical signals generated by the eye camera assembly 228. The processor executable code can include machine-readable instructions that, when executed by the processor, cause the processor to generate z coordinate scan control signals for the objective lens assembly 214. In some cases, the x,y coordinate scan control signals, the z coordinate scan control signals, or both the x,y coordinate scan control signals and the z coordinate scan control signals, can be based on an image of the eye. In some cases, the x,y coordinate scan control signals, the z coordinate scan control signals, or both the x,y coordinate scan control signals and the z coordinate scan control signals, can be generated independent of an image of the eye. In some cases, the x,y coordinate scan control signals, the z coordinate scan control signals, or both the x,y coordinate scan control signals and the z coordinate scan control signals, can be generated according to a pre-defined or pre-determined scan pattern. The processor executable code can include machine-readable instructions that, when executed by the processor, cause the processor to generate an elastic stiffness map 240 for a volume of ophthalmic tissue of the eye 222 based on Brillouin signals. In some cases, the optical scanning assembly 210 may include a prism pair, for example a prism pair as depicted in FIGS. 3A and 3B.

In some instances, it is possible to point, aim, or otherwise orient the patient interface system 200 relative to the patient eye 222, and then execute a pre-defined beam scanning pattern so as to gather biomechanical information regarding the tissue of the eye. Execution of the pre-defined beam scanning pattern could be controlled in part by operation of the optical scanning assembly 210 and/or the objective lens assembly 214, so as to scan the diagnostic beam to various points on or within the eye according to the pre-defined beam scanning pattern. For example, the pre-defined scan pattern may include a grid of 5×5 points in an x,y plane at a z depth, and operation of motorized elements of the optical scanning assembly 210 and the objective lens assembly 214 can facilitate analysis of the 25 grid points within the eye by the patient interface system 200, optionally without the use of the eye camera assembly 228. Often, the patient and/or the patient eye is moving throughout the beam scanning procedure. The eye camera assembly 228 can operate to track movement of the eye relative to the patient interface system 200. For example, the eye camera assembly 228 can be used to track the movement or location of a particular reference (e.g. center coordinate) of the eye. In this sense, the reference can be considered as a moving target. As the beam scanning pattern (e.g. pattern 320 depicted in FIG. 3C) is executed and spectrometer data is collected at various points throughout the eye tissue, the eye camera assembly 228 can track the movement of the eye (e.g. by tracking the pupil, or the center of the pupil). In this way, the processing assembly 232 can use the eye tracking data to register the spectrometer data to the appropriate locations of the eye tissue. In some cases, the eye movement data can be used by the processing assembly 232 to adjust or compute control signals for motorized elements of the optical scanning assembly 210 and/or the objective lens assembly 214, so that as the eye moves, the scanning pattern is adjusted or computed so as to accommodate for such eye movement. In this way, the eye camera assembly 228 can be used to determine where the eye is at any given moment, and before the system obtains information from another scan point, the eye location can be used to calculate a desired deflection of the laser beam, so as to match the current position of the eye. In some cases, it can be calculated where the laser is on the eye for the predefined scan point rather than trying to track and update the actual position accordingly. In this sense, the eye camera assembly can be used to actively guide the scanning system to ensure that the diagnostic laser focused point is directed to the desired position. Such tracking can be helpful, because even where a patient has their head secured within or relative to a headrest, there can still be eye motion or movement within tissues of the patient eye, due to the patient's heartbeat, involuntary eye movements, changes in gaze direction, slight bodily movements, and the like. Such movements can have a significant impact on the location or orientation of the patient cornea, which may have a thickness on the range of 0.5 mm. In some cases, the thickness can have a value between 0.4 mm and 0.7 mm. For example, such movements can otherwise cause the scanning beam focused spot to be localized slightly off-target relative to a pre-defined or computed scan pattern, within the tissue.

Operation of the spectrometer assembly 234 can be used to generate a tissue (e.g. cornea) stiffness map, and the map can be registered to points within the corneal tissue using information obtained by the eye camera assembly 228, so as to provide a spatial map for the patient eye. In some cases, the system 200 can be configured to maintain a history of scanned points relative to the eye's position, and this history can be used in the calculation of an elasticity or stiffness map. In this way, a physician can read the map 240 and determine which locations on the patient eye correspond to various stiffness values, because the acquired biomechanical data is co-registered with the actual coordinate system of the eye using imaging information obtained by the eye camera assembly 228. In some cases, information from the eye camera assembly 228 is used to generate the map 240. In some cases, no information from the eye camera assembly 228 is used to generate the map. In some cases, a map 240 is not generated. In some cases, only information related to the measured z-axis is obtained, so as to produce a one-dimensional elastic stiffness profile (as compared to a higher dimensional elastic stiffness map).

In some embodiments, spectrometer information related to points within the tissue that are interrogated with the focused spot is used to generate a map. In some cases, data from points within a particular region can be averaged (e.g. averaging data obtained from multiple points along a z axis). In some cases, data from points within a particular region is not averaged. In some cases, the averaging can be performed so as to accommodate for eye movement. In some cases, an axial scan can be performed to create a characteristic curve as Brillouin signal from different media are detected. For example, this may involve the transition from air to cornea to water-like aqueous humor. Similarly, it may be desirable to start deeper and go in the opposite direction since the thickness is larger for the crystalline lens and aqueous humor relative to the cornea. Also, this may limit or eliminate the need to address back reflections from the air cornea interface. There is a characteristic Gaussian transition between the cornea and the aqueous humor, with known frequency shift ranges for the Brillouin signals from those tissue types. Also, based on the scan rate, known structure thickness ranges, and curve fitting, the characteristic curve can be analyzed for scan quality and points to averaged can be appropriately extracted. Additionally, individually scanned points Brillouin frequency can be curve fit for their own quality metrics and included/excluded in the average based on the sensitivity and standard deviation of the measurement. Embodiments of the present invention can encompass any of a variety of different scan sequences for control algorithms of the scan. For example, some embodiments may involve scanning in a spiral pattern rather than raster scanning. Some embodiments may involve using and retraining information from adjacent scan points and the patient moves.

In some cases, the optical scanning assembly 210 may include a prism pair. FIGS. 3A, 3B, and 3C depict aspects of a Risley prism pair 300 according to embodiments of the present invention. By rotating either of both of the prisms (300a, 300b) of the pair, it is possible to achieve a desired (e.g. spherical) scanning pattern on the person's eye through angular deviation of the probing electromagnetic radiation. Prism rotation can enable the relocation or redirection of the beam on the x,y space on the person's eye.

FIG. 3A depicts a front view and a side view of an exemplary prism 310. As shown in FIG. 3B, two wedge prisms can be used to create an angular deviation of a beam from its optical axis. In this way, it is possible to generate a desired scan pattern or discrete beam pointing 320 as depicted in FIG. 3C. Often, the prisms themselves are rotated about their own axis. In some embodiments, a Risley scanner can involve rotating two wedged prisms to scan the beam in a circular arc or a circular pattern. In some embodiments, light 330 entering the prism pair 300 is collimated and light 340 exiting the prism pair is collimated.

A first wedge prism 300a and a second wedge prism 300b can be rotated as desired. In some cases, the prisms are rotated independently and/or sequentially. In some cases, the prisms are rotated in tandem. In some cases, the prisms are rotated in the same direction. In some cases, the prisms are rotated in opposite directions. In some cases, only one prism is rotated. Accordingly, the rotation enables the deviation or redirection of the beam, by a known or predetermined amount, depending on the relative angle between the prisms. Operation of the prisms may rely upon the angular deviation and refraction of the prisms.

As desired, the rotation can be converted into cartesian coordinates as well as polar coordinates. In some cases, the optical scanning assembly can operate to redirect or reposition the beam from one scan grid coordinate to another (e.g. as depicted in FIG. 3C), once every two to three seconds. This frequency can give the patient time to blink, so as to re-hydrate their eye. In this way, it can be seen that controlled operation of the optical scanning assembly can effect scanning of the beam in the x,y plane on a scan grid 320. The optical scanning assembly can reposition the laser beam as desired. In some cases, if a patient blinks, the eye camera can be used to indicate that the patient has blinked, and the associated scan data can be excluded, or optionally obtained again.

In some embodiments, the focused spot of the diagnostic beam can be scanned to the individual discrete locations of the scan grid 320. In addition to scanning in a single x,y plane, it is also possible to scan in multiple x,y planes, by adjusting the z depth. Information corresponding to each of the locations on the scan grid can be used to generate a characteristic profile from which elasticity information can be extracted. In some cases, information for various points can be interpolated together to generate a heat map of elasticity, and such a heat map can be overlaid to an image of the eye. In the case of keratoconus, the patient may have a weakening of the cornea in a region located in the lower portion of the eye. Based on such information, a physician may decide to disqualify a patient from a particular refractive surgery procedure, to treat the patient with a cross-linking procedure, or to perform or not perform another treatment on the eye.

Figure 4:
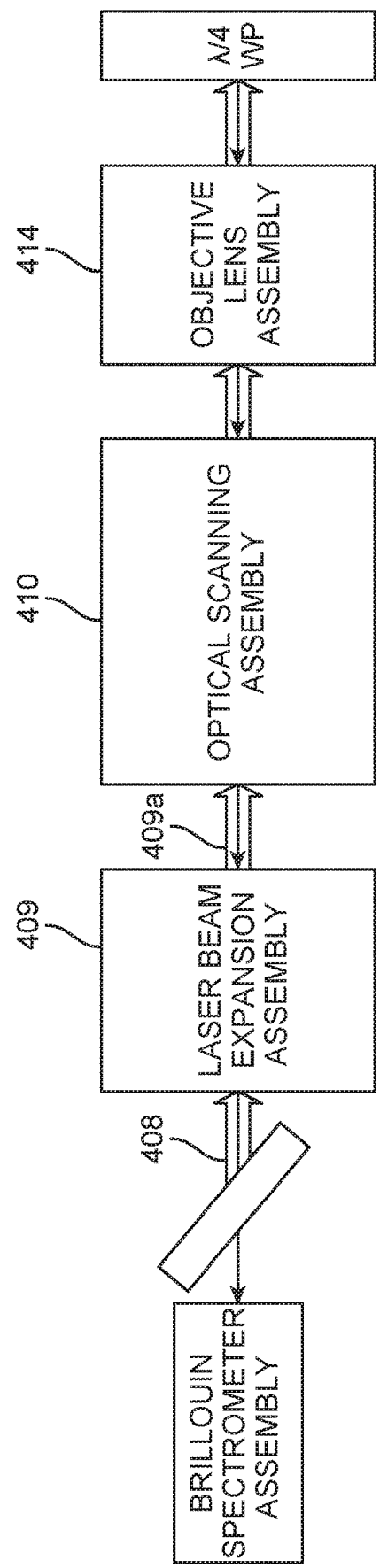
FIG. 4 depicts aspects of a system for generating an elastic stiffness map for a volume of an ophthalmic tissue of an eye of a patient, according to embodiments of the present invention.

As shown in FIG. 4, a beam expansion assembly 409, such as a laser beam expansion assembly, can be positioned upstream (with regard to the direction of the scanning diagnostic laser beam 408) of the optical scanning assembly 410. In many cases, it is desirable to use a beam expansion assembly so as to ensure filling of the back aperture of an objective lens of the objective lens assembly 414. According to some embodiments, the optical scanning assembly 410 includes a prism pair, the individual prisms of the pair are positioned very close to one another, the prism pair provides a relatively large clear aperture, and there is no consequence to increasing their aperture. In some cases, such positioning may not be necessary for operation of the instrument, and if there is more wobble due to larger spacing, then this unwanted beam steering can be accounted for elsewhere in the instrument design. In some cases, increasing the clear aperture for a combined XY mirror paddle like a galvo can result in the paddles needing to be separated further apart (since this is a combined XY setup). In some cases, if an instrument uses prisms which are rotated about the optical axis, increasing their CA may not grow their size along the optical axis. So, no additional separation between the prisms may be incurred. In some cases, this this can be advantageous because it is possible to do beam expansion before instead of after the angular deviation has been imparted on the laser source. One or more of these principles can also generally apply to a multiaxis mirror or similar device. Accordingly, it is possible to have the laser beam expansion assembly 409 positioned upstream of the optical scanning assembly 410 and/or the objective lens assembly 414 (as opposed to being positioned in the scanning space), and it is also possible to have a large collimated beam 409a coming into the optical scanning assembly 410, and hence wobble for the system is maintained at a small amount.

In the embodiments depicted in FIGS. 2 and 4, it is possible to position the optical scanning assembly (e.g. 210, 410) very close to the back of the objective lens assembly (e.g. 214, 414), and it is also possible to maintain a very short or small angular deviation of the beam, whereby the ratio of the angular deviation through the prism pair to the angular deviation on the eye is minimal or minimized.

According to some embodiments, operation of the objective lens assembly 414 can perform the axial scanning in the z (depth) direction. In some cases, the optical scanning assembly 410 and the objective lens assembly 414 can be moved together in tandem. When the optical scanning assembly 410 and the objective lens assembly 414 are moved together in tandem, it is possible to maintain a constant distance between them, and this distance may be a short distance. In some cases, having a short distance between 410 and 414 can be advantageous because it can help keep the objective size smaller. In some cases, if there is an angle on the beam, the farther the objective is away from the scan assembly, the larger the objective will need to be in order prevent vignetting. In some case, the optical scanning assembly 410 and the objective lens assembly 414 can be moved independently from one another.

FIG. 5 depicts aspects of a patient interface system 500 according to embodiments of the present invention. As discussed elsewhere herein, system 500 can be used to generate an elastic stiffness map 540 for a volume of an ophthalmic tissue of an eye of a patient. As shown here, system 500 includes a laser assembly or light source 502 that generates a collimated diagnostic laser beam 504, a polarizing beam splitter 506 that reflects a portion 508 of the collimated diagnostic laser beam 504, and the reflected portion 508 is then transmitted to a laser beam expansion assembly 509, which converts beam 508 to an expanded beam 509a. In some cases, light source 502 can be a device that produces electromagnetic radiation characterized by one or more wavelengths or one or more frequencies. According to some embodiments, the electromagnetic radiation beam expansion assembly 509 expands a collimated scanning diagnostic laser beam from a first diameter to a second diameter that is larger than the first diameter. The laser beam expansion assembly 509 may include multiple lenses. In some cases, the laser beam expansion assembly 509 includes lenses disposed in a Galilean configuration, with a negative lens followed by a positive lens. In some case, the laser beam expansion assembly 509 can be provided as a Galilean type beam expander. In some cases, the collimated scanning diagnostic laser beam has a linear polarization orientation. In turn, expanded beam 509a is transmitted to an optical scanning assembly 510.

As shown here, the polarizing beam splitter 506 can be positioned before the laser beam expansion assembly 509. The polarizing beam splitter 506 can operate to split the diagnostic laser beam 504 into a scanning portion (508) and a non-scanning portion (not shown). In some cases, the beam splitter 506 allows for the measurement (e.g. concurrent) of a reference sample. In some cases, the beam splitter 506 operates to provide an additional amount of filtration of back reflections of light. In some cases, the polarizing beam splitter 506 transmits light at a 90 degrees orientation and on the return path the light goes to 90 degrees. According to some embodiments, the beam splitter 506 works in conjunction with the quarter wave plate 517. For example, after two passes through the waveplate 517, the returning light can be passed back to the spectrometer assembly 534, and light that has only passed once (e.g. reflections from lenses) will be excluded. In some cases, when the light first enters the quarter wave plate 517, some amount can be portioned to a calibrated reference sample. As described elsewhere herein (e.g. FIGS. 11-15), a half-waveplate element may also be positioned after the laser source which sets up a ratio of linearly polarized s and p. This can control the light split through the polarizing beam splitter (PBS). According to some embodiments, a Brillouin signal from a sample can be used as a built in reference to the instrument for accurate calculation of the Brillouin signal. There may also be a quarter waveplate on the reference path to provide an isolated signal that will make its way back to the spectrometer.

According to some embodiments, the optical scanning assembly 510 operates to adjust or redirect a beam path of the expanded collimated scanning diagnostic laser beam. In some cases, the patient interface system 500 may not include the polarizing beam splitter 506. The optical scanning assembly 510 operates to redirect a beam path of the reflected portion 508 of the collimated scanning diagnostic laser beam. The redirected reflected portion 512 of the collimated scanning diagnostic laser beam is then transmitted to an objective lens assembly 514, which operates to focus the redirected portion 512 of the collimated scanning diagnostic laser beam to produce a focused scanning diagnostic laser beam 516.

According to some embodiments, the objective lens assembly 514 operates to focus the expanded collimated scanning diagnostic laser beam 512 to produce a focused scanning diagnostic laser beam 516 having a beam waist or focused spot. In some cases, the objective lens assembly 514 operates to adjust a scan position of the beam waist or focused spot. In some cases, the objective lens assembly 514 includes a motorized stage that allows the objective lens assembly to travel toward and away from the optical scanning assembly 510. In some cases, the optical scanning assembly 510 includes a motorized stage that allows the optical scanning assembly to travel toward and away from the objective lens assembly 514. In some cases, the optical scanning assembly and the objective lens assembly include or are disposed on respective motorized stages, or are disposed on a common motorized stage, so that the optical scanning assembly and the objective lens assembly can move in tandem.

As shown here, system 500 may include a quarter-wave plate assembly 517. In some embodiments, the quarter-wave plate assembly 517 operates to convert the focused scanning diagnostic laser beam 516 from a linear polarization orientation to a circular polarization orientation. In some embodiments, the quarter-wave plate assembly 517 operates to provide a 45 degree rotation to the focused scanning diagnostic laser beam 516. In some cases, the quarter-wave plate assembly 517 operates to convert the focused scanning diagnostic laser beam 516 from p-polarized light to s-polarized light. In a double pass embodiment, s-polarized light can be converted to p-polarized light (e.g. whatever is orthogonal to the input wave). In some cases, the quarter-wave plate assembly 517 operates to convert the focused scanning diagnostic laser beam 516 from s-polarized light to p-polarized light. The quarter-wave plate assembly 517 can be placed along the beam path, for example between the objective lens assembly 514 and the shortpass dichroic filter 518*a*. In some embodiments, the quarter-wave plate assembly 517 can be placed upstream of the objective lens assembly 514 or downstream of the shortpass dichroic filter 518*a*. In some cases, the quarter-wave plate assembly 517 can be placed anywhere as desired, between the sample (e.g. eye) and the PBS. In some cases, the quarter wave plate assembly operates to isolate out back reflections from system, for example as described elsewhere herein. In some case, the quarter-wave plate is configured to perform the classical operation of an optical isolator.

The focused scanning diagnostic laser beam 516 is reflected by a shortpass dichroic filter 518*a*, and the reflected focused portion 520 is transmitted toward an eye 522 of the patient. In some cases, the focused scanning diagnostic laser beam has a circular polarization orientation and is reflected by the shortpass dichroic filter 518*a* toward the eye 522. In some cases, isolation and redirecting are the core functions performed on the beam. In some cases, the returning beam is transformed back to linear polarization again when it passes back through the waveplate.

According to some embodiments, a dichroic filter can operate as a beam splitter that splits light based on wavelength or color, rather than splitting light based on power. In some cases, a dichroic filter will transmit light within a certain wavelength band or range and/or reflect light within a certain wavelength band or range. As shown here, dichroic filters can operate to fold together, or to separate out, different wavelengths of light (e.g. into a common optical path).

In some case, the dichroic filters can operate to fold together fixation light 529*a*, imaging light 530, and scanning diagnostic light 520, into a common optical path (e.g. between the shortpass dichroic filter 518*a* and the eye 522). Similarly, a dichroic can operate to peel apart light from a common path into separate optical paths, for example imaging light 530 and returned scanning diagnostic light travel along a common optical path from the eye to the shortpass dichroic filter 518*a*, and then the imaging light is transmitted through the shortpass dichroic filter 518*a* and the returned scanning diagnostic light is reflected by the shortpass dichroic filter 518*a*.

The reflected focused scanning diagnostic laser beam 520 has focused spot 524, and operation of the optical scanning assembly 510 or the objective lens assembly 514, or the combined operation of the optical scanning assembly 510 and the objective lens assembly 514, can adjust a scan position of the focused spot 524 to various discrete locations on or within one or more tissues of the eye 522.

The patient interface system 500 also includes an eye camera assembly 528 that receives imaging light 530 from the eye (which optionally may have passed through a shortpass dichroic filter 518*a* and a longpass dichroic filter 518*b* of a beam control assembly) and that generates electrical signals in response to the received imaging light 530. The imaging light 530 can provide registration information regarding the position and/or orientation of the eye. In some cases, this registration information can be used (e.g. by processing assembly 532) to provide locate elasticity measurement data obtained by the Brillouin spectrometer assembly 534 to particular points of the eye. In some cases, the imaging light 530 can help to provide feedback, which may be continuous feedback, to the processing assembly. The imaging light 530 can be processed to provide information regarding a center coordinate of the eye, a central reference of the eye, or more generically, a reference coordinate on the eye, which can be registered to the biomechanical data. Such a reference coordinate can be determined by processing the imaging data.

In some cases, the processing assembly 532 can operate to generate two images, specifically an image of the eye and a Brillouin heat map (e.g. stiffness values at discrete points), and to accurately superimpose those images on top of each other using registration. In this way, the mechanical information is relevant in the physical space. In some cases, the processing assembly does not perform a superimposition. Rather, a camera is used to provide a reference point to begin a scan pattern, and thereafter a scan is performed according to the pattern, so as to generate the stiffness map. The map can indicate whether there are any abnormal spots or points of interest on the eye, without providing the exact location on the eye of the abnormal spots or points of interest. In some cases, a camera is not used to provide a reference point to begin a scan pattern. For example, the physician or operate could manually inspect the person's eye, and then aim the beam, without using a camera. In some cases, it is possible to illuminate the person's eye using a certain wattage, observe a reflection off the person's eye, and determine that the alignment of the scanning beam and the eye is sufficient.

Hence, input techniques for aiming the diagnostic beam can include using a camera image or data, manually aiming the beam, or using feedback from the Brillouin spectrometer. For example, data obtained by the spectrometer can provide an indication of whether the system is in focus. The Brillouin spectrometer can be used to differentiate spectral shifts that are characteristic of different tissues. In some cases, as the focused spot is scanned in the z depth direction, it is possible to detect fundamentally different frequency shifts (or different information) as the focused spot goes through different layers (e.g. going from the air, to the cornea surface, to the aqueous humor, to the crystalline lens, and so on) which can correspond to different elastic properties (e.g. elastic modulus). In this sense, the Brillouin approach can provide aspects of an imaging modality. Hence, it may be possible to determine where the focused spot is located (e.g. along a z-axis), by observing or analyzing the spectrometer image. In some cases, it is possible to align or position the patient interface system, by observing or using a reflection off of a person's eye, then moving the system into focus based on feedback from the spectrometer camera, and then initiating the scan. In some cases, the camera is parfocal with the laser beam, and the focus of the eye can also be used.

In some embodiments, system 500 also includes a fixation assembly 529 that provides the eye with a gaze target. In some cases, fixation light 529a is generated by the fixation assembly 529, travels from the fixation assembly 529, is reflected by the longpass dichroic filter 518b, travels through the shortpass dichroic filter 518a, and to the eye 522. According to some embodiments, the fixation assembly 529 includes a matrix of light-emitting diode (LEDs).

The patient interface system 500 can further include a Brillouin spectrometer assembly 534 having a Brillouin spectrometer 534a and a spatial filter 534b that is parfocal with the focused spot 524 (e.g. in a conjugate focal plane). The Brillouin spectrometer can generate Brillouin signals as the focused spot 524 is scanned to discrete locations throughout a volume or plane thickness of ophthalmic tissue of the eye 522. Brillouin scattered light from the focused spot at the discrete locations is returned to the spatial filter 534b. According to some embodiments, the spatial filter 534b operates as an input for the Brillouin spectrometer, and is in conjugate alignment with the focused spot 524 or beam waist of the focused scanning diagnostic laser beam, and the Brillouin spectrometer 534a can generate Brillouin signals as the focused spot 524 or beam waist of the focused scanning diagnostic beam is scanned to discrete locations throughout the volume of the ophthalmic tissue of the eye 522. In some cases, the spatial filter 534b can operate to exclude information associated with out of focus focal planes, and include information associated with the focal plane of interest. The filter 534b can provide sensitivity to locations where the focused spot 524 is positioned, and little or no sensitivity to extraneous locations. In some cases, a spatial filter can be provided without using a fiber. In some cases, the spatial filter 534b can operate to prime the incoming light, which is then measured by the spectrometer 534a, which in turn generates the spectrum (e.g. Brillouin) signals.

By using a fiber input, it is possible to provide modularity to the system, whereby the patient scanning interface can be decoupled and coupled with the spectrometer via the optical fiber. Such modularity can provide enhanced testing and serviceability advantages. For example, the optical fiber could be uncoupled from one patient interface system, and coupled with another patient interface system. Hence, if one patient interface were to malfunction, it could be replaced with another patient interface. This could also allow patient interfaces to be tested as modules, which can improve manufacturability.

From an optical standpoint, a fiber can provide a highly functional pinhole. In some cases, such embodiments can provide a separate input and output. It is possible to physically decouple with free space optics the input and output of the system. In some embodiments, the input is not separated from the output. For example, the same light can be coupled back into the same input path and optionally the beam could be redirected to the spectrometer after traveling back down the fibe.

According to some embodiments, an optical output out of a single mode fiber can provide or approach a perfect Gaussian distribution, which has desirable beam shape and optical quality characteristics, and can be well suited for use with sensitive optical elements. As such, this feature can help optimize the optical performance of the overall system, particularly when multiple optical elements are involved.

In some cases, a fiber can operate as a conjugate pinhole or aperture (or spatial filter) for the focus spot in the tissue that is being analyzed. The fiber can operate to provide a focal plane resolution and specificity, filtering out the out of focus light that is not of interest. In some cases, a spatial filter can be provided as a radial aperture or a circular aperture. In some cases, an aperture can have a diameter of about 1 mm aperture. In some cases, the focus of the light is aligned with the core of a fiber, whereby only that light which is properly aligned to the core of the fiber will make it into that fiber. Thereafter, that light will be propagated down the fiber. In this sense, the core of the fiber can operate as a filter, spatial mask, or pinhole aperture, whereby light coupled into the core of the fiber is propagated, and undesired light is filtered or masked out. Often, a fiber will operate in conjunction with a lens. In some embodiments, the fiber can be provided as a collimated fiber optic. In some cases, light is focused into the fiber, or into the core of the fiber, using a lens. The light can be propagated in the fiber by way of total internal reflection. Where light is not properly aligned with the fiber core, such light may not propagate down the fiber, or be coupled into that fiber.

Put another way, light that is at a different focal plane, in the tissue, will not be at the same focal plane, over at the pinhole or spatial filter side, and hence becomes filtered out. The out of focus light will not make it into the pinhole or spatial aperture, and won't be coupled into the fiber, because that light is not aligned (e.g. not at the same focal plane, confocal, or conjugate).

As shown here, the patient interface system 500 can include a processing assembly 532 in operative association with the optical scanning assembly 510, the objective lens assembly 514, the eye camera assembly 528, the fixation assembly 529, and the Brillouin spectrometer assembly 534. The processing assembly 532 can include a processor, an electronic storage location operatively coupled with the processor, and processor executable code stored on the electronic storage location and embodied in a tangible non-transitory computer readable medium. In some cases, the patient interface system 500 may include peripheral embedded IO boards for digital or analog sensing and control of peripheral devices. For example, the system 500 may include a general-purpose input/output (GPIO) embedded processor board (e.g. "Arduino-like") to set the illumination intensity, the fixation pattern, to read from photodiode, and the like. The processor executable code can include machine-readable instructions that, when executed by the processor, cause the processor to generate x,y coordinate scan control signals for the optical scanning assembly 510. In some cases, x,y coordinate scan control signals for the optical scanning assembly 510 can be generated based on the electrical signals generated by the eye camera assembly 528. The processor executable code can include machine-readable instructions that, when executed by the processor, cause the processor to generate z coordinate scan control signals for the objective lens assembly 514. In some cases, the x,y coordinate scan control signals, the z coordinate scan control signals, or both the x,y coordinate scan control signals and the z coordinate scan control signals, can be based on an image of the eye. In some cases, the x,y coordinate scan control signals, the z coordinate scan control signals, or both the x,y coordinate scan control signals and the z coordinate scan control signals, can be generated independent of an image of the eye. In some cases, the x,y coordinate scan control signals, the z coordinate scan control signals, or both the x,y coordinate scan control signals and the z coordinate scan control signals, can be generated according to a pre-defined or pre-determined scan pattern. The processor executable code can include machine-readable instructions that, when executed by the processor, cause the processor to generate an elastic stiffness map for a volume of ophthalmic tissue of the eye 522 based on Brillouin signals. In some cases, the optical scanning assembly 510 may include a prism pair, for example a prism pair as depicted in FIG. 3.

As shown in FIG. 5, the eye 522 can be at a 90 degree angle of orientation relative to the general trajectory of the scanning diagnostic beam after the scanning diagnostic beam exits the objective lens assembly 514. In this way, the reflected focused portion 520 of the scanning diagnostic beam and the imaging light 530 that travels from the eye to the eye camera assembly are aligned in a colinear path. According to some embodiments, such a configuration (e.g. reflecting the beam off the shortpass dichroic filter 518a) may produce less astigmatism (or more generally, less optical aberration) than a different configuration (e.g. scanning or transmitting the beam through the shortpass dichroic filter 518a). This advantage may be particularly helpful for maintaining high beam quality when the scanning diagnostic beam is diffraction limited and involves a confocal focused spot. In some embodiments, the finer axial resolution spot will also minimize contaminating back-reflections from the front surface of the eye, allow for scanning of more of the eye thickness with better spatial resolution. Dichroic filters can operate to reflect or reject light having certain wavelengths, and to transmit light having certain wavelengths.

According to some embodiments, the system 500 can include one or more illumination lamps or light devices 526 that direct illumination light or radiation 527 toward the eye. In some cases, an illumination device 526 can be or include a light emitting diode (LED). In some cases, the illumination light or radiation 527 can be infrared light. In some cases, the illumination light or radiation 527 can be non-visible light. In some cases, the illumination light 527 can have a wavelength value within a range from about 700 nm to about 1,000,000 nm. In some case, the illumination light 527 can have a wavelength value of about 940 nm. According to some embodiments, the eye camera assembly 528 is sensitive to the wavelength of the illumination light 527 (which can also be the same as or similar to the wavelength of the imaging light 530).

In some cases, the illumination light 527 can have a wavelength value that is greater than a wavelength value of the diagnostic scanning light or radiation. In some cases, the diagnostic beam (e.g. 504, 520) has a wavelength value within a range from about 450 to about 1350 nm. In some cases, the wavelength of the scanning diagnostic beam has a value of about 780 nm. In some cases, the scanning diagnostic radiation can have a wavelength value within a range from about 450 to about 1350 nm. In some cases, the fixation light 529a is visible light. In some cases, the fixation light 529a is visible green light. In some cases, the fixation light 529a has a wavelength value of about 520 to about 560 nm. According to some embodiments, the fixation assembly 529 generates light 529a that provides the eye with a gaze target, which can be helpful in a clinical setting or application. In some cases, a system or method can include a gaze target that is not provided by a light emitting fixation assembly.

As shown in FIG. 5, the shortpass dichroic filter 518a can operate to reflect the incoming and returning scanning diagnostic beam, to transmit the imaging light 530 (which can be illumination light 527 reflected from the eye), and to transmit the fixation light 529a. Relatedly, the longpass dichroic filter 518b can operate to reflect the fixation light 529a and to transmit the imaging light 530 (which can be illumination light 527 reflected from the eye). In some cases, instead of using a shortpass dichroic filter 518a, it is possible to instead use a dichroic (e.g. longpass) or some other filter that reflects a certain wavelength range and passes another wavelength range.

According to some embodiments, the focused scanning diagnostic laser beam 520 optical path and the imaging light 530 optical path are provided as integrated colinear optical paths, as a result of the operation of one or more dichroic filters. In some cases, the respective optical paths may not be integrated in a colinear fashion. In some cases, by providing integrated colinear optical paths, it is possible to avoid or eliminate geometric distortions of the image that may otherwise be present when using an off-axis camera (even though it may be possible to achieve the same focal point for a laser, relative to the focus of the imaging camera).

In some cases, by providing integrated colinear optical paths, it is possible to more efficiently register biomechanical data to eye location and/or orientation data pertaining to a real world eye space. In some cases, it is possible to use eye tracker or camera information to register and track where those points have been scanned, relative to certain features and/or registration coordinates on the eye.

According to some embodiments, astigmatism can be incurred for the eye camera illumination or an image of the eye by transmitting through the dichroic, and a perfect 3D orthogonal orientation (e.g. of the illumination lamp 526) can cancel out that astigmatism.

As seen here, the longpass dichroic filter 518b operates to fold together the light 529a from the fixation assembly 529 and the imaging light 530 from the eye (integrated). Embodiments of the present invention also encompass designs where the fixation light 529a is not folded into the same path with the imaging light 530 (unintegrated). As shown in FIG. 5, in this embodiment there may be no lens between the shortpass dichroic filter 518a and the longpass dichroic filter 518b.

According to some embodiments, the eye camera assembly 528 of patient interface system 500 can image through a path that is not the same as the laser path. Patient interface system 500 can involve a co-axial scanning laser that is reflected at 90 degrees. Lateral xy scanning can be achieved by a Risley prism scanning method. A Risley prism pair can provide an optical x,y scanning capability. In some cases, the quarter wave plate assembly 517 can be positioned downstream of the objective lens assembly 514 for purposes of optical isolation. According to some embodiments, there is a mechanical coupling between the eye camera assembly 528 and the laser scanning. As discussed herein with reference to FIG. 6, embodiments of the present invention may also encompass mechanically decoupled systems. Patient interface system 500 can provide a diffraction limited focused spot over an entire focal volume. It is understood that an eye or any other sample with aberrations may make it so the spot is not diffraction limited.

Figure 11:
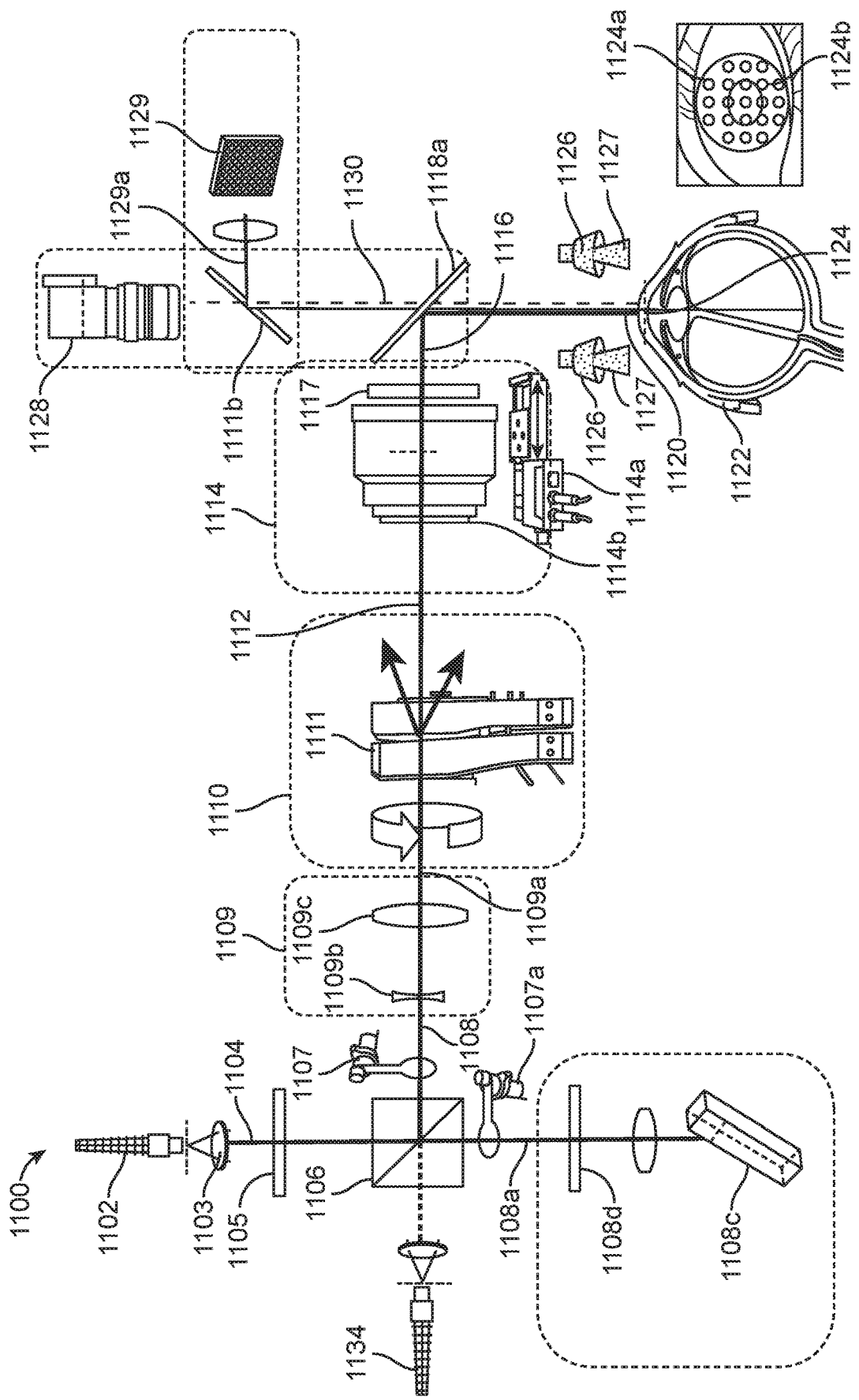
FIG. 11 depicts aspects of a system for generating an elastic stiffness map for a volume of an ophthalmic tissue of an eye of a patient, according to embodiments of the present invention.

In some cases, the patient interface system 500 depicted in FIG. 5 can incorporate one or more features of the embodiment depicted in FIG. 11. For example, FIG. 11 shows additional details regarding a reference path that is used to measure a sample containing plastic and water, that has known elastic properties. This can be used to normalize the data that is received from the actual tissue being analyzed, for example the cornea or the crystalline lens. Light can be controlled by a pair of shutters, and operation of the shutters can determine whether the laser light is going to hit the reference path, or whether the laser is going to hit the sample path. FIG. 11 also illustrates that a fixation assembly can include a grid of light points or light emitting diodes. The system can be configured to illuminate one or more points of the grid, so as to control where the patient directs their gaze. In this way, it is possible to facilitate the measurement of certain areas of the eye that otherwise may be difficult to scan or measure when the patient is looking directly straightforward. Accordingly, the system can facilitate a computerized control of the orientation of the eye, by changing the gaze angle. Performance graphs for the dichroic filters are illustrated, indicating transmission percentage (y axis) and wavelength (x axis). According to some embodiments, the dashed line boxes are provided to illustrate various submodules that are isolated based on their function. In some cases, multiple submodules with different functions can cooperatively work together as a system to achieve the overall function.

Figure 6:
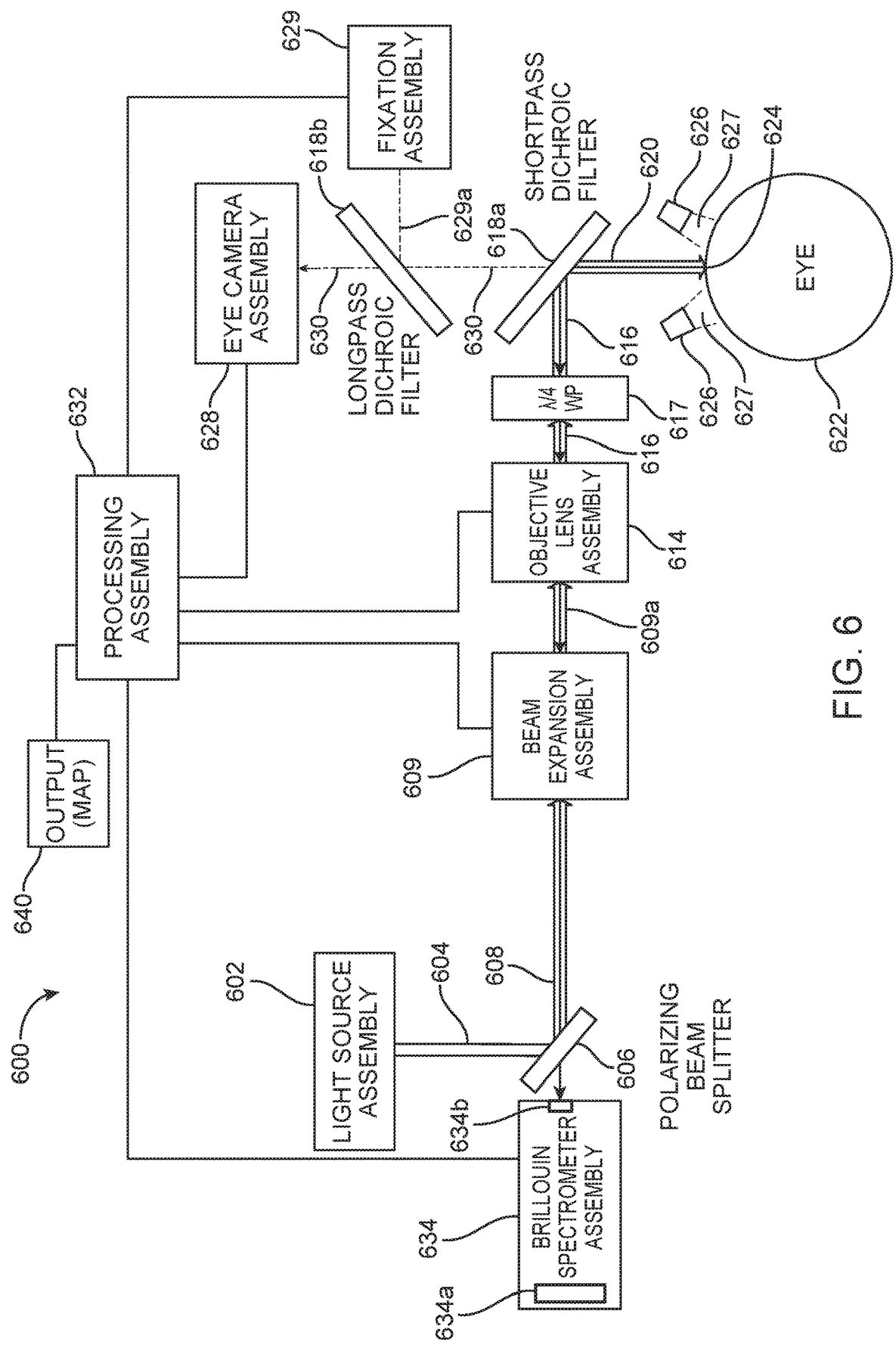
FIG. 6 depicts aspects of a system for generating an elastic stiffness map for a volume of an ophthalmic tissue of an eye of a patient, according to embodiments of the present invention.

FIG. 6 depicts aspects of a patient interface system 600 according to embodiments of the present invention. As discussed elsewhere herein, system 600 can be used to generate an elastic stiffness map for a volume of an ophthalmic tissue of an eye of a patient. As shown here, system 600 includes a laser assembly or light source 602 that generates a collimated diagnostic laser beam 604, a polarizing beam splitter 606 that reflects a portion 608 of the collimated diagnostic laser beam 604, and the reflected portion 608 is then transmitted to a laser beam expansion assembly 609, which converts beam 608 to an expanded beam 609a. In some cases, light source 602 can be a device that produces electromagnetic radiation characterized by one or more wavelengths or one or more frequencies. According to some embodiments, the electromagnetic radiation beam expansion assembly 609 expands a collimated scanning diagnostic laser beam from a first diameter to a second diameter that is larger than the first diameter. The laser beam expansion assembly 609 may include multiple lenses. In some cases, the laser beam expansion assembly 609 includes lenses disposed in a Galilean configuration, with a negative lens followed by a positive lens. In some case, the laser beam expansion assembly 609 can be provided as a Galilean type beam expander. In some cases, the collimated scanning diagnostic laser beam has a linear polarization orientation. In turn, expanded beam 609a is transmitted to an objective lens assembly 614.

As shown here, the polarizing beam splitter 606 can be positioned before the laser beam expansion assembly 609. The polarizing beam splitter 606 can operate to split the diagnostic laser beam 604 into a scanning portion (608) and a non-scanning portion (not shown). In some cases, the beam splitter 606 allows for the measurement (e.g. concurrent) of a reference sample. In some cases, the beam splitter 606 operates to provide an additional amount of filtration of back reflections of light. In some cases, the polarizing beam splitter 606 transmits light at a 90 degrees orientation and on the return path the light goes to 90 degrees According to some embodiments, the beam splitter 606 works in conjunction with the quarter wave plate 617. For example, after two passes through the waveplate 617, the returning light can be passed back to the spectrometer assembly 634, and light that has only passed once (e.g. reflections from lenses) will be excluded. In some cases, when the light first enters the quarter wave plate 617, some amount can be portioned to a calibrated reference sample. As described elsewhere herein (e.g. FIGS. 11-15), a half-waveplate element may also be positioned after the laser source which sets up a ratio of linearly polarized s and p. This can control the light split through the polarizing beam splitter (PBS). According to some embodiments, a Brillouin signal from a sample can be used as a built in reference to the instrument for accurate calculation of the Brillouin signal. There may also be a quarter waveplate on the reference path to provide an isolated signal that will make its way back to the spectrometer.

According to some embodiments, the beam expansion assembly 609 operates to adjust or redirect a beam path of the expanded collimated scanning diagnostic laser beam. In some cases, the patient interface system 600 may not include the polarizing beam splitter 606. The beam expansion assembly 609 operates to redirect a beam path of the reflected portion 608 of the collimated scanning diagnostic laser beam. The redirected reflected portion 609a of the collimated scanning diagnostic laser beam is then transmitted to an objective lens assembly 614, which operates to focus the redirected portion 609a of the collimated scanning diagnostic laser beam to produce a focused scanning diagnostic laser beam 616.

According to some embodiments, the objective lens assembly 614 operates to focus the expanded collimated scanning diagnostic laser beam 609a to produce a focused scanning diagnostic laser beam 616 having a beam waist or focused spot. In some cases, the objective lens assembly 614 operates to adjust a scan position of the beam waist or focused spot. In some cases, the objective lens assembly 614 includes a motorized stage that allows the objective lens assembly to travel toward and away from the beam expansion assembly 609. In some cases, the beam expansion assembly 609 includes a motorized stage that allows the optical scanning assembly to travel toward and away from the objective lens assembly 614, and/or in a plane perpendicular to the beam path. In some cases, movement of the beam expander or the beam expander and the objective together along the optical axis (e.g. in optical z) can achieve an axial translation along the z axis of the interrogating beam focus. In some cases, the beam expansion assembly and the objective lens assembly include or are disposed on respective motorized stages, or are disposed on a common motorized stage, so that the beam expansion assembly and the objective lens assembly can move in tandem.

As shown here, system 600 may include a quarter-wave plate assembly 617. In some embodiments, the quarter-wave plate assembly 617 operates to convert the focused scanning diagnostic laser beam 616 from a linear polarization orientation to a circular polarization orientation. In some embodiments, the quarter-wave plate assembly 617 operates to provide a 45 degree rotation to the focused scanning diagnostic laser beam 616. In some cases, the quarter-wave plate assembly 617 operates to convert the focused scanning diagnostic laser beam 616 from p-polarized light to s-polarized light. In some cases, the quarter-wave plate assembly 617 operates to convert the focused scanning diagnostic laser beam 616 from s-polarized light to p-polarized light. The quarter-wave plate assembly 617 can be placed along the beam path, for example between the objective lens assembly 614 and the shortpass dichroic filter 618a. In some embodiments, the quarter-wave plate assembly 617 can be placed upstream of the objective lens assembly 614 or downstream of the shortpass dichroic filter 618a. In some cases, the closer the quarter-wave plate is to the sample, the more back-reflections can be filtered out by the PBS. In exemplary embodiments, the quarter-wave plate is the last element in the objective lens followed by the dichroic in front of the eye.

The focused scanning diagnostic laser beam 616 is reflected by a shortpass dichroic filter 618a, and the reflected focused portion 620 is transmitted toward an eye 622 of the patient. In some cases, the focused scanning diagnostic laser beam has a circular polarization orientation and is reflected by the shortpass dichroic filter 618*a* toward the eye 622.

According to some embodiments, a dichroic filter can operate as a beam splitter that splits light based on wavelength or color, rather than splitting light based on power. In some cases, a dichroic filter will transmit light within a certain wavelength band or range and/or reflect light within a certain wavelength band or range. As shown here, dichroic filters can operate to fold together, or to separate out, different wavelengths of light (e.g. into a common optical path).

In some case, the dichroic filters can operate to fold together fixation light 629*a*, imaging light 630, and scanning diagnostic light 620, into a common optical path (e.g. between the shortpass dichroic filter 618*a* and the eye 622). Similarly, a dichroic can operate to split or redirect light from a common path into separate optical paths, for example imaging light 630 and returned scanning diagnostic light travel along a common optical path from the eye to the shortpass dichroic filter 618*a*, and then the imaging light is transmitted through the shortpass dichroic filter 618*a* and the returned scanning diagnostic light is reflected by the shortpass dichroic filter 618*a*.

The reflected focused scanning diagnostic laser beam 620 has focused spot 624, and operation of the beam expansion assembly 609 or the objective lens assembly 614, or the combined operation of the beam expansion assembly 609 and the objective lens assembly 614, can adjust a scan position of the focused spot 624 to various discrete locations on or within one or more tissues of the eye 622. In some instances, the scanning technique provided by system 600 can involve a mechanical xy scanning approach.

The patient interface system 600 also includes an eye camera assembly 628 that receives imaging light 630 from the eye (which optionally may have passed through a shortpass dichroic filter 618*a* and a longpass dichroic filter 618*b* of a beam control assembly) and that generates electrical signals in response to the received imaging light 630. The imaging light 630 can provide registration information regarding the position and/or orientation of the eye. In some cases, this registration information can be used (e.g. by processing assembly 632) to provide locate elasticity measurement data obtained by the Brillouin spectrometer assembly 634 to particular points of the eye. In some cases, the imaging light 630 can help to provide feedback, which may be continuous feedback, to the processing assembly. The imaging light 630 can be processed to provide information regarding a center coordinate of the eye, a central reference of the eye, or more generically, a reference coordinate on the eye, which can be registered to the biomechanical data. Such a reference coordinate can be determined by processing the imaging data.

In some cases, the processing assembly 632 can operate to generate two images, specifically an image of the eye and a Brillouin heat map (e.g. stiffness values at discrete points), and to accurately superimpose those images on top of each other using registration. In this way, the mechanical information is relevant in the physical space. In some cases, the processing assembly does not perform a superimposition. Rather, a camera is used to provide a reference point to begin a scan pattern, and thereafter a scan is performed according to the pattern, so as to generate the stiffness map. The map can indicate whether there are any abnormal spots or points of interest on the eye, without providing the exact location on the eye of the abnormal spots or points of interest. In some cases, a camera is not used to provide a reference point to begin a scan pattern. For example, the physician or operate could manually inspect the person's eye, and then aim the beam, without using a camera. In some cases, it is possible to illuminate the person's eye using a certain wattage, observe a reflection off the person's eye, and determine that the alignment of the scanning beam relative to the patient's eye is sufficient.

Hence, input techniques for aiming the diagnostic beam can include using a camera image or data, manually aiming the beam, or using feedback from the Brillouin spectrometer. For example, data obtained by the spectrometer can provide an indication of whether the system is in focus. The Brillouin spectrometer can be used to differentiate spectral shifts that are characteristic of different tissues. In some cases, as the focused spot is scanned in the z depth direction, it is possible to detect fundamentally different frequency shifts (or different information) as the focused spot goes through different layers (e.g. going from the air, to the cornea surface, to the aqueous humor, to the crystalline lens, and so on) which can correspond to different elastic properties (e.g. elastic modulus). In this sense, the Brillouin approach can provide aspects of an imaging modality. In some embodiments, Brillouin spectroscopy is used an imaging modality because multiple pixels of information are put together to generate a map. This map can be considered to be an image (e.g. more than 1 pixel), and accordingly, Brillouin spectroscopy can be considered to be an imaging modality. Hence, it may be possible to determine where the focused spot is located, by observing or analyzing the spectrometer image. In some cases, it is possible to align or position the patient interface system, by observing or using a reflection off of a person's eye, then moving the system into focus based on feedback from the spectrometer camera, and then initiating the scan.

In some embodiments, system 600 also includes a fixation assembly 629 that provides the eye with a gaze target. In some cases, fixation light 629*a* is generated by the fixation assembly 629, travels from the fixation assembly 629, is reflected by the longpass dichroic filter 618*b*, travels through the shortpass dichroic filter 618*a*, and to the eye 622. According to some embodiments, the fixation assembly 629 includes a matrix of light-emitting diode (LEDs).

The patient interface system 600 can further include a Brillouin spectrometer assembly 634 having a Brillouin spectrometer 634*a* and a spatial filter 634*b* that is parfocal with the focused spot 624 (e.g. in a conjugate focal plane). The Brillouin spectrometer can generate Brillouin signals as the focused spot 624 is scanned to discrete locations throughout a volume or plane thickness of ophthalmic tissue of the eye 622. Brillouin scattered light from the focused spot at the discrete locations is returned to the spatial filter 634*b*. According to some embodiments, the spatial filter 634*b* operates as an input for the Brillouin spectrometer, and is in conjugate alignment with the focused spot 624 or beam waist of the focused scanning diagnostic laser beam, and the Brillouin spectrometer 634*a* can generate Brillouin signals as the focused spot 624 or beam waist of the focused scanning diagnostic beam is scanned to discrete locations throughout the volume of the ophthalmic tissue of the eye 622. In some cases, the spatial filter 634*b* can operate to exclude information associated with out of focus focal planes, and include information associated with the focal plane of interest. The filter 634*b* can provide sensitivity to locations where the focused spot 624 is positioned, and little or no sensitivity to extraneous locations. In some cases, a spatial filter can be provided without using a fiber. In some cases, the spatial filter 634*b* can operate to prime the incoming light, which is then measured by the spectrometer 634a, which in turn generates the spectrum (e.g. Brillouin) signals.

By using a fiber input, it is possible to provide modularity to the system, whereby the patient scanning interface can be decoupled and coupled with the spectrometer via the optical fiber. Such modularity can provide enhanced testing and serviceability advantages. For example, the optical fiber could be uncoupled from one patient interface system, and coupled with another patient interface system. Hence, if one patient interface were to malfunction, it could be replaced with another patient interface. This could also allow patient interfaces to be tested as modules, which can improve manufacturability and serviceability.

From an optical standpoint, a fiber can provide a highly functional pinhole. In some cases, such embodiments can provide a separate input and output. It is possible to physically decouple with free space optics the input and output of the system. In some cases, such configurations can be considered to provide a free space optical circulator, for example using the PBS.

According to some embodiments, an optical output out of a single mode fiber can provide or approach a perfect Gaussian distribution, which has desirable beam shape and optical quality characteristics, and can be well suited for use with sensitive optical elements. As such, this feature can help optimize the optical performance of the overall system, particularly when multiple optical elements are involved.

In some cases, a fiber can operate as a conjugate pinhole or aperture (or spatial filter) for the focus spot in the tissue that is being analyzed. The fiber can operate to provide a focal plane resolution and specificity, filtering out the out of focus light that is not of interest. In some cases, a spatial filter can be provided as a radial aperture or a circular aperture. In some cases, an aperture can have a diameter of about 1 mm aperture. In some cases, the focus of the light is aligned with the core of a fiber, whereby only that light which is properly aligned to the core of the fiber will make it into that fiber. Thereafter, that light will be propagated down the fiber. In this sense, the core of the fiber can operate as a filter, spatial mask, or pinhole aperture, whereby light coupled into the core of the fiber is propagated, and undesired light is filtered or masked out. Often, a fiber will operate in conjunction with a lens. In some embodiments, the fiber can be provided as a collimated fiber optic. In some cases, light is focused into the fiber, or into the core of the fiber, using a lens. The light can be propagated in the fiber by way of total internal reflection. Where light is not properly aligned with the fiber core, such light may not propagate down the fiber, or be coupled into that fiber.

Put another way, light that is at a different focal plane, in the tissue, will not be at the same focal plane, over at the pinhole or spatial filter side, and hence becomes filtered out. The out of focus light will not make it into the pinhole or spatial aperture, and won't be coupled into the fiber, because that light is not aligned (e.g. not at the same focal plane, confocal, or conjugate).

As shown here, the patient interface system 600 can include a processing assembly 632 in operative association with the beam expansion assembly 609, the objective lens assembly 614, the eye camera assembly 628, the fixation assembly 629, and the Brillouin spectrometer assembly 634. The processing assembly 632 can include a processor, an electronic storage location operatively coupled with the processor, and processor executable code stored on the electronic storage location and embodied in a tangible non-transitory computer readable medium. The processor executable code can include machine-readable instructions that, when executed by the processor, cause the processor to generate x,y coordinate scan control signals for the beam expansion assembly 609. In some cases, x,y coordinate scan control signals for the beam expansion assembly 609 can be generated based on the electrical signals generated by the eye camera assembly 628. The processor executable code can include machine-readable instructions that, when executed by the processor, cause the processor to generate z coordinate scan control signals for the objective lens assembly 614. In some cases, the x,y coordinate scan control signals, the z coordinate scan control signals, or both the x,y coordinate scan control signals and the z coordinate scan control signals, can be based on an image of the eye. In some cases, the x,y coordinate scan control signals, the z coordinate scan control signals, or both the x,y coordinate scan control signals and the z coordinate scan control signals, can be generated independent of an image of the eye. In some cases, the x,y coordinate scan control signals, the z coordinate scan control signals, or both the x,y coordinate scan control signals and the z coordinate scan control signals, can be generated according to a pre-defined or pre-determined scan pattern. The processor executable code can include machine-readable instructions that, when executed by the processor, cause the processor to generate an elastic stiffness map for a volume of ophthalmic tissue of the eye 622 based on Brillouin signals.

As shown in FIG. 6, the eye 622 can be at a 90 degree angle of orientation relative to the general trajectory of the scanning diagnostic beam after the scanning diagnostic beam exits the objective lens assembly 614. In this way, the reflected focused portion 620 of the scanning diagnostic beam and the imaging light 630 that travels from the eye to the eye camera assembly are aligned in a colinear path. According to some embodiments, such a configuration (e.g. reflecting the beam off the shortpass dichroic filter 618a) may produce less astigmatism (or more generally, less optical aberration) than a different configuration (e.g. scanning or transmitting the beam through the shortpass dichroic filter 618a). This advantage may be particularly helpful for maintaining high beam quality when the scanning diagnostic beam is diffraction limited and involves a confocal focused spot. In some embodiments, the finer axial resolution spot will also minimize contaminating back-reflections from the front surface of the eye, allow for scanning of more of the eye thickness with better spatial resolution. Dichroic filters can operate to reflect or reject light having certain wavelengths, and to transmit light having certain wavelengths.

According to some embodiments, the system 600 can include one or more illumination lamps or light devices 626 that direct illumination light or radiation 627 toward the eye. In some cases, the illumination light or radiation 627 can be infrared light. In some cases, the illumination light or radiation 627 can be non-visible light. In some cases, the illumination light 627 can have a wavelength value within a range from about 700 nm to about 1,000,000 nm. In some case, the illumination light 627 can have a wavelength value of about 940 nm. According to some embodiments, the eye camera assembly 628 is sensitive to the wavelength of the illumination light 627 (which can also be the same as or similar to the wavelength of the imaging light 630).

In some cases, the illumination light 627 can have a wavelength value that is greater than a wavelength value of the diagnostic scanning light or radiation. In some cases, the diagnostic beam (e.g. 604, 620) has a wavelength value within a range from about 450 to about 1350 nm. In some cases, the wavelength of the scanning diagnostic beam has a value of about 780 nm. In some cases, the scanning diagnostic radiation can have a wavelength value within a range from about 450 to about 1350 nm. In some cases, the fixation light 629a is visible light. In some cases, the fixation light 629a is visible green light. In some cases, the fixation light 629a has a wavelength value of about 520 to about 560 nm. According to some embodiments, the fixation assembly 629 generates light 629a that provides the eye with a gaze target, which can be helpful in a clinical setting or application. In some cases, a system or method can include a gaze target that is not provided by a light emitting fixation assembly.

As shown in FIG. 6, the shortpass dichroic filter 618a can operate to reflect the incoming and returning scanning diagnostic beam, to transmit the imaging light 630 (which can be illumination light 627 reflected from the eye), and to transmit the fixation light 629a. Related, the longpass dichroic filter 618b can operate to reflect the fixation light 629a and to transmit the imaging light 630 (which can be illumination light 627 reflected from the eye).

According to some embodiments, the focused scanning diagnostic laser beam 620 optical path and the imaging light 630 optical path are provided as integrated colinear optical paths, as a result of the operation of one or more dichroic filters. In some cases, the respective optical paths may not be integrated in a colinear fashion. In some cases, by providing integrated colinear optical paths, it is possible to avoid or eliminate geometric distortions of the image that may otherwise be present when using an off-axis camera (even though it may be possible to achieve the same focal point for a laser, relative to the focus of the imaging camera).

In some cases, by providing integrated colinear optical paths, it is possible to more efficiently register biomechanical data to eye location and/or orientation data pertaining to a real world eye space. In some cases, it is possible to use eye tracker or camera information to register and track where those points have been scanned, relative to certain features and/or registration coordinates on the eye.

According to some embodiments, astigmatism can be incurred for the eye camera illumination or an image of the eye by transmitting through the dichroic, and a perfect 3D orthogonal orientation (e.g. of the illumination lamp 626) can cancel out that astigmatism.

As seen here, the longpass dichroic filter 618b operates to fold together the light 629a from the fixation assembly 629 and the imaging light 630 from the eye (integrated). Embodiments of the present invention also encompass designs where the fixation light 629a is not folded into the same path with the imaging light 630 (unintegrated). As shown in FIG. 6, in this embodiment there may be no lens between the shortpass dichroic filter 618a and the longpass dichroic filter 618b.

According to some embodiments, system 600 provides a working distance of about 50 mm between the shortpass dichroic filter 618a and the eye 622. The working distance can be defined as the distance between the eye and the optical element that is closes to the eye along the beam path. In some cases, the system can be designed with a minimum working distance as to provide any unwanted interference between the instrument and the patient. In some cases, larger working distances can be achieved, with a concomitant increase in size of the optics for the same NA. At some point, in particular in the 90 degree configuration, the size of the objective becomes the largest element. Hence, even though the working distance is increasing, the distance between the patient's face and the objective may not because the size is also growing. As shown here, the scanning beam 620, the imaging light 630, and the fixation light 629a are all colinear with one another in the working distance. Advantageously, such a configuration allows the system to establish a clear correspondence or registration between the position of the focused spot 624 (and the data collected for that position) and a physical location on or in the tissue of the eye 622. Similarly, such a colinear configuration can help to avoid or reduce geometric distortion that may otherwise be present in an off-axis configuration. In some cases, an off-axis camera may result in a keystone effect. It is possible to calibrate this out with a software correction. In some cases, the focal plane also becomes an image slice at angle, which may make identifying the correct focal plane more difficult. In some imaging modalities, this is desirable as in Scheimpflug imaging. In some cases, the numerical aperture of the objective lens assembly 614 can be relatively large, for example greater than 0.1. In some cases, the numerical aperture is about 0.125. In some cases, the quarter wave plate 617 can operate to filter any back reflections from any of the optics that may be positioned upstream of the quarter wave plate.

According to some embodiments, scanning of the beam can be achieved at least in part by effecting motorized x,y, z movement of an objective lens of the objective lens assembly 614 while maintaining a boresighted beam down the center of the objective lens, such that the actual laser beam would not be scanned optically with mirrors, or any rotational mechanisms (in contrast to other embodiments which are disclosed herein).

According to some embodiments, the eye camera assembly 628 of patient interface system 600 can image through a path that is not the same as the laser path. Patient interface system 600 can involve a co-axial scanning laser that is reflected at 90 degrees. Lateral xy scanning can be achieved by motor translation of the entire laser scan path. In some cases, the entire laser scan path can exclude the fixation assembly, the eye camera, the processing assembly the laser head/controller, and the spectrometer. According to some embodiments, beam expansion assembly 609 can include a plano-convex afocal relay. In some embodiments, objective lens assembly 614 includes a 3 singlet objective. In some cases, the quarter wave plate assembly 617 can be positioned downstream of the objective lens assembly 614 for purposes of optical isolation. In some embodiments, this configured can be considered to be a simple camera setup with a lens, and it can be integrated colinearly into the overall path by function of the dichroics which only pass the illuminating infrared imaging light providing the image of the eye to the camera. According to some embodiments, there is a mechanical decoupling between the eye camera assembly 628 and the laser scanning. FIG. 6 encompasses a system without an integrated optical scanning system, and the light is focused on the eye. Rather than angularly steering the beam using the scanning assembly, the XYZ motors used for aligning the eye to the system can also be used to reposition the laser light on the patients eye. This could be embodied as a system where the eye camera image is mechanically decoupled, so the eye image does not also move, or mechanically coupled with a moving eye image. System 600 can provide a configuration where all optics are on axis, where testing for alignment can be achieved with only a line scan instead of a 3D scan volume, where there is no optical scanning, and/or there is an inherently telecentric arrangement.

Figure 12:
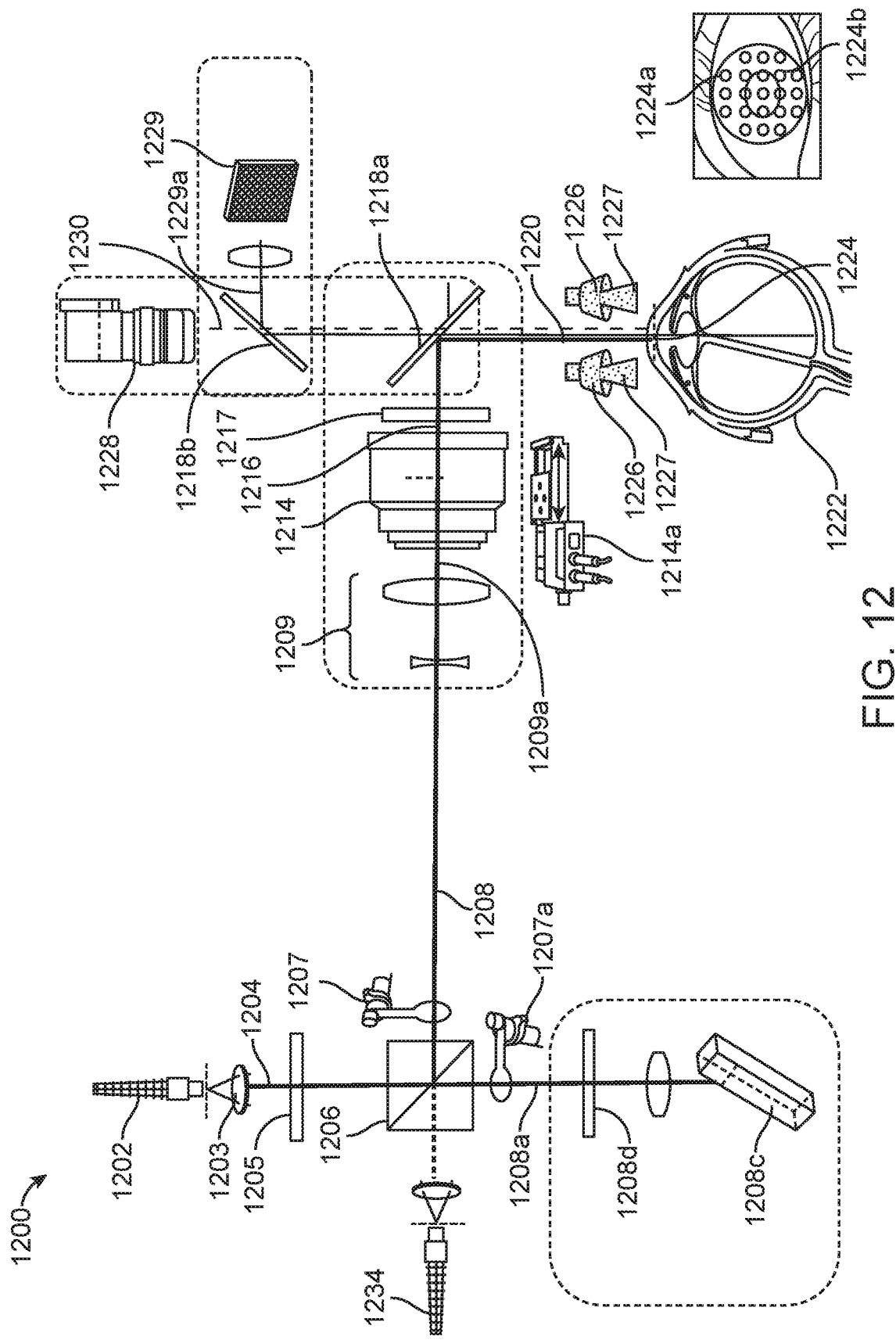
FIG. 12 depicts aspects of a system for generating an elastic stiffness map for a volume of an ophthalmic tissue of an eye of a patient, according to embodiments of the present invention.

In some cases, the patient interface system 600 depicted in FIG. 6 can incorporate one or more features of the embodiment depicted in FIG. 12. For example, FIG. 12 shows additional details regarding a reference path that is used to measure a sample containing plastic and water, that has known elastic properties. This can be used to normalize the data that is received from the actual tissue being analyzed, for example the cornea or the crystalline lens. Light can be controlled by a pair of shutters, and operation of the shutters can determine whether the laser light is going to hit the reference path, or whether the laser is going to hit the sample path. FIG. 12 also illustrates that a fixation assembly can include a grid of light points or light emitting diodes. The system can be configured to illuminate one or more points of the grid, so as to control where the patient directs their gaze. In this way, it is possible to facilitate the measurement of certain areas of the eye that otherwise may be difficult to scan or measure when the patient is looking directly straightforward. Accordingly, the system can facilitate a computerized control of the orientation of the eye, by changing the gaze angle.

Figure 7:
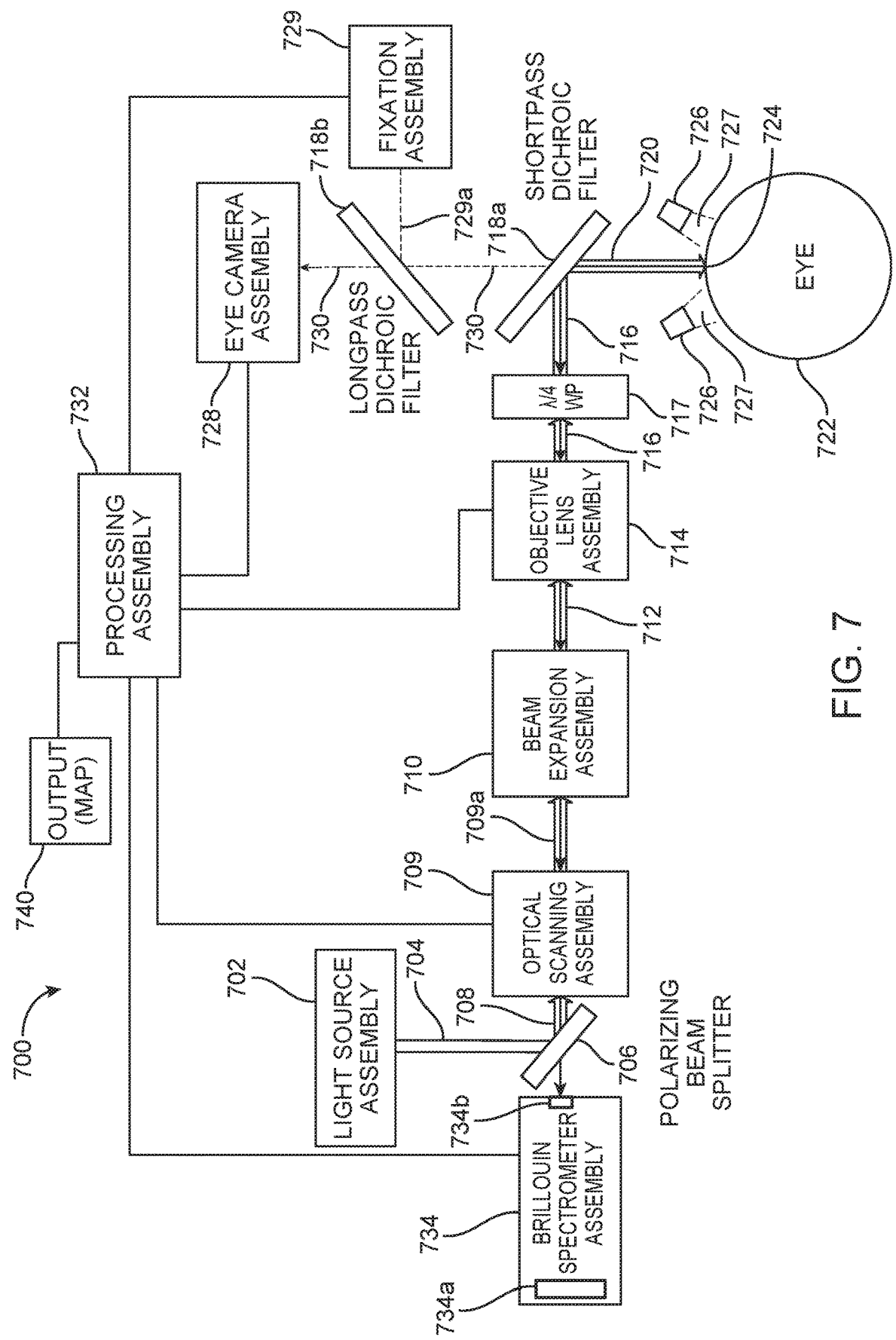
FIG. 7 depicts aspects of a system for generating an elastic stiffness map for a volume of an ophthalmic tissue of an eye of a patient, according to embodiments of the present invention.

FIG. 7 depicts aspects of a patient interface system 700 according to embodiments of the present invention. As discussed elsewhere herein, system 700 can be used to generate an elastic stiffness map 740 for a volume of an ophthalmic tissue of an eye of a patient. As shown here, system 700 includes a laser assembly or light source 702 that generates a collimated diagnostic laser beam 704, a polarizing beam splitter 706 that reflects a portion 708 of the collimated diagnostic laser beam 704, and the reflected portion 708 is then transmitted to an optical scanning assembly 709, which operates to adjust or redirect a beam path of the scanning diagnostic laser beam portion 708 to produce a redirected portion 709a that is transmitted to an electromagnetic radiation beam expansion assembly 710, which converts beam 709a to an expanded beam 712. In some cases, light source 702 can be a device that produces electromagnetic radiation characterized by one or more wavelengths or one or more frequencies. According to some embodiments, the electromagnetic radiation beam expansion assembly 710 expands a collimated scanning diagnostic laser beam from a first diameter to a second diameter that is larger than the first diameter. The laser beam expansion assembly 710 may include multiple lenses. In some cases, the laser beam expansion assembly 710 includes telephoto lens configuration. For example, the beam expansion assembly 710 can include a telephoto lens group that extends the light path to create a long-focus lens (e.g. 400 mm). In some cases, the laser beam expansion assembly 710 can include an afocal relay system. In turn, expanded beam 712 is transmitted to an objective lens assembly 714.

As shown here, the polarizing beam splitter 706 can be positioned before the optical scanning assembly 709. The polarizing beam splitter 706 can operate to split the diagnostic laser beam 704 into a scanning portion (708) and a non-scanning portion (not shown). In some cases, the beam splitter 706 allows for the measurement (e.g. concurrent) of a reference sample. In some cases, the beam splitter 706 operates to provide an additional amount of filtration of back reflections of light. Filtration can be based on polarization, and may involve aspects of a conventional optical isolator based on polarizing optics and a quarter wave plate. In some cases, the polarizing beam splitter 706 transmits light at a 90 degrees orientation and on the return path the light goes to 90 degrees. According to some embodiments, the beam splitter 706 works in conjunction with the quarter wave plate 717. For example, after two passes through the waveplate 717, the returning light can be passed back to the spectrometer assembly 734, and light that has only passed once (e.g. reflections from lenses) will be excluded. In some cases, when the light first enters the quarter wave plate 717, some amount can be portioned to a calibrated reference sample. As described elsewhere herein (e.g. FIGS. 11-15), a half-waveplate element may also be positioned after the laser source which sets up a ratio of linearly polarized s and p. This can control the light split through the polarizing beam splitter (PBS). According to some embodiments, a Brillouin signal from a sample can be used as a built in reference to the instrument for accurate calculation of the Brillouin signal. There may also be a quarter waveplate on the reference path to provide an isolated signal that will make its way back to the spectrometer.

According to some embodiments, the optical scanning assembly 709 operates to adjust or redirect a beam path of the collimated scanning diagnostic laser beam 708. In some cases, the patient interface system 700 may not include the polarizing beam splitter 706. The optical scanning assembly 709 operates to redirect a beam path of the reflected portion 708 of the collimated scanning diagnostic laser beam. The redirected reflected portion 709a of the collimated scanning diagnostic laser beam is then transmitted to a beam expansion assembly 710, and the resulting expanded beam 712 is transmitted to an objective lens assembly 714, which operates to focus the portion 712 of the collimated scanning diagnostic laser beam to produce a focused scanning diagnostic laser beam 716.

According to some embodiments, the objective lens assembly 714 operates to focus the expanded collimated scanning diagnostic laser beam 712 to produce a focused scanning diagnostic laser beam 716 having a beam waist or focused spot. In some cases, the objective lens assembly 714 operates to adjust a scan position of the beam waist or focused spot. In some cases, the objective lens assembly 714 includes a motorized stage that allows the objective lens assembly to travel toward and away from the beam expansion assembly 710. In some cases, the optical scanning assembly 709 includes motorized elements such as scanning mirrors, or an XY galvanometer scanner, the optical scanning assembly 709 to redirect the trajectory of the beam 708. Relatedly, the optical scanning assembly 709 can include a system of mirrors that can be adjusted, in terms of their orientation, so as to direct the beam in the desired directions. Hence, this design can include some optics to place the focused spot 724 at the desired location at the cornea.

As shown here, system 700 may include a quarter-wave plate assembly 717. In some embodiments, the quarter-wave plate assembly 717 operates to convert the focused scanning diagnostic laser beam 716 from a linear polarization orientation to a circular polarization orientation. In some embodiments, the quarter-wave plate assembly 717 operates to provide a 45 degree rotation to the focused scanning diagnostic laser beam 716. In some cases, the quarter-wave plate assembly 717 operates to convert the focused scanning diagnostic laser beam 716 from p-polarized light to s-polarized light. In some cases, the quarter-wave plate assembly 717 operates to convert the focused scanning diagnostic laser beam 716 from s-polarized light to p-polarized light. The quarter-wave plate assembly 717 can be placed along the beam path, for example between the objective lens assembly 714 and the shortpass dichroic filter 718a. In some embodiments, the quarter-wave plate assembly 717 can be placed upstream of the objective lens assembly 714 or downstream of the shortpass dichroic filter 718a In some cases, the quarter-wave plate assembly 717 can be placed anywhere as desired, between the sample (e.g. eye) and the PBS.

The focused scanning diagnostic laser beam 716 is reflected by a shortpass dichroic filter 718a, and the reflected focused portion 720 is transmitted toward an eye 722 of the patient. In some cases, the focused scanning diagnostic laser beam has a circular polarization orientation and is reflected by the shortpass dichroic filter 718a toward the eye 722.

According to some embodiments, a dichroic filter can operate as a beam splitter that splits light based on wavelength or color, rather than splitting light based on power. In some cases, a dichroic filter will transmit light within a certain wavelength band or range and/or reflect light within a certain wavelength band or range. As shown here, dichroic filters can operate to fold together, or to separate out, different wavelengths of light (e.g. into a common optical path).

In some case, the dichroic filters can operate to fold together fixation light 729a, imaging light 730, and scanning diagnostic light 720, into a common optical path (e.g. between the shortpass dichroic filter 718a and the eye 722). Similarly, a dichroic can operate to peel apart light from a common path into separate optical paths, for example imaging light 730 and returned scanning diagnostic light travel along a common optical path from the eye to the shortpass dichroic filter 718a, and then the imaging light is transmitted through the shortpass dichroic filter 718a and the returned scanning diagnostic light is reflected by the shortpass dichroic filter 718a.

The reflected focused scanning diagnostic laser beam 720 has focused spot 724, and operation of the optical scanning assembly 709 or the objective lens assembly 714, or the combined operation of the optical scanning assembly 709 and the objective lens assembly 714, can adjust a scan position of the focused spot 724 to various discrete locations on or within one or more tissues of the eye 722.

The patient interface system 700 also includes an eye camera assembly 728 that receives imaging light 730 from the eye (which optionally may have passed through a shortpass dichroic filter 718a and a longpass dichroic filter 718b of a beam control assembly) and that generates electrical signals in response to the received imaging light 730. The imaging light 730 can provide registration information regarding the position and/or orientation of the eye. In some cases, this registration information can be used (e.g. by processing assembly 732) to provide locate elasticity measurement data obtained by the Brillouin spectrometer assembly 734 to particular points of the eye. In some cases, the imaging light 730 can help to provide feedback, which may be continuous feedback, to the processing assembly. The imaging light 730 can be processed to provide information regarding a center coordinate of the eye, a central reference of the eye, or more generically, a reference coordinate on the eye, which can be registered to the biomechanical data. Such a reference coordinate can be determined by processing the imaging data.

In some cases, the processing assembly 732 can operate to generate two images, specifically an image of the eye and a Brillouin heat map (e.g. stiffness values at discrete points), and to accurately superimpose those images on top of each other using registration. In this way, the mechanical information is relevant in the physical space. In some cases, the processing assembly does not perform a superimposition. Rather, a camera is used to provide a reference point to begin a scan pattern, and thereafter a scan is performed according to the pattern, so as to generate the stiffness map. The map can indicate whether there are any abnormal spots or points of interest on the eye, without providing the exact location on the eye of the abnormal spots or points of interest. In some cases, a camera is not used to provide a reference point to begin a scan pattern. For example, the physician or operate could manually inspect the person's eye, and then aim the beam, without using a camera. In some cases, it is possible to illuminate the person's eye using a certain wattage, observe a reflection off the person's eye, and determine that the alignment of the scanning beam and the eye is sufficient.

Hence, input techniques for aiming the diagnostic beam can include using a camera image or data, manually aiming the beam, or using feedback from the Brillouin spectrometer. For example, data obtained by the spectrometer can provide an indication of whether the system is in focus. The Brillouin spectrometer can be used to differentiate spectral shifts that are characteristic of different tissues. In some cases, as the focused spot is scanned in the z depth direction, it is possible to detect fundamentally different frequency shifts (or different information) as the focused spot goes through different layers (e.g. going from the air, to the cornea surface, to the aqueous humor, to the crystalline lens, and so on) which can correspond to different elastic properties (e.g. elastic modulus). In this sense, the Brillouin approach can provide aspects of an imaging modality. Hence, it may be possible to determine where the focused spot is located (e.g. along a z-axis), by observing or analyzing the spectrometer image. In some cases, it is possible to align or position the patient interface system, by observing or using a reflection off of a person's eye, then moving the system into focus based on feedback from the spectrometer camera, and then initiating the scan. In some cases, the camera is parfocal with the laser beam, and the focus of the eye can also be used.

In some embodiments, system 700 also includes a fixation assembly 729 that provides the eye with a gaze target. In some cases, fixation light 729a is generated by the fixation assembly 729, travels from the fixation assembly 729, is reflected by the longpass dichroic filter 718b, travels through the shortpass dichroic filter 718a, and to the eye 722. According to some embodiments, the fixation assembly 729 includes a matrix of light-emitting diode (LEDs).

The patient interface system 700 can further include a Brillouin spectrometer assembly 734 having a Brillouin spectrometer 734a and a spatial filter 734b that is parfocal with the focused spot 724 (e.g. in a conjugate focal plane). The Brillouin spectrometer can generate Brillouin signals as the focused spot 724 is scanned to discrete locations throughout a volume or plane thickness of ophthalmic tissue of the eye 722. Brillouin scattered light from the focused spot at the discrete locations is returned to the spatial filter 734b. According to some embodiments, the spatial filter 734b operates as an input for the Brillouin spectrometer, and is in conjugate alignment with the focused spot 724 or beam waist of the focused scanning diagnostic laser beam, and the Brillouin spectrometer 734a can generate Brillouin signals as the focused spot 724 or beam waist of the focused scanning diagnostic beam is scanned to discrete locations throughout the volume of the ophthalmic tissue of the eye 722. In some cases, the spatial filter 734b can operate to exclude information associated with out of focus focal planes, and include information associated with the focal plane of interest. The filter 734b can provide sensitivity to locations where the focused spot 724 is positioned, and little or no sensitivity to extraneous locations. In some cases, a spatial filter can be provided without using a fiber. In some cases, the spatial filter 734b can operate to prime the incoming light, which is then measured by the spectrometer 734a, which in turn generates the spectrum (e.g. Brillouin) signals.

By using a fiber input, it is possible to provide modularity to the system, whereby the patient scanning interface can be decoupled and coupled with the spectrometer via the optical fiber. Such modularity can provide enhanced testing and serviceability advantages. For example, the optical fiber could be uncoupled from one patient interface system, and coupled with another patient interface system. Hence, if one patient interface were to malfunction, it could be replaced with another patient interface. This could also allow patient interfaces to be tested as modules, which can improve manufacturability.

From an optical standpoint, a fiber can provide a highly functional pinhole. In some cases, such embodiments can provide a separate input and output. It is possible to physically decouple with free space optics the input and output of the system In some embodiments, the input is not separated from the output. For example, the same light can be coupled back into the same input path and optionally the beam could be redirected to the spectrometer after traveling back down the fiber.

According to some embodiments, an optical output out of a single mode fiber can provide or approach a perfect Gaussian distribution, which has desirable beam shape and optical quality characteristics, and can be well suited for use with sensitive optical elements. As such, this feature can help optimize the optical performance of the overall system, particularly when multiple optical elements are involved.

In some cases, a fiber can operate as a conjugate pinhole or aperture (or spatial filter) for the focus spot in the tissue that is being analyzed. The fiber can operate to provide a focal plane resolution and specificity, filtering out the out of focus light that is not of interest. In some cases, a spatial filter can be provided as a radial aperture or a circular aperture. In some cases, an aperture can have a diameter of about 1 mm aperture. In some cases, the focus of the light is aligned with the core of a fiber, whereby only that light which is properly aligned to the core of the fiber will make it into that fiber. Thereafter, that light will be propagated down the fiber. In this sense, the core of the fiber can operate as a filter, spatial mask, or pinhole aperture, whereby light coupled into the core of the fiber is propagated, and undesired light is filtered or masked out. Often, a fiber will operate in conjunction with a lens. In some embodiments, the fiber can be provided as a collimated fiber optic. In some cases, light is focused into the fiber, or into the core of the fiber, using a lens. The light can be propagated in the fiber by way of total internal reflection. Where light is not properly aligned with the fiber core, such light may not propagate down the fiber, or be coupled into that fiber.

Put another way, light that is at a different focal plane, in the tissue, will not be at the same focal plane, over at the pinhole or spatial filter side, and hence becomes filtered out. The out of focus light will not make it into the pinhole or spatial aperture, and won't be coupled into the fiber, because that light is not aligned (e.g. not at the same focal plane, confocal, or conjugate).

As shown here, the patient interface system 700 can include a processing assembly 732 in operative association with the optical scanning assembly 710, the objective lens assembly 714, the eye camera assembly 728, the fixation assembly 729, and the Brillouin spectrometer assembly 734. The processing assembly 732 can include a processor, an electronic storage location operatively coupled with the processor, and processor executable code stored on the electronic storage location and embodied in a tangible non-transitory computer readable medium. The processor executable code can include machine-readable instructions that, when executed by the processor, cause the processor to generate x,y coordinate scan control signals for the optical scanning assembly 709. In some cases, x,y coordinate scan control signals for the optical scanning assembly 709 can be generated based on the electrical signals generated by the eye camera assembly 728. The processor executable code can include machine-readable instructions that, when executed by the processor, cause the processor to generate z coordinate scan control signals for the objective lens assembly 714. In some cases, the x,y coordinate scan control signals, the z coordinate scan control signals, or both the x,y coordinate scan control signals and the z coordinate scan control signals, can be based on an image of the eye. In some cases, the x,y coordinate scan control signals, the z coordinate scan control signals, or both the x,y coordinate scan control signals and the z coordinate scan control signals, can be generated independent of an image of the eye. In some cases, the x,y coordinate scan control signals, the z coordinate scan control signals, or both the x,y coordinate scan control signals and the z coordinate scan control signals, can be generated according to a pre-defined or pre-determined scan pattern. The processor executable code can include machine-readable instructions that, when executed by the processor, cause the processor to generate an elastic stiffness map for a volume of ophthalmic tissue of the eye 722 based on Brillouin signals.

As shown in FIG. 7, the eye 722 can be at a 90 degree angle of orientation relative to the general trajectory of the scanning diagnostic beam after the scanning diagnostic beam exits the objective lens assembly 714. In this way, the reflected focused portion 720 of the scanning diagnostic beam and the imaging light 730 that travels from the eye to the eye camera assembly are aligned in a colinear path. According to some embodiments, such a configuration (e.g. reflecting the beam off the shortpass dichroic filter 718a) may produce less astigmatism (or more generally, less optical aberration) than a different configuration (e.g. scanning or transmitting the beam through the shortpass dichroic filter 718a). This advantage may be particularly helpful for maintaining high beam quality when the scanning diagnostic beam is diffraction limited and involves a confocal focused spot. In some embodiments, the finer axial resolution spot will also minimize contaminating back-reflections from the front surface of the eye, allow for scanning of more of the eye thickness with better spatial resolution. Dichroic filters can operate to reflect or reject light having certain wavelengths, and to transmit light having certain wavelengths.

According to some embodiments, the system 700 can include one or more illumination lamps or light devices 726 that direct illumination light or radiation 727 toward the eye. In some cases, the illumination light or radiation 727 can be infrared light. In some cases, the illumination light or radiation 727 can be non-visible light. In some cases, the illumination light 727 can have a wavelength value within a range from about 700 nm to about 1,000,000 nm. In some case, the illumination light 727 can have a wavelength value of about 940 nm. According to some embodiments, the eye camera assembly 728 is sensitive to the wavelength of the illumination light 727 (which can also be the same as or similar to the wavelength of the imaging light 730).

In some cases, the illumination light 727 can have a wavelength value that is greater than a wavelength value of the diagnostic scanning light or radiation. In some cases, the diagnostic beam (e.g. 704, 720) has a wavelength value within a range from about 450 to about 1350 nm. In some cases, the wavelength of the scanning diagnostic beam has a value of about 780 nm. In some cases, the scanning diagnostic radiation can have a wavelength value within a range from about 450 to about 1350 nm. In some cases, the fixation light 729a is visible light. In some cases, the fixation light 729a is visible green light. In some cases, the fixation light 729a has a wavelength value of about 520 to about 560 nm. According to some embodiments, the fixation assembly 729 generates light 729a that provides the eye with a gaze target, which can be helpful in a clinical setting or application. In some cases, a system or method can include a gaze target that is not provided by a light emitting fixation assembly.

As shown in FIG. 7, the shortpass dichroic filter 718a can operate to reflect the incoming and returning scanning diagnostic beam, to transmit the imaging light 730 (which can be illumination light 727 reflected from the eye), and to transmit the fixation light 729a. Related, the longpass dichroic filter 718b can operate to reflect the fixation light 729a and to transmit the imaging light 730 (which can be illumination light 727 reflected from the eye). According to some embodiments, the eye camera assembly 728 does not image through the laser path and/or the co-axial scanning laser can be reflected at 90 degrees. In some cases, the quarter wave plate assembly 717 can be positioned downstream of the objective lens assembly 714 for purposes of optical isolation. The optical scanning assembly 709 can be configured to provide lateral xy scanning, optionally by implementation of galvanometer mirrors. In some cases, the optical scanning assembly 709 can be followed by an afocal relay, which may include a beam magnification or expansion mechanism and/or a pupil scanning mechanism. Optical scanning can be achieved by system 700 without changing the field of view of the eye camera assembly 728.

According to some embodiments, the focused scanning diagnostic laser beam 720 optical path and the imaging light 730 optical path are provided as integrated colinear optical paths, as a result of the operation of one or more dichroic filters. In some cases, the respective optical paths may not be integrated in a colinear fashion. In some cases, by providing integrated colinear optical paths, it is possible to avoid or eliminate geometric distortions of the image that may otherwise be present when using an off-axis camera (even though it may be possible to achieve the same focal point for a laser, relative to the focus of the imaging camera).

In some cases, by providing integrated colinear optical paths, it is possible to more efficiently register biomechanical data to eye location and/or orientation data pertaining to a real world eye space. In some cases, it is possible to use eye tracker or camera information to register and track where those points have been scanned, relative to certain features and/or registration coordinates on the eye.

According to some embodiments, astigmatism can be incurred for the eye camera illumination or an image of the eye by transmitting through the dichroic, and a perfect 3D orthogonal orientation (e.g. of the illumination lamp 726) can cancel out that astigmatism.

As seen here, the longpass dichroic filter 718b operates to fold together the light 529a from the fixation assembly 729 and the imaging light 730 from the eye (integrated). Embodiments of the present invention also encompass designs where the fixation light 729a is not folded into the same path with the imaging light 730 (unintegrated). As shown in FIG. 7, in this embodiment there may be no lens between the shortpass dichroic filter 718a and the longpass dichroic filter 718b.

In the embodiment depicted in FIG. 7, as well as in other embodiments disclosed herein, it may be desirable for a beam that enters an optical scanning system 709 to be collimated, and to have a beam that is collimated in a space between the beam expansion assembly 710 and the back entrance of an objective of the objective lens assembly 714. According to some embodiments, the objective lens assembly 714 can include a motorized element, such as z scan motor, which can move or translate the position of an objective of the objective lens assembly 714. Such movement can operate to shift the location of a focused spot 724 (e.g. confocal focused spot) to deeper or shallower locations within the patient tissue.

According to some embodiments, the focused spot 724 can be initially positioned in the space anterior to the patient eye, and then scanned in the z direction toward a central part of the patient's eye, through the cornea, through the aqueous humor, and into deeper tissues or structures of the eye. The system 700 can operate to take measurements at any position along this trajectory. Hence, the system can scan along a depth line, sampling periodically, and then from that data, determine one or more points corresponding to the air, one or more points corresponding to the cornea, one or more points corresponding to the aqueous humor or liquid posterior to the cornea. The system 700 can also operate to isolate the data points corresponding to the cornea, and use those data points to generate a corneal elasticity map for that location, either by averaging the data points, or treating them separately.

Figure 13:
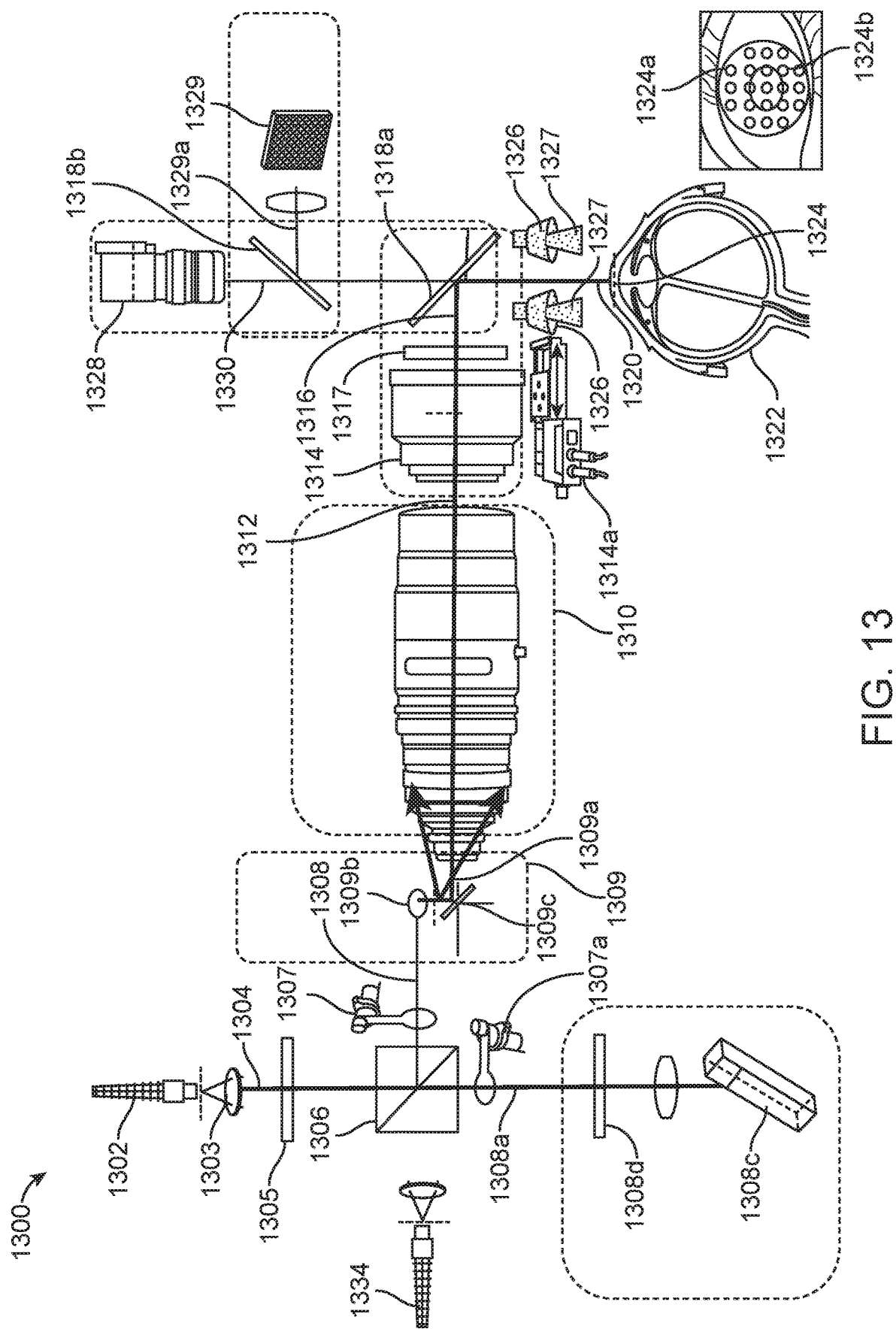
FIG. 13 depicts aspects of a system for generating an elastic stiffness map for a volume of an ophthalmic tissue of an eye of a patient, according to embodiments of the present invention.

In some cases, the patient interface system 700 depicted in FIG. 7 can incorporate one or more features of the embodiment depicted in FIG. 13. For example, FIG. 13 shows additional details regarding a reference path that is used to measure a sample containing plastic and water, that has known elastic properties. This can be used to normalize the data that is received from the actual tissue being analyzed, for example the cornea or the crystalline lens. Light can be controlled by a pair of shutters, and operation of the shutters can determine whether the laser light is going to hit the reference path, or whether the laser is going to hit the sample path. FIG. 13 also illustrates that a fixation assembly can include a grid of light points or light emitting diodes. The system can be configured to illuminate one or more points of the grid, so as to control where the patient directs their gaze. In this way, it is possible to facilitate the measurement of certain areas of the eye that otherwise may be difficult to scan or measure when the patient is looking directly straightforward. Accordingly, the system can facilitate a computerized control of the orientation of the eye, by changing the gaze angle.

Figure 8:
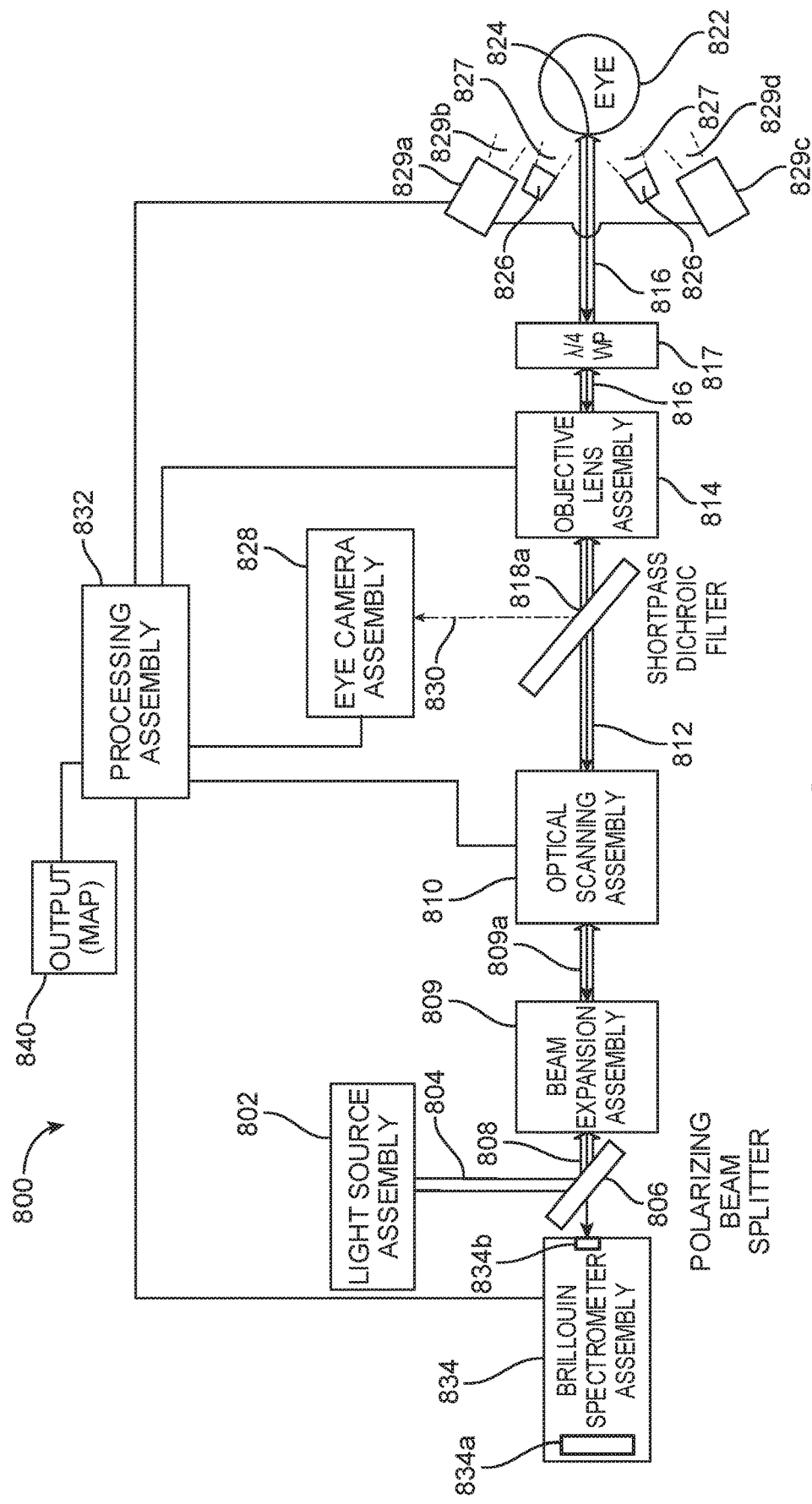
FIG. 8 depicts aspects of a system for generating an elastic stiffness map for a volume of an ophthalmic tissue of an eye of a patient, according to embodiments of the present invention.

FIG. 8 depicts aspects of a patient interface system 800 according to embodiments of the present invention. As discussed elsewhere herein, system 800 can be used to generate an elastic stiffness map 840 for a volume of an ophthalmic tissue of an eye of a patient. As shown here, system 800 includes a laser assembly or light source 802 that generates a collimated diagnostic laser beam 804, a polarizing beam splitter 806 that reflects a portion 808 of the collimated diagnostic laser beam 804, and the reflected portion 808 is then transmitted to a laser beam expansion assembly 809, which converts beam 808 to an expanded beam 809a. In some cases, light source 802 can be a device that produces electromagnetic radiation characterized by one or more wavelengths or one or more frequencies. According to some embodiments, the electromagnetic radiation beam expansion assembly 809 expands a collimated scanning diagnostic laser beam from a first diameter to a second diameter that is larger than the first diameter. The laser beam expansion assembly 809 may include multiple lenses. In some cases, the laser beam expansion assembly 809 includes lenses disposed in a Galilean configuration, with a negative lens followed by a positive lens. In some case, the laser beam expansion assembly 809 can be provided as a Galilean type beam expander. In some cases, the collimated scanning diagnostic laser beam has a linear polarization orientation. In turn, expanded beam 809a is transmitted to an optical scanning assembly 810.

As shown here, the polarizing beam splitter 806 can be positioned before the laser beam expansion assembly 809. The polarizing beam splitter 806 can operate to split the diagnostic laser beam 804 into a scanning portion (808) and a non-scanning portion (not shown). In some cases, the beam splitter 806 allows for the measurement (e.g. concurrent) of a reference sample. In some cases, the beam splitter 806 operates to provide an additional amount of filtration of back reflections of light. Filtration can be based on polarization, and may involve aspects of a conventional optical isolator based on polarizing optics and a quarter wave plate. In some cases, the polarizing beam splitter 806 transmits light at a 90 degrees orientation and on the return path the light goes to 90 degrees. In some embodiments, the beam splitter 806 works in conjunction with the quarter wave plate 817. For example, after two passes through the waveplate 817, the returning light can be passed back to the spectrometer assembly 834, and light that has only passed once (e.g. reflections from lenses) will be excluded. In some cases, when the light first enters the quarter wave plate 817, some amount can be portioned to a calibrated reference sample. As described elsewhere herein (e.g. FIGS. 11-15), a half-waveplate element may also be positioned after the laser source which sets up a ratio of linearly polarized s and p. This can control the light split through the polarizing beam splitter (PBS). According to some embodiments, a Brillouin signal from a sample can be used as a built in reference to the instrument for accurate calculation of the Brillouin signal. There may also be a quarter waveplate on the reference path to provide an isolated signal that will make its way back to the spectrometer.

According to some embodiments, the optical scanning assembly 810 operates to adjust or redirect a beam path of the expanded collimated scanning diagnostic laser beam. In some cases, the patient interface system 800 may not include the polarizing beam splitter 806. The optical scanning assembly 810 operates to redirect a beam path of the reflected portion 808 of the collimated scanning diagnostic laser beam. The redirected reflected portion 812 of the collimated scanning diagnostic laser beam is then transmitted through a shortpass dichroic filter 818a and to an objective lens assembly 814, which operates to focus the redirected portion 812 of the collimated scanning diagnostic laser beam to produce a focused scanning diagnostic laser beam 816.

According to some embodiments, the objective lens assembly 814 operates to focus the expanded collimated scanning diagnostic laser beam 812 to produce a focused scanning diagnostic laser beam 816 having a beam waist or focused spot. In some cases, the objective lens assembly 814 operates to adjust a scan position of the beam waist or focused spot. In some cases, the objective lens assembly 814 includes a motorized stage that allows the objective lens assembly to travel toward and away from the optical scanning assembly 810. In some cases, the optical scanning assembly 810 includes a motorized stage that allows the optical scanning assembly to travel toward and away from the objective lens assembly 814. In some cases, the optical scanning assembly and the objective lens assembly include or are disposed on respective motorized stages, or are disposed on a common motorized stage, so that the optical scanning assembly and the objective lens assembly can move in tandem.

As shown here, system 800 may include a quarter-wave plate assembly 817. In some embodiments, the quarter-wave plate assembly 817 operates to convert the focused scanning diagnostic laser beam 816 from a linear polarization orientation to a circular polarization orientation. In some embodiments, the quarter-wave plate assembly 817 operates to provide a 45 degree rotation to the focused scanning diagnostic laser beam 816. In some cases, the quarter-wave plate assembly 817 operates to convert the focused scanning diagnostic laser beam 816 from p-polarized light to s-polarized light. In some cases, the quarter-wave plate assembly 817 operates to convert the focused scanning diagnostic laser beam 816 from s-polarized light to p-polarized light. The quarter-wave plate assembly 817 can be placed along the beam path, for example between the objective lens assembly 814 and the eye 822. In some embodiments, the quarter-wave plate assembly 817 can be placed upstream of the objective lens assembly 814. In some cases, the quarter-wave plate assembly 817 can be placed anywhere as desired, between the sample (e.g. eye) and the PBS.

The focused scanning diagnostic laser beam 816 is transmitted toward an eye 822 of the patient. In some cases, the focused scanning diagnostic laser beam has a circular polarization orientation. In some cases, a dichroic filter will transmit light within a certain wavelength band or range and/or reflect light within a certain wavelength band or range. As shown here, dichroic filters can operate to fold together, or to separate out, different wavelengths of light (e.g. into a common optical path).

In some case, the dichroic filters can operate to fold together imaging light 830, and scanning diagnostic light 816, into a common optical path (e.g. between the shortpass dichroic filter 818a and the eye 822). Similarly, a dichroic can operate to peel apart light from a common path into separate optical paths, for example imaging light 830 and returned scanning diagnostic light travel along a common optical path from the eye to the shortpass dichroic filter 818a, and then the returned scanning diagnostic light is transmitted through the shortpass dichroic filter 818a and the imaging light is reflected by the shortpass dichroic filter 818a.

The focused scanning diagnostic laser beam 816 has focused spot 824, and operation of the optical scanning assembly 810 or the objective lens assembly 814, or the combined operation of the optical scanning assembly 810 and the objective lens assembly 814, can adjust a scan position of the focused spot 824 to various discrete locations on or within one or more tissues of the eye 822.

The patient interface system 800 also includes an eye camera assembly 828 that receives imaging light 830 from the eye (which optionally may have been reflected by a shortpass dichroic filter 818a of a beam control assembly) and that generates electrical signals in response to the received imaging light 830. The imaging light 830 can provide registration information regarding the position and/or orientation of the eye. In some cases, this registration information can be used (e.g. by processing assembly 832) to provide locate elasticity measurement data obtained by the Brillouin spectrometer assembly 834 to particular points of the eye. In some cases, the imaging light 830 can help to provide feedback, which may be continuous feedback, to the processing assembly. The imaging light 830 can be processed to provide information regarding a center coordinate of the eye, a central reference of the eye, or more generically, a reference coordinate on the eye, which can be registered to the biomechanical data. Such a reference coordinate can be determined by processing the imaging data.

In some cases, the processing assembly 832 can operate to generate two images, specifically an image of the eye and a Brillouin heat map (e.g. stiffness values at discrete points), and to accurately superimpose those images on top of each other using registration. In this way, the mechanical information is relevant in the physical space. In some cases, the processing assembly does not perform a superimposition. Rather, a camera is used to provide a reference point to begin a scan pattern, and thereafter a scan is performed according to the pattern, so as to generate the stiffness map. The map can indicate whether there are any abnormal spots or points of interest on the eye, without providing the exact location on the eye of the abnormal spots or points of interest. In some cases, a camera is not used to provide a reference point to begin a scan pattern. For example, the physician or operate could manually inspect the person's eye, and then aim the beam, without using a camera. In some cases, it is possible to illuminate the person's eye using a certain wattage, observe a reflection off the person's eye, and determine that the alignment of the scanning beam and the eye is sufficient.

Hence, input techniques for aiming the diagnostic beam can include using a camera image or data, manually aiming the beam, or using feedback from the Brillouin spectrometer. For example, data obtained by the spectrometer can provide an indication of whether the system is in focus. The Brillouin spectrometer can be used to differentiate spectral shifts that are characteristic of different tissues. In some cases, as the focused spot is scanned in the z depth direction, it is possible to detect fundamentally different frequency shifts (or different information) as the focused spot goes through different layers (e.g. going from the air, to the cornea surface, to the aqueous humor, to the crystalline lens, and so on) which can correspond to different elastic properties (e.g. elastic modulus). In this sense, the Brillouin approach can provide aspects of an imaging modality. Hence, it may be possible to determine where the focused spot is located (e.g. along a z-axis), by observing or analyzing the spectrometer image. In some cases, it is possible to align or position the patient interface system, by observing or using a reflection off of a person's eye, then moving the system into focus based on feedback from the spectrometer camera, and then initiating the scan. In some cases, the camera is parfocal with the laser beam, and the focus of the eye can also be used.

In some embodiments, system 800 also includes a fixation assembly that provides the eye with a gaze target, the fixation assembly having a first fixation mechanism 829a that transmits a first fixation light 829b toward the eye, and a second fixation mechanism 829c that transmits a second fixation light 829d toward the eye. According to some embodiments, the fixation assembly includes light-emitting diodes (LEDs). In some cases, the fixation light is a collimated green light produced by a light emitting diode.

The patient interface system 800 can further include a Brillouin spectrometer assembly 834 having a Brillouin spectrometer 834a and a spatial filter 834b that is parfocal with the focused spot 824 (e.g. in a conjugate focal plane). The Brillouin spectrometer can generate Brillouin signals as the focused spot 824 is scanned to discrete locations throughout a volume or plane thickness of ophthalmic tissue of the eye 822. Brillouin scattered light from the focused spot at the discrete locations is returned to the spatial filter 834b. According to some embodiments, the spatial filter 834b operates as an input for the Brillouin spectrometer, and is in conjugate alignment with the focused spot 824 or beam waist of the focused scanning diagnostic laser beam, and the Brillouin spectrometer 834a can generate Brillouin signals as the focused spot 824 or beam waist of the focused scanning diagnostic beam is scanned to discrete locations throughout the volume of the ophthalmic tissue of the eye 822. In some cases, the spatial filter 834b can operate to exclude information associated with out of focus focal planes, and include information associated with the focal plane of interest. The filter 834b can provide sensitivity to locations where the focused spot 824 is positioned, and little or no sensitivity to extraneous locations. In some cases, a spatial filter can be provided without using a fiber. In some cases, the spatial filter 834b can operate to prime the incoming light, which is then measured by the spectrometer 834a, which in turn generates the spectrum (e.g. Brillouin) signals.

By using a fiber input, it is possible to provide modularity to the system, whereby the patient scanning interface can be decoupled and coupled with the spectrometer via the optical fiber. Such modularity can provide enhanced testing and serviceability advantages. For example, the optical fiber could be uncoupled from one patient interface system, and coupled with another patient interface system. Hence, if one patient interface were to malfunction, it could be replaced with another patient interface. This could also allow patient interfaces to be tested as modules, which can improve manufacturability.

From an optical standpoint, a fiber can provide a highly functional pinhole. In some cases, such embodiments can provide a separate input and output. It is possible to physically decouple with free space optics the input and output of the system. In some embodiments, the input is not separated from the output. For example, the same light can be coupled back into the same input path and optionally the beam could be redirected to the spectrometer after traveling back down the fiber.

According to some embodiments, an optical output out of a single mode fiber can provide or approach a perfect Gaussian distribution, which has desirable beam shape and optical quality characteristics, and can be well suited for use with sensitive optical elements. As such, this feature can help optimize the optical performance of the overall system, particularly when multiple optical elements are involved.

In some cases, a fiber can operate as a conjugate pinhole or aperture (or spatial filter) for the focus spot in the tissue that is being analyzed. The fiber can operate to provide a focal plane resolution and specificity, filtering out the out of focus light that is not of interest. In some cases, a spatial filter can be provided as a radial aperture or a circular aperture. In some cases, an aperture can have a diameter of about 1 mm aperture. In some cases, the focus of the light is aligned with the core of a fiber, whereby only that light which is properly aligned to the core of the fiber will make it into that fiber. Thereafter, that light will be propagated down the fiber. In this sense, the core of the fiber can operate as a filter, spatial mask, or pinhole aperture, whereby light coupled into the core of the fiber is propagated, and undesired light is filtered or masked out. Often, a fiber will operate in conjunction with a lens. In some embodiments, the fiber can be provided as a collimated fiber optic. In some cases, light is focused into the fiber, or into the core of the fiber, using a lens. The light can be propagated in the fiber by way of total internal reflection. Where light is not properly aligned with the fiber core, such light may not propagate down the fiber, or be coupled into that fiber.

Put another way, light that is at a different focal plane, in the tissue, will not be at the same focal plane, over at the pinhole or spatial filter side, and hence becomes filtered out. The out of focus light will not make it into the pinhole or spatial aperture, and won't be coupled into the fiber, because that light is not aligned (e.g. not at the same focal plane, confocal, or conjugate).

As shown here, the patient interface system 800 can include a processing assembly 832 in operative association with the optical scanning assembly 810, the objective lens assembly 814, the eye camera assembly 828, the fixation assembly (829a, 829c), and the Brillouin spectrometer assembly 834. The processing assembly 832 can include a processor, an electronic storage location operatively coupled with the processor, and processor executable code stored on the electronic storage location and embodied in a tangible non-transitory computer readable medium. The processor executable code can include machine-readable instructions that, when executed by the processor, cause the processor to generate x,y coordinate scan control signals for the optical scanning assembly 810. In some cases, x,y coordinate scan control signals for the optical scanning assembly 810 can be generated based on the electrical signals generated by the eye camera assembly 828. The processor executable code can include machine-readable instructions that, when executed by the processor, cause the processor to generate z coordinate scan control signals for the objective lens assembly 814. In some cases, the x,y coordinate scan control signals, the z coordinate scan control signals, or both the x,y coordinate scan control signals and the z coordinate scan control signals, can be based on an image of the eye. In some cases, the x,y coordinate scan control signals, the z coordinate scan control signals, or both the x,y coordinate scan control signals and the z coordinate scan control signals, can be generated independent of an image of the eye. In some cases, the x,y coordinate scan control signals, the z coordinate scan control signals, or both the x,y coordinate scan control signals and the z coordinate scan control signals, can be generated according to a pre-defined or pre-determined scan pattern. The processor executable code can include machine-readable instructions that, when executed by the processor, cause the processor to generate an elastic stiffness map for a volume of ophthalmic tissue of the eye 822 based on Brillouin signals. In some cases, the optical scanning assembly 810 may include a prism pair, for example a prism pair as depicted in FIG. 3.

As shown in FIG. 8, the eye 822 can be at an on-axis orientation relative to the general trajectory of the scanning diagnostic beam after the scanning diagnostic beam exits the objective lens assembly 814. In this way, the focused portion 816 of the scanning diagnostic beam and the imaging light 830 that travels from the eye to the shortpass dichroic filter are aligned in a colinear path. Dichroic filters can operate to reflect or reject light having certain wavelengths, and to transmit light having certain wavelengths.

According to some embodiments, the system 800 can include one or more illumination lamps or light devices 826 that direct illumination light or radiation 827 toward the eye. In some cases, the illumination light or radiation 827 can be infrared light. In some cases, the illumination light or radiation 827 can be non-visible light. In some cases, the illumination light 827 can have a wavelength value within a range from about 700 nm to about 1,000,000 nm. In some case, the illumination light 827 can have a wavelength value of about 940 nm. According to some embodiments, the eye camera assembly 828 is sensitive to the wavelength of the illumination light 827 (which can also be the same as or similar to the wavelength of the imaging light 830).

In some cases, the illumination light 827 can have a wavelength value that is greater than a wavelength value of the diagnostic scanning light or radiation. In some cases, the diagnostic beam (e.g. 804, 816) has a wavelength value within a range from about 450 to about 1350 nm. In some cases, the wavelength of the scanning diagnostic beam has a value of about 780 nm. In some cases, the scanning diagnostic radiation can have a wavelength value within a range from about 450 to about 1350 nm. In some cases, the fixation light 829b, 829d is visible light. In some cases, the fixation light 829b, 829d is visible green light. In some cases, the fixation light 829b, 829d has a wavelength value of about 520 to about 560 nm. According to some embodiments, the fixation assembly generates light 829b, 829d that provides the eye with a gaze target, which can be helpful in a clinical setting or application. In some cases, a system or method can include a gaze target that is not provided by a light emitting fixation assembly.

As shown in FIG. 8, the shortpass dichroic filter 818a can operate to transmit the incoming and returning scanning diagnostic beam, and to reflect the imaging light 830 (which can be illumination light 827 reflected from the eye).

According to some embodiments, the focused scanning diagnostic laser beam 816 optical path and the imaging light 830 optical path are provided as integrated colinear optical paths. In some cases, the respective optical paths may not be integrated in a colinear fashion. In some cases, by providing integrated colinear optical paths, it is possible to avoid or eliminate geometric distortions of the image that may otherwise be present when using an off-axis camera (even though it may be possible to achieve the same focal point for a laser, relative to the focus of the imaging camera).

In some cases, by providing integrated colinear optical paths, it is possible to more efficiently register biomechanical data to eye location and/or orientation data pertaining to a real world eye space. In some cases, it is possible to use eye tracker or camera information to register and track where those points have been scanned, relative to certain features and/or registration coordinates on the eye.

As shown in FIG. 8, in this embodiment there may be no lens between the shortpass dichroic filter 818a and the eye camera assembly 828. In some cases, the eye camera assembly includes an imaging lens or a lens assembly/objective. Also, in this embodiment the shortpass dichroic filter 818a is positioned in the collimated space between the optical scanning assembly 810 and the objective lens assembly 814, and a portion of the camera path is also positioned in the collimated space between the optical scanning assembly 810 and the objective lens assembly 814.

According to some embodiments, the eye camera assembly 828 of patient interface system 800 can image through a path that is aligned with the laser path. Patient interface system 800 can involve a co-axial scanning laser that is reflected at 90 degrees. Lateral xy scanning can be achieved by a Risley prism pair. In some cases, the Risley prism pair can provide direct eye scanning. Optical xy scanning can be achieved with a Risley prism pair. In some cases, the quarter wave plate assembly 817 can be positioned downstream of the objective lens assembly 814 for purposes of optical isolation. In some cases, mechanical configurations can involve transmitting the laser through a splitter. One aspect of such a mechanical configuration is that there may be no 90 degree reflection required by the laser path. This may make it easier to achieve a desired working distance easier or making it even larger without necessarily putting constraints on the objective lens. In some cases, the optical challenges may be more substantial with additional aberrations from introducing the dichroic before the objective and constraints on distance imaging to achieve the desired eye FOV with certain image quality through the laser scanning objective. According to some embodiments, there is a mechanical decoupling between the eye camera assembly 828 and the laser scanning. System 800 can provide a configuration where all optics are on axis, where testing for alignment can be achieved with only a line scan instead of a 3D scan volume, where there is no optical scanning, and/or there is an inherently telecentric arrangement. Patient interface system 800 can provide a diffraction limited focused spot over an entire focal volume. It is understood that an eye or any other sample with aberrations may make it so the spot is not diffraction limited.

Figure 14:
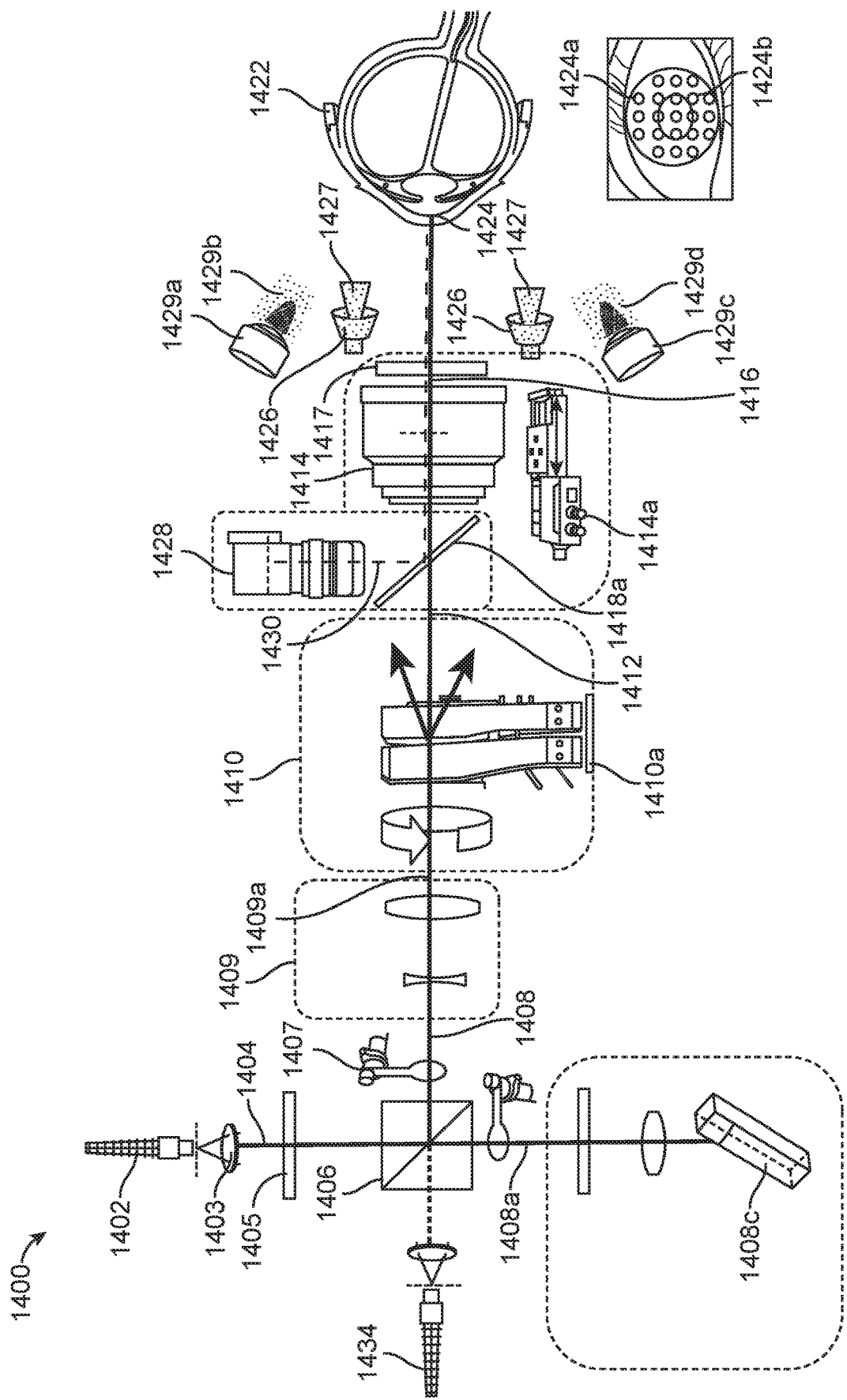
FIG. 14 depicts aspects of a system for generating an elastic stiffness map for a volume of an ophthalmic tissue of an eye of a patient, according to embodiments of the present invention.

In some cases, the patient interface system 800 depicted in FIG. 8 can incorporate one or more features of the embodiment depicted in FIG. 14. For example, FIG. 14 shows additional details regarding a reference path that is used to measure a sample containing plastic and water, that has known elastic properties. This can be used to normalize the data that is received from the actual tissue being analyzed, for example the cornea or the crystalline lens. Light can be controlled by a pair of shutters, and operation of the shutters can determine whether the laser light is going to hit the reference path, or whether the laser is going to hit the sample path. FIG. 14 also illustrates that a fixation assembly can include separate fixation mechanisms. The system can be configured to illuminate one or both fixation mechanisms, so as to control where the patient directs their gaze. In this way, it is possible to facilitate the measurement of certain areas of the eye that otherwise may be difficult to scan or measure when the patient is looking directly straightforward. Accordingly, the system can facilitate a computerized control of the orientation of the eye, by changing the gaze angle.

Figure 9:
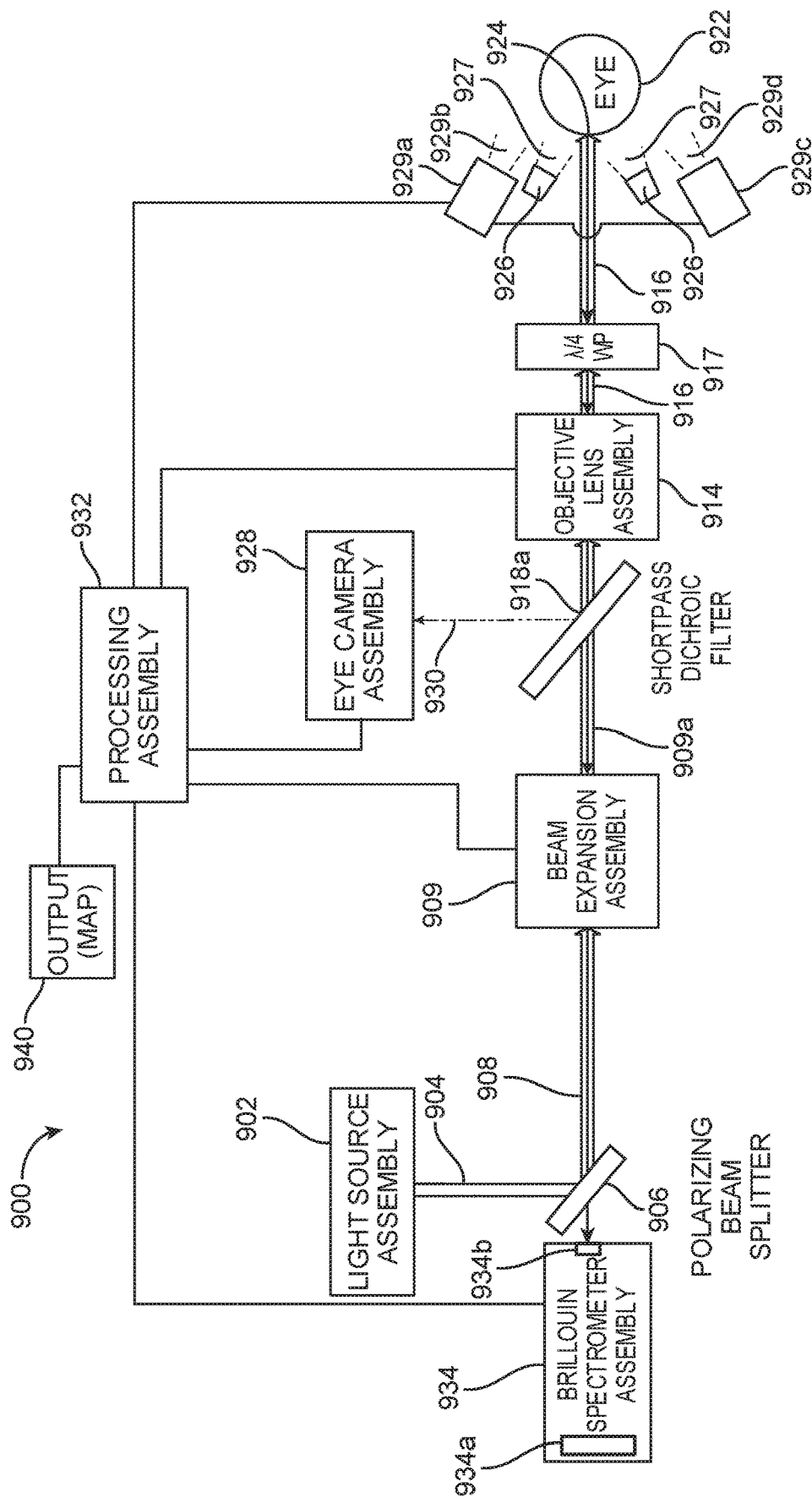
FIG. 9 depicts aspects of a system for generating an elastic stiffness map for a volume of an ophthalmic tissue of an eye of a patient, according to embodiments of the present invention.

FIG. 9 depicts aspects of a patient interface system 900 according to embodiments of the present invention. As discussed elsewhere herein, system 900 can be used to generate an elastic stiffness map 940 for a volume of an ophthalmic tissue of an eye of a patient. As shown here, system 900 includes a laser assembly or light source 902 that generates a collimated diagnostic laser beam 904, a polarizing beam splitter 906 that reflects a portion 908 of the collimated diagnostic laser beam 904, and the reflected portion 908 is then transmitted to a laser beam expansion assembly 909, which converts beam 908 to an expanded beam 909a. In some cases, light source 902 can be a device that produces electromagnetic radiation characterized by one or more wavelengths or one or more frequencies. According to some embodiments, the electromagnetic radiation beam expansion assembly 909 expands a collimated scanning diagnostic laser beam from a first diameter to a second diameter that is larger than the first diameter. The laser beam expansion assembly 909 may include multiple lenses. In some cases, the laser beam expansion assembly 909 includes lenses disposed in a Galilean configuration, with a negative lens followed by a positive lens. In some case, the laser beam expansion assembly 909 can be provided as a Galilean type beam expander. In some cases, the collimated scanning diagnostic laser beam has a linear polarization orientation. In turn, expanded beam 909a is transmitted to an objective lens assembly 914.

As shown here, the polarizing beam splitter 906 can be positioned before the laser beam expansion assembly 909. The polarizing beam splitter 906 can operate to split the diagnostic laser beam 904 into a scanning portion (908) and a non-scanning portion (not shown). In some cases, the beam splitter 906 allows for the measurement (e.g. concurrent) of a reference sample. In some cases, the beam splitter 906 operates to provide an additional amount of filtration of back reflections of light. Filtration can be based on polarization, and may involve aspects of a conventional optical isolator based on polarizing optics and a quarter wave plate. In some cases, the polarizing beam splitter 906 transmits light at a 90 degrees orientation and on the return path the light goes to 90 degrees. According to some embodiments, the beam splitter 906 works in conjunction with the quarter wave plate 917. For example, after two passes through the waveplate 917, the returning light can be passed back to the spectrometer assembly 934, and light that has only passed once (e.g. reflections from lenses) will be excluded. In some cases, when the light first enters the quarter wave plate 917, some amount can be portioned to a calibrated reference sample. As described elsewhere herein (e.g. FIGS. 11-15), a half-waveplate element may also be positioned after the laser source which sets up a ratio of linearly polarized s and p. This can control the light split through the polarizing beam splitter (PBS). According to some embodiments, a Brillouin signal from a sample can be used as a built in reference to the instrument for accurate calculation of the Brillouin signal. There may also be a quarter waveplate on the reference path to provide an isolated signal that will make its way back to the spectrometer.

According to some embodiments, the beam expansion assembly 909 operates to adjust or redirect a beam path of the expanded collimated scanning diagnostic laser beam. In some cases, the patient interface system 900 may not include the polarizing beam splitter 906.

The beam expansion assembly 909 operates to redirect a beam path of the reflected portion 908 of the collimated scanning diagnostic laser beam. The redirected reflected portion 909a of the collimated scanning diagnostic laser beam is then transmitted to an objective lens assembly 914, which operates to focus the redirected portion 909a of the collimated scanning diagnostic laser beam to produce a focused scanning diagnostic laser beam 916.

According to some embodiments, the objective lens assembly 914 operates to focus the expanded collimated scanning diagnostic laser beam 909a to produce a focused scanning diagnostic laser beam 916 having a beam waist or focused spot. In some cases, the objective lens assembly 914 operates to adjust a scan position of the beam waist or focused spot. In some cases, the objective lens assembly 914 includes a motorized stage that allows the objective lens assembly to travel toward and away from the beam expansion assembly 909. In some cases, the beam expansion assembly 909 includes a motorized stage that allows the optical scanning assembly to travel toward and away from the objective lens assembly 914, and/or in a plane perpendicular to the beam path. In some cases, the beam expansion assembly and the objective lens assembly include or are disposed on respective motorized stages, or are disposed on a common motorized stage, so that the beam expansion assembly and the objective lens assembly can move in tandem.

As shown here, system 900 may include a quarter-wave plate assembly 917. In some embodiments, the quarter-wave plate assembly 917 operates to convert the focused scanning diagnostic laser beam 916 from a linear polarization orientation to a circular polarization orientation. In some embodiments, the quarter-wave plate assembly 917 operates to provide a 45 degree rotation to the focused scanning diagnostic laser beam 916. In some cases, the quarter-wave plate assembly 917 operates to convert the focused scanning diagnostic laser beam 916 from p-polarized light to s-polarized light. In some cases, the quarter-wave plate assembly 917 operates to convert the focused scanning diagnostic laser beam 916 from s-polarized light to p-polarized light. The quarter-wave plate assembly 917 can be placed along the beam path, for example between the objective lens assembly 914 and the eye 922. In some embodiments, the quarter-wave plate assembly 917 can be placed upstream of the objective lens assembly 914. In some cases, the quarter-wave plate assembly 917 can be placed anywhere as desired, between the sample (e.g. eye) and the PBS.

The focused scanning diagnostic laser beam 916 is transmitted toward an eye 922 of the patient. In some cases, the focused scanning diagnostic laser beam has a circular polarization orientation. In some cases, a dichroic filter will transmit light within a certain wavelength band or range and/or reflect light within a certain wavelength band or range. As shown here, dichroic filters can operate to fold together, or to separate out, different wavelengths of light (e.g. into a common optical path).

In some case, the dichroic filters can operate to fold together imaging light 930, and scanning diagnostic light 916, into a common optical path (e.g. between the shortpass dichroic filter 918*a* and the eye 922). Similarly, a dichroic can operate to peel apart light from a common path into separate optical paths, for example imaging light 930 and returned scanning diagnostic light travel along a common optical path from the eye to the shortpass dichroic filter 918*a*, and then the returned scanning diagnostic light is transmitted through the shortpass dichroic filter 918*a* and the imaging light is reflected by the shortpass dichroic filter 918*a*.

The focused scanning diagnostic laser beam 916 has focused spot 924, and operation of the beam expansion assembly 909 or the objective lens assembly 914, or the combined operation of the beam expansion assembly 909 and the objective lens assembly 914, can adjust a scan position of the focused spot 924 to various discrete locations on or within one or more tissues of the eye 922.

The patient interface system 900 also includes an eye camera assembly 928 that receives imaging light 930 from the eye (which optionally may have been reflected by a shortpass dichroic filter 918*a* of a beam control assembly) and that generates electrical signals in response to the received imaging light 930. The imaging light 930 can provide registration information regarding the position and/or orientation of the eye. In some cases, this registration information can be used (e.g. by processing assembly 932) to provide locate elasticity measurement data obtained by the Brillouin spectrometer assembly 934 to particular points of the eye. In some cases, the imaging light 930 can help to provide feedback, which may be continuous feedback, to the processing assembly. The imaging light 930 can be processed to provide information regarding a center coordinate of the eye, a central reference of the eye, or more generically, a reference coordinate on the eye, which can be registered to the biomechanical data. Such a reference coordinate can be determined by processing the imaging data.

In some cases, the processing assembly 932 can operate to generate two images, specifically an image of the eye and a Brillouin heat map (e.g. stiffness values at discrete points), and to accurately superimpose those images on top of each other using registration. In this way, the mechanical information is relevant in the physical space. In some cases, the processing assembly does not perform a superimposition. Rather, a camera is used to provide a reference point to begin a scan pattern, and thereafter a scan is performed according to the pattern, so as to generate the stiffness map. The map can indicate whether there are any abnormal spots or points of interest on the eye, without providing the exact location on the eye of the abnormal spots or points of interest. In some cases, a camera is not used to provide a reference point to begin a scan pattern. For example, the physician or operate could manually inspect the person's eye, and then aim the beam, without using a camera. In some cases, it is possible to illuminate the person's eye using a certain wattage, observe a reflection off the person's eye, and determine that the alignment of the scanning beam and the eye is sufficient.

Hence, input techniques for aiming the diagnostic beam can include using a camera image or data, manually aiming the beam, or using feedback from the Brillouin spectrometer. For example, data obtained by the spectrometer can provide an indication of whether the system is in focus. The Brillouin spectrometer can be used to differentiate spectral shifts that are characteristic of different tissues. In some cases, as the focused spot is scanned in the z depth direction, it is possible to detect fundamentally different frequency shifts (or different information) as the focused spot goes through different layers (e.g. going from the air, to the cornea surface, to the aqueous humor, to the crystalline lens, and so on) which can correspond to different elastic properties (e.g. elastic modulus). In this sense, the Brillouin approach can provide aspects of an imaging modality. Hence, it may be possible to determine where the focused spot is located (e.g. along a z-axis), by observing or analyzing the spectrometer image. In some cases, it is possible to align or position the patient interface system, by observing or using a reflection off of a person's eye, then moving the system into focus based on feedback from the spectrometer camera, and then initiating the scan. In some cases, the camera is parfocal with the laser beam, and the focus of the eye can also be used.

In some embodiments, system 900 also includes a fixation assembly that provides the eye with a gaze target, the fixation assembly having a first fixation mechanism 929*a* that transmits a first fixation light 929*b* toward the eye, and a second fixation mechanism 929*c* that transmits a second fixation light 929*d* toward the eye. According to some embodiments, the fixation assembly includes light-emitting diodes (LEDs). In some cases, the fixation light is a collimated green light produced by a light emitting diode.

The patient interface system 900 can further include a Brillouin spectrometer assembly 934 having a Brillouin spectrometer 934*a* and a spatial filter 934*b* that is parfocal with the focused spot 924 (e.g. in a conjugate focal plane). The Brillouin spectrometer can generate Brillouin signals as the focused spot 924 is scanned to discrete locations throughout a volume or plane thickness of ophthalmic tissue of the eye 922. Brillouin scattered light from the focused spot at the discrete locations is returned to the spatial filter 934*b*. According to some embodiments, the spatial filter 934*b* operates as an input for the Brillouin spectrometer, and is in conjugate alignment with the focused spot 924 or beam waist of the focused scanning diagnostic laser beam, and the Brillouin spectrometer 934*a* can generate Brillouin signals as the focused spot 924 or beam waist of the focused scanning diagnostic beam is scanned to discrete locations throughout the volume of the ophthalmic tissue of the eye 922. In some cases, the spatial filter 934*b* can operate to exclude information associated with out of focus focal planes, and include information associated with the focal plane of interest. The filter 934*b* can provide sensitivity to locations where the focused spot 924 is positioned, and little or no sensitivity to extraneous locations. In some cases, a spatial filter can be provided without using a fiber. In some cases, the spatial filter 934b can operate to prime the incoming light, which is then measured by the spectrometer 934a, which in turn generates the spectrum (e.g. Brillouin) signals.

By using a fiber input, it is possible to provide modularity to the system, whereby the patient scanning interface can be decoupled and coupled with the spectrometer via the optical fiber. Such modularity can provide enhanced testing and serviceability advantages. For example, the optical fiber could be uncoupled from one patient interface system, and coupled with another patient interface system. Hence, if one patient interface were to malfunction, it could be replaced with another patient interface. This could also allow patient interfaces to be tested as modules, which can improve manufacturability.

From an optical standpoint, a fiber can provide a highly functional pinhole. In some cases, such embodiments can provide a separate input and output. It is possible to physically decouple with free space optics the input and output of the system. In some embodiments, the input is not separated from the output. For example, the same light can be coupled back into the same input path and optionally the beam could be redirected to the spectrometer after traveling back down the fiber.

According to some embodiments, an optical output out of a single mode fiber can provide or approach a perfect Gaussian distribution, which has desirable beam shape and optical quality characteristics, and can be well suited for use with sensitive optical elements. As such, this feature can help optimize the optical performance of the overall system, particularly when multiple optical elements are involved.

In some cases, a fiber can operate as a conjugate pinhole or aperture (or spatial filter) for the focus spot in the tissue that is being analyzed. The fiber can operate to provide a focal plane resolution and specificity, filtering out the out of focus light that is not of interest. In some cases, a spatial filter can be provided as a radial aperture or a circular aperture. In some cases, an aperture can have a diameter of about 1 mm aperture. In some cases, the focus of the light is aligned with the core of a fiber, whereby only that light which is properly aligned to the core of the fiber will make it into that fiber. Thereafter, that light will be propagated down the fiber. In this sense, the core of the fiber can operate as a filter, spatial mask, or pinhole aperture, whereby light coupled into the core of the fiber is propagated, and undesired light is filtered or masked out. Often, a fiber will operate in conjunction with a lens. In some embodiments, the fiber can be provided as a collimated fiber optic. In some cases, light is focused into the fiber, or into the core of the fiber, using a lens. The light can be propagated in the fiber by way of total internal reflection. Where light is not properly aligned with the fiber core, such light may not propagate down the fiber, or be coupled into that fiber.

Put another way, light that is at a different focal plane, in the tissue, will not be at the same focal plane, over at the pinhole or spatial filter side, and hence becomes filtered out. The out of focus light will not make it into the pinhole or spatial aperture, and won't be coupled into the fiber, because that light is not aligned (e.g. not at the same focal plane, confocal, or conjugate).

As shown here, the patient interface system 900 can include a processing assembly 932 in operative association with the beam expansion assembly 909, the objective lens assembly 914, the eye camera assembly 928, the fixation assembly (929a, 929c), and the Brillouin spectrometer assembly 934. The processing assembly 932 can include a processor, an electronic storage location operatively coupled with the processor, and processor executable code stored on the electronic storage location and embodied in a tangible non-transitory computer readable medium. The processor executable code can include machine-readable instructions that, when executed by the processor, cause the processor to generate x,y coordinate scan control signals for the beam expansion assembly 909. In some cases, x,y coordinate scan control signals for the beam expansion assembly 909 can be generated based on the electrical signals generated by the eye camera assembly 928. The processor executable code can include machine-readable instructions that, when executed by the processor, cause the processor to generate z coordinate scan control signals for the objective lens assembly 914. In some cases, the x,y coordinate scan control signals, the z coordinate scan control signals, or both the x,y coordinate scan control signals and the z coordinate scan control signals, can be based on an image of the eye. In some cases, the x,y coordinate scan control signals, the z coordinate scan control signals, or both the x,y coordinate scan control signals and the z coordinate scan control signals, can be generated independent of an image of the eye. In some cases, the x,y coordinate scan control signals, the z coordinate scan control signals, or both the x,y coordinate scan control signals and the z coordinate scan control signals, can be generated according to a pre-defined or pre-determined scan pattern. The processor executable code can include machine-readable instructions that, when executed by the processor, cause the processor to generate an elastic stiffness map for a volume of ophthalmic tissue of the eye 922 based on Brillouin signals.

As shown in FIG. 9, the eye 922 can be at an on-axis orientation relative to the general trajectory of the scanning diagnostic beam after the scanning diagnostic beam exits the objective lens assembly 914. In this way, the focused portion 916 of the scanning diagnostic beam and the imaging light 930 that travels from the eye to the shortpass dichroic filter are aligned in a colinear path. Dichroic filters can operate to reflect or reject light having certain wavelengths, and to transmit light having certain wavelengths.

According to some embodiments, the system 900 can include one or more illumination lamps or light devices 926 that direct illumination light or radiation 927 toward the eye. In some cases, the illumination light or radiation 927 can be infrared light. In some cases, the illumination light or radiation 927 can be non-visible light. In some cases, the illumination light 927 can have a wavelength value within a range from about 700 nm to about 1,000,000 nm. In some case, the illumination light 927 can have a wavelength value of about 940 nm. According to some embodiments, the eye camera assembly 928 is sensitive to the wavelength of the illumination light 927 (which can also be the same as or similar to the wavelength of the imaging light 930).

In some cases, the illumination light 927 can have a wavelength value that is greater than a wavelength value of the diagnostic scanning light or radiation. In some cases, the diagnostic beam (e.g. 904, 916) has a wavelength value within a range from about 450 to about 1350 nm. In some cases, the wavelength of the scanning diagnostic beam has a value of about 780 nm. In some cases, the scanning diagnostic radiation can have a wavelength value within a range from about 450 to about 1350 nm. In some cases, fixation light 929b, 929d is visible light. In some cases, the fixation light 929b, 929d is visible green light. In some cases, the fixation light 929b, 929d has a wavelength value of about 520 to about 560 nm. According to some embodiments, the fixation assembly generates light 929b, 929d that provides the eye with a gaze target, which can be helpful in a clinical setting or application. In some cases, a system or method can include a gaze target that is not provided by a light emitting fixation assembly.

As shown in FIG. 9, the shortpass dichroic filter 918a can operate to transmit the incoming and returning scanning diagnostic beam, and to reflect the imaging light 930 (which can be illumination light 927 reflected from the eye).

According to some embodiments, the focused scanning diagnostic laser beam 916 optical path and the imaging light 930 optical path are provided as integrated colinear optical paths. In some cases, the respective optical paths may not be integrated in a colinear fashion. In some cases, by providing integrated colinear optical paths, it is possible to avoid or eliminate geometric distortions of the image that may otherwise be present when using an off-axis camera (even though it may be possible to achieve the same focal point for a laser, relative to the focus of the imaging camera).

In some cases, by providing integrated colinear optical paths, it is possible to more efficiently register biomechanical data to eye location and/or orientation data pertaining to a real world eye space. In some cases, it is possible to use eye tracker or camera information to register and track where those points have been scanned, relative to certain features and/or registration coordinates on the eye.

As shown in FIG. 9, in this embodiment there may be no lens between the shortpass dichroic filter 918a and the eye camera assembly 928. In some cases, the eye camera assembly includes an imaging lens or a lens assembly/objective. Also, in this embodiment the shortpass dichroic filter 918a is positioned in the collimated space between the optical scanning assembly (or beam expansion assembly 909) and the objective lens assembly 914, and a portion of the camera path is also positioned in the collimated space between the optical scanning assembly (or beam expansion assembly 909) and the objective lens assembly 914.

Figure 15:
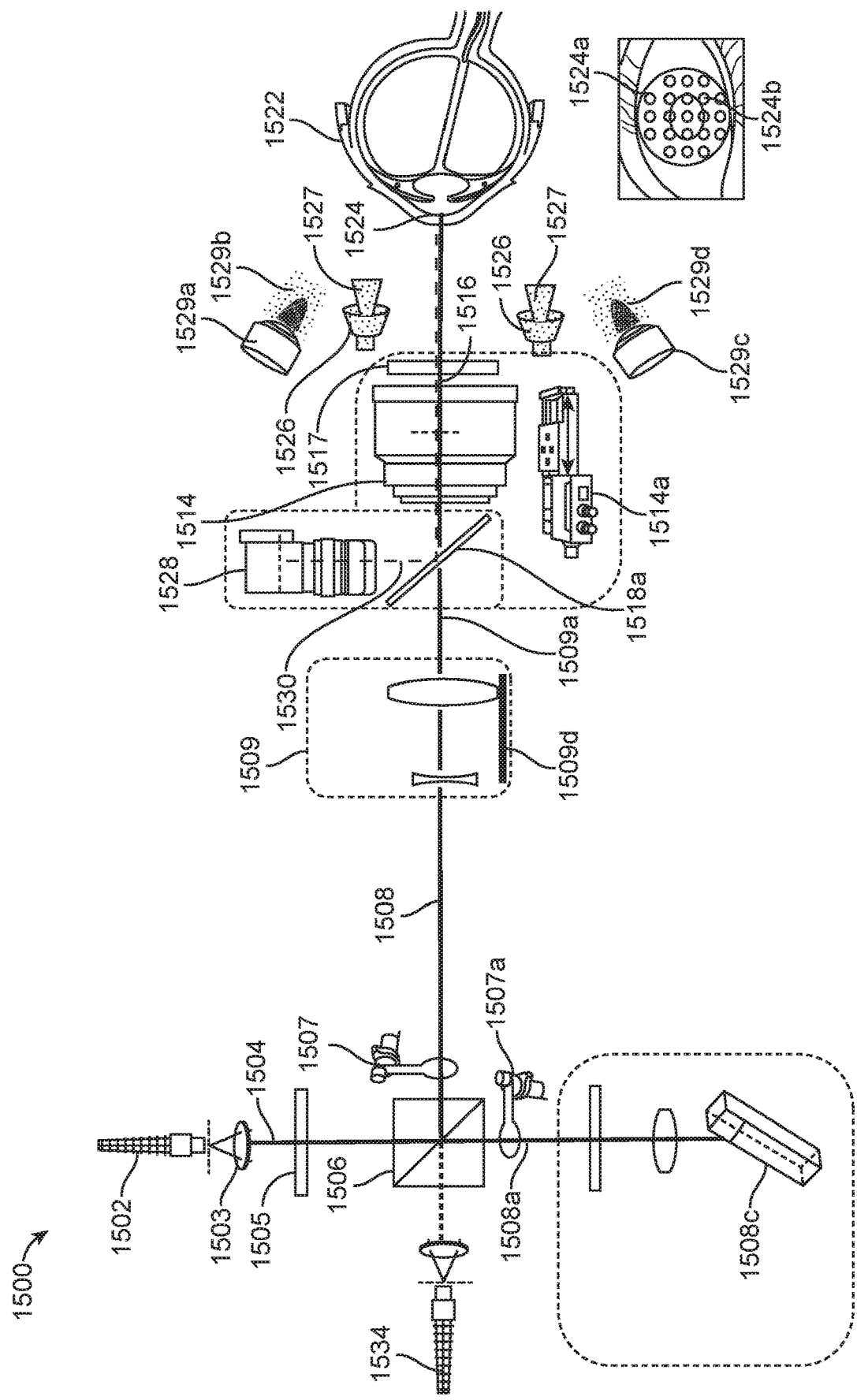
FIG. 15 depicts aspects of a system for generating an elastic stiffness map for a volume of an ophthalmic tissue of an eye of a patient, according to embodiments of the present invention.

In some cases, the patient interface system 900 depicted in FIG. 9 can incorporate one or more features of the embodiment depicted in FIG. 15. For example, FIG. 15 shows additional details regarding a reference path that is used to measure a sample containing plastic and water, that has known elastic properties. This can be used to normalize the data that is received from the actual tissue being analyzed, for example the cornea or the crystalline lens. Light can be controlled by a pair of shutters, and operation of the shutters can determine whether the laser light is going to hit the reference path, or whether the laser is going to hit the sample path. FIG. 15 also illustrates that a fixation assembly can include separate fixation mechanisms. The system can be configured to illuminate one or both fixation mechanisms, so as to control where the patient directs their gaze. In this way, it is possible to facilitate the measurement of certain areas of the eye that otherwise may be difficult to scan or measure when the patient is looking directly straightforward. Accordingly, the system can facilitate a computerized control of the orientation of the eye, by changing the gaze angle.

In some cases, optic elements such as lenses can include a coating. For example, lenses of a beam expansion assembly can include a V coating for 780, so as to provide at least 99.9% transmission efficiency for the optics (e.g. minimum scanning path % transmission), thus maximizing light transmission efficiency through imaging optics. Such coatings can be helpful when working with low-light Brillouin scattered signals. In some cases, it is desirable to remove or minimize back reflections from optical surfaces of the system. Typically, an optical element has an index change as it interfaces with the surrounding medium (in this case air), thus creating a reflection which may contaminate the signal (for example, when a beam is transmitted from glass to air and/or from air to glass). However, such reflection may lead to undesirable light entering the spectrometer and/or optical system. The Brillouin analysis techniques disclosed herein may operate under high sensitivities, where there is a substantial differential between the scanning beam that is projected toward the eye and the return beam that is being detected by the spectrometer. In some embodiments, a returning Brillouin signal that is being measured can be up to 10 orders of magnitude less than the input beam that is being used to illuminate the eye. Hence, it may be desirable to separate and filter the returning beam (weaker) from the input beam (stronger), thus providing an improved dynamic range for the signal to noise ratio. Such filtration can be enhanced by using polarization, wavelength, signal processing, or other spatial filtering techniques.

In some embodiments, the Brillouin spectrometer assembly operates in a light starved regime, measuring or detecting very few photons (e.g. on the order of hundreds of photons), so it can be important to minimize light loss as much as possible through reflections from optical surfaces, and such photons can also be potential sources of noise. In this sense, transmission losses and reflections can contribute to noise in the system.

So if a design has many optical surfaces in it, that increases the frequency of potential contamination of the signal, and signal transmission losses. So, it is advantageous to have a simple optical system. Hence, it is possible to optimize the coatings on the optical surfaces, to as to achieve a desired transmission performance.

According to some embodiments, it is possible to tilt or orient the optics so as to minimize or isolate reflections from the surface of the optics, and improve the quality of the light that enters the spatial filter or fiber of the Brillouin spectrometer assembly. In some cases, a quarter wave plate filter can be placed between two optics so as to provide filtering. In some cases, a patient interface system may not include a quarter wave plate filter. In some cases, it may be desirable to place a quarter wave plate filter further downstream along the beam path, at a location that is closer toward the eye. In some embodiments, a patient interface system may include a spectrometer modification that operates to enhance the filtration of the carrier wave, such that back reflections are less disruptive to the Brillouin signal analysis.

According to some embodiments, filtering can be based on the extinction ratio that is associated with the beam splitter. Typically, polarization based optics have an extinction ratio (ER) or extinction efficiency, which can relate to how many of the undesired photons they will let through. This is typically specified in dB. A high efficient PBS is usually at least 50 dB or 100,000:1.

Figure 10:
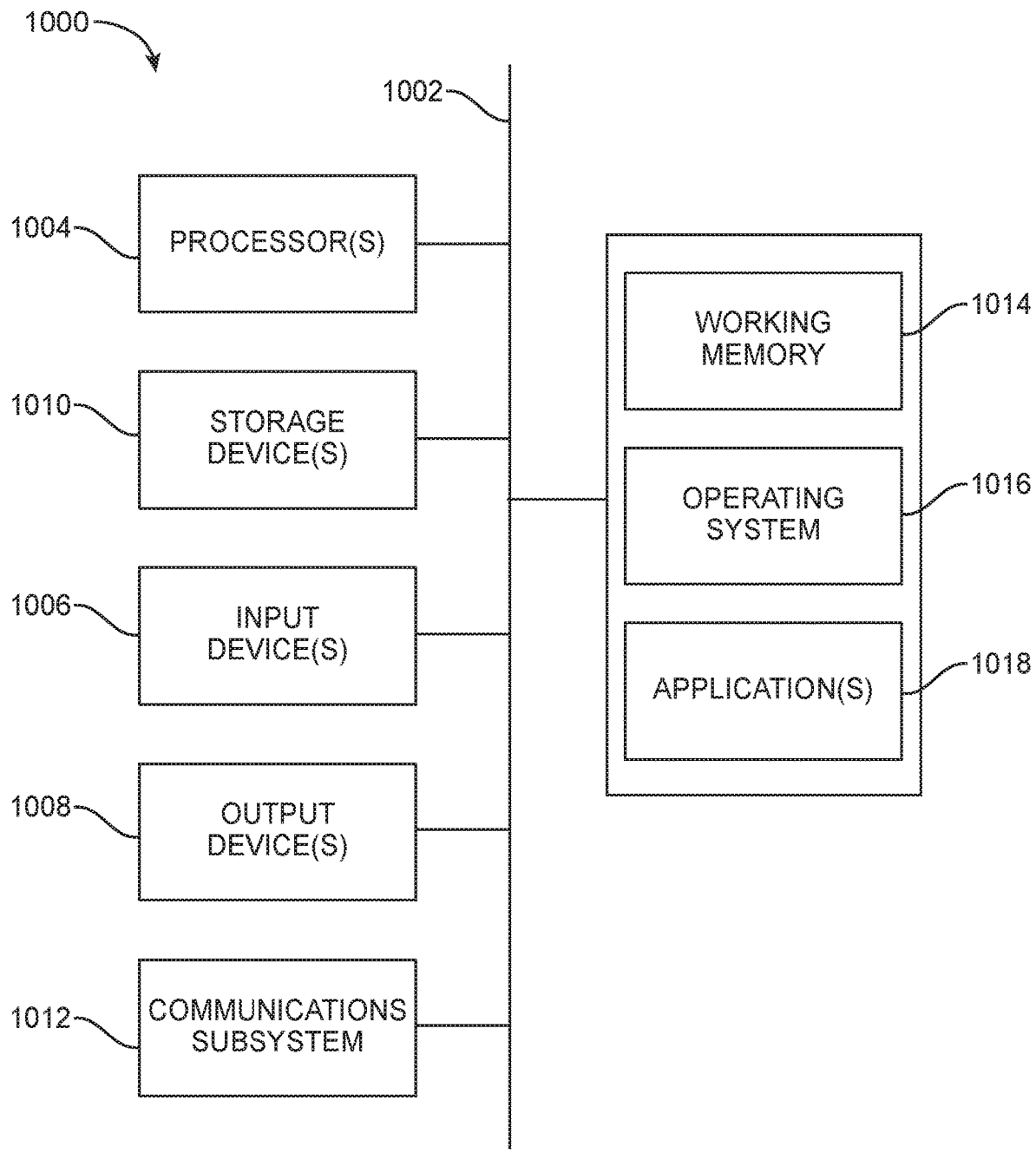
FIG. 10 depicts aspects of a computer system for use in a scanning, imaging, or mapping system, according to embodiments of the present invention.

FIG. 10 depicts aspects of an exemplary computer system or device 1000 configured for use with any of the scanning, imaging, and/or mapping systems disclosed herein, according to embodiments of the present invention. An example of a computer system or device 1000 may include an enterprise server, blade server, desktop computer, laptop computer, tablet computer, personal data assistant, smartphone, any combination thereof, and/or any other type of machine configured for performing calculations. Any computing devices encompassed by embodiments of the present invention may be wholly or at least partially configured to exhibit features similar to the computer system 1000.

The computer system 1000 of FIG. 10 is shown comprising hardware elements that may be electrically coupled via a bus 1002 (or may otherwise be in communication, as appropriate). The hardware elements may include a processing unit with one or more processors 1004, including without limitation one or more general-purpose processors and/or one or more special-purpose processors (such as digital signal processing chips, graphics acceleration processors, and/or the like); one or more input devices 1006, which may include without limitation a remote control, a mouse, a keyboard, and/or the like; and one or more output devices 1008, which may include without limitation a presentation device (e.g., controller screen), a printer, and/or the like.

The computer system 1000 may further include (and/or be in communication with) one or more non-transitory storage devices 1010, which may comprise, without limitation, local and/or network accessible storage, and/or may include, without limitation, a disk drive, a drive array, an optical storage device, a solid-state storage device, such as a random access memory, and/or a read-only memory, which may be programmable, flash-updateable, and/or the like. Such storage devices may be configured to implement any appropriate data stores, including without limitation, various file systems, database structures, and/or the like.

The computer system 1000 can also include a communications subsystem 1012, which may include without limitation a modem, a network card (wireless and/or wired), an infrared communication device, a wireless communication device and/or a chipset such as a Bluetooth device, 802.11 device, WiFi device, WiMax device, cellular communication facilities such as GSM (Global System for Mobile Communications), W-CDMA (Wideband Code Division Multiple Access), LTE (Long Term Evolution), and the like. The communications subsystem 1012 may permit data to be exchanged with a network (such as the network described below, to name one example), other computer systems, controllers, and/or any other devices described herein. In many embodiments, the computer system 1000 can further comprise a working memory 1014, which may include a random access memory and/or a read-only memory device, as described above.

The computer system 1000 also can comprise software elements, shown as being currently located within the working memory 1014, including an operating system 1016, device drivers, executable libraries, and/or other code, such as one or more application programs 1018, which may comprise computer programs provided by various embodiments, and/or may be designed to implement methods, and/or configure systems, provided by other embodiments, as described herein. By way of example, one or more procedures described with respect to the method(s) discussed herein, and/or system components might be implemented as code and/or instructions executable by a computer (and/or a processor within a computer); in an aspect, then, such code and/or instructions may be used to configure and/or adapt a general purpose computer (or other device) to perform one or more operations in accordance with the described methods.

A set of these instructions and/or code can be stored on a non-transitory computer-readable storage medium, such as the storage device(s) 1010 described above. In some cases, the storage medium might be incorporated within a computer system, such as computer system 1000. In other embodiments, the storage medium might be separate from a computer system (e.g., a removable medium, such as flash memory), and/or provided in an installation package, such that the storage medium may be used to program, configure, and/or adapt a general purpose computer with the instructions/code stored thereon. These instructions might take the form of executable code, which is executable by the computer system 1000 and/or might take the form of source and/or installable code, which, upon compilation and/or installation on the computer system 1000 (e.g., using any of a variety of generally available compilers, installation programs, compression/decompression utilities, and the like), then takes the form of executable code.

It is apparent that substantial variations may be made in accordance with specific requirements. For example, customized hardware might also be used, and/or particular elements might be implemented in hardware, software (including portable software, such as applets, and the like), or both. Further, connection to other computing devices such as network input/output devices may be employed.

As mentioned elsewhere herein, in one aspect, some embodiments may employ a computer system (such as the computer system 1000) to perform methods in accordance with various embodiments of the disclosure. According to a set of embodiments, some or all of the procedures of such methods are performed by the computer system 1000 in response to processor 1004 executing one or more sequences of one or more instructions (which might be incorporated into the operating system 1016 and/or other code, such as an application program 1018) contained in the working memory 1014. Such instructions may be read into the working memory 1014 from another computer-readable medium, such as one or more of the storage device(s) 1010. Merely by way of example, execution of the sequences of instructions contained in the working memory 1014 may cause the processor(s) 1004 to perform one or more procedures of the methods described herein.

The terms "machine-readable medium" and "computer-readable medium," as used herein, can refer to any non-transitory medium that participates in providing data that causes a machine to operate in a specific fashion. In an embodiment implemented using the computer system 1000, various computer-readable media might be involved in providing instructions/code to processor(s) 1004 for execution and/or might be used to store and/or carry such instructions/code. In many implementations, a computer-readable medium is a physical and/or tangible storage medium. Such a medium may take the form of a non-volatile media or volatile media. Non-volatile media may include, for example, optical and/or magnetic disks, such as the storage device(s) 1010. Volatile media may include, without limitation, dynamic memory, such as the working memory 1014.

Exemplary forms of physical and/or tangible computer-readable media may include a floppy disk, a flexible disk, hard disk, magnetic tape, or any other magnetic medium, a compact disc, any other optical medium, ROM, RAM, and the like, any other memory chip or cartridge, or any other medium from which a computer may read instructions and/or code. Various forms of computer-readable media may be involved in carrying one or more sequences of one or more instructions to the processor(s) 1004 for execution. By way of example, the instructions may initially be carried on a magnetic disk and/or optical disc of a remote computer. A remote computer might load the instructions into its dynamic memory and send the instructions as signals over a transmission medium to be received and/or executed by the computer system 1000.

The communications subsystem 1012 (and/or components thereof) generally can receive signals, and the bus 1002 then can carry the signals (and/or the data, instructions, and the like, carried by the signals) to the working memory 1014, from which the processor(s) 1004 retrieves and executes the instructions. The instructions received by the working memory 1014 may optionally be stored on a non-transitory storage device 1010 either before or after execution by the processor(s) 1004.

It should further be understood that the components of computer system 1000 can be distributed across a network. For example, some processing may be performed in one location using a first processor while other processing may be performed by another processor remote from the first processor. Other components of computer system 1000 may be similarly distributed. As such, computer system 700 may be interpreted as a distributed computing system that performs processing in multiple locations. In some instances, computer system 1000 may be interpreted as a single computing device, such as a distinct laptop, desktop computer, or the like, depending on the context.

A processor may be a hardware processor such as a central processing unit (CPU), a graphic processing unit (GPU), or a general-purpose processing unit. A processor can be any suitable integrated circuits, such as computing platforms or microprocessors, logic devices and the like. Although the disclosure is described with reference to a processor, other types of integrated circuits and logic devices are also applicable. The processors or machines may not be limited by the data operation capabilities. The processors or machines may perform 512 bit, 256 bit, 128 bit, 64 bit, 32 bit, or 16 bit data operations.

Each of the calculations or operations discussed herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described herein. All features of the described systems are applicable to the described methods mutatis mutandis, and vice versa. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like. While the exemplary embodiments have been described in some detail, by way of example and for clarity of understanding, those of skill in the art will recognize that a variety of modification, adaptations, and changes may be employed.

Any of the patient interface system or method embodiments disclosed herein can incorporate one or more features described in U.S. Patent Publication Numbers US 2007/0233056, US 2012/0302862, US 2016/0151202, US 2017/0254749, and US 2017/0360297, in U.S. Pat. Nos. 7,898,656, 8,115,919, 9,777,053, and/or in G. Scarcelli and S. H. Yun, "In vivo Brillouin optical microscopy of the human eye," Opt. Express 20(8), 9197-9202 (2012), the contents of each of which are incorporated herein by reference for all purposes.

FIG. 11 depicts aspects of a patient interface system 1100 according to embodiments of the present invention. As discussed elsewhere herein, system 1100 can be used to generate an elastic stiffness map for a volume of an ophthalmic tissue of an eye of a patient. As shown here, system 1100 includes a laser assembly or light source 1102 (e.g. collimated fiber input, 780 nm) and lens 1103 (e.g. 4 mm beam expansion) that generate a collimated diagnostic laser beam 1104, a polarizing beam splitter 1106 that reflects a portion 1108 of the collimated diagnostic laser beam 1104, and the reflected portion 1108 is then transmitted to a laser beam expansion assembly 1109, which converts beam 1108 to an expanded beam 1109a. Optionally, a shutter mechanism 1107 having one or more shutters can be disposed between the polarizing beam splitter 1106 and the laser beam expansion assembly 1109. In some cases, light source 1102 can be a device that produces electromagnetic radiation characterized by one or more wavelengths or one or more frequencies. According to some embodiments, the electromagnetic radiation beam expansion assembly 1109 expands a collimated scanning diagnostic laser beam from a first diameter to a second diameter that is larger than the first diameter. The laser beam expansion assembly 1109 may include multiple lenses (e.g. lenses 1109b, 1109c). In some cases, the laser beam expansion assembly 1109 includes lenses disposed in a Galilean configuration, with a negative lens followed by a positive lens. In some case, the laser beam expansion assembly 1109 can be provided as a Galilean type beam expander. In some cases, the collimated scanning diagnostic laser beam has a linear polarization orientation. In turn, expanded beam 1109a is transmitted to an optical scanning assembly 1110.

As shown here, the polarizing beam splitter 1106 can be positioned before the laser beam expansion assembly 1109. The polarizing beam splitter 1106 can operate to split the diagnostic laser beam 1104 into a scanning portion (1108) and a non-scanning portion (1108a). In some cases, the beam splitter 1106 allows for the measurement (e.g. concurrent) of a reference sample 1108c. In some cases, the beam splitter 1106 operates to provide an additional amount of filtration of back reflections of light. In some cases, the polarizing beam splitter 1106 transmits light at a 90 degrees orientation and on the return path the light goes to 90 degrees. According to some embodiments, the beam splitter 1106 works in conjunction with the quarter wave plate 1117. For example, after two passes through the waveplate 1117, the returning light can be passed back to the spectrometer assembly 1134, and light that has only passed once (e.g. reflections from lenses) will be excluded. In some cases, when the light first enters the quarter wave plate 1117, some amount can be portioned to a calibrated reference sample. A half-waveplate element 1105 may also be positioned after the laser source which sets up a ratio of linearly polarized s and p. This can control the light split through the polarizing beam splitter (PBS). According to some embodiments, a Brillouin signal from a sample can be used as a built in reference to the instrument for accurate calculation of the Brillouin signal. There may also be a quarter waveplate ($\lambda/4$) 1108d on the reference path to provide an isolated signal that will make its way back to the spectrometer.

According to some embodiments, the optical scanning assembly 1110 operates to adjust or redirect a beam path of the expanded collimated scanning diagnostic laser beam. In some cases, the patient interface system 1100 may not include the polarizing beam splitter 1106. The optical scanning assembly 1110 operates to redirect a beam path of the reflected portion 1108 of the collimated scanning diagnostic laser beam. The redirected reflected portion 1112 of the collimated scanning diagnostic laser beam is then transmitted to an objective lens assembly 1114, which operates to focus the redirected portion 1112 of the collimated scanning diagnostic laser beam to produce a focused scanning diagnostic laser beam 1116.

According to some embodiments, the objective lens assembly 1114 operates to focus the expanded collimated scanning diagnostic laser beam 1112 to produce a focused scanning diagnostic laser beam 1116 having a beam waist or focused spot. In some cases, objective lens assembly 1114 includes a waveplate 1117 and an objective lens 1114*b*. In some cases, objective lens 1114*b* is a 0.125 NA objective lens. In some cases, the objective lens assembly 1114 operates to adjust a scan position of the beam waist or focused spot. In some cases, the objective lens assembly 1114 includes a motorized stage 1114*a* that allows the objective lens assembly to travel toward and away from the optical scanning assembly 1110. In some cases, the optical scanning assembly 1110 includes a motorized stage that allows the optical scanning assembly to travel toward and away from the objective lens assembly 1114. In some cases, the optical scanning assembly and the objective lens assembly include or are disposed on respective motorized stages, or are disposed on a common motorized stage, so that the optical scanning assembly and the objective lens assembly can move in tandem.

As shown here, system 1100 may include a quarter-wave plate assembly 1117. In some embodiments, the quarter-wave plate assembly 1117 operates to convert the focused scanning diagnostic laser beam 1116 from a linear polarization orientation to a circular polarization orientation. In some embodiments, the quarter-wave plate assembly 1117 operates to provide a 45 degree rotation to the focused scanning diagnostic laser beam 1116. In some cases, the quarter-wave plate assembly 1117 operates to convert the focused scanning diagnostic laser beam 1116 from p-polarized light to s-polarized light. In a double pass embodiment, s-polarized light can be converted to p-polarized light (e.g. whatever is orthogonal to the input wave). In some cases, the quarter-wave plate assembly 1117 operates to convert the focused scanning diagnostic laser beam 1116 from s-polarized light to p-polarized light. The quarter-wave plate assembly 1117 can be placed along the beam path, for example between the objective lens assembly 1114 and the shortpass dichroic filter 1118*a*. In some embodiments, the quarter-wave plate assembly 1117 can be placed upstream of the objective lens assembly 1114 or downstream of the shortpass dichroic filter 1118*a*. In some cases, the quarter-wave plate assembly 1117 can be placed anywhere as desired, between the sample (e.g. eye) and the PBS. In some cases, the quarter wave plate assembly operates to isolate out back reflections from system, for example as described elsewhere herein. In some case, the quarter-wave plate is configured to perform the classical operation of an optical isolator.

The focused scanning diagnostic laser beam 1116 is reflected by a shortpass dichroic filter 1118*a*, and the reflected focused portion is transmitted toward an eye 1122 of the patient. In some cases, the focused scanning diagnostic laser beam has a circular polarization orientation and is reflected by the shortpass dichroic filter 1118*a* toward the eye 1122. In some cases, isolation and redirecting are the core functions performed on the beam. In some cases, the returning beam is transformed back to linear polarization again when it passes back through the waveplate.

According to some embodiments, a dichroic filter can operate as a beam splitter that splits light based on wavelength or color, rather than splitting light based on power. In some cases, a dichroic filter will transmit light within a certain wavelength band or range and/or reflect light within a certain wavelength band or range. As shown here, dichroic filters can operate to fold together, or to separate out, different wavelengths of light (e.g. into a common optical path).

In some case, the dichroic filters can operate to fold together fixation light 1129*a*, imaging light 1130, and scanning diagnostic light 1120, into a common optical path (e.g. between the shortpass dichroic filter 1118*a* and the eye 1122). Similarly, a dichroic can operate to peel apart light from a common path into separate optical paths, for example imaging light 1130 and returned scanning diagnostic light travel along a common optical path from the eye to the shortpass dichroic filter 1118*a*, and then the imaging light is transmitted through the shortpass dichroic filter 1118*a* and the returned scanning diagnostic light is reflected by the shortpass dichroic filter 1118*a*.

The reflected focused scanning diagnostic laser beam 1120 has focused spot 1124, and operation of the optical scanning assembly 1110 or the objective lens assembly 1114, or the combined operation of the optical scanning assembly 1110 and the objective lens assembly 1114, can adjust a scan position of the focused spot 1124 to various discrete locations (e.g. 1124*a*, 1124*b*) on or within one or more tissues of the eye 1122.

The patient interface system 1100 also includes an eye camera assembly 1128 that receives imaging light 1130 from the eye (which optionally may have passed through a shortpass dichroic filter 1118*a* and a longpass dichroic filter 1118*b* of a beam control assembly) and that generates electrical signals in response to the received imaging light 1130. The imaging light 1130 can provide registration information regarding the position and/or orientation of the eye. In some cases, this registration information can be used (e.g. by a processing assembly, such as the processing assembly described in FIG. 5) to provide locate elasticity measurement data obtained by the Brillouin spectrometer assembly 1134 to particular points of the eye. In some cases, the imaging light 1130 can help to provide feedback, which may be continuous feedback, to the processing assembly. The imaging light 1130 can be processed to provide information regarding a center coordinate of the eye, a central reference of the eye, or more generically, a reference coordinate on the eye, which can be registered to the biomechanical data. Such a reference coordinate can be determined by processing the imaging data.

In some cases, the processing assembly can operate to generate two images, specifically an image of the eye and a Brillouin heat map (e.g. stiffness values at discrete points), and to accurately superimpose those images on top of each other using registration. In this way, the mechanical information is relevant in the physical space. In some cases, the processing assembly does not perform a superimposition. Rather, a camera is used to provide a reference point to begin a scan pattern, and thereafter a scan is performed according to the pattern, so as to generate the stiffness map. The map can indicate whether there are any abnormal spots or points of interest on the eye, without providing the exact location on the eye of the abnormal spots or points of interest. In some cases, a camera is not used to provide a reference point to begin a scan pattern. For example, the physician or operate could manually inspect the person's eye, and then aim the beam, without using a camera. In some cases, it is possible to illuminate the person's eye using a certain wattage, observe a reflection off the person's eye, and determine that the alignment of the scanning beam and the eye is sufficient.

Hence, input techniques for aiming the diagnostic beam can include using a camera image or data, manually aiming the beam, or using feedback from the Brillouin spectrometer. For example, data obtained by the spectrometer can provide an indication of whether the system is in focus. The Brillouin spectrometer can be used to differentiate spectral shifts that are characteristic of different tissues. In some cases, as the focused spot is scanned in the z depth direction, it is possible to detect fundamentally different frequency shifts (or different information) as the focused spot goes through different layers (e.g. going from the air, to the cornea surface, to the aqueous humor, to the crystalline lens, and so on) which can correspond to different elastic properties (e.g. elastic modulus). In this sense, the Brillouin approach can provide aspects of an imaging modality. Hence, it may be possible to determine where the focused spot is located (e.g. along a z-axis), by observing or analyzing the spectrometer image. In some cases, it is possible to align or position the patient interface system, by observing or using a reflection off of a person's eye, then moving the system into focus based on feedback from the spectrometer camera, and then initiating the scan. In some cases, the camera is parfocal with the laser beam, and the focus of the eye can also be used.

In some embodiments, system 1100 also includes a fixation assembly 1129 that provides the eye with a gaze target. In some cases, fixation light 1129a is generated by the fixation assembly 1129, travels from the fixation assembly 1129, is reflected by the longpass dichroic filter 1118b, travels through the shortpass dichroic filter 1118a, and to the eye 1122. According to some embodiments, the fixation assembly 1129 includes a matrix of light-emitting diode (LEDs).

The patient interface system 1100 can further include a Brillouin spectrometer assembly 1134 having a Brillouin spectrometer and a spatial filter that is parfocal with the focused spot 1124 (e.g. in a conjugate focal plane). The Brillouin spectrometer can generate Brillouin signals as the focused spot 1124 is scanned to discrete locations throughout a volume or plane thickness of ophthalmic tissue of the eye 1122. Brillouin scattered light from the focused spot at the discrete locations is returned to the spatial filter. According to some embodiments, the spatial filter operates as an input for the Brillouin spectrometer, and is in conjugate alignment with the focused spot 1124 or beam waist of the focused scanning diagnostic laser beam, and the Brillouin spectrometer can generate Brillouin signals as the focused spot 1124 or beam waist of the focused scanning diagnostic beam is scanned to discrete locations throughout the volume of the ophthalmic tissue of the eye 1122. In some cases, the spatial filter can operate to exclude information associated with out of focus focal planes, and include information associated with the focal plane of interest. The filter can provide sensitivity to locations where the focused spot is positioned, and little or no sensitivity to extraneous locations. In some cases, a spatial filter can be provided without using a fiber. In some cases, the spatial filter can operate to prime the incoming light, which is then measured by the spectrometer, which in turn generates the spectrum (e.g. Brillouin) signals.

By using a fiber input, it is possible to provide modularity to the system, whereby the patient scanning interface can be decoupled and coupled with the spectrometer via the optical fiber. Such modularity can provide enhanced testing and serviceability advantages. For example, the optical fiber could be uncoupled from one patient interface system, and coupled with another patient interface system. Hence, if one patient interface were to malfunction, it could be replaced with another patient interface. This could also allow patient interfaces to be tested as modules, which can improve manufacturability.

From an optical standpoint, a fiber can provide a highly functional pinhole. In some cases, such embodiments can provide a separate input and output. It is possible to physically decouple with free space optics the input and output of the system. In some embodiments, the input is not separated from the output. For example, the same light can be coupled back into the same input path and optionally the beam could be redirected to the spectrometer after traveling back down the fiber.

According to some embodiments, an optical output out of a single mode fiber can provide or approach a perfect Gaussian distribution, which has desirable beam shape and optical quality characteristics, and can be well suited for use with sensitive optical elements. As such, this feature can help optimize the optical performance of the overall system, particularly when multiple optical elements are involved.

In some cases, a fiber can operate as a conjugate pinhole or aperture (or spatial filter) for the focus spot in the tissue that is being analyzed. The fiber can operate to provide a focal plane resolution and specificity, filtering out the out of focus light that is not of interest. In some cases, a spatial filter can be provided as a radial aperture or a circular aperture. In some cases, an aperture can have a diameter of about 1 mm aperture. In some cases, the focus of the light is aligned with the core of a fiber, whereby only that light which is properly aligned to the core of the fiber will make it into that fiber. Thereafter, that light will be propagated down the fiber. In this sense, the core of the fiber can operate as a filter, spatial mask, or pinhole aperture, whereby light coupled into the core of the fiber is propagated, and undesired light is filtered or masked out. Often, a fiber will operate in conjunction with a lens. In some embodiments, the fiber can be provided as a collimated fiber optic. In some cases, light is focused into the fiber, or into the core of the fiber, using a lens. The light can be propagated in the fiber by way of total internal reflection. Where light is not properly aligned with the fiber core, such light may not propagate down the fiber, or be coupled into that fiber.

Put another way, light that is at a different focal plane, in the tissue, will not be at the same focal plane, over at the pinhole or spatial filter side, and hence becomes filtered out. The out of focus light will not make it into the pinhole or spatial aperture, and won't be coupled into the fiber, because that light is not aligned (e.g. not at the same focal plane, confocal, or conjugate).

In some embodiments, the patient interface system 1100 can include a processing assembly (e.g. such as the processing assembly depicted in FIG. 5) in operative association with the optical scanning assembly 1110, the objective lens assembly 1114, the eye camera assembly 1128, the fixation assembly 1129, and the Brillouin spectrometer assembly 1134. The processing assembly can include a processor, an electronic storage location operatively coupled with the processor, and processor executable code stored on the electronic storage location and embodied in a tangible non-transitory computer readable medium. In some cases, the patient interface system 1100 may include peripheral embedded IO boards for digital or analog sensing and control of peripheral devices. For example, the system 1100 may include a general-purpose input/output (GPIO) embedded processor board (e.g. "Arduino-like") to set the illumination intensity, the fixation pattern, to read from photodiode, and the like. The processor executable code can include machine-readable instructions that, when executed by the processor, cause the processor to generate x,y coordinate scan control signals for the optical scanning assembly 1110. In some cases, x,y coordinate scan control signals for the optical scanning assembly 1110 can be generated based on the electrical signals generated by the eye camera assembly 1128. The processor executable code can include machine-readable instructions that, when executed by the processor, cause the processor to generate z coordinate scan control signals for the objective lens assembly 1114. In some cases, the x,y coordinate scan control signals, the z coordinate scan control signals, or both the x,y coordinate scan control signals and the z coordinate scan control signals, can be based on an image of the eye. In some cases, the x,y coordinate scan control signals, the z coordinate scan control signals, or both the x,y coordinate scan control signals and the z coordinate scan control signals, can be generated independent of an image of the eye. In some cases, the x,y coordinate scan control signals, the z coordinate scan control signals, or both the x,y coordinate scan control signals and the z coordinate scan control signals, can be generated according to a pre-defined or pre-determined scan pattern. The processor executable code can include machine-readable instructions that, when executed by the processor, cause the processor to generate an elastic stiffness map for a volume of ophthalmic tissue of the eye 1122 based on Brillouin signals. In some cases, the optical scanning assembly 1110 may include a prism pair, for example a prism pair as depicted in FIG. 3. FIG. 11 depicts a Risley prism pair 1111 with an operational range of $\theta=\pm 10°$.

As shown in FIG. 11, the eye 1122 can be at a 90 degree angle of orientation relative to the general trajectory of the scanning diagnostic beam after the scanning diagnostic beam exits the objective lens assembly 1114. In this way, the reflected focused portion 1120 of the scanning diagnostic beam and the imaging light 1130 that travels from the eye to the eye camera assembly are aligned in a colinear path. According to some embodiments, such a configuration (e.g. reflecting the beam off the shortpass dichroic filter 1118a) may produce less astigmatism (or more generally, less optical aberration) than a different configuration (e.g. scanning or transmitting the beam through the shortpass dichroic filter 1118a). This advantage may be particularly helpful for maintaining high beam quality when the scanning diagnostic beam is diffraction limited and involves a confocal focused spot. In some embodiments, the finer axial resolution spot will also minimize contaminating back-reflections from the front surface of the eye, allow for scanning of more of the eye thickness with better spatial resolution. Dichroic filters can operate to reflect or reject light having certain wavelengths, and to transmit light having certain wavelengths.

According to some embodiments, the system 1100 can include one or more illumination lamps or light devices 1126 that direct illumination light or radiation 1127 toward the eye. In some cases, an illumination device 1126 can be or include a light emitting diode (LED). In some cases, the illumination light or radiation 1127 can be infrared light. In some cases, the illumination light or radiation 1127 can be non-visible light. In some cases, the illumination light 1127 can have a wavelength value within a range from about 700 nm to about 1,000,000 nm. In some case, the illumination light 1127 can have a wavelength value of about 940 nm. According to some embodiments, the eye camera assembly 1128 is sensitive to the wavelength of the illumination light 1127 (which can also be the same as or similar to the wavelength of the imaging light 1130).

In some cases, the illumination light 1127 can have a wavelength value that is greater than a wavelength value of the diagnostic scanning light or radiation. In some cases, the diagnostic beam (e.g. 1104, 1120) has a wavelength value within a range from about 450 to about 1350 nm. In some cases, the wavelength of the scanning diagnostic beam has a value of about 780 nm. In some cases, the scanning diagnostic radiation can have a wavelength value within a range from about 450 to about 1350 nm. In some cases, the fixation light 1129a is visible light. In some cases, the fixation light 1129a is visible green light. In some cases, the fixation light 1129a has a wavelength value of about 520 to about 560 nm. According to some embodiments, the fixation assembly 1129 generates light 1129a that provides the eye with a gaze target, which can be helpful in a clinical setting or application. In some cases, a system or method can include a gaze target that is not provided by a light emitting fixation assembly.

As shown in FIG. 11, the shortpass dichroic filter 1118a can operate to reflect the incoming and returning scanning diagnostic beam, to transmit the imaging light 1130 (which can be illumination light 1127 reflected from the eye), and to transmit the fixation light 1129a. Relatedly, the longpass dichroic filter 1118b can operate to reflect the fixation light 1129a and to transmit the imaging light 1130 (which can be illumination light 1127 reflected from the eye). In some cases, instead of using a shortpass dichroic filter 1118a, it is possible to instead use a dichroic (e.g. longpass) or some other filter that reflects a certain wavelength range and passes another wavelength range.

According to some embodiments, the focused scanning diagnostic laser beam 1120 optical path and the imaging light 1130 optical path are provided as integrated colinear optical paths, as a result of the operation of one or more dichroic filters. In some cases, the respective optical paths may not be integrated in a colinear fashion. In some cases, by providing integrated colinear optical paths, it is possible to avoid or eliminate geometric distortions of the image that may otherwise be present when using an off-axis camera (even though it may be possible to achieve the same focal point for a laser, relative to the focus of the imaging camera).

In some cases, by providing integrated colinear optical paths, it is possible to more efficiently register biomechanical data to eye location and/or orientation data pertaining to a real world eye space. In some cases, it is possible to use eye tracker or camera information to register and track where those points have been scanned, relative to certain features and/or registration coordinates on the eye.

According to some embodiments, astigmatism can be incurred for the eye camera illumination or an image of the eye by transmitting through the dichroic, and a perfect 3D orthogonal orientation (e.g. of the illumination lamp 1126) can cancel out that astigmatism.

As seen here, the longpass dichroic filter 1118b operates to fold together the light 1129a from the fixation assembly 1129 and the imaging light 1130 from the eye (integrated). Embodiments of the present invention also encompass designs where the fixation light 1129a is not folded into the same path with the imaging light 1130 (unintegrated). As shown in FIG. 11, in this embodiment there may be no lens between the shortpass dichroic filter 1118a and the longpass dichroic filter 1118b.

According to some embodiments, the eye camera assembly 1128 of patient interface system 1100 can image through a path that is not the same as the laser path. In some cases, the eye camera assembly 1128 includes an eye tracker camera and an imaging lens (e.g. f=~25 mm). Patient interface system 1100 can involve a co-axial scanning laser that is reflected at 90 degrees. Lateral xy scanning can be achieved by a Risley prism scanning method. A Risley prism pair can provide an optical x,y scanning capability. In some cases, the quarter wave plate assembly 1117 can be positioned downstream of the objective lens assembly 1114 for purposes of optical isolation. According to some embodiments, there is a mechanical coupling between the eye camera assembly 1128 and the laser scanning. As discussed herein with reference to FIG. 6, embodiments of the present invention may also encompass mechanically decoupled systems. Patient interface system 1100 can provide a diffraction limited focused spot over an entire focal volume. It is understood that an eye or any other sample with aberrations may make it so the spot is not diffraction limited.

In some cases, the patient interface system 1100 depicted in FIG. 11 can incorporate one or more features of the embodiment depicted in FIG. 5. FIG. 11 shows additional details regarding a reference path that is used to measure a sample containing plastic and water, that has known elastic properties. This can be used to normalize the data that is received from the actual tissue being analyzed, for example the cornea or the crystalline lens. Light can be controlled by a pair of shutters 1107, 1107a, and operation of the shutters can determine whether the laser light is going to hit the reference path, or whether the laser is going to hit the sample path. FIG. 11 also illustrates that a fixation assembly can include a grid of light points or light emitting diodes. The system can be configured to illuminate one or more points of the grid, so as to control where the patient directs their gaze. In this way, it is possible to facilitate the measurement of certain areas of the eye that otherwise may be difficult to scan or measure when the patient is looking directly straightforward. Accordingly, the system can facilitate a computerized control of the orientation of the eye, by changing the gaze angle. Performance graphs for the dichroic filters are illustrated, indicating transmission percentage (y axis) and wavelength (x axis). According to some embodiments, the dashed line boxes are provided to illustrate various submodules that are isolated based on their function. In some cases, multiple submodules with different functions can cooperatively work together as a system to achieve the overall function.

FIG. 12 depicts aspects of a patient interface system 1200 according to embodiments of the present invention. As discussed elsewhere herein, system 1200 can be used to generate an elastic stiffness map for a volume of an ophthalmic tissue of an eye of a patient. As shown here, system 1200 includes a laser assembly or light source 1202 that generates a collimated diagnostic laser beam 1204 (e.g. by operation of lens 1203 (e.g. 4 mm beam expansion)), a polarizing beam splitter 1206 that reflects a portion 1208 of the collimated diagnostic laser beam 1204, and the reflected portion 1208 is then transmitted to a laser beam expansion assembly 1209, which converts beam 1208 to an expanded beam 609a. In some cases, beam 1204 may pass through a wave plate 1205, such as a λ/2 wave plate, prior to reaching the splitter 1206. In some cases, light source 1202 can be a device that produces electromagnetic radiation characterized by one or more wavelengths or one or more frequencies. According to some embodiments, the electromagnetic radiation beam expansion assembly 1209 expands a collimated scanning diagnostic laser beam from a first diameter to a second diameter that is larger than the first diameter. The laser beam expansion assembly 1209 may include multiple lenses. In some cases, the laser beam expansion assembly 1209 includes lenses disposed in a Galilean configuration, with a negative lens followed by a positive lens. In some case, the laser beam expansion assembly 1209 can be provided as a Galilean type beam expander. In some cases, the collimated scanning diagnostic laser beam has a linear polarization orientation. In turn, expanded beam 1209a is transmitted to an objective lens assembly 1214.

As shown here, the polarizing beam splitter 1206 can be positioned before the laser beam expansion assembly 1209. The polarizing beam splitter 1206 can operate to split the diagnostic laser beam 1204 into a scanning portion 1208 and a non-scanning portion 1208a. Optionally, a shutter mechanism 1207 having one or more shutters can be disposed between the polarizing beam splitter 1206 and the laser beam expansion assembly 1209. In some cases, the beam splitter 1206 allows for the measurement (e.g. concurrent) of a reference sample 1208c. In some cases, the beam splitter 1206 operates to provide an additional amount of filtration of back reflections of light. In some cases, the polarizing beam splitter 1206 transmits light at a 90 degrees orientation and on the return path the light goes to 90 degrees According to some embodiments, the beam splitter 1206 works in conjunction with the quarter wave plate 1217. For example, after two passes through the waveplate 1217, the returning light can be passed back to the spectrometer assembly 1234, and light that has only passed once (e.g. reflections from lenses) will be excluded. In some cases, when the light first enters the quarter wave plate 1217, some amount can be portioned to a calibrated reference sample. A half-waveplate element 1205 may also be positioned after the laser source which sets up a ratio of linearly polarized s and p. This can control the light split through the polarizing beam splitter (PBS). According to some embodiments, a Brillouin signal from a sample can be used as a built in reference to the instrument for accurate calculation of the Brillouin signal. There may also be a quarter waveplate on the reference path to provide an isolated signal that will make its way back to the spectrometer.

According to some embodiments, the beam expansion assembly 1209 operates to adjust or redirect a beam path of the expanded collimated scanning diagnostic laser beam. In some cases, the patient interface system 1200 may not include the polarizing beam splitter 1206. The beam expansion assembly 1209 operates to redirect a beam path of the reflected portion 1208 of the collimated scanning diagnostic laser beam. The redirected reflected portion 1209a of the collimated scanning diagnostic laser beam is then transmitted to an objective lens assembly 1214, which operates to focus the redirected portion 1209a of the collimated scanning diagnostic laser beam to produce a focused scanning diagnostic laser beam 1216.

According to some embodiments, the objective lens assembly 1214 operates to focus the expanded collimated scanning diagnostic laser beam 1209a to produce a focused scanning diagnostic laser beam 1216 having a beam waist or focused spot. In some cases, the objective lens assembly 1214 operates to adjust a scan position of the beam waist or focused spot. In some cases, the objective lens assembly 1214 includes a motorized stage that allows the objective lens assembly to travel toward and away from the beam expansion assembly 609. In some cases, the beam expansion assembly 609 includes a motorized stage 1214a that allows the optical scanning assembly to travel toward and away from the objective lens assembly 1214, and/or in a plane perpendicular to the beam path. In some cases, movement of the beam expander or the beam expander and the objective together along the optical axis (e.g. in optical z) can achieve an axial translation along the z axis of the interrogating beam focus. In some cases, the beam expansion assembly and the objective lens assembly include or are disposed on respective motorized stages, or are disposed on a common motorized stage, so that the beam expansion assembly and the objective lens assembly can move in tandem.

As shown here, system 1200 may include a quarter-wave plate assembly 1217. In some embodiments, the quarter-wave plate assembly 1217 operates to convert the focused scanning diagnostic laser beam 1216 from a linear polarization orientation to a circular polarization orientation. In some embodiments, the quarter-wave plate assembly 1217 operates to provide a 45 degree rotation to the focused scanning diagnostic laser beam 1216. In some cases, the quarter-wave plate assembly 1217 operates to convert the focused scanning diagnostic laser beam 1216 from p-polarized light to s-polarized light. In some cases, the quarter-wave plate assembly 1217 operates to convert the focused scanning diagnostic laser beam 1216 from s-polarized light to p-polarized light. The quarter-wave plate assembly 1217 can be placed along the beam path, for example between the objective lens assembly 1214 and the shortpass dichroic filter 1218*a*. In some embodiments, the quarter-wave plate assembly 1217 can be placed upstream of the objective lens assembly 1214 or downstream of the shortpass dichroic filter 1218*a*. In some cases, the closer the quarter-wave plate is to the sample, the more back-reflections can be filtered out by the PBS. In exemplary embodiments, the quarter-wave plate is the last element in the objective lens followed by the dichroic in front of the eye.

The focused scanning diagnostic laser beam 1216 is reflected by a shortpass dichroic filter 1218*a*, and the reflected focused portion 1220 is transmitted toward an eye 1222 of the patient. In some cases, the focused scanning diagnostic laser beam has a circular polarization orientation and is reflected by the shortpass dichroic filter 1218*a* toward the eye 1222.

According to some embodiments, a dichroic filter can operate as a beam splitter that splits light based on wavelength or color, rather than splitting light based on power. In some cases, a dichroic filter will transmit light within a certain wavelength band or range and/or reflect light within a certain wavelength band or range. As shown here, dichroic filters can operate to fold together, or to separate out, different wavelengths of light (e.g. into a common optical path).

In some case, the dichroic filters can operate to fold together fixation light 1229*a*, imaging light 630, and scanning diagnostic light 1220, into a common optical path (e.g. between the shortpass dichroic filter 1218*a* and the eye 1222). Similarly, a dichroic can operate to split or redirect light from a common path into separate optical paths, for example imaging light 1230 and returned scanning diagnostic light travel along a common optical path from the eye to the shortpass dichroic filter 1218*a*, and then the imaging light is transmitted through the shortpass dichroic filter 1218*a* and the returned scanning diagnostic light is reflected by the shortpass dichroic filter 1218*a*.

The reflected focused scanning diagnostic laser beam 1220 has focused spot 1224, and operation of the beam expansion assembly 1209 or the objective lens assembly 1214, or the combined operation of the beam expansion assembly 1209 and the objective lens assembly 1214, can adjust a scan position of the focused spot 1224 to various discrete locations (e.g. 1224*a*, 1224*b*) on or within one or more tissues of the eye 1222. In some instances, the scanning technique provided by system 1200 can involve a mechanical xy scanning approach.

The patient interface system 1200 also includes an eye camera assembly 1228 that receives imaging light 1230 from the eye (which optionally may have passed through a shortpass dichroic filter 1218*a* and a longpass dichroic filter 1218*b* of a beam control assembly) and that generates electrical signals in response to the received imaging light 1230. The imaging light 1230 can provide registration information regarding the position and/or orientation of the eye. In some cases, this registration information can be used (e.g. by a processing assembly, such as the processing assembly which is depicted in FIG. 6) to provide locate elasticity measurement data obtained by the Brillouin spectrometer assembly 1234 to particular points of the eye. In some cases, the imaging light 1230 can help to provide feedback, which may be continuous feedback, to the processing assembly. The imaging light 1230 can be processed to provide information regarding a center coordinate of the eye, a central reference of the eye, or more generically, a reference coordinate on the eye, which can be registered to the biomechanical data. Such a reference coordinate can be determined by processing the imaging data.

In some cases, the processing assembly can operate to generate two images, specifically an image of the eye and a Brillouin heat map (e.g. stiffness values at discrete points), and to accurately superimpose those images on top of each other using registration. In this way, the mechanical information is relevant in the physical space. In some cases, the processing assembly does not perform a superimposition. Rather, a camera is used to provide a reference point to begin a scan pattern, and thereafter a scan is performed according to the pattern, so as to generate the stiffness map. The map can indicate whether there are any abnormal spots or points of interest on the eye, without providing the exact location on the eye of the abnormal spots or points of interest. In some cases, a camera is not used to provide a reference point to begin a scan pattern. For example, the physician or operate could manually inspect the person's eye, and then aim the beam, without using a camera. In some cases, it is possible to illuminate the person's eye using a certain wattage, observe a reflection off the person's eye, and determine that the alignment of the scanning beam relative to the patient's eye is sufficient.

Hence, input techniques for aiming the diagnostic beam can include using a camera image or data, manually aiming the beam, or using feedback from the Brillouin spectrometer. For example, data obtained by the spectrometer can provide an indication of whether the system is in focus. The Brillouin spectrometer can be used to differentiate spectral shifts that are characteristic of different tissues. In some cases, as the focused spot is scanned in the z depth direction, it is possible to detect fundamentally different frequency shifts (or different information) as the focused spot goes through different layers (e.g. going from the air, to the cornea surface, to the aqueous humor, to the crystalline lens, and so on) which can correspond to different elastic properties (e.g. elastic modulus). In this sense, the Brillouin approach can provide aspects of an imaging modality. In some embodiments, Brillouin spectroscopy is used an imaging modality because multiple pixels of information are put together to generate a map. This map can be considered to be an image (e.g. more than 1 pixel), and accordingly, Brillouin spectroscopy can be considered to be an imaging modality. Hence, it may be possible to determine where the focused spot is located, by observing or analyzing the spectrometer image. In some cases, it is possible to align or position the patient interface system, by observing or using a reflection off of a person's eye, then moving the system into focus based on feedback from the spectrometer camera, and then initiating the scan.

In some embodiments, system 1200 also includes a fixation assembly 1229 that provides the eye with a gaze target. In some cases, fixation light 1229*a* is generated by the fixation assembly 1229, travels from the fixation assembly 1229, is reflected by the longpass dichroic filter 1218*b*, travels through the shortpass dichroic filter 1218*a*, and to the eye 1222. According to some embodiments, the fixation assembly 1229 includes a matrix of light-emitting diode (LEDs).

The patient interface system 1200 can further include a Brillouin spectrometer assembly 1234 having a Brillouin spectrometer and a spatial filter that is parfocal with the focused spot 1224 (e.g. in a conjugate focal plane). The Brillouin spectrometer can generate Brillouin signals as the focused spot 1224 is scanned to discrete locations throughout a volume or plane thickness of ophthalmic tissue of the eye 1222. Brillouin scattered light from the focused spot at the discrete locations is returned to the spatial filter. According to some embodiments, the spatial filter operates as an input for the Brillouin spectrometer, and is in conjugate alignment with the focused spot 1224 or beam waist of the focused scanning diagnostic laser beam, and the Brillouin spectrometer can generate Brillouin signals as the focused spot 1224 or beam waist of the focused scanning diagnostic beam is scanned to discrete locations throughout the volume of the ophthalmic tissue of the eye 1222. In some cases, the spatial filter can operate to exclude information associated with out of focus focal planes, and include information associated with the focal plane of interest. The filter can provide sensitivity to locations where the focused spot 1224 is positioned, and little or no sensitivity to extraneous locations. In some cases, a spatial filter can be provided without using a fiber. In some cases, the spatial filter can operate to prime the incoming light, which is then measured by the spectrometer, which in turn generates the spectrum (e.g. Brillouin) signals.

By using a fiber input, it is possible to provide modularity to the system, whereby the patient scanning interface can be decoupled and coupled with the spectrometer via the optical fiber. Such modularity can provide enhanced testing and serviceability advantages. For example, the optical fiber could be uncoupled from one patient interface system, and coupled with another patient interface system. Hence, if one patient interface were to malfunction, it could be replaced with another patient interface. This could also allow patient interfaces to be tested as modules, which can improve manufacturability and serviceability.

From an optical standpoint, a fiber can provide a highly functional pinhole. In some cases, such embodiments can provide a separate input and output. It is possible to physically decouple with free space optics the input and output of the system. In some cases, such configurations can be considered to provide a free space optical circulator, for example using the PBS.

According to some embodiments, an optical output out of a single mode fiber can provide or approach a perfect Gaussian distribution, which has desirable beam shape and optical quality characteristics, and can be well suited for use with sensitive optical elements. As such, this feature can help optimize the optical performance of the overall system, particularly when multiple optical elements are involved.

In some cases, a fiber can operate as a conjugate pinhole or aperture (or spatial filter) for the focus spot in the tissue that is being analyzed. The fiber can operate to provide a focal plane resolution and specificity, filtering out the out of focus light that is not of interest. In some cases, a spatial filter can be provided as a radial aperture or a circular aperture. In some cases, an aperture can have a diameter of about 1 mm aperture. In some cases, the focus of the light is aligned with the core of a fiber, whereby only that light which is properly aligned to the core of the fiber will make it into that fiber. Thereafter, that light will be propagated down the fiber. In this sense, the core of the fiber can operate as a filter, spatial mask, or pinhole aperture, whereby light coupled into the core of the fiber is propagated, and undesired light is filtered or masked out. Often, a fiber will operate in conjunction with a lens. In some embodiments, the fiber can be provided as a collimated fiber optic. In some cases, light is focused into the fiber, or into the core of the fiber, using a lens. The light can be propagated in the fiber by way of total internal reflection. Where light is not properly aligned with the fiber core, such light may not propagate down the fiber, or be coupled into that fiber.

Put another way, light that is at a different focal plane, in the tissue, will not be at the same focal plane, over at the pinhole or spatial filter side, and hence becomes filtered out. The out of focus light will not make it into the pinhole or spatial aperture, and won't be coupled into the fiber, because that light is not aligned (e.g. not at the same focal plane, confocal, or conjugate).

As shown here, the patient interface system 1200 can include a processing assembly (e.g. such as the processing assembly depicted in FIG. 6) in operative association with the beam expansion assembly 1209, the objective lens assembly 1214, the eye camera assembly 1228, the fixation assembly 1229, and the Brillouin spectrometer assembly 1234. The processing assembly can include a processor, an electronic storage location operatively coupled with the processor, and processor executable code stored on the electronic storage location and embodied in a tangible non-transitory computer readable medium. The processor executable code can include machine-readable instructions that, when executed by the processor, cause the processor to generate x,y coordinate scan control signals for the beam expansion assembly 1209. In some cases, x,y coordinate scan control signals for the beam expansion assembly 1209 can be generated based on the electrical signals generated by the eye camera assembly 1228. The processor executable code can include machine-readable instructions that, when executed by the processor, cause the processor to generate z coordinate scan control signals for the objective lens assembly 1214. In some cases, the x,y coordinate scan control signals, the z coordinate scan control signals, or both the x,y coordinate scan control signals and the z coordinate scan control signals, can be based on an image of the eye. In some cases, the x,y coordinate scan control signals, the z coordinate scan control signals, or both the x,y coordinate scan control signals and the z coordinate scan control signals, can be generated independent of an image of the eye. In some cases, the x,y coordinate scan control signals, the z coordinate scan control signals, or both the x,y coordinate scan control signals and the z coordinate scan control signals, can be generated according to a pre-defined or pre-determined scan pattern. The processor executable code can include machine-readable instructions that, when executed by the processor, cause the processor to generate an elastic stiffness map for a volume of ophthalmic tissue of the eye 1222 based on Brillouin signals.

As shown in FIG. 12, the eye 1222 can be at a 90 degree angle of orientation relative to the general trajectory of the scanning diagnostic beam after the scanning diagnostic beam exits the objective lens assembly 1214. In this way, the reflected focused portion 1220 of the scanning diagnostic beam and the imaging light 1230 that travels from the eye to the eye camera assembly are aligned in a colinear path. According to some embodiments, such a configuration (e.g. reflecting the beam off the shortpass dichroic filter 1218*a*) may produce less astigmatism (or more generally, less optical aberration) than a different configuration (e.g. scanning or transmitting the beam through the shortpass dichroic filter 1218*a*). This advantage may be particularly helpful for maintaining high beam quality when the scanning diagnostic beam is diffraction limited and involves a confocal focused spot. In some embodiments, the finer axial resolution spot will also minimize contaminating back-reflections from the front surface of the eye, allow for scanning of more of the eye thickness with better spatial resolution. Dichroic filters can operate to reflect or reject light having certain wavelengths, and to transmit light having certain wavelengths.

According to some embodiments, the system 1200 can include one or more illumination lamps or light devices 1226 that direct illumination light or radiation 1227 toward the eye. In some cases, the illumination light or radiation 1227 can be infrared light. In some cases, the illumination light or radiation 1227 can be non-visible light. In some cases, the illumination light 1227 can have a wavelength value within a range from about 700 nm to about 1,000,000 nm. In some case, the illumination light 1227 can have a wavelength value of about 940 nm. According to some embodiments, the eye camera assembly 1228 is sensitive to the wavelength of the illumination light 1227 (which can also be the same as or similar to the wavelength of the imaging light 1230).

In some cases, the illumination light 1227 can have a wavelength value that is greater than a wavelength value of the diagnostic scanning light or radiation. In some cases, the diagnostic beam (e.g. 1204, 1220) has a wavelength value within a range from about 450 to about 1350 nm. In some cases, the wavelength of the scanning diagnostic beam has a value of about 780 nm. In some cases, the scanning diagnostic radiation can have a wavelength value within a range from about 450 to about 1350 nm. In some cases, the fixation light 1229*a* is visible light. In some cases, the fixation light 1229*a* is visible green light. In some cases, the fixation light 1229*a* has a wavelength value of about 520 to about 560 nm. According to some embodiments, the fixation assembly 1229 generates light 1229*a* that provides the eye with a gaze target, which can be helpful in a clinical setting or application. In some cases, a system or method can include a gaze target that is not provided by a light emitting fixation assembly.

As shown in FIG. 12, the shortpass dichroic filter 1218*a* can operate to reflect the incoming and returning scanning diagnostic beam, to transmit the imaging light 1230 (which can be illumination light 1227 reflected from the eye), and to transmit the fixation light 1229*a*. Related, the longpass dichroic filter 1218*b* can operate to reflect the fixation light 1229*a* and to transmit the imaging light 1230 (which can be illumination light 1227 reflected from the eye).

According to some embodiments, the focused scanning diagnostic laser beam 1220 optical path and the imaging light 1230 optical path are provided as integrated colinear optical paths, as a result of the operation of one or more dichroic filters. In some cases, the respective optical paths may not be integrated in a colinear fashion. In some cases, by providing integrated colinear optical paths, it is possible to avoid or eliminate geometric distortions of the image that may otherwise be present when using an off-axis camera (even though it may be possible to achieve the same focal point for a laser, relative to the focus of the imaging camera).

In some cases, by providing integrated colinear optical paths, it is possible to more efficiently register biomechanical data to eye location and/or orientation data pertaining to a real world eye space. In some cases, it is possible to use eye tracker or camera information to register and track where those points have been scanned, relative to certain features and/or registration coordinates on the eye.

According to some embodiments, astigmatism can be incurred for the eye camera illumination or an image of the eye by transmitting through the dichroic, and a perfect 3D orthogonal orientation (e.g. of the illumination lamp 1226) can cancel out that astigmatism.

As seen here, the longpass dichroic filter 1218*b* operates to fold together the light 1229*a* from the fixation assembly 1229 and the imaging light 1230 from the eye (integrated). Embodiments of the present invention also encompass designs where the fixation light 1229*a* is not folded into the same path with the imaging light 1230 (unintegrated). As shown in FIG. 12, in this embodiment there may be no lens between the shortpass dichroic filter 1218*a* and the longpass dichroic filter 1218*b*.

According to some embodiments, system 1200 provides a working distance of about 50 mm between the shortpass dichroic filter 1218*a* and the eye 1222. The working distance can be defined as the distance between the eye and the optical element that is closes to the eye along the beam path. In some cases, the system can be designed with a minimum working distance as to provide any unwanted interference between the instrument and the patient. In some cases, larger working distances can be achieved, with a concomitant increase in size of the optics for the same NA. At some point, in particular in the 90 degree configuration, the size of the objective becomes the largest element. Hence, even though the working distance is increasing, the distance between the patient's face and the objective may not because the size is also growing. As shown here, the scanning beam 1220, the imaging light 1230, and the fixation light 1229*a* are all colinear with one another in the working distance. Advantageously, such a configuration allows the system to establish a clear correspondence or registration between the position of the focused spot 1224 (and the data collected for that position) and a physical location on or in the tissue of the eye 1222. Similarly, such a colinear configuration can help to avoid or reduce geometric distortion that may otherwise be present in an off-axis configuration. In some cases, an off-axis camera may result in a keystone effect. It is possible to calibrate this out with a software correction. In some cases, the focal plane also becomes an image slice at angle, which may make identifying the correct focal plane more difficult. In some imaging modalities, this is desirable as in Scheimpflug imaging. In some cases, the numerical aperture of the objective lens assembly 1214 can be relatively large, for example greater than 0.1. In some cases, the numerical aperture is about 0.125. In some cases, the quarter wave plate 1217 can operate to filter any back reflections from any of the optics that may be positioned upstream of the quarter wave plate.

According to some embodiments, scanning of the beam can be achieved at least in part by effecting motorized x,y, z movement of an objective lens of the objective lens assembly 1214 while maintaining a boresighted beam down the center of the objective lens, such that the actual laser beam would not be scanned optically with mirrors, or any rotational mechanisms (in contrast to other embodiments which are disclosed herein).

According to some embodiments, the eye camera assembly 1228 of patient interface system 1200 can image through a path that is not the same as the laser path. In some cases, the eye camera assembly 1228 includes an eye tracker camera and an imaging lens (e.g. f=~25 mm). Patient interface system 1200 can involve a co-axial scanning laser that is reflected at 90 degrees. Lateral xy scanning can be achieved by motor translation of the entire laser scan path. In some cases, the entire laser scan path can exclude the fixation assembly, the eye camera, the processing assembly the laser head/controller, and the spectrometer. According to some embodiments, beam expansion assembly 1209 can include a plano-convex afocal relay. In some embodiments, objective lens assembly 1214 includes a 3 singlet objective. In some cases, the quarter wave plate assembly 1217 can be positioned downstream of the objective lens assembly 1214 for purposes of optical isolation. In some embodiments, this configured can be considered to be a simple camera setup with a lens, and it can be integrated colinearly into the overall path by function of the dichroics which only pass the illuminating infrared imaging light providing the image of the eye to the camera. According to some embodiments, there is a mechanical decoupling between the eye camera assembly 1228 and the laser scanning. FIG. 12 encompasses a system without an integrated optical scanning system, and the light is focused on the eye. Rather than angularly steering the beam using the scanning assembly, the XYZ motors used for aligning the eye to the system can also be used to reposition the laser light on the patients eye. This could be embodied as a system where the eye camera image is mechanically decoupled, so the eye image does not also move, or mechanically coupled with a moving eye image. System 1200 can provide a configuration where all optics are on axis, where testing for alignment can be achieved with only a line scan instead of a 3D scan volume, where there is no optical scanning, and/or there is an inherently telecentric arrangement.

In some cases, the patient interface system 1200 depicted in FIG. 12 can incorporate one or more features of the embodiment depicted in FIG. 6. FIG. 12 shows additional details regarding a reference path that is used to measure a sample containing plastic and water, that has known elastic properties. This can be used to normalize the data that is received from the actual tissue being analyzed, for example the cornea or the crystalline lens. Light can be controlled by a pair of shutters, and operation of the shutters 1207, 1207*a* can determine whether the laser light is going to hit the reference path (e.g. through a wave plate 1208*d*, such as a λ/4 wave plate), or whether the laser is going to hit the sample path. FIG. 12 also illustrates that a fixation assembly can include a grid of light points or light emitting diodes. The system can be configured to illuminate one or more points of the grid, so as to control where the patient directs their gaze. In this way, it is possible to facilitate the measurement of certain areas of the eye that otherwise may be difficult to scan or measure when the patient is looking directly straightforward. Accordingly, the system can facilitate a computerized control of the orientation of the eye, by changing the gaze angle.

FIG. 13 depicts aspects of a patient interface system 1300 according to embodiments of the present invention. As discussed elsewhere herein, system 1300 can be used to generate an elastic stiffness map for a volume of an ophthalmic tissue of an eye of a patient. As shown here, system 1300 includes a laser assembly or light source 1302 that generates a collimated diagnostic laser beam 1304 (e.g. by using a lens 1303, such as a 4 mm beam expansion lens), a polarizing beam splitter 1306 that reflects a portion 1308 of the collimated diagnostic laser beam 1304, and the reflected portion 1308 is then transmitted to an optical scanning assembly 1309, which operates to adjust or redirect a beam path of the scanning diagnostic laser beam portion 1308 to produce a redirected portion 1309*a* that is transmitted to an electromagnetic radiation beam expansion assembly 1310, which converts beam 1309*a* to an expanded beam 1312. In some cases, light source 1302 can be a device that produces electromagnetic radiation characterized by one or more wavelengths or one or more frequencies. According to some embodiments, the electromagnetic radiation beam expansion assembly 1310 expands a collimated scanning diagnostic laser beam from a first diameter to a second diameter that is larger than the first diameter. The laser beam expansion assembly 1310 may include multiple lenses. In some cases, the laser beam expansion assembly 1310 includes telephoto lens configuration. For example, the beam expansion assembly 1310 can include a telephoto lens group that extends the light path to create a long-focus lens (e.g. 400 mm). In some cases, the laser beam expansion assembly 1310 can include an afocal relay system. In turn, expanded beam 1312 is transmitted to an objective lens assembly 1314.

As shown here, the polarizing beam splitter 1306 can be positioned before the optical scanning assembly 1309. The polarizing beam splitter 1306 can operate to split the diagnostic laser beam 1304 into a scanning portion 1308 and a non-scanning portion 1308*a*. In some cases, the beam splitter 1306 allows for the measurement (e.g. concurrent) of a reference sample 1308 (e.g. through a waveplate 1308*d*, such as a λ/4 waveplate). In some cases, the beam splitter 1306 operates to provide an additional amount of filtration of back reflections of light. Filtration can be based on polarization, and may involve aspects of a conventional optical isolator based on polarizing optics and a quarter wave plate. In some cases, the polarizing beam splitter 1306 transmits light at a 90 degrees orientation and on the return path the light goes to 90 degrees. According to some embodiments, the beam splitter 1306 works in conjunction with the quarter wave plate 1317. For example, after two passes through the waveplate 1317, the returning light can be passed back to the spectrometer assembly 1334, and light that has only passed once (e.g. reflections from lenses) will be excluded. In some cases, when the light first enters the quarter wave plate 1317, some amount can be portioned to a calibrated reference sample. A half-waveplate element 1305 may also be positioned after the laser source which sets up a ratio of linearly polarized s and p. This can control the light split through the polarizing beam splitter (PBS). According to some embodiments, a Brillouin signal from a sample can be used as a built in reference to the instrument for accurate calculation of the Brillouin signal. There may also be a quarter waveplate on the reference path to provide an isolated signal that will make its way back to the spectrometer.

According to some embodiments, the optical scanning assembly 1309 operates to adjust or redirect a beam path of the collimated scanning diagnostic laser beam 1308. In some cases, the patient interface system 1300 may not include the polarizing beam splitter 1306. The optical scanning assembly 1309 operates to redirect a beam path of the reflected portion 1308 of the collimated scanning diagnostic laser beam. The redirected reflected portion 1309*a* of the collimated scanning diagnostic laser beam is then transmitted to a beam expansion assembly 1310, and the resulting expanded beam 1312 is transmitted to an objective lens assembly 1314, which operates to focus the portion 1312 of the collimated scanning diagnostic laser beam to produce a focused scanning diagnostic laser beam 1316.

According to some embodiments, the objective lens assembly 1314 operates to focus the expanded collimated scanning diagnostic laser beam 1312 to produce a focused scanning diagnostic laser beam 1316 having a beam waist or focused spot. In some cases, the objective lens assembly 1314 operates to adjust a scan position of the beam waist or focused spot. In some cases, the objective lens assembly 1314 includes a motorized stage 1314*a* that allows the objective lens assembly to travel toward and away from the beam expansion assembly 1310. In some cases, the optical scanning assembly 1309 includes motorized elements such as scanning mirrors, or an XY galvanometer scanner, the optical scanning assembly 1309 to redirect the trajectory of the beam 1308. Relatedly, the optical scanning assembly 709 can include a system of mirrors that can be adjusted, in terms of their orientation, so as to direct the beam in the desired directions. Hence, this design can include some optics to place the focused spot 1324 at the desired location at the cornea. As shown here, optical scanning assembly 1309 can include a pair of xy galvo scanning mirrors 1309*b*, 1309*c*. In some cases, the galvo mirrors can provide an operational range of θ=±20°.

As shown here, system 1300 may include a quarter-wave plate assembly 1317. In some embodiments, the quarter-wave plate assembly 1317 operates to convert the focused scanning diagnostic laser beam 1316 from a linear polarization orientation to a circular polarization orientation. In some embodiments, the quarter-wave plate assembly 1317 operates to provide a 45 degree rotation to the focused scanning diagnostic laser beam 1316. In some cases, the quarter-wave plate assembly 1317 operates to convert the focused scanning diagnostic laser beam 1316 from p-polarized light to s-polarized light. In some cases, the quarter-wave plate assembly 1317 operates to convert the focused scanning diagnostic laser beam 1316 from s-polarized light to p-polarized light. The quarter-wave plate assembly 1317 can be placed along the beam path, for example between the objective lens assembly 1314 and the shortpass dichroic filter 1318*a*. In some embodiments, the quarter-wave plate assembly 1317 can be placed upstream of the objective lens assembly 1314 or downstream of the shortpass dichroic filter 1318*a*. In some cases, the quarter-wave plate assembly 1317 can be placed anywhere as desired, between the sample (e.g. eye) and the PBS. According to some embodiments, system 1300 provides a working distance of about 27 mm.

The focused scanning diagnostic laser beam 1316 is reflected by a shortpass dichroic filter 1318*a*, and the reflected focused portion 1320 is transmitted toward an eye 1322 of the patient. In some cases, the focused scanning diagnostic laser beam has a circular polarization orientation and is reflected by the shortpass dichroic filter 1318*a* toward the eye 1322.

According to some embodiments, a dichroic filter can operate as a beam splitter that splits light based on wavelength or color, rather than splitting light based on power. In some cases, a dichroic filter will transmit light within a certain wavelength band or range and/or reflect light within a certain wavelength band or range. As shown here, dichroic filters can operate to fold together, or to separate out, different wavelengths of light (e.g. into a common optical path).

In some case, the dichroic filters can operate to fold together fixation light 1329*a*, imaging light 1330, and scanning diagnostic light 1320, into a common optical path (e.g. between the shortpass dichroic filter 1318*a* and the eye 1322). Similarly, a dichroic can operate to peel apart light from a common path into separate optical paths, for example imaging light 1330 and returned scanning diagnostic light travel along a common optical path from the eye to the shortpass dichroic filter 1318*a*, and then the imaging light is transmitted through the shortpass dichroic filter 1318*a* and the returned scanning diagnostic light is reflected by the shortpass dichroic filter 1318*a*.

The reflected focused scanning diagnostic laser beam 1320 has focused spot 1324, and operation of the optical scanning assembly 1309 or the objective lens assembly 1314, or the combined operation of the optical scanning assembly 1309 and the objective lens assembly 1314, can adjust a scan position of the focused spot 1324 to various discrete locations on or within one or more tissues of the eye 1322.

The patient interface system 1300 also includes an eye camera assembly 1328 that receives imaging light 1330 from the eye (which optionally may have passed through a shortpass dichroic filter 1318*a* and a longpass dichroic filter 1318*b* of a beam control assembly) and that generates electrical signals in response to the received imaging light 1330. In some cases, the eye camera assembly 1328 includes an eye tracker camera and an imaging lens (e.g. f=~25 mm). The imaging light 1330 can provide registration information regarding the position and/or orientation of the eye. In some cases, this registration information can be used (e.g. by a processing assembly, such as the processing assembly depicted in FIG. 7) to provide locate elasticity measurement data obtained by the Brillouin spectrometer assembly 1334 to particular points of the eye. In some cases, the imaging light 1330 can help to provide feedback, which may be continuous feedback, to the processing assembly. The imaging light 1330 can be processed to provide information regarding a center coordinate of the eye, a central reference of the eye, or more generically, a reference coordinate on the eye, which can be registered to the biomechanical data. Such a reference coordinate can be determined by processing the imaging data.

In some cases, the processing assembly can operate to generate two images, specifically an image of the eye and a Brillouin heat map (e.g. stiffness values at discrete points), and to accurately superimpose those images on top of each other using registration. In this way, the mechanical information is relevant in the physical space. In some cases, the processing assembly does not perform a superimposition. Rather, a camera is used to provide a reference point to begin a scan pattern, and thereafter a scan is performed according to the pattern, so as to generate the stiffness map. The map can indicate whether there are any abnormal spots or points of interest on the eye, without providing the exact location on the eye of the abnormal spots or points of interest. In some cases, a camera is not used to provide a reference point to begin a scan pattern. For example, the physician or operate could manually inspect the person's eye, and then aim the beam, without using a camera. In some cases, it is possible to illuminate the person's eye using a certain wattage, observe a reflection off the person's eye, and determine that the alignment of the scanning beam and the eye is sufficient.

Hence, input techniques for aiming the diagnostic beam can include using a camera image or data, manually aiming the beam, or using feedback from the Brillouin spectrometer. For example, data obtained by the spectrometer can provide an indication of whether the system is in focus. The Brillouin spectrometer can be used to differentiate spectral shifts that are characteristic of different tissues. In some cases, as the focused spot is scanned in the z depth direction, it is possible to detect fundamentally different frequency shifts (or different information) as the focused spot goes through different layers (e.g. going from the air, to the cornea surface, to the aqueous humor, to the crystalline lens, and so on) which can correspond to different elastic properties (e.g. elastic modulus). In this sense, the Brillouin approach can provide aspects of an imaging modality. Hence, it may be possible to determine where the focused spot is located (e.g. along a z-axis), by observing or analyzing the spectrometer image. In some cases, it is possible to align or position the patient interface system, by observing or using a reflection off of a person's eye, then moving the system into focus based on feedback from the spectrometer camera, and then initiating the scan. In some cases, the camera is parfocal with the laser beam, and the focus of the eye can also be used.

In some embodiments, system 1300 also includes a fixation assembly 1329 that provides the eye with a gaze target. In some cases, fixation light 1329a is generated by the fixation assembly 1329, travels from the fixation assembly 1329, is reflected by the longpass dichroic filter 1318b, travels through the shortpass dichroic filter 1318a, and to the eye 1322. According to some embodiments, the fixation assembly 1329 includes a matrix of light-emitting diode (LEDs).

The patient interface system 1300 can further include a Brillouin spectrometer assembly 1334 having a Brillouin spectrometer and a spatial filter that is parfocal with the focused spot 1324 (e.g. in a conjugate focal plane). The Brillouin spectrometer can generate Brillouin signals as the focused spot 1324 is scanned to discrete locations (e.g. 1324a, 1324b) throughout a volume or plane thickness of ophthalmic tissue of the eye 1322. Brillouin scattered light from the focused spot at the discrete locations is returned to the spatial filter. According to some embodiments, the spatial filter operates as an input for the Brillouin spectrometer, and is in conjugate alignment with the focused spot 1324 or beam waist of the focused scanning diagnostic laser beam, and the Brillouin spectrometer can generate Brillouin signals as the focused spot 1324 or beam waist of the focused scanning diagnostic beam is scanned to discrete locations throughout the volume of the ophthalmic tissue of the eye 1322. In some cases, the spatial filter can operate to exclude information associated with out of focus focal planes, and include information associated with the focal plane of interest. The filter can provide sensitivity to locations where the focused spot 1324 is positioned, and little or no sensitivity to extraneous locations. In some cases, a spatial filter can be provided without using a fiber. In some cases, the spatial filter can operate to prime the incoming light, which is then measured by the spectrometer, which in turn generates the spectrum (e.g. Brillouin) signals.

By using a fiber input, it is possible to provide modularity to the system, whereby the patient scanning interface can be decoupled and coupled with the spectrometer via the optical fiber. Such modularity can provide enhanced testing and serviceability advantages. For example, the optical fiber could be uncoupled from one patient interface system, and coupled with another patient interface system. Hence, if one patient interface were to malfunction, it could be replaced with another patient interface. This could also allow patient interfaces to be tested as modules, which can improve manufacturability.

From an optical standpoint, a fiber can provide a highly functional pinhole. In some cases, such embodiments can provide a separate input and output. It is possible to physically decouple with free space optics the input and output of the system In some embodiments, the input is not separated from the output. For example, the same light can be coupled back into the same input path and optionally the beam could be redirected to the spectrometer after traveling back down the fiber.

According to some embodiments, an optical output out of a single mode fiber can provide or approach a perfect Gaussian distribution, which has desirable beam shape and optical quality characteristics, and can be well suited for use with sensitive optical elements. As such, this feature can help optimize the optical performance of the overall system, particularly when multiple optical elements are involved.

In some cases, a fiber can operate as a conjugate pinhole or aperture (or spatial filter) for the focus spot in the tissue that is being analyzed. The fiber can operate to provide a focal plane resolution and specificity, filtering out the out of focus light that is not of interest. In some cases, a spatial filter can be provided as a radial aperture or a circular aperture. In some cases, an aperture can have a diameter of about 1 mm aperture. In some cases, the focus of the light is aligned with the core of a fiber, whereby only that light which is properly aligned to the core of the fiber will make it into that fiber. Thereafter, that light will be propagated down the fiber. In this sense, the core of the fiber can operate as a filter, spatial mask, or pinhole aperture, whereby light coupled into the core of the fiber is propagated, and undesired light is filtered or masked out. Often, a fiber will operate in conjunction with a lens. In some embodiments, the fiber can be provided as a collimated fiber optic. In some cases, light is focused into the fiber, or into the core of the fiber, using a lens. The light can be propagated in the fiber by way of total internal reflection. Where light is not properly aligned with the fiber core, such light may not propagate down the fiber, or be coupled into that fiber.

Put another way, light that is at a different focal plane, in the tissue, will not be at the same focal plane, over at the pinhole or spatial filter side, and hence becomes filtered out. The out of focus light will not make it into the pinhole or spatial aperture, and won't be coupled into the fiber, because that light is not aligned (e.g. not at the same focal plane, confocal, or conjugate).

As shown here, the patient interface system 1300 can include a processing assembly (e.g. such as the processing assembly depicted in FIG. 7) in operative association with the optical scanning assembly 1310, the objective lens assembly 1314, the eye camera assembly 1328, the fixation assembly 1329, and the Brillouin spectrometer assembly 1334. The processing assembly can include a processor, an electronic storage location operatively coupled with the processor, and processor executable code stored on the electronic storage location and embodied in a tangible non-transitory computer readable medium. The processor executable code can include machine-readable instructions that, when executed by the processor, cause the processor to generate x,y coordinate scan control signals for the optical scanning assembly 1309. In some cases, x,y coordinate scan control signals for the optical scanning assembly 1309 can be generated based on the electrical signals generated by the eye camera assembly 1328. The processor executable code can include machine-readable instructions that, when executed by the processor, cause the processor to generate z coordinate scan control signals for the objective lens assembly 1314. In some cases, the x,y coordinate scan control signals, the z coordinate scan control signals, or both the x,y coordinate scan control signals and the z coordinate scan control signals, can be based on an image of the eye. In some cases, the x,y coordinate scan control signals, the z coordinate scan control signals, or both the x,y coordinate scan control signals and the z coordinate scan control signals, can be generated independent of an image of the eye. In some cases, the x,y coordinate scan control signals, the z coordinate scan control signals, or both the x,y coordinate scan control signals and the z coordinate scan control signals, can be generated according to a pre-defined or pre-determined scan pattern. The processor executable code can include machine-readable instructions that, when executed by the processor, cause the processor to generate an elastic stiffness map for a volume of ophthalmic tissue of the eye 1322 based on Brillouin signals.

As shown in FIG. 13, the eye 1322 can be at a 90 degree angle of orientation relative to the general trajectory of the scanning diagnostic beam after the scanning diagnostic beam exits the objective lens assembly 1314. In this way, the reflected focused portion 1320 of the scanning diagnostic beam and the imaging light 1330 that travels from the eye to the eye camera assembly are aligned in a colinear path. According to some embodiments, such a configuration (e.g. reflecting the beam off the shortpass dichroic filter 1318a) may produce less astigmatism (or more generally, less optical aberration) than a different configuration (e.g. scanning or transmitting the beam through the shortpass dichroic filter 1318a). This advantage may be particularly helpful for maintaining high beam quality when the scanning diagnostic beam is diffraction limited and involves a confocal focused spot. In some embodiments, the finer axial resolution spot will also minimize contaminating back-reflections from the front surface of the eye, allow for scanning of more of the eye thickness with better spatial resolution. Dichroic filters can operate to reflect or reject light having certain wavelengths, and to transmit light having certain wavelengths.

According to some embodiments, the system 1300 can include one or more illumination lamps or light devices 1326 that direct illumination light or radiation 1327 toward the eye. In some cases, the illumination light or radiation 1327 can be infrared light. In some cases, the illumination light or radiation 1327 can be non-visible light. In some cases, the illumination light 1327 can have a wavelength value within a range from about 700 nm to about 1,000,000 nm. In some case, the illumination light 1327 can have a wavelength value of about 940 nm. According to some embodiments, the eye camera assembly 1328 is sensitive to the wavelength of the illumination light 1327 (which can also be the same as or similar to the wavelength of the imaging light 1330).

In some cases, the illumination light 1327 can have a wavelength value that is greater than a wavelength value of the diagnostic scanning light or radiation. In some cases, the diagnostic beam (e.g. 1304, 1320) has a wavelength value within a range from about 450 to about 1350 nm. In some cases, the wavelength of the scanning diagnostic beam has a value of about 780 nm. In some cases, the scanning diagnostic radiation can have a wavelength value within a range from about 450 to about 1350 nm. In some cases, the fixation light 1329a is visible light. In some cases, the fixation light 1329a is visible green light. In some cases, the fixation light 1329a has a wavelength value of about 520 to about 560 nm. According to some embodiments, the fixation assembly 1329 generates light 1329a that provides the eye with a gaze target, which can be helpful in a clinical setting or application. In some cases, a system or method can include a gaze target that is not provided by a light emitting fixation assembly.

As shown in FIG. 13, the shortpass dichroic filter 1318a can operate to reflect the incoming and returning scanning diagnostic beam, to transmit the imaging light 1330 (which can be illumination light 1327 reflected from the eye), and to transmit the fixation light 1329a. Related, the longpass dichroic filter 1318b can operate to reflect the fixation light 1329a and to transmit the imaging light 1330 (which can be illumination light 1327 reflected from the eye). According to some embodiments, the eye camera assembly 1328 does not image through the laser path and/or the co-axial scanning laser can be reflected at 90 degrees. In some cases, the quarter wave plate assembly 1317 can be positioned downstream of the objective lens assembly 1314 for purposes of optical isolation. The optical scanning assembly 1309 can be configured to provide lateral xy scanning, optionally by implementation of galvanometer mirrors. In some cases, the optical scanning assembly 1309 can be followed by an afocal relay, which may include a beam magnification or expansion mechanism and/or a pupil scanning mechanism. Optical scanning can be achieved by system 1300 without changing the field of view of the eye camera assembly 1328.

According to some embodiments, the focused scanning diagnostic laser beam 1320 optical path and the imaging light 1330 optical path are provided as integrated colinear optical paths, as a result of the operation of one or more dichroic filters. In some cases, the respective optical paths may not be integrated in a colinear fashion. In some cases, by providing integrated colinear optical paths, it is possible to avoid or eliminate geometric distortions of the image that may otherwise be present when using an off-axis camera (even though it may be possible to achieve the same focal point for a laser, relative to the focus of the imaging camera).

In some cases, by providing integrated colinear optical paths, it is possible to more efficiently register biomechanical data to eye location and/or orientation data pertaining to a real world eye space. In some cases, it is possible to use eye tracker or camera information to register and track where those points have been scanned, relative to certain features and/or registration coordinates on the eye.

According to some embodiments, astigmatism can be incurred for the eye camera illumination or an image of the eye by transmitting through the dichroic, and a perfect 3D orthogonal orientation (e.g. of the illumination lamp 1326) can cancel out that astigmatism.

As seen here, the longpass dichroic filter 1318b operates to fold together the light 1329a from the fixation assembly 1329 and the imaging light 1330 from the eye (integrated). Embodiments of the present invention also encompass designs where the fixation light 1329a is not folded into the same path with the imaging light 1330 (unintegrated). As shown in FIG. 13, in this embodiment there may be no lens between the shortpass dichroic filter 1318a and the longpass dichroic filter 1318b.

In the embodiment depicted in FIG. 13, as well as in other embodiments disclosed herein, it may be desirable for a beam that enters an optical scanning system 1309 to be collimated, and to have a beam that is collimated in a space between the beam expansion assembly 1310 and the back entrance of an objective of the objective lens assembly 1314. According to some embodiments, the objective lens assembly 1314 can include a motorized element, such as z scan motor, which can move or translate the position of an objective of the objective lens assembly 1314. Such movement can operate to shift the location of a focused spot 1324 (e.g. confocal focused spot) to deeper or shallower locations within the patient tissue.

According to some embodiments, the focused spot 1324 can be initially positioned in the space anterior to the patient eye, and then scanned in the z direction toward a central part of the patient's eye, through the cornea, through the aqueous humor, and into deeper tissues or structures of the eye. The system 1300 can operate to take measurements at any position along this trajectory. Hence, the system can scan along a depth line, sampling periodically, and then from that data, determine one or more points corresponding to the air, one or more points corresponding to the cornea, one or more points corresponding to the aqueous humor or liquid posterior to the cornea. The system 1300 can also operate to isolate the data points corresponding to the cornea, and use those data points to generate a corneal elasticity map for that location, either by averaging the data points, or treating them separately.

In some cases, the patient interface system 1300 depicted in FIG. 13 can incorporate one or more features of the embodiment depicted in FIG. 7. FIG. 13 shows additional details regarding a reference path 1308a that is used to measure a sample 1308c containing plastic and water, that has known elastic properties. This can be used to normalize the data that is received from the actual tissue being analyzed, for example the cornea or the crystalline lens. Light can be controlled by a pair of shutters 1307, 1307a, and operation of the shutters can determine whether the laser light is going to hit the reference path, or whether the laser is going to hit the sample path. FIG. 13 also illustrates that a fixation assembly 1329 can include a grid of light points or light emitting diodes. The system can be configured to illuminate one or more points of the grid, so as to control where the patient directs their gaze. In this way, it is possible to facilitate the measurement of certain areas of the eye that otherwise may be difficult to scan or measure when the patient is looking directly straightforward. Accordingly, the system can facilitate a computerized control of the orientation of the eye, by changing the gaze angle.

FIG. 14 depicts aspects of a patient interface system 1400 according to embodiments of the present invention. As discussed elsewhere herein, system 1400 can be used to generate an elastic stiffness map for a volume of an ophthalmic tissue of an eye of a patient. As shown here, system 1400 includes a laser assembly or light source 1402 that generates a collimated diagnostic laser beam 1404 (e.g. by passing through a lens 1403, such as a 4 mm beam expansion lens), a polarizing beam splitter 1406 that reflects a portion 1408 of the collimated diagnostic laser beam 1404, and the reflected portion 1408 is then transmitted to a laser beam expansion assembly 1409, which converts beam 1408 to an expanded beam 1409a. In some cases, light source 1402 can be a device that produces electromagnetic radiation characterized by one or more wavelengths or one or more frequencies. According to some embodiments, the electromagnetic radiation beam expansion assembly 1409 expands a collimated scanning diagnostic laser beam from a first diameter to a second diameter that is larger than the first diameter. The laser beam expansion assembly 1409 may include multiple lenses. In some cases, the laser beam expansion assembly 1409 includes lenses disposed in a Galilean configuration, with a negative lens followed by a positive lens. In some case, the laser beam expansion assembly 1409 can be provided as a Galilean type beam expander. In some cases, the collimated scanning diagnostic laser beam has a linear polarization orientation. In turn, expanded beam 1409a is transmitted to an optical scanning assembly 1410.

As shown here, the polarizing beam splitter 1406 can be positioned before the laser beam expansion assembly 1409. The polarizing beam splitter 1406 can operate to split the diagnostic laser beam 1404 into a scanning portion 1408 and a non-scanning portion 1408a. In some cases, the beam splitter 1406 allows for the measurement (e.g. concurrent) of a reference sample 1408c. In some cases, the beam splitter 1406 operates to provide an additional amount of filtration of back reflections of light. Filtration can be based on polarization, and may involve aspects of a conventional optical isolator based on polarizing optics and a quarter wave plate. In some cases, the polarizing beam splitter 1406 transmits light at a 90 degrees orientation and on the return path the light goes to 90 degrees. In some embodiments, the beam splitter 1406 works in conjunction with the quarter wave plate 1417. For example, after two passes through the waveplate 1417, the returning light can be passed back to the spectrometer assembly 1434, and light that has only passed once (e.g. reflections from lenses) will be excluded. In some cases, when the light first enters the quarter wave plate 1417, some amount can be portioned to a calibrated reference sample. A half-waveplate element 1405 may also be positioned after the laser source which sets up a ratio of linearly polarized s and p. This can control the light split through the polarizing beam splitter (PBS). According to some embodiments, a Brillouin signal from a sample can be used as a built in reference to the instrument for accurate calculation of the Brillouin signal. There may also be a quarter waveplate on the reference path to provide an isolated signal that will make its way back to the spectrometer.

According to some embodiments, the optical scanning assembly 1410 operates to adjust or redirect a beam path of the expanded collimated scanning diagnostic laser beam. In some cases, the patient interface system 1400 may not include the polarizing beam splitter 1406. The optical scanning assembly 1410 operates to redirect a beam path of the reflected portion 1408 of the collimated scanning diagnostic laser beam. The redirected reflected portion 1412 of the collimated scanning diagnostic laser beam is then transmitted through a shortpass dichroic filter 1418a and to an objective lens assembly 1414, which operates to focus the redirected portion 1412 of the collimated scanning diagnostic laser beam to produce a focused scanning diagnostic laser beam 1416. According to some embodiments, system 1400 provides a working distance of about 50 mm.

According to some embodiments, the objective lens assembly 1414 operates to focus the expanded collimated scanning diagnostic laser beam 1412 to produce a focused scanning diagnostic laser beam 1416 having a beam waist or focused spot. In some cases, the objective lens assembly 1414 operates to adjust a scan position of the beam waist or focused spot. In some cases, the objective lens assembly 1414 includes a motorized stage that allows the objective lens assembly to travel toward and away from the optical scanning assembly 1410. In some cases, the optical scanning assembly 1410 includes a motorized stage 1410a that allows the optical scanning assembly to travel toward and away from the objective lens assembly 1414. In some cases, the optical scanning assembly and the objective lens assembly include or are disposed on respective motorized stages, or are disposed on a common motorized stage, so that the optical scanning assembly and the objective lens assembly can move in tandem.

As shown here, system 1400 may include a quarter-wave plate assembly 1417. In some embodiments, the quarter-wave plate assembly 1417 operates to convert the focused scanning diagnostic laser beam 1416 from a linear polarization orientation to a circular polarization orientation. In some embodiments, the quarter-wave plate assembly 1417 operates to provide a 45 degree rotation to the focused scanning diagnostic laser beam 1416. In some cases, the quarter-wave plate assembly 1417 operates to convert the focused scanning diagnostic laser beam 1416 from p-polarized light to s-polarized light. In some cases, the quarter-wave plate assembly 1417 operates to convert the focused scanning diagnostic laser beam 1416 from s-polarized light to p-polarized light. The quarter-wave plate assembly 1417 can be placed along the beam path, for example between the objective lens assembly 1414 and the eye 1422. In some embodiments, the quarter-wave plate assembly 1417 can be placed upstream of the objective lens assembly 1414. In some cases, the quarter-wave plate assembly 1417 can be placed anywhere as desired, between the sample (e.g. eye) and the PBS.

The focused scanning diagnostic laser beam 1416 is transmitted toward an eye 1422 of the patient. In some cases, the focused scanning diagnostic laser beam has a circular polarization orientation. In some cases, a dichroic filter will transmit light within a certain wavelength band or range and/or reflect light within a certain wavelength band or range. As shown here, dichroic filters can operate to fold together, or to separate out, different wavelengths of light (e.g. into a common optical path).

In some case, the dichroic filters can operate to fold together imaging light 1430, and scanning diagnostic light 1416, into a common optical path (e.g. between the shortpass dichroic filter 1418a and the eye 1422). Similarly, a dichroic can operate to peel apart light from a common path into separate optical paths, for example imaging light 1430 and returned scanning diagnostic light travel along a common optical path from the eye to the shortpass dichroic filter 1418a, and then the returned scanning diagnostic light is transmitted through the shortpass dichroic filter 1418a and the imaging light is reflected by the shortpass dichroic filter 1418a.

The focused scanning diagnostic laser beam 1416 has focused spot 1424, and operation of the optical scanning assembly 1410 or the objective lens assembly 1414, or the combined operation of the optical scanning assembly 1410 and the objective lens assembly 1414, can adjust a scan position of the focused spot 1424 to various discrete locations (e.g. 1424a, 1424b) on or within one or more tissues of the eye 1422.

The patient interface system 1400 also includes an eye camera assembly 1428 that receives imaging light 1430 from the eye (which optionally may have been reflected by a shortpass dichroic filter 1418a of a beam control assembly) and that generates electrical signals in response to the received imaging light 1430. The imaging light 1430 can provide registration information regarding the position and/or orientation of the eye. In some cases, this registration information can be used (e.g. by a processing assembly, such as the processing assembly depicted in FIG. 8) to provide locate elasticity measurement data obtained by the Brillouin spectrometer assembly 1434 to particular points of the eye. In some cases, the imaging light 1430 can help to provide feedback, which may be continuous feedback, to the processing assembly. The imaging light 1430 can be processed to provide information regarding a center coordinate of the eye, a central reference of the eye, or more generically, a reference coordinate on the eye, which can be registered to the biomechanical data. Such a reference coordinate can be determined by processing the imaging data.

In some cases, the processing assembly can operate to generate two images, specifically an image of the eye and a Brillouin heat map (e.g. stiffness values at discrete points), and to accurately superimpose those images on top of each other using registration. In this way, the mechanical information is relevant in the physical space. In some cases, the processing assembly does not perform a superimposition. Rather, a camera is used to provide a reference point to begin a scan pattern, and thereafter a scan is performed according to the pattern, so as to generate the stiffness map. The map can indicate whether there are any abnormal spots or points of interest on the eye, without providing the exact location on the eye of the abnormal spots or points of interest. In some cases, a camera is not used to provide a reference point to begin a scan pattern. For example, the physician or operate could manually inspect the person's eye, and then aim the beam, without using a camera. In some cases, it is possible to illuminate the person's eye using a certain wattage, observe a reflection off the person's eye, and determine that the alignment of the scanning beam and the eye is sufficient.

Hence, input techniques for aiming the diagnostic beam can include using a camera image or data, manually aiming the beam, or using feedback from the Brillouin spectrometer. For example, data obtained by the spectrometer can provide an indication of whether the system is in focus. The Brillouin spectrometer can be used to differentiate spectral shifts that are characteristic of different tissues. In some cases, as the focused spot is scanned in the z depth direction, it is possible to detect fundamentally different frequency shifts (or different information) as the focused spot goes through different layers (e.g. going from the air, to the cornea surface, to the aqueous humor, to the crystalline lens, and so on) which can correspond to different elastic properties (e.g. elastic modulus). In this sense, the Brillouin approach can provide aspects of an imaging modality. Hence, it may be possible to determine where the focused spot is located (e.g. along a z-axis), by observing or analyzing the spectrometer image. In some cases, it is possible to align or position the patient interface system, by observing or using a reflection off of a person's eye, then moving the system into focus based on feedback from the spectrometer camera, and then initiating the scan. In some cases, the camera is parfocal with the laser beam, and the focus of the eye can also be used.

In some embodiments, system 1400 also includes a fixation assembly that provides the eye with a gaze target, the fixation assembly having a first fixation mechanism 1429a that transmits a first fixation light 1429b toward the eye, and a second fixation mechanism 1429c that transmits a second fixation light 1429d toward the eye. According to some embodiments, the fixation assembly includes light-emitting diodes (LEDs). In some cases, the fixation light is a collimated green light produced by a light emitting diode.

The patient interface system 1400 can further include a Brillouin spectrometer assembly 1434 having a Brillouin spectrometer and a spatial filter that is parfocal with the focused spot 1424 (e.g. in a conjugate focal plane). The Brillouin spectrometer can generate Brillouin signals as the focused spot 1424 is scanned to discrete locations throughout a volume or plane thickness of ophthalmic tissue of the eye 1422. Brillouin scattered light from the focused spot at the discrete locations is returned to the spatial filter. According to some embodiments, the spatial filter operates as an input for the Brillouin spectrometer, and is in conjugate alignment with the focused spot 1424 or beam waist of the focused scanning diagnostic laser beam, and the Brillouin spectrometer can generate Brillouin signals as the focused spot 1424 or beam waist of the focused scanning diagnostic beam is scanned to discrete locations throughout the volume of the ophthalmic tissue of the eye 1422. In some cases, the spatial filter can operate to exclude information associated with out of focus focal planes, and include information associated with the focal plane of interest. The filter can provide sensitivity to locations where the focused spot 1424 is positioned, and little or no sensitivity to extraneous locations. In some cases, a spatial filter can be provided without using a fiber. In some cases, the spatial filter can operate to prime the incoming light, which is then measured by the spectrometer, which in turn generates the spectrum (e.g. Brillouin) signals.

By using a fiber input, it is possible to provide modularity to the system, whereby the patient scanning interface can be decoupled and coupled with the spectrometer via the optical fiber. Such modularity can provide enhanced testing and serviceability advantages. For example, the optical fiber could be uncoupled from one patient interface system, and coupled with another patient interface system. Hence, if one patient interface were to malfunction, it could be replaced with another patient interface. This could also allow patient interfaces to be tested as modules, which can improve manufacturability.

From an optical standpoint, a fiber can provide a highly functional pinhole. In some cases, such embodiments can provide a separate input and output. It is possible to physically decouple with free space optics the input and output of the system. In some embodiments, the input is not separated from the output. For example, the same light can be coupled back into the same input path and optionally the beam could be redirected to the spectrometer after traveling back down the fiber.

According to some embodiments, an optical output out of a single mode fiber can provide or approach a perfect Gaussian distribution, which has desirable beam shape and optical quality characteristics, and can be well suited for use with sensitive optical elements. As such, this feature can help optimize the optical performance of the overall system, particularly when multiple optical elements are involved.

In some cases, a fiber can operate as a conjugate pinhole or aperture (or spatial filter) for the focus spot in the tissue that is being analyzed. The fiber can operate to provide a focal plane resolution and specificity, filtering out the out of focus light that is not of interest. In some cases, a spatial filter can be provided as a radial aperture or a circular aperture. In some cases, an aperture can have a diameter of about 1 mm aperture. In some cases, the focus of the light is aligned with the core of a fiber, whereby only that light which is properly aligned to the core of the fiber will make it into that fiber. Thereafter, that light will be propagated down the fiber. In this sense, the core of the fiber can operate as a filter, spatial mask, or pinhole aperture, whereby light coupled into the core of the fiber is propagated, and undesired light is filtered or masked out. Often, a fiber will operate in conjunction with a lens. In some embodiments, the fiber can be provided as a collimated fiber optic. In some cases, light is focused into the fiber, or into the core of the fiber, using a lens. The light can be propagated in the fiber by way of total internal reflection. Where light is not properly aligned with the fiber core, such light may not propagate down the fiber, or be coupled into that fiber.

Put another way, light that is at a different focal plane, in the tissue, will not be at the same focal plane, over at the pinhole or spatial filter side, and hence becomes filtered out. The out of focus light will not make it into the pinhole or spatial aperture, and won't be coupled into the fiber, because that light is not aligned (e.g. not at the same focal plane, confocal, or conjugate).

As shown here, the patient interface system 1400 can include a processing assembly (e.g. such as the processing assembly depicted in FIG. 8) in operative association with the optical scanning assembly 1410, the objective lens assembly 1414, the eye camera assembly 1428, the fixation assembly (1429a, 1429c), and the Brillouin spectrometer assembly 1434. The processing assembly can include a processor, an electronic storage location operatively coupled with the processor, and processor executable code stored on the electronic storage location and embodied in a tangible non-transitory computer readable medium. The processor executable code can include machine-readable instructions that, when executed by the processor, cause the processor to generate x,y coordinate scan control signals for the optical scanning assembly 1410. In some cases, x,y coordinate scan control signals for the optical scanning assembly 1410 can be generated based on the electrical signals generated by the eye camera assembly 1428. The processor executable code can include machine-readable instructions that, when executed by the processor, cause the processor to generate z coordinate scan control signals for the objective lens assembly 1414. In some cases, the x,y coordinate scan control signals, the z coordinate scan control signals, or both the x,y coordinate scan control signals and the z coordinate scan control signals, can be based on an image of the eye. In some cases, the x,y coordinate scan control signals, the z coordinate scan control signals, or both the x,y coordinate scan control signals and the z coordinate scan control signals, can be generated independent of an image of the eye. In some cases, the x,y coordinate scan control signals, the z coordinate scan control signals, or both the x,y coordinate scan control signals and the z coordinate scan control signals, can be generated according to a pre-defined or pre-determined scan pattern. The processor executable code can include machine-readable instructions that, when executed by the processor, cause the processor to generate an elastic stiffness map for a volume of ophthalmic tissue of the eye 1422 based on Brillouin signals. In some cases, the optical scanning assembly 1410 may include a prism pair, for example a prism pair as depicted in FIG. 3. In some cases, the prism pair can provide an operational range of $\theta = \pm 10°$.

As shown in FIG. 14, the eye 1422 can be at an on-axis orientation relative to the general trajectory of the scanning diagnostic beam after the scanning diagnostic beam exits the objective lens assembly 1414. In this way, the focused portion 1416 of the scanning diagnostic beam and the imaging light 1430 that travels from the eye to the shortpass dichroic filter are aligned in a colinear path. Dichroic filters can operate to reflect or reject light having certain wavelengths, and to transmit light having certain wavelengths.

According to some embodiments, the system 1400 can include one or more illumination lamps or light devices 1426 that direct illumination light or radiation 1427 toward the eye. In some cases, the illumination light or radiation 1427 can be infrared light. In some cases, the illumination light or radiation 1427 can be non-visible light. In some cases, the illumination light 1427 can have a wavelength value within a range from about 700 nm to about 1,000,000 nm. In some case, the illumination light 1427 can have a wavelength value of about 940 nm. According to some embodiments, the eye camera assembly 1428 is sensitive to the wavelength of the illumination light 1427 (which can also be the same as or similar to the wavelength of the imaging light 1430).

In some cases, the illumination light 1427 can have a wavelength value that is greater than a wavelength value of the diagnostic scanning light or radiation. In some cases, the diagnostic beam (e.g. 1404, 1416) has a wavelength value within a range from about 450 to about 1350 nm. In some cases, the wavelength of the scanning diagnostic beam has a value of about 780 nm. In some cases, the scanning diagnostic radiation can have a wavelength value within a range from about 450 to about 1350 nm. In some cases, the fixation light 1429b, 1429d is visible light. In some cases, the fixation light 1429b, 1429d is visible green light. In some cases, the fixation light 1429b, 1429d has a wavelength value of about 520 to about 560 nm. According to some embodiments, the fixation assembly generates light 1429b, 1429d that provides the eye with a gaze target, which can be helpful in a clinical setting or application. In some cases, a system or method can include a gaze target that is not provided by a light emitting fixation assembly.

As shown in FIG. 14, the shortpass dichroic filter 1418a can operate to transmit the incoming and returning scanning diagnostic beam, and to reflect the imaging light 1430 (which can be illumination light 1427 reflected from the eye).

According to some embodiments, the focused scanning diagnostic laser beam 1416 optical path and the imaging light 1430 optical path are provided as integrated colinear optical paths. In some cases, the respective optical paths may not be integrated in a colinear fashion. In some cases, by providing integrated colinear optical paths, it is possible to avoid or eliminate geometric distortions of the image that may otherwise be present when using an off-axis camera (even though it may be possible to achieve the same focal point for a laser, relative to the focus of the imaging camera).

In some cases, by providing integrated colinear optical paths, it is possible to more efficiently register biomechanical data to eye location and/or orientation data pertaining to a real world eye space. In some cases, it is possible to use eye tracker or camera information to register and track where those points have been scanned, relative to certain features and/or registration coordinates on the eye.

As shown in FIG. 14, in this embodiment there may be no lens between the shortpass dichroic filter 1418a and the eye camera assembly 1428. In some cases, the eye camera assembly 1428 includes an eye tracker camera and an imaging lens (e.g. f=~25 mm). In some cases, the eye camera assembly includes an imaging lens or a lens assembly/objective. Also, in this embodiment the shortpass dichroic filter 1418a is positioned in the collimated space between the optical scanning assembly 1410 and the objective lens assembly 1414, and a portion of the camera path is also positioned in the collimated space between the optical scanning assembly 1410 and the objective lens assembly 1414.

According to some embodiments, the eye camera assembly 1428 of patient interface system 1400 can image through a path that is aligned with the laser path. Patient interface system 1400 can involve a co-axial scanning laser that is reflected at 90 degrees. Lateral xy scanning can be achieved by a Risley prism pair. In some cases, the Risley prism pair can provide direct eye scanning. Optical xy scanning can be achieved with a Risley prism pair. In some cases, the quarter wave plate assembly 1417 can be positioned downstream of the objective lens assembly 1414 for purposes of optical isolation. In some cases, mechanical configurations can involve transmitting the laser through a splitter. One aspect of such a mechanical configuration is that there may be no 90 degree reflection required by the laser path. This may make it easier to achieve a desired working distance easier or making it even larger without necessarily putting constraints on the objective lens. In some cases, the optical challenges may be more substantial with additional aberrations from introducing the dichroic before the objective and constraints on distance imaging to achieve the desired eye FOV with certain image quality through the laser scanning objective. According to some embodiments, there is a mechanical decoupling between the eye camera assembly 1428 and the laser scanning. System 1400 can provide a configuration where all optics are on axis, where testing for alignment can be achieved with only a line scan instead of a 3D scan volume, where there is no optical scanning, and/or there is an inherently telecentric arrangement. Patient interface system 1400 can provide a diffraction limited focused spot over an entire focal volume. It is understood that an eye or any other sample with aberrations may make it so the spot is not diffraction limited.

In some cases, the patient interface system 1400 depicted in FIG. 14 can incorporate one or more features of the embodiment depicted in FIG. 8. FIG. 14 shows details regarding a reference path 1408a that is used to measure a sample 1408c containing plastic and water, that has known elastic properties. This can be used to normalize the data that is received from the actual tissue being analyzed, for example the cornea or the crystalline lens. Light can be controlled by a pair of shutters 1407, 1407a, and operation of the shutters can determine whether the laser light is going to hit the reference path, or whether the laser is going to hit the sample path. FIG. 14 also illustrates that a fixation assembly can include separate fixation mechanisms. The system can be configured to illuminate one or both fixation mechanisms, so as to control where the patient directs their gaze. In this way, it is possible to facilitate the measurement of certain areas of the eye that otherwise may be difficult to scan or measure when the patient is looking directly straight-forward. Accordingly, the system can facilitate a computerized control of the orientation of the eye, by changing the gaze angle.

FIG. 15 depicts aspects of a patient interface system 1500 according to embodiments of the present invention. As discussed elsewhere herein, system 1500 can be used to generate an elastic stiffness map for a volume of an ophthalmic tissue of an eye of a patient. As shown here, system 1500 includes a laser assembly or light source 1502 that generates a collimated diagnostic laser beam 1504 (e.g. by using a lens 1503, such as a 4 mm beam expansion lens), a polarizing beam splitter 1506 that reflects a portion 1508 of the collimated diagnostic laser beam 1504, and the reflected portion 1508 is then transmitted to a laser beam expansion assembly 1509, which converts beam 1508 to an expanded beam 1509a. In some cases, light source 1502 can be a device that produces electromagnetic radiation characterized by one or more wavelengths or one or more frequencies. According to some embodiments, the electromagnetic radiation beam expansion assembly 1509 expands a collimated scanning diagnostic laser beam from a first diameter to a second diameter that is larger than the first diameter. The laser beam expansion assembly 1509 may include multiple lenses. In some cases, the laser beam expansion assembly 1509 includes lenses disposed in a Galilean configuration, with a negative lens followed by a positive lens. In some case, the laser beam expansion assembly 1509 can be provided as a Galilean type beam expander. In some cases, the collimated scanning diagnostic laser beam has a linear polarization orientation. In turn, expanded beam 1509a is transmitted to an objective lens assembly 1514.

As shown here, the polarizing beam splitter 1506 can be positioned before the laser beam expansion assembly 1509. The polarizing beam splitter 1506 can operate to split the diagnostic laser beam 1504 into a scanning portion 1508 and a non-scanning portion 1508a. In some cases, the beam splitter 1506 allows for the measurement (e.g. concurrent) of a reference sample. In some cases, the beam splitter 1506 operates to provide an additional amount of filtration of back reflections of light. Filtration can be based on polarization, and may involve aspects of a conventional optical isolator based on polarizing optics and a quarter wave plate. In some cases, the polarizing beam splitter 1506 transmits light at a 90 degrees orientation and on the return path the light goes to 90 degrees. According to some embodiments, the beam splitter 1506 works in conjunction with the quarter wave plate 1517. For example, after two passes through the waveplate 1517, the returning light can be passed back to the spectrometer assembly 1534, and light that has only passed once (e.g. reflections from lenses) will be excluded. In some cases, when the light first enters the quarter wave plate 1517, some amount can be portioned to a calibrated reference sample. A half-waveplate element 1505 may also be positioned after the laser source which sets up a ratio of linearly polarized s and p. This can control the light split through the polarizing beam splitter (PBS). According to some embodiments, a Brillouin signal from a sample can be used as a built in reference to the instrument for accurate calculation of the Brillouin signal. There may also be a quarter waveplate on the reference path to provide an isolated signal that will make its way back to the spectrometer.

According to some embodiments, the beam expansion assembly 1509 operates to adjust or redirect a beam path of the expanded collimated scanning diagnostic laser beam. In some cases, the patient interface system 1500 may not include the polarizing beam splitter 1506.

The beam expansion assembly 1509 operates to redirect a beam path of the reflected portion 1508 of the collimated scanning diagnostic laser beam. The redirected reflected portion 1509a of the collimated scanning diagnostic laser beam is then transmitted to an objective lens assembly 1514, which operates to focus the redirected portion 1509a of the collimated scanning diagnostic laser beam to produce a focused scanning diagnostic laser beam 1516. According to some embodiments, system 1500 provides a working distance of about 50 mm.

According to some embodiments, the objective lens assembly 1514 operates to focus the expanded collimated scanning diagnostic laser beam 1509a to produce a focused scanning diagnostic laser beam 1516 having a beam waist or focused spot. In some cases, the objective lens assembly 1514 operates to adjust a scan position of the beam waist or focused spot. In some cases, the objective lens assembly 1514 includes a motorized stage 1514a that allows the objective lens assembly to travel toward and away from the beam expansion assembly 1509. In some cases, the operation of motorized stage 1514a moves both the objective lens assembly 1514a and the eye camera assembly 1528 in unison (e.g. toward or away from the eye). In some cases, the beam expansion assembly 1509 includes a motorized stage 1509d that allows the optical scanning assembly (or beam expansion assembly) to travel toward and away from the objective lens assembly 1514, and/or in a plane perpendicular to the beam path. In some cases, the beam expansion assembly and the objective lens assembly include or are disposed on respective motorized stages, or are disposed on a common motorized stage, so that the beam expansion assembly and the objective lens assembly can move in tandem.

As shown here, system 1500 may include a quarter-wave plate assembly 1517. In some embodiments, the quarter-wave plate assembly 1517 operates to convert the focused scanning diagnostic laser beam 1516 from a linear polarization orientation to a circular polarization orientation. In some embodiments, the quarter-wave plate assembly 1517 operates to provide a 45 degree rotation to the focused scanning diagnostic laser beam 1516. In some cases, the quarter-wave plate assembly 1517 operates to convert the focused scanning diagnostic laser beam 1516 from p-polarized light to s-polarized light. In some cases, the quarter-wave plate assembly 1517 operates to convert the focused scanning diagnostic laser beam 1516 from s-polarized light to p-polarized light. The quarter-wave plate assembly 1517 can be placed along the beam path, for example between the objective lens assembly 1514 and the eye 1522. In some embodiments, the quarter-wave plate assembly 1517 can be placed upstream of the objective lens assembly 1514. In some cases, the quarter-wave plate assembly 1517 can be placed anywhere as desired, between the sample (e.g. eye) and the PBS.

The focused scanning diagnostic laser beam 1516 is transmitted toward an eye 1522 of the patient. In some cases, the focused scanning diagnostic laser beam has a circular polarization orientation. In some cases, a dichroic filter will transmit light within a certain wavelength band or range and/or reflect light within a certain wavelength band or range. As shown here, dichroic filters can operate to fold together, or to separate out, different wavelengths of light (e.g. into a common optical path).

In some case, the dichroic filters can operate to fold together imaging light 1530, and scanning diagnostic light 1516, into a common optical path (e.g. between the shortpass dichroic filter 1518a and the eye 1522). Similarly, a dichroic can operate to peel apart light from a common path into separate optical paths, for example imaging light 1530 and returned scanning diagnostic light travel along a common optical path from the eye to the shortpass dichroic filter 1518a, and then the returned scanning diagnostic light is transmitted through the shortpass dichroic filter 1518a and the imaging light is reflected by the shortpass dichroic filter 1518a.

The focused scanning diagnostic laser beam 1516 has focused spot 1524, and operation of the beam expansion assembly 1509 or the objective lens assembly 1514, or the combined operation of the beam expansion assembly 1509 and the objective lens assembly 1514, can adjust a scan position of the focused spot 1524 to various discrete locations on or within one or more tissues of the eye 1522.

The patient interface system 1500 also includes an eye camera assembly 1528 that receives imaging light 1530 from the eye (which optionally may have been reflected by a shortpass dichroic filter 1518a of a beam control assembly) and that generates electrical signals in response to the received imaging light 1530. The imaging light 1530 can provide registration information regarding the position and/or orientation of the eye. In some cases, this registration information can be used (e.g. by a processing assembly, such as a processing assembly as depicted in FIG. 9) to provide locate elasticity measurement data obtained by the Brillouin spectrometer assembly 1534 to particular points of the eye. In some cases, the imaging light 1530 can help to provide feedback, which may be continuous feedback, to the processing assembly. The imaging light 1530 can be processed to provide information regarding a center coordinate of the eye, a central reference of the eye, or more generically, a reference coordinate on the eye, which can be registered to the biomechanical data. Such a reference coordinate can be determined by processing the imaging data.

In some cases, a processing assembly (such as the processing assembly depicted in FIG. 9) can operate to generate two images, specifically an image of the eye and a Brillouin heat map (e.g. stiffness values at discrete points), and to accurately superimpose those images on top of each other using registration. In this way, the mechanical information is relevant in the physical space. In some cases, the processing assembly does not perform a superimposition. Rather, a camera is used to provide a reference point to begin a scan pattern, and thereafter a scan is performed according to the pattern, so as to generate the stiffness map. The map can indicate whether there are any abnormal spots or points of interest on the eye, without providing the exact location on the eye of the abnormal spots or points of interest. In some cases, a camera is not used to provide a reference point to begin a scan pattern. For example, the physician or operate could manually inspect the person's eye, and then aim the beam, without using a camera. In some cases, it is possible to illuminate the person's eye using a certain wattage, observe a reflection off the person's eye, and determine that the alignment of the scanning beam and the eye is sufficient.

Hence, input techniques for aiming the diagnostic beam can include using a camera image or data, manually aiming the beam, or using feedback from the Brillouin spectrometer. For example, data obtained by the spectrometer can provide an indication of whether the system is in focus. The Brillouin spectrometer can be used to differentiate spectral shifts that are characteristic of different tissues. In some cases, as the focused spot is scanned in the z depth direction, it is possible to detect fundamentally different frequency shifts (or different information) as the focused spot goes through different layers (e.g. going from the air, to the cornea surface, to the aqueous humor, to the crystalline lens, and so on) which can correspond to different elastic properties (e.g. elastic modulus). In this sense, the Brillouin approach can provide aspects of an imaging modality. Hence, it may be possible to determine where the focused spot is located (e.g. along a z-axis), by observing or analyzing the spectrometer image. In some cases, it is possible to align or position the patient interface system, by observing or using a reflection off of a person's eye, then moving the system into focus based on feedback from the spectrometer camera, and then initiating the scan. In some cases, the camera is parfocal with the laser beam, and the focus of the eye can also be used.

In some embodiments, system 1500 also includes a fixation assembly that provides the eye with a gaze target, the fixation assembly having a first fixation mechanism 1529a that transmits a first fixation light 1529b toward the eye, and a second fixation mechanism 1529c that transmits a second fixation light 1529d toward the eye. According to some embodiments, the fixation assembly includes light-emitting diodes (LEDs). In some cases, the fixation light is a collimated green light produced by a light emitting diode.

The patient interface system 1500 can further include a Brillouin spectrometer assembly 1534 having a Brillouin spectrometer and a spatial filter that is parfocal with the focused spot 1524 (e.g. in a conjugate focal plane). The Brillouin spectrometer can generate Brillouin signals as the focused spot 1524 is scanned to discrete locations throughout a volume or plane thickness of ophthalmic tissue of the eye 1522. Brillouin scattered light from the focused spot at the discrete locations is returned to the spatial filter. According to some embodiments, the spatial filter operates as an input for the Brillouin spectrometer, and is in conjugate alignment with the focused spot 1524 or beam waist of the focused scanning diagnostic laser beam, and the Brillouin spectrometer can generate Brillouin signals as the focused spot 1524 or beam waist of the focused scanning diagnostic beam is scanned to discrete locations throughout the volume of the ophthalmic tissue of the eye 1522. In some cases, the spatial filter can operate to exclude information associated with out of focus focal planes, and include information associated with the focal plane of interest. The filter can provide sensitivity to locations where the focused spot 1524 is positioned, and little or no sensitivity to extraneous locations. In some cases, a spatial filter can be provided without using a fiber. In some cases, the spatial filter can operate to prime the incoming light, which is then measured by the spectrometer, which in turn generates the spectrum (e.g. Brillouin) signals.

By using a fiber input, it is possible to provide modularity to the system, whereby the patient scanning interface can be decoupled and coupled with the spectrometer via the optical fiber. Such modularity can provide enhanced testing and serviceability advantages. For example, the optical fiber could be uncoupled from one patient interface system, and coupled with another patient interface system. Hence, if one patient interface were to malfunction, it could be replaced with another patient interface. This could also allow patient interfaces to be tested as modules, which can improve manufacturability.

From an optical standpoint, a fiber can provide a highly functional pinhole. In some cases, such embodiments can provide a separate input and output. It is possible to physically decouple with free space optics the input and output of the system. In some embodiments, the input is not separated from the output. For example, the same light can be coupled back into the same input path and optionally the beam could be redirected to the spectrometer after traveling back down the fiber.

According to some embodiments, an optical output out of a single mode fiber can provide or approach a perfect Gaussian distribution, which has desirable beam shape and optical quality characteristics, and can be well suited for use with sensitive optical elements. As such, this feature can help optimize the optical performance of the overall system, particularly when multiple optical elements are involved.

In some cases, a fiber can operate as a conjugate pinhole or aperture (or spatial filter) for the focus spot in the tissue that is being analyzed. The fiber can operate to provide a focal plane resolution and specificity, filtering out the out of focus light that is not of interest. In some cases, a spatial filter can be provided as a radial aperture or a circular aperture. In some cases, an aperture can have a diameter of about 1 mm aperture. In some cases, the focus of the light is aligned with the core of a fiber, whereby only that light which is properly aligned to the core of the fiber will make it into that fiber. Thereafter, that light will be propagated down the fiber. In this sense, the core of the fiber can operate as a filter, spatial mask, or pinhole aperture, whereby light coupled into the core of the fiber is propagated, and undesired light is filtered or masked out. Often, a fiber will operate in conjunction with a lens. In some embodiments, the fiber can be provided as a collimated fiber optic. In some cases, light is focused into the fiber, or into the core of the fiber, using a lens. The light can be propagated in the fiber by way of total internal reflection. Where light is not properly aligned with the fiber core, such light may not propagate down the fiber, or be coupled into that fiber.

Put another way, light that is at a different focal plane, in the tissue, will not be at the same focal plane, over at the pinhole or spatial filter side, and hence becomes filtered out. The out of focus light will not make it into the pinhole or spatial aperture, and won't be coupled into the fiber, because that light is not aligned (e.g. not at the same focal plane, confocal, or conjugate).

As shown here, the patient interface system 1500 can include a processing assembly (such as the processing assembly depicted in FIG. 9) in operative association with the beam expansion assembly 1509, the objective lens assembly 1514, the eye camera assembly 1528, the fixation assembly (1529a, 1529c), and the Brillouin spectrometer assembly 1534. The processing assembly can include a processor, an electronic storage location operatively coupled with the processor, and processor executable code stored on the electronic storage location and embodied in a tangible non-transitory computer readable medium. The processor executable code can include machine-readable instructions that, when executed by the processor, cause the processor to generate x,y coordinate scan control signals for the beam expansion assembly 1509. In some cases, x,y coordinate scan control signals for the beam expansion assembly 1509 can be generated based on the electrical signals generated by the eye camera assembly 1528. The processor executable code can include machine-readable instructions that, when executed by the processor, cause the processor to generate z coordinate scan control signals for the objective lens assembly 1514. In some cases, the x,y coordinate scan control signals, the z coordinate scan control signals, or both the x,y coordinate scan control signals and the z coordinate scan control signals, can be based on an image of the eye. In some cases, the x,y coordinate scan control signals, the z coordinate scan control signals, or both the x,y coordinate scan control signals and the z coordinate scan control signals, can be generated independent of an image of the eye. In some cases, the x,y coordinate scan control signals, the z coordinate scan control signals, or both the x,y coordinate scan control signals and the z coordinate scan control signals, can be generated according to a pre-defined or pre-determined scan pattern. The processor executable code can include machine-readable instructions that, when executed by the processor, cause the processor to generate an elastic stiffness map for a volume of ophthalmic tissue of the eye 1522 based on Brillouin signals.

As shown in FIG. 15, the eye 1522 can be at an on-axis orientation relative to the general trajectory of the scanning diagnostic beam after the scanning diagnostic beam exits the objective lens assembly 1514. In this way, the focused portion 1516 of the scanning diagnostic beam and the imaging light 1530 that travels from the eye to the shortpass dichroic filter are aligned in a colinear path. Dichroic filters can operate to reflect or reject light having certain wavelengths, and to transmit light having certain wavelengths.

According to some embodiments, the system 1500 can include one or more illumination lamps or light devices 1526 that direct illumination light or radiation 1527 toward the eye. In some cases, the illumination light or radiation 1527 can be infrared light. In some cases, the illumination light or radiation 1527 can be non-visible light. In some cases, the illumination light 1527 can have a wavelength value within a range from about 700 nm to about 1,000,000 nm. In some case, the illumination light 1527 can have a wavelength value of about 940 nm. According to some embodiments, the eye camera assembly 1528 is sensitive to the wavelength of the illumination light 1527 (which can also be the same as or similar to the wavelength of the imaging light 1530).

In some cases, the illumination light 1527 can have a wavelength value that is greater than a wavelength value of the diagnostic scanning light or radiation. In some cases, the diagnostic beam (e.g. 1504, 1516) has a wavelength value within a range from about 450 to about 1350 nm. In some cases, the wavelength of the scanning diagnostic beam has a value of about 780 nm. In some cases, the scanning diagnostic radiation can have a wavelength value within a range from about 450 to about 1350 nm. In some cases, the fixation light 1529b, 1529d is visible light. In some cases, the fixation light 1529b, 1529d is visible green light. In some cases, the fixation light 1529b, 1529d has a wavelength value of about 520 to about 560 nm. According to some embodiments, the fixation assembly generates light 1529b, 1529d that provides the eye with a gaze target, which can be helpful in a clinical setting or application. In some cases, a system or method can include a gaze target that is not provided by a light emitting fixation assembly.

As shown in FIG. 15, the shortpass dichroic filter 1518a can operate to transmit the incoming and returning scanning diagnostic beam, and to reflect the imaging light 1530 (which can be illumination light 1527 reflected from the eye).

According to some embodiments, the focused scanning diagnostic laser beam 1516 optical path and the imaging light 1530 optical path are provided as integrated colinear optical paths. In some cases, the respective optical paths may not be integrated in a colinear fashion. In some cases, by providing integrated colinear optical paths, it is possible to avoid or eliminate geometric distortions of the image that may otherwise be present when using an off-axis camera (even though it may be possible to achieve the same focal point for a laser, relative to the focus of the imaging camera).

In some cases, by providing integrated colinear optical paths, it is possible to more efficiently register biomechanical data to eye location and/or orientation data pertaining to a real world eye space. In some cases, it is possible to use eye tracker or camera information to register and track where those points have been scanned, relative to certain features and/or registration coordinates on the eye.

As shown in FIG. 15, in this embodiment there may be no lens between the shortpass dichroic filter 1518a and the eye camera assembly 1528. In some cases, the eye camera assembly 1528 includes an eye tracker camera and an imaging lens (e.g. f=~25 mm). In some cases, the eye camera assembly includes an imaging lens or a lens assembly/objective. Also, in this embodiment the shortpass dichroic filter 1518a is positioned in the collimated space between the optical scanning assembly 1510 and the objective lens assembly 1514, and a portion of the camera path is also positioned in the collimated space between the optical scanning assembly (or beam expansion assembly 1509) and the objective lens assembly 1514.

In some cases, the patient interface system 1500 depicted in FIG. 15 can incorporate one or more features of the embodiment depicted in FIG. 9. FIG. 15 shows details regarding a reference path 1508a that is used to measure a sample 1508c containing plastic and water, that has known elastic properties. This can be used to normalize the data that is received from the actual tissue being analyzed, for example the cornea or the crystalline lens. Light can be controlled by a pair of shutters 1507, 1507a, and operation of the shutters can determine whether the laser light is going to hit the reference path 1508a, or whether the laser is going to hit the sample path 1508. FIG. 15 also illustrates that a fixation assembly can include separate fixation mechanisms. The system can be configured to illuminate one or both fixation mechanisms, so as to control where the patient directs their gaze. In this way, it is possible to facilitate the measurement of certain areas of the eye that otherwise may be difficult to scan or measure when the patient is looking directly straightforward. Accordingly, the system can facilitate a computerized control of the orientation of the eye, by changing the gaze angle.

Figure 16:
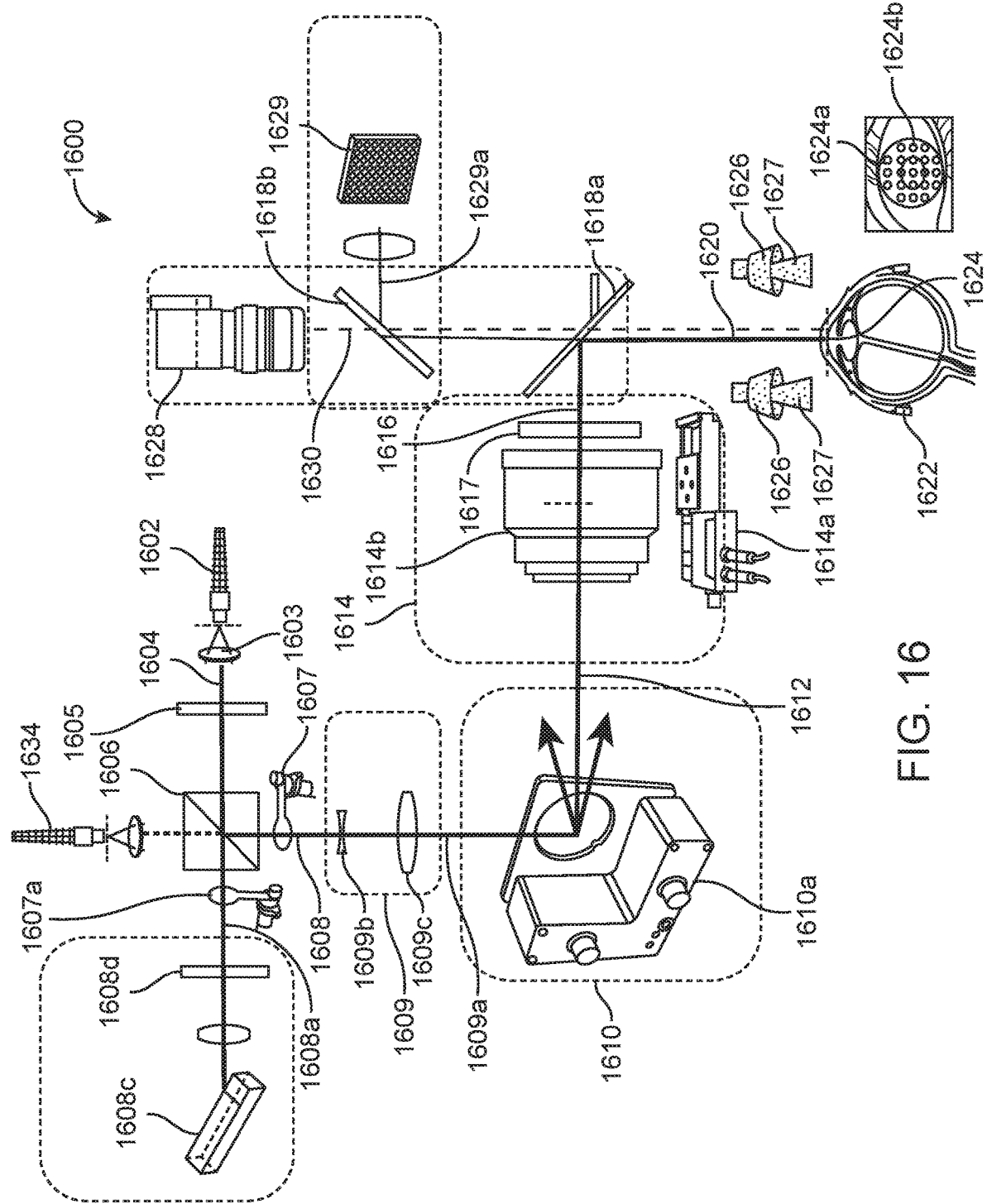
FIG. 16 depicts aspects of a system for generating an elastic stiffness map for a volume of an ophthalmic tissue of an eye of a patient, according to embodiments of the present invention.

FIG. 16 depicts aspects of a patient interface system 1600 according to embodiments of the present invention. As discussed elsewhere herein, system 1600 can be used to generate an elastic stiffness map for a volume of an ophthalmic tissue of an eye of a patient. As shown here, system 1600 includes a laser assembly or light source 1602 (e.g. collimated fiber input, 780 nm) and lens 1603 (e.g. 4 mm beam expansion) that generate a collimated diagnostic laser beam 1604, a polarizing beam splitter 1606 that reflects a portion 1608 of the collimated diagnostic laser beam 1604, and the reflected portion 1608 is then transmitted to a laser beam expansion assembly 1609, which converts beam 1608 to an expanded beam 1609a. Optionally, a shutter mechanism 1607 having one or more shutters can be disposed between the polarizing beam splitter 1606 and the laser beam expansion assembly 1609. In some cases, light source 1602 can be a device that produces electromagnetic radiation characterized by one or more wavelengths or one or more frequencies. According to some embodiments, the electromagnetic radiation beam expansion assembly 1609 expands a collimated scanning diagnostic laser beam from a first diameter to a second diameter that is larger than the first diameter. The laser beam expansion assembly 1609 may include multiple lenses (e.g. lenses 1609b, 1609c). In some cases, the laser beam expansion assembly 1609 includes lenses disposed in a Galilean configuration, with a negative lens followed by a positive lens. In some case, the laser beam expansion assembly 1609 can be provided as a Galilean type beam expander. In some cases, the collimated scanning diagnostic laser beam has a linear polarization orientation. In turn, expanded beam 1609a is transmitted to an optical scanning assembly 1610.

As shown here, the polarizing beam splitter 1606 can be positioned before the laser beam expansion assembly 1609. The polarizing beam splitter 1606 can operate to split the diagnostic laser beam 1604 into a scanning portion 1608 and a non-scanning portion 1608a. In some cases, the beam splitter 1606 allows for the measurement (e.g. concurrent) of a reference sample 1608c. In some cases, the beam splitter 1606 operates to provide an additional amount of filtration of back reflections of light. In some cases, the polarizing beam splitter 1606 transmits light at a 90 degrees orientation and on the return path the light goes to 90 degrees. According to some embodiments, the beam splitter 1606 works in conjunction with the quarter wave plate 1617. For example, after two passes through the waveplate 1617, the returning light can be passed back to the spectrometer assembly 1634, and light that has only passed once (e.g. reflections from lenses) will be excluded. In some cases, when the light first enters the quarter wave plate 1617, some amount can be portioned to a calibrated reference sample. A half-waveplate element 1605 may also be positioned after the laser source which sets up a ratio of linearly polarized s and p. This can control the light split through the polarizing beam splitter (PBS). According to some embodiments, a Brillouin signal from a sample can be used as a built in reference to the instrument for accurate calculation of the Brillouin signal. There may also be a quarter waveplate (λ/4) 1608d on the reference path to provide an isolated signal that will make its way back to the spectrometer.

According to some embodiments, the optical scanning assembly 1610 operates to adjust or redirect a beam path of the expanded collimated scanning diagnostic laser beam. In some cases, the patient interface system 1600 may not include the polarizing beam splitter 1606. The optical scanning assembly 1610 operates to redirect a beam path of the reflected portion 1608 of the collimated scanning diagnostic laser beam. The redirected reflected portion 1612 of the collimated scanning diagnostic laser beam is then transmitted to an objective lens assembly 1614, which operates to focus the redirected portion 1612 of the collimated scanning diagnostic laser beam to produce a focused scanning diagnostic laser beam 1616.

According to some embodiments, the objective lens assembly 1614 operates to focus the expanded collimated scanning diagnostic laser beam 1612 to produce a focused scanning diagnostic laser beam 1616 having a beam waist or focused spot. According to some embodiments, system 1600 provides a working distance of about 50 mm. In some cases, objective lens assembly 1614 includes a waveplate 1617 and an objective lens 1614b. In some cases, objective lens 1614b is a 0.125 NA objective lens. In some cases, the objective lens assembly 1614 operates to adjust a scan position of the beam waist or focused spot. In some cases, the objective lens assembly 1614 includes a motorized stage 1614a that allows the objective lens assembly to travel toward and away from the optical scanning assembly 1610. In some cases, the optical scanning assembly 1610 includes a motorized stage that allows the optical scanning assembly to travel toward and away from the objective lens assembly 1614. In some cases, the optical scanning assembly and the objective lens assembly include or are disposed on respective motorized stages, or are disposed on a common motorized stage, so that the optical scanning assembly and the objective lens assembly can move in tandem.

As shown here, system 1600 may include a quarter-wave plate assembly 1617. In some embodiments, the quarter-wave plate assembly 1617 operates to convert the focused scanning diagnostic laser beam 1616 from a linear polarization orientation to a circular polarization orientation. In some embodiments, the quarter-wave plate assembly 1617 operates to provide a 45 degree rotation to the focused scanning diagnostic laser beam 1616. In some cases, the quarter-wave plate assembly 1117 operates to convert the focused scanning diagnostic laser beam 1116 from p-polarized light to s-polarized light. In a double pass embodiment, s-polarized light can be converted to p-polarized light (e.g. whatever is orthogonal to the input wave). In some cases, the quarter-wave plate assembly 1617 operates to convert the focused scanning diagnostic laser beam 1616 from s-polarized light to p-polarized light. The quarter-wave plate assembly 1617 can be placed along the beam path, for example between the objective lens assembly 1614 and the shortpass dichroic filter 1618a. In some embodiments, the quarter-wave plate assembly 1617 can be placed upstream of the objective lens assembly 1614 or downstream of the shortpass dichroic filter 1618a. In some cases, the quarter-wave plate assembly 1617 can be placed anywhere as desired, between the sample (e.g. eye) and the PBS. In some cases, the quarter wave plate assembly operates to isolate out back reflections from system, for example as described elsewhere herein. In some case, the quarter-wave plate is configured to perform the classical operation of an optical isolator.

The focused scanning diagnostic laser beam 1616 is reflected by a shortpass dichroic filter 1618a, and the reflected focused portion is transmitted toward an eye 1622 of the patient. In some cases, the focused scanning diagnostic laser beam has a circular polarization orientation and is reflected by the shortpass dichroic filter 1118a toward the eye 1122. In some cases, isolation and redirecting are the core functions performed on the beam. In some cases, the returning beam is transformed back to linear polarization again when it passes back through the waveplate.

According to some embodiments, a dichroic filter can operate as a beam splitter that splits light based on wavelength or color, rather than splitting light based on power. In some cases, a dichroic filter will transmit light within a certain wavelength band or range and/or reflect light within a certain wavelength band or range. As shown here, dichroic filters can operate to fold together, or to separate out, different wavelengths of light (e.g. into a common optical path).

In some case, the dichroic filters can operate to fold together fixation light 1629a, imaging light 1630, and scanning diagnostic light 1620, into a common optical path (e.g. between the shortpass dichroic filter 1618a and the eye 1622). Similarly, a dichroic can operate to peel apart light from a common path into separate optical paths, for example imaging light 1630 and returned scanning diagnostic light travel along a common optical path from the eye to the shortpass dichroic filter 1618a, and then the imaging light is transmitted through the shortpass dichroic filter 1618a and the returned scanning diagnostic light is reflected by the shortpass dichroic filter 1618a.

The reflected focused scanning diagnostic laser beam 1620 has focused spot 1624, and operation of the optical scanning assembly 1610 or the objective lens assembly 1614, or the combined operation of the optical scanning assembly 1610 and the objective lens assembly 1614, can adjust a scan position of the focused spot 1624 to various discrete locations (e.g. 1624a, 1624b) on or within one or more tissues of the eye 1622.

The patient interface system 1600 also includes an eye camera assembly 1628 that receives imaging light 1630 from the eye (which optionally may have passed through a shortpass dichroic filter 1618a and a longpass dichroic filter 1618b of a beam control assembly) and that generates electrical signals in response to the received imaging light 1630. The imaging light 1630 can provide registration information regarding the position and/or orientation of the eye. In some cases, this registration information can be used (e.g. by a processing assembly, such as the processing assembly described in FIG. 5) to provide locate elasticity measurement data obtained by the Brillouin spectrometer assembly 1634 to particular points of the eye. In some cases, the imaging light 1630 can help to provide feedback, which may be continuous feedback, to the processing assembly. The imaging light 1630 can be processed to provide information regarding a center coordinate of the eye, a central reference of the eye, or more generically, a reference coordinate on the eye, which can be registered to the biomechanical data. Such a reference coordinate can be determined by processing the imaging data.

In some cases, the processing assembly can operate to generate two images, specifically an image of the eye and a Brillouin heat map (e.g. stiffness values at discrete points), and to accurately superimpose those images on top of each other using registration. In this way, the mechanical information is relevant in the physical space. In some cases, the processing assembly does not perform a superimposition. Rather, a camera is used to provide a reference point to begin a scan pattern, and thereafter a scan is performed according to the pattern, so as to generate the stiffness map. The map can indicate whether there are any abnormal spots or points of interest on the eye, without providing the exact location on the eye of the abnormal spots or points of interest. In some cases, a camera is not used to provide a reference point to begin a scan pattern. For example, the physician or operate could manually inspect the person's eye, and then aim the beam, without using a camera. In some cases, it is possible to illuminate the person's eye using a certain wattage, observe a reflection off the person's eye, and determine that the alignment of the scanning beam and the eye is sufficient.

Hence, input techniques for aiming the diagnostic beam can include using a camera image or data, manually aiming the beam, or using feedback from the Brillouin spectrometer. For example, data obtained by the spectrometer can provide an indication of whether the system is in focus. The Brillouin spectrometer can be used to differentiate spectral shifts that are characteristic of different tissues. In some cases, as the focused spot is scanned in the z depth direction, it is possible to detect fundamentally different frequency shifts (or different information) as the focused spot goes through different layers (e.g. going from the air, to the cornea surface, to the aqueous humor, to the crystalline lens, and so on) which can correspond to different elastic properties (e.g. elastic modulus). In this sense, the Brillouin approach can provide aspects of an imaging modality. Hence, it may be possible to determine where the focused spot is located (e.g. along a z-axis), by observing or analyzing the spectrometer image. In some cases, it is possible to align or position the patient interface system, by observing or using a reflection off of a person's eye, then moving the system into focus based on feedback from the spectrometer camera, and then initiating the scan. In some cases, the camera is parfocal with the laser beam, and the focus of the eye can also be used.

In some embodiments, system 1600 also includes a fixation assembly 1629 that provides the eye with a gaze target. In some cases, fixation light 1629a is generated by the fixation assembly 1629, travels from the fixation assembly 1629, is reflected by the longpass dichroic filter 1618b, travels through the shortpass dichroic filter 1618a, and to the eye 1622. According to some embodiments, the fixation assembly 1629 includes a matrix of light-emitting diode (LEDs).

The patient interface system 1600 can further include a Brillouin spectrometer assembly 1634 having a Brillouin spectrometer and a spatial filter that is parfocal with the focused spot 1624 (e.g. in a conjugate focal plane). The Brillouin spectrometer can generate Brillouin signals as the focused spot 1624 is scanned to discrete locations throughout a volume or plane thickness of ophthalmic tissue of the eye 1622. Brillouin scattered light from the focused spot at the discrete locations is returned to the spatial filter. According to some embodiments, the spatial filter operates as an input for the Brillouin spectrometer, and is in conjugate alignment with the focused spot 1624 or beam waist of the focused scanning diagnostic laser beam, and the Brillouin spectrometer can generate Brillouin signals as the focused spot 1624 or beam waist of the focused scanning diagnostic beam is scanned to discrete locations throughout the volume of the ophthalmic tissue of the eye 1622. In some cases, the spatial filter can operate to exclude information associated with out of focus focal planes, and include information associated with the focal plane of interest. The filter can provide sensitivity to locations where the focused spot is positioned, and little or no sensitivity to extraneous locations. In some cases, a spatial filter can be provided without using a fiber. In some cases, the spatial filter can operate to prime the incoming light, which is then measured by the spectrometer, which in turn generates the spectrum (e.g. Brillouin) signals.

By using a fiber input, it is possible to provide modularity to the system, whereby the patient scanning interface can be decoupled and coupled with the spectrometer via the optical fiber. Such modularity can provide enhanced testing and serviceability advantages. For example, the optical fiber could be uncoupled from one patient interface system, and coupled with another patient interface system. Hence, if one patient interface were to malfunction, it could be replaced with another patient interface. This could also allow patient interfaces to be tested as modules, which can improve manufacturability.

From an optical standpoint, a fiber can provide a highly functional pinhole. In some cases, such embodiments can provide a separate input and output. It is possible to physically decouple with free space optics the input and output of the system. In some embodiments, the input is not separated from the output. For example, the same light can be coupled back into the same input path and optionally the beam could be redirected to the spectrometer after traveling back down the fiber.

According to some embodiments, an optical output out of a single mode fiber can provide or approach a perfect Gaussian distribution, which has desirable beam shape and optical quality characteristics, and can be well suited for use with sensitive optical elements. As such, this feature can help optimize the optical performance of the overall system, particularly when multiple optical elements are involved.

In some cases, a fiber can operate as a conjugate pinhole or aperture (or spatial filter) for the focus spot in the tissue that is being analyzed. The fiber can operate to provide a focal plane resolution and specificity, filtering out the out of focus light that is not of interest. In some cases, a spatial filter can be provided as a radial aperture or a circular aperture. In some cases, an aperture can have a diameter of about 1 mm aperture. In some cases, the focus of the light is aligned with the core of a fiber, whereby only that light which is properly aligned to the core of the fiber will make it into that fiber. Thereafter, that light will be propagated down the fiber. In this sense, the core of the fiber can operate as a filter, spatial mask, or pinhole aperture, whereby light coupled into the core of the fiber is propagated, and undesired light is filtered or masked out. Often, a fiber will operate in conjunction with a lens. In some embodiments, the fiber can be provided as a collimated fiber optic. In some cases, light is focused into the fiber, or into the core of the fiber, using a lens. The light can be propagated in the fiber by way of total internal reflection. Where light is not properly aligned with the fiber core, such light may not propagate down the fiber, or be coupled into that fiber.

Put another way, light that is at a different focal plane, in the tissue, will not be at the same focal plane, over at the pinhole or spatial filter side, and hence becomes filtered out. The out of focus light will not make it into the pinhole or spatial aperture, and won't be coupled into the fiber, because that light is not aligned (e.g. not at the same focal plane, confocal, or conjugate).

In some embodiments, the patient interface system 1600 can include a processing assembly (e.g. such as the processing assembly depicted in FIG. 5) in operative association with the optical scanning assembly 1610, the objective lens assembly 1614, the eye camera assembly 1628, the fixation assembly 1629, and the Brillouin spectrometer assembly 1634. The processing assembly can include a processor, an electronic storage location operatively coupled with the processor, and processor executable code stored on the electronic storage location and embodied in a tangible non-transitory computer readable medium. In some cases, the patient interface system 1600 may include peripheral embedded IO boards for digital or analog sensing and control of peripheral devices. For example, the system 1600 may include a general-purpose input/output (GPIO) embedded processor board (e.g. "Arduino-like") to set the illumination intensity, the fixation pattern, to read from photodiode, and the like. The processor executable code can include machine-readable instructions that, when executed by the processor, cause the processor to generate x,y coordinate scan control signals for the optical scanning assembly 1610. In some cases, x,y coordinate scan control signals for the optical scanning assembly 1610 can be generated based on the electrical signals generated by the eye camera assembly 1628. The processor executable code can include machine-readable instructions that, when executed by the processor, cause the processor to generate z coordinate scan control signals for the objective lens assembly 1614. In some cases, the x,y coordinate scan control signals, the z coordinate scan control signals, or both the x,y coordinate scan control signals and the z coordinate scan control signals, can be based on an image of the eye. In some cases, the x,y coordinate scan control signals, the z coordinate scan control signals, or both the x,y coordinate scan control signals and the z coordinate scan control signals, can be generated independent of an image of the eye. In some cases, the x,y coordinate scan control signals, the z coordinate scan control signals, or both the x,y coordinate scan control signals and the z coordinate scan control signals, can be generated according to a pre-defined or pre-determined scan pattern. The processor executable code can include machine-readable instructions that, when executed by the processor, cause the processor to generate an elastic stiffness map for a volume of ophthalmic tissue of the eye 1622 based on Brillouin signals. In some cases, the optical scanning assembly 1610 may include a tip-tilt mirror 1610a. In some cases, the tip-tilt mirror 1610a can have an operational range of $\theta=\pm2°$. In some cases, the tip-tilt mirror 1610a can be a T-MM2 Series with motorized two axis mirror mounts (Zaber Technologies Inc., Vancouver Canada). In some cases, the tip-tilt mirror 1610a can have a two-axis kinematic mount with ±5° range. Operation of the tip-tilt mirror 1610a can adjust x,y positioning of a focused spot 1624. In some cases, operation of the tip-tilt mirror 1610a can adjust x,y positioning of a focused spot 1624 throughout a field of view or range. In some cases, the field of view or scan range is ±5 mm or 6 mm. In some cases, x,y positioning is adjusted by operation of the tip-tilt mirror 1610a in combination with operation of the objective lens 1614b. A ±2° tip-tilt adjustment may be sufficient to achieve a ±6 mm scan range.

As shown in FIG. 16, the eye 1622 can be at a 90 degree angle of orientation relative to the general trajectory of the scanning diagnostic beam after the scanning diagnostic beam exits the objective lens assembly 1614. In this way, the reflected focused portion 1620 of the scanning diagnostic beam and the imaging light 1630 that travels from the eye to the eye camera assembly are aligned in a colinear path. According to some embodiments, such a configuration (e.g. reflecting the beam off the shortpass dichroic filter 1618a) may produce less astigmatism (or more generally, less optical aberration) than a different configuration (e.g. scanning or transmitting the beam through the shortpass dichroic filter 1618a). This advantage may be particularly helpful for maintaining high beam quality when the scanning diagnostic beam is diffraction limited and involves a confocal focused spot. In some embodiments, the finer axial resolution spot will also minimize contaminating back-reflections from the front surface of the eye, allow for scanning of more of the eye thickness with better spatial resolution. Dichroic filters can operate to reflect or reject light having certain wavelengths, and to transmit light having certain wavelengths.

According to some embodiments, the system 1600 can include one or more illumination lamps or light devices 1626 that direct illumination light or radiation 1627 toward the eye. In some cases, an illumination device 1626 can be or include a light emitting diode (LED). In some cases, the illumination light or radiation 1627 can be infrared light. In some cases, the illumination light or radiation 1627 can be non-visible light. In some cases, the illumination light 1627 can have a wavelength value within a range from about 700 nm to about 1,000,000 nm. In some case, the illumination light 1627 can have a wavelength value of about 940 nm. According to some embodiments, the eye camera assembly 1628 is sensitive to the wavelength of the illumination light 1627 (which can also be the same as or similar to the wavelength of the imaging light 1630).

In some cases, the illumination light 1627 can have a wavelength value that is greater than a wavelength value of the diagnostic scanning light or radiation. In some cases, the diagnostic beam (e.g. 1604, 1620) has a wavelength value within a range from about 450 to about 1350 nm. In some cases, the wavelength of the scanning diagnostic beam has a value of about 780 nm. In some cases, the scanning diagnostic radiation can have a wavelength value within a range from about 450 to about 1350 nm. In some cases, the fixation light 1629a is visible light. In some cases, the fixation light 1629a is visible green light. In some cases, the fixation light 1629a has a wavelength value of about 520 to about 560 nm. According to some embodiments, the fixation assembly 1629 generates light 1629a that provides the eye with a gaze target, which can be helpful in a clinical setting or application. In some cases, a system or method can include a gaze target that is not provided by a light emitting fixation assembly.

As shown in FIG. 16, the shortpass dichroic filter 1618a can operate to reflect the incoming and returning scanning diagnostic beam, to transmit the imaging light 1630 (which can be illumination light 1627 reflected from the eye), and to transmit the fixation light 1629a. Relatedly, the longpass dichroic filter 1618b can operate to reflect the fixation light 1629a and to transmit the imaging light 1630 (which can be illumination light 1627 reflected from the eye). In some cases, instead of using a shortpass dichroic filter 1618a, it is possible to instead use a dichroic (e.g. longpass) or some other filter that reflects a certain wavelength range and passes another wavelength range.

According to some embodiments, the focused scanning diagnostic laser beam 1620 optical path and the imaging light 1630 optical path are provided as integrated colinear optical paths, as a result of the operation of one or more dichroic filters. In some cases, the respective optical paths may not be integrated in a colinear fashion. In some cases, by providing integrated colinear optical paths, it is possible to avoid or eliminate geometric distortions of the image that may otherwise be present when using an off-axis camera (even though it may be possible to achieve the same focal point for a laser, relative to the focus of the imaging camera).

In some cases, by providing integrated colinear optical paths, it is possible to more efficiently register biomechanical data to eye location and/or orientation data pertaining to a real world eye space. In some cases, it is possible to use eye tracker or camera information to register and track where those points have been scanned, relative to certain features and/or registration coordinates on the eye.

According to some embodiments, astigmatism can be incurred for the eye camera illumination or an image of the eye by transmitting through the dichroic, and a perfect 3D orthogonal orientation (e.g. of the illumination lamp 1626) can cancel out that astigmatism.

As seen here, the longpass dichroic filter 1618b operates to fold together the light 1629a from the fixation assembly 1629 and the imaging light 1630 from the eye (integrated). Embodiments of the present invention also encompass designs where the fixation light 1629a is not folded into the same path with the imaging light 1630 (unintegrated). As shown in FIG. 16, in this embodiment there may be no lens between the shortpass dichroic filter 1618a and the longpass dichroic filter 1618b.

According to some embodiments, the eye camera assembly 1628 of patient interface system 1600 can image through a path that is not the same as the laser path. In some cases, the eye camera assembly 1628 includes an eye tracker camera and an imaging lens (e.g. f=~25 mm). Patient interface system 1600 can involve a co-axial scanning laser that is reflected at 90 degrees. Lateral xy scanning can be achieved by a Risley prism scanning method. A Risley prism pair can provide an optical x,y scanning capability. In some cases, the quarter wave plate assembly 1617 can be positioned downstream of the objective lens assembly 1614 for purposes of optical isolation. According to some embodiments, there is a mechanical coupling between the eye camera assembly 1628 and the laser scanning. As discussed herein with reference to FIG. 6, embodiments of the present invention may also encompass mechanically decoupled systems. Patient interface system 1600 can provide a diffraction limited focused spot over an entire focal volume. It is understood that an eye or any other sample with aberrations may make it so the spot is not diffraction limited.

In some cases, the patient interface system 1600 depicted in FIG. 16 can incorporate one or more features of the embodiment depicted in FIG. 5 or 11. FIG. 16 shows a reference path 1608a that is used to measure a sample 1608c containing plastic and water, that has known elastic properties. This can be used to normalize the data that is received from the actual tissue being analyzed, for example the cornea or the crystalline lens. Light can be controlled by a pair of shutters 1607, 1607a, and operation of the shutters can determine whether the laser light is going to hit the reference path, or whether the laser is going to hit the sample path. FIG. 16 also illustrates that a fixation assembly 1629 can include a grid of light points or light emitting diodes. The system can be configured to illuminate one or more points of the grid, so as to control where the patient directs their gaze. In this way, it is possible to facilitate the measurement of certain areas of the eye that otherwise may be difficult to scan or measure when the patient is looking directly straightforward. Accordingly, the system can facilitate a computerized control of the orientation of the eye, by changing the gaze angle. Performance graphs for the dichroic filters are illustrated, indicating transmission percentage (y axis) and wavelength (x axis). According to some embodiments, the dashed line boxes are provided to illustrate various submodules that are isolated based on their function. In some cases, multiple submodules with different functions can cooperatively work together as a system to achieve the overall function.

Figure 17:
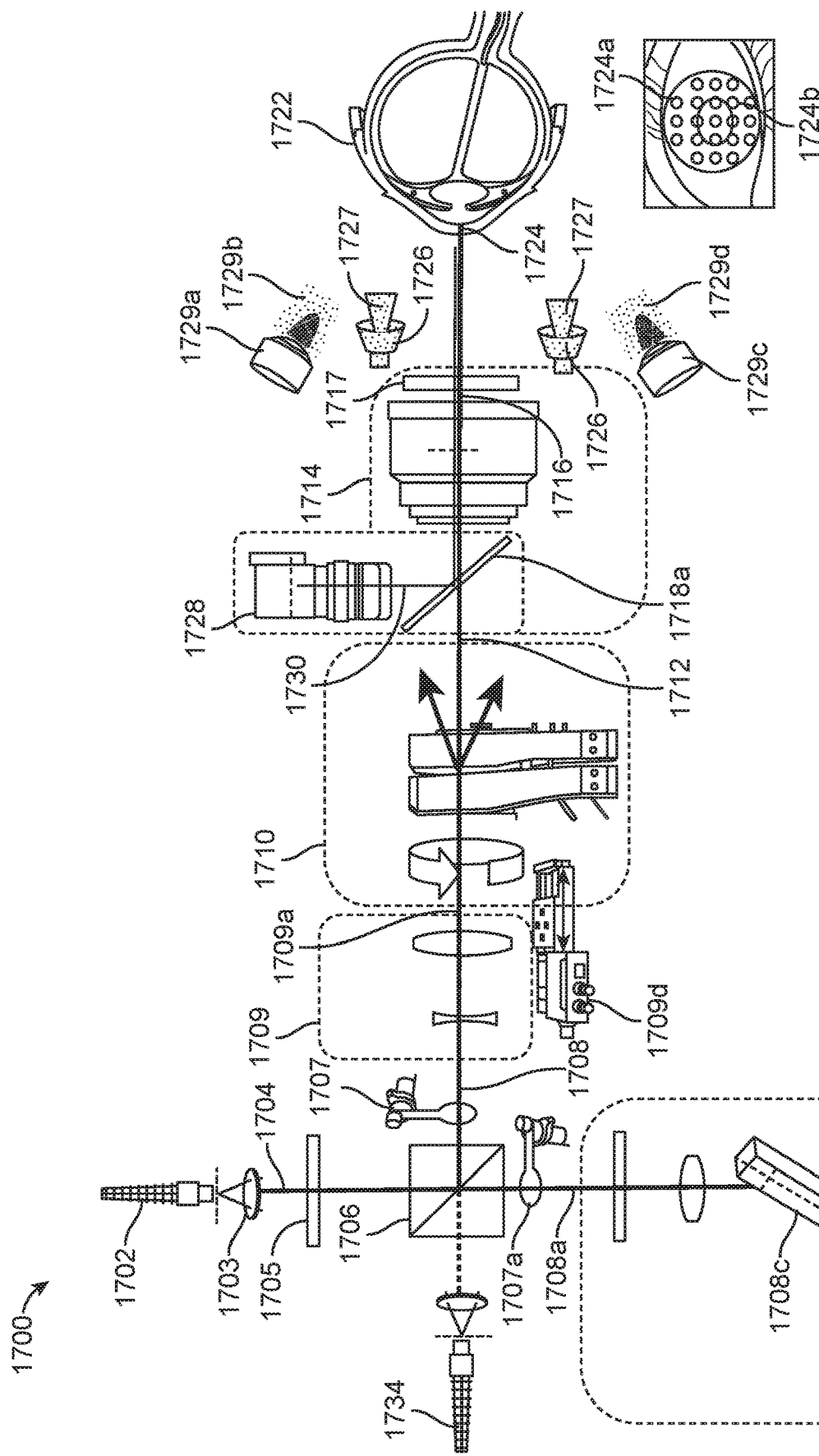
FIG. 17 depicts aspects of a system for generating an elastic stiffness map for a volume of an ophthalmic tissue of an eye of a patient, according to embodiments of the present invention.

FIG. 17 depicts aspects of a patient interface system 1700 according to embodiments of the present invention. As discussed elsewhere herein, system 1700 can be used to generate an elastic stiffness map for a volume of an ophthalmic tissue of an eye of a patient. As shown here, system 1700 includes a laser assembly or light source 1702 that generates a collimated diagnostic laser beam 1704 (e.g. by passing through a lens 1703, such as a 4 mm beam expansion lens), a polarizing beam splitter 1706 that reflects a portion 1708 of the collimated diagnostic laser beam 1704, and the reflected portion 1708 is then transmitted to a laser beam expansion assembly 1709, which converts beam 1708 to an expanded beam 1709*a*. In some cases, light source 1702 can be a device that produces electromagnetic radiation characterized by one or more wavelengths or one or more frequencies. According to some embodiments, the electromagnetic radiation beam expansion assembly 1709 expands a collimated scanning diagnostic laser beam from a first diameter to a second diameter that is larger than the first diameter. The laser beam expansion assembly 1709 may include multiple lenses. In some cases, the laser beam expansion assembly 1709 includes lenses disposed in a Galilean configuration, with a negative lens followed by a positive lens. In some case, the laser beam expansion assembly 1709 can be provided as a Galilean type beam expander. In some cases, the collimated scanning diagnostic laser beam has a linear polarization orientation. In turn, expanded beam 1709*a* is transmitted to an optical scanning assembly 1710.

As shown here, the polarizing beam splitter 1706 can be positioned before the laser beam expansion assembly 1709. The polarizing beam splitter 1706 can operate to split the diagnostic laser beam 1704 into a scanning portion 1708 and a non-scanning portion 1708*a*. In some cases, the beam splitter 1706 allows for the measurement (e.g. concurrent) of a reference sample 1708*c*. In some cases, the beam splitter 1706 operates to provide an additional amount of filtration of back reflections of light. Filtration can be based on polarization, and may involve aspects of a conventional optical isolator based on polarizing optics and a quarter wave plate. In some cases, the polarizing beam splitter 1706 transmits light at a 90 degrees orientation and on the return path the light goes to 90 degrees. In some embodiments, the beam splitter 1706 works in conjunction with the quarter wave plate 1717. For example, after two passes through the waveplate 1717, the returning light can be passed back to the spectrometer assembly 1734, and light that has only passed once (e.g. reflections from lenses) will be excluded. In some cases, when the light first enters the quarter wave plate 1717, some amount can be portioned to a calibrated reference sample. A half-waveplate element 1705 may also be positioned after the laser source which sets up a ratio of linearly polarized s and p. This can control the light split through the polarizing beam splitter (PBS). According to some embodiments, a Brillouin signal from a sample can be used as a built in reference to the instrument for accurate calculation of the Brillouin signal. There may also be a quarter waveplate on the reference path to provide an isolated signal that will make its way back to the spectrometer.

According to some embodiments, the optical scanning assembly 1710 operates to adjust or redirect a beam path of the expanded collimated scanning diagnostic laser beam. In some cases, the patient interface system 1700 may not include the polarizing beam splitter 1706. The optical scanning assembly 1710 operates to redirect a beam path of the reflected portion 1708 of the collimated scanning diagnostic laser beam. The redirected reflected portion 1712 of the collimated scanning diagnostic laser beam is then transmitted through a shortpass dichroic filter 1718*a* and to an objective lens assembly 1714, which operates to focus the redirected portion 1712 of the collimated scanning diagnostic laser beam to produce a focused scanning diagnostic laser beam 1716. According to some embodiments, system 1700 provides a working distance of about 50 mm.

According to some embodiments, the objective lens assembly 1714 operates to focus the expanded collimated scanning diagnostic laser beam 1712 to produce a focused scanning diagnostic laser beam 1716 having a beam waist or focused spot. In some cases, the objective lens assembly 1714 operates to adjust a scan position of the beam waist or focused spot. In some cases, the objective lens assembly 1714 includes a motorized stage that allows the objective lens assembly to travel toward and away from the optical scanning assembly 1710. In some cases, the optical scanning assembly 1710 includes a motorized stage that allows the optical scanning assembly to travel toward and away from the objective lens assembly 1714. In some cases, the optical scanning assembly and the objective lens assembly include or are disposed on respective motorized stages, or are disposed on a common motorized stage, so that the optical scanning assembly and the objective lens assembly can move in tandem.

Figure 18:
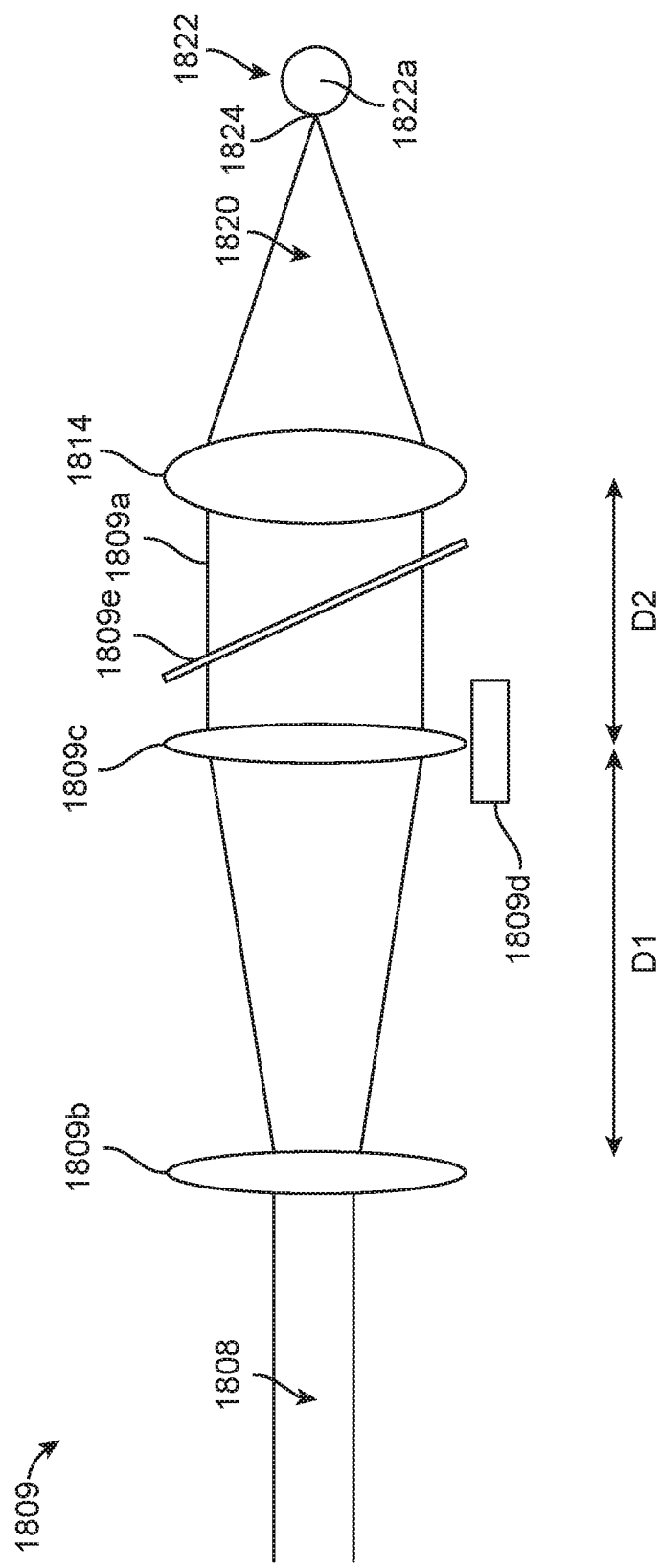
FIG. 18 depicts aspects of a system for generating an elastic stiffness map for a volume of an ophthalmic tissue of an eye of a patient, according to embodiments of the present invention.

In some cases, the laser beam expansion assembly 1709 includes a motorized stage 1709*d* that allows one or more components of the laser beam expansion assembly 1709 to travel toward and away from the optical scanning assembly 1710, or otherwise along the light propagation path traveled by reflected portion 1708. FIG. 18 depicts additional aspects of a laser beam expansion assembly having a motorized stage or otherwise axially adjustable lens elements.

With returning reference to FIG. 17, system 1700 may include a quarter-wave plate assembly 1717. In some embodiments, the quarter-wave plate assembly 1717 operates to convert the focused scanning diagnostic laser beam 1716 from a linear polarization orientation to a circular polarization orientation. In some embodiments, the quarter-wave plate assembly 1717 operates to provide a 45 degree rotation to the focused scanning diagnostic laser beam 1716. In some cases, the quarter-wave plate assembly 1717 operates to convert the focused scanning diagnostic laser beam 1716 from p-polarized light to s-polarized light. In some cases, the quarter-wave plate assembly 1717 operates to convert the focused scanning diagnostic laser beam 1716 from s-polarized light to p-polarized light. The quarter-wave plate assembly 1717 can be placed along the beam path, for example between the objective lens assembly 1714 and the eye 1722. In some embodiments, the quarter-wave plate assembly 1717 can be placed upstream of the objective lens assembly 1714. In some cases, the quarter-wave plate assembly 1717 can be placed anywhere as desired, between the sample (e.g. eye) and the PBS.

The focused scanning diagnostic laser beam 1716 is transmitted toward an eye 1722 of the patient. In some cases, the focused scanning diagnostic laser beam has a circular polarization orientation. In some cases, a dichroic filter will transmit light within a certain wavelength band or range and/or reflect light within a certain wavelength band or range. As shown here, dichroic filters can operate to fold together, or to separate out, different wavelengths of light (e.g. into a common optical path).

In some case, the dichroic filters can operate to fold together imaging light 1730, and scanning diagnostic light 1716, into a common optical path (e.g. between the shortpass dichroic filter 1718*a* and the eye 1722). Similarly, a dichroic can operate to peel apart light from a common path into separate optical paths, for example imaging light 1730 and returned scanning diagnostic light travel along a common optical path from the eye to the shortpass dichroic filter 1718*a*, and then the returned scanning diagnostic light is transmitted through the shortpass dichroic filter 1718*a* and the imaging light is reflected by the shortpass dichroic filter 1718*a*.

The focused scanning diagnostic laser beam 1716 has focused spot 1724, and operation of the laser beam expansion assembly 1709, the optical scanning assembly 1710, and/or the objective lens assembly 1714 (alone or in combination), can adjust a scan position of the focused spot 1724 to various discrete locations (e.g. 1724a, 1724b) on or within one or more tissues of the eye 1722.

The patient interface system 1700 also includes an eye camera assembly 1728 that receives imaging light 1730 from the eye (which optionally may have been reflected by a shortpass dichroic filter 1718a of a beam control assembly) and that generates electrical signals in response to the received imaging light 1730. The imaging light 1730 can provide registration information regarding the position and/or orientation of the eye. In some cases, this registration information can be used (e.g. by a processing assembly, such as the processing assembly depicted in FIG. 8) to provide locate elasticity measurement data obtained by the Brillouin spectrometer assembly 1734 to particular points of the eye. In some cases, the imaging light 1730 can help to provide feedback, which may be continuous feedback, to the processing assembly. The imaging light 1730 can be processed to provide information regarding a center coordinate of the eye, a central reference of the eye, or more generically, a reference coordinate on the eye, which can be registered to the biomechanical data. Such a reference coordinate can be determined by processing the imaging data.

In some cases, the processing assembly can operate to generate two images, specifically an image of the eye and a Brillouin heat map (e.g. stiffness values at discrete points), and to accurately superimpose those images on top of each other using registration. In this way, the mechanical information is relevant in the physical space. In some cases, the processing assembly does not perform a superimposition. Rather, a camera is used to provide a reference point to begin a scan pattern, and thereafter a scan is performed according to the pattern, so as to generate the stiffness map. The map can indicate whether there are any abnormal spots or points of interest on the eye, without providing the exact location on the eye of the abnormal spots or points of interest. In some cases, a camera is not used to provide a reference point to begin a scan pattern. For example, the physician or operate could manually inspect the person's eye, and then aim the beam, without using a camera. In some cases, it is possible to illuminate the person's eye using a certain wattage, observe a reflection off the person's eye, and determine that the alignment of the scanning beam and the eye is sufficient.

Hence, input techniques for aiming the diagnostic beam can include using a camera image or data, manually aiming the beam, or using feedback from the Brillouin spectrometer. For example, data obtained by the spectrometer can provide an indication of whether the system is in focus. The Brillouin spectrometer can be used to differentiate spectral shifts that are characteristic of different tissues. In some cases, as the focused spot is scanned in the z depth direction, it is possible to detect fundamentally different frequency shifts (or different information) as the focused spot goes through different layers (e.g. going from the air, to the cornea surface, to the aqueous humor, to the crystalline lens, and so on) which can correspond to different elastic properties (e.g. elastic modulus). In this sense, the Brillouin approach can provide aspects of an imaging modality. Hence, it may be possible to determine where the focused spot is located (e.g. along a z-axis), by observing or analyzing the spectrometer image. In some cases, it is possible to align or position the patient interface system, by observing or using a reflection off of a person's eye, then moving the system into focus based on feedback from the spectrometer camera, and then initiating the scan. In some cases, the camera is parfocal with the laser beam, and the focus of the eye can also be used.

In some embodiments, system 1700 also includes a fixation assembly that provides the eye with a gaze target, the fixation assembly having a first fixation mechanism 1729a that transmits a first fixation light 1729b toward the eye, and a second fixation mechanism 1729c that transmits a second fixation light 1729d toward the eye. According to some embodiments, the fixation assembly includes light-emitting diodes (LEDs). In some cases, the fixation light is a collimated green light produced by a light emitting diode.

The patient interface system 1700 can further include a Brillouin spectrometer assembly 1734 having a Brillouin spectrometer and a spatial filter that is parfocal with the focused spot 1724 (e.g. in a conjugate focal plane). The Brillouin spectrometer can generate Brillouin signals as the focused spot 1724 is scanned to discrete locations throughout a volume or plane thickness of ophthalmic tissue of the eye 1722. Brillouin scattered light from the focused spot at the discrete locations is returned to the spatial filter. According to some embodiments, the spatial filter operates as an input for the Brillouin spectrometer, and is in conjugate alignment with the focused spot 1724 or beam waist of the focused scanning diagnostic laser beam, and the Brillouin spectrometer can generate Brillouin signals as the focused spot 1724 or beam waist of the focused scanning diagnostic beam is scanned to discrete locations throughout the volume of the ophthalmic tissue of the eye 1722. In some cases, the spatial filter can operate to exclude information associated with out of focus focal planes, and include information associated with the focal plane of interest. The filter can provide sensitivity to locations where the focused spot 1724 is positioned, and little or no sensitivity to extraneous locations. In some cases, a spatial filter can be provided without using a fiber. In some cases, the spatial filter can operate to prime the incoming light, which is then measured by the spectrometer, which in turn generates the spectrum (e.g. Brillouin) signals.

By using a fiber input, it is possible to provide modularity to the system, whereby the patient scanning interface can be decoupled and coupled with the spectrometer via the optical fiber. Such modularity can provide enhanced testing and serviceability advantages. For example, the optical fiber could be uncoupled from one patient interface system, and coupled with another patient interface system. Hence, if one patient interface were to malfunction, it could be replaced with another patient interface. This could also allow patient interfaces to be tested as modules, which can improve manufacturability.

From an optical standpoint, a fiber can provide a highly functional pinhole. In some cases, such embodiments can provide a separate input and output. It is possible to physically decouple with free space optics the input and output of the system. In some embodiments, the input is not separated from the output. For example, the same light can be coupled back into the same input path and optionally the beam could be redirected to the spectrometer after traveling back down the fiber.

According to some embodiments, an optical output out of a single mode fiber can provide or approach a perfect Gaussian distribution, which has desirable beam shape and optical quality characteristics, and can be well suited for use with sensitive optical elements. As such, this feature can help optimize the optical performance of the overall system, particularly when multiple optical elements are involved.

In some cases, a fiber can operate as a conjugate pinhole or aperture (or spatial filter) for the focus spot in the tissue that is being analyzed. The fiber can operate to provide a focal plane resolution and specificity, filtering out the out of focus light that is not of interest. In some cases, a spatial filter can be provided as a radial aperture or a circular aperture. In some cases, an aperture can have a diameter of about 1 mm aperture. In some cases, the focus of the light is aligned with the core of a fiber, whereby only that light which is properly aligned to the core of the fiber will make it into that fiber. Thereafter, that light will be propagated down the fiber. In this sense, the core of the fiber can operate as a filter, spatial mask, or pinhole aperture, whereby light coupled into the core of the fiber is propagated, and undesired light is filtered or masked out. Often, a fiber will operate in conjunction with a lens. In some embodiments, the fiber can be provided as a collimated fiber optic. In some cases, light is focused into the fiber, or into the core of the fiber, using a lens. The light can be propagated in the fiber by way of total internal reflection. Where light is not properly aligned with the fiber core, such light may not propagate down the fiber, or be coupled into that fiber.

Put another way, light that is at a different focal plane, in the tissue, will not be at the same focal plane, over at the pinhole or spatial filter side, and hence becomes filtered out. The out of focus light will not make it into the pinhole or spatial aperture, and won't be coupled into the fiber, because that light is not aligned (e.g. not at the same focal plane, confocal, or conjugate).

As shown here, the patient interface system 1700 can include a processing assembly (e.g. such as the processing assembly depicted in FIG. 8) in operative association with the beam expansion assembly 1709, the optical scanning assembly 1710, the objective lens assembly 1714, the eye camera assembly 1728, the fixation assembly (1729*a*, 1729*c*), and the Brillouin spectrometer assembly 1734. The processing assembly can include a processor, an electronic storage location operatively coupled with the processor, and processor executable code stored on the electronic storage location and embodied in a tangible non-transitory computer readable medium. The processor executable code can include machine-readable instructions that, when executed by the processor, cause the processor to generate x,y coordinate scan control signals for the optical scanning assembly 1710. In some cases, x,y coordinate scan control signals for the optical scanning assembly 1710 can be generated based on the electrical signals generated by the eye camera assembly 1428. The processor executable code can include machine-readable instructions that, when executed by the processor, cause the processor to generate z coordinate scan control signals for the beam expansion assembly 1709 and/or the objective lens assembly 1714. In some cases, the x,y coordinate scan control signals, the z coordinate scan control signals, or both the x,y coordinate scan control signals and the z coordinate scan control signals, can be based on an image of the eye. In some cases, the x,y coordinate scan control signals, the z coordinate scan control signals, or both the x,y coordinate scan control signals and the z coordinate scan control signals, can be generated independent of an image of the eye. In some cases, the x,y coordinate scan control signals, the z coordinate scan control signals, or both the x,y coordinate scan control signals and the z coordinate scan control signals, can be generated according to a pre-defined or pre-determined scan pattern. The processor executable code can include machine-readable instructions that, when executed by the processor, cause the processor to generate an elastic stiffness map for a volume of ophthalmic tissue of the eye 1722 based on Brillouin signals. In some cases, the optical scanning assembly 1710 may include a prism pair, for example a prism pair as depicted in FIG. 3. In some cases, the prism pair can provide an operational range of $\theta = \pm 10°$.

As shown in FIG. 17, the eye 1722 can be at an on-axis orientation relative to the general trajectory of the scanning diagnostic beam after the scanning diagnostic beam exits the objective lens assembly 1714. In this way, the focused portion 1716 of the scanning diagnostic beam and the imaging light 1730 that travels from the eye to the shortpass dichroic filter are aligned in a colinear path. Dichroic filters can operate to reflect or reject light having certain wavelengths, and to transmit light having certain wavelengths.

According to some embodiments, the system 1700 can include one or more illumination lamps or light devices 1726 that direct illumination light or radiation 1727 toward the eye. In some cases, the illumination light or radiation 1727 can be infrared light. In some cases, the illumination light or radiation 1727 can be non-visible light. In some cases, the illumination light 1727 can have a wavelength value within a range from about 700 nm to about 1,000,000 nm. In some case, the illumination light 1727 can have a wavelength value of about 940 nm. According to some embodiments, the eye camera assembly 1728 is sensitive to the wavelength of the illumination light 1727 (which can also be the same as or similar to the wavelength of the imaging light 1730).

In some cases, the illumination light 1727 can have a wavelength value that is greater than a wavelength value of the diagnostic scanning light or radiation. In some cases, the diagnostic beam (e.g. 1704, 1716) has a wavelength value within a range from about 450 to about 1350 nm. In some cases, the wavelength of the scanning diagnostic beam has a value of about 780 nm. In some cases, the scanning diagnostic radiation can have a wavelength value within a range from about 450 to about 1350 nm. In some cases, the fixation light 1729*b*, 1729*d* is visible light. In some cases, the fixation light 1729*b*, 1729*d* is visible green light. In some cases, the fixation light 1729*b*, 1729*d* has a wavelength value of about 520 to about 560 nm. According to some embodiments, the fixation assembly generates light 1729*b*, 1729*d* that provides the eye with a gaze target, which can be helpful in a clinical setting or application. In some cases, a system or method can include a gaze target that is not provided by a light emitting fixation assembly.

As shown in FIG. 17, the shortpass dichroic filter 1718*a* can operate to transmit the incoming and returning scanning diagnostic beam, and to reflect the imaging light 1730 (which can be illumination light 1727 reflected from the eye).

According to some embodiments, the focused scanning diagnostic laser beam 1716 optical path and the imaging light 1730 optical path are provided as integrated colinear optical paths. In some cases, the respective optical paths may not be integrated in a colinear fashion. In some cases, by providing integrated colinear optical paths, it is possible to avoid or eliminate geometric distortions of the image that may otherwise be present when using an off-axis camera (even though it may be possible to achieve the same focal point for a laser, relative to the focus of the imaging camera).

In some cases, by providing integrated colinear optical paths, it is possible to more efficiently register biomechanical data to eye location and/or orientation data pertaining to a real world eye space. In some cases, it is possible to use eye tracker or camera information to register and track where those points have been scanned, relative to certain features and/or registration coordinates on the eye.

As shown in FIG. 17, in this embodiment there may be no lens between the shortpass dichroic filter 1718a and the eye camera assembly 1728. In some cases, the eye camera assembly 1728 includes an eye tracker camera and an imaging lens (e.g. f=~25 mm). In some cases, the eye camera assembly includes an imaging lens or a lens assembly/objective. Also, in this embodiment the shortpass dichroic filter 1718a is positioned in the collimated space between the optical scanning assembly 1710 and the objective lens assembly 1714, and a portion of the camera path is also positioned in the collimated space between the optical scanning assembly 1710 and the objective lens assembly 1714.

According to some embodiments, the eye camera assembly 1728 of patient interface system 1700 can image through a path that is aligned with the laser path. Patient interface system 1700 can involve a co-axial scanning laser that is reflected at 90 degrees. Lateral xy scanning can be achieved by a Risley prism pair. In some cases, the Risley prism pair can provide direct eye scanning. Optical xy scanning can be achieved with a Risley prism pair. In some cases, the quarter wave plate assembly 1717 can be positioned downstream of the objective lens assembly 1714 for purposes of optical isolation. In some cases, mechanical configurations can involve transmitting the laser through a splitter. One aspect of such a mechanical configuration is that there may be no 90 degree reflection required by the laser path. This may make it easier to achieve a desired working distance easier or making it even larger without necessarily putting constraints on the objective lens. In some cases, the optical challenges may be more substantial with additional aberrations from introducing the dichroic before the objective and constraints on distance imaging to achieve the desired eye FOV with certain image quality through the laser scanning objective. According to some embodiments, there is a mechanical decoupling between the eye camera assembly 1728 and the laser scanning. System 1700 can provide a configuration where all optics are on axis, where testing for alignment can be achieved with only a line scan instead of a 3D scan volume, where there is no optical scanning, and/or there is an inherently telecentric arrangement. Patient interface system 1700 can provide a diffraction limited focused spot over an entire focal volume. It is understood that an eye or any other sample with aberrations may make it so the spot is not diffraction limited.

In some cases, the patient interface system 1700 depicted in FIG. 17 can incorporate one or more features of the embodiments depicted in FIG. 8 or 14. FIG. 17 shows a reference path 1708a that is used to measure a sample 1708c containing plastic and water, that has known elastic properties. This can be used to normalize the data that is received from the actual tissue being analyzed, for example the cornea or the crystalline lens. Light can be controlled by a pair of shutters 1707, 1707a, and operation of the shutters can determine whether the laser light is going to hit the reference path, or whether the laser is going to hit the sample path. FIG. 17 also illustrates that a fixation assembly can include separate fixation mechanisms. The system can be configured to illuminate one or both fixation mechanisms, so as to control where the patient directs their gaze. In this way, it is possible to facilitate the measurement of certain areas of the eye that otherwise may be difficult to scan or measure when the patient is looking directly straightforward. Accordingly, the system can facilitate a computerized control of the orientation of the eye, by changing the gaze angle.

FIG. 18 depicts aspects of a laser beam expansion assembly 1809 according to embodiments of the present invention. As shown here, a laser beam expansion assembly 1809 can include a first lens 1809b, a second lens 1809c, a motorized or moveable translation stage 1809d, a dichroic 1809e, and an objective 1814. The beam expansion assembly 1809 can receive light or reflected light 1808 originating from a fiber output, as discussed elsewhere herein. In some cases, lens 1809b can have a focal length (f1) of about −20 mm. In some cases, lens 1809c can have a focal length (f2) of about 100 mm. Such a ratio (−20:100) can provide a 5× beam expansion. Other ratios and beam expansion amounts can be used. With a 5× beam expansion, a 3.3 mm input beam 1808 can be expanded to approximately a 16.5 mm expanded beam 1809a. In some cases, objective 1814 can include one or more lenses. In some cases, objective 1814 can have a focal length (f3) of about 100 mm. In some cases, an objective or objective lens assembly 1814 can include an objective lens having a relatively large numerical aperture (NA). For example, the NA can have a value of 0.1, or higher. In some cases, the NA can be 0.125.

As shown here, motorized stage 1809d can be coupled with second lens 1809c. Motorized stage 1809d can operate to move second lens away from or toward first lens 1809b, thus either increasing or decreasing a distance D1 between first lens 1809b and second lens 1809c. In some cases, D1 can be about 80 mm. In some cases, D1 can be greater than or lesser than 80 mm. Motorized stage 1809d can operate to move second lens away from or toward objective 1814, thus either increasing or decreasing a distance D2 between first lens 1809b and objective 1814. Objective 1814 operates to focus the expanded beam 1809a to produce a focused beam 1820. In some cases, D2 can be about 150 mm. In some cases, D2 can be greater than or lesser than 150 mm.

As shown here, the expanded beam 1809a can be collimated. When lens 1809c moves toward first lens 1809b and D1 is decreased, the expanded beam 1809a can diverge (uncollimated), and the focused spot 1824 can move toward a central portion 1822a of the eye (e.g. through one or more deeper tissue layers). Conversely, when lens 1809c moves away from first lens 1809b and D1 is increased, the expanded beam 1809a can converge (uncollimated), and the focused spot 1824 can move away from a central portion 1822a of the eye (e.g. through one or more shallower tissue layers). Hence, it can be seen that operation of the motorized stage 1809d or movement of the second lens 1809c can adjust the positioning of the focused spot 1824 in the z direction. Hence, the expanded beam 1809a may or may not be collimated when it reaches the objective 1814.

The objective 1814 can remain stationary throughout the adjustment (e.g. axial or z axis) of the second lens 1809c. In this way, it is possible to more fully use the working distance provided by the system. For example, it is easier to consistently maintain a suitable or desired distance between the final optic in the system and the patient's eye. This can reduce the probability of having undesired contact between the objective 1814 and the patient's eye 1822. Relatedly, when the objective 1814 remains stationary, it is possible to more fully use the focal length or distance (e.g. f3=100 mm) of the objective 1814. Further advantageously, in this configuration, it is possible to position the dichroic 1809e before the objective 1814.

By providing an objective 1814 that is stationary, and a dichroic 1809e positioned before the stationary objective 1814, it is possible to achieve improved performance for the eye tracker camera field of view (e.g. by maintaining a more consistent aspect ratio).

In some cases, movement of second lens 1809*c* can result in about a 1:1 corresponding movement (or some other known fixed ratio) of the focused spot 1824. For example, moving the second lens 1809*c* toward the first lens 1809*b* by about 1 mm can move the focused spot 1824 toward the eye center 1822*a* (or otherwise to a deeper location along the z axis) by about 1 mm. Given the movement ratio, it is possible to determine what z axis movement is needed for second lens 1809*c* in order to achieve a desired z axis movement in the focused spot 1824. Typically, when moving the second lens 1809*c* at relatively small operational amounts (e.g. 10 mm or 15 mm), the size of the focused spot 1824 does not change significantly, and performance of the Brillouin imaging remains effective.

Increasing the focal length of second lens 1809*c* can operate to reduce the sensitivity and/or reduce the movement ratio. For example, if the focal length of second lens 1809*c* is increased from 100 mm to 200 mm, the movement ratio will be changed to less than a 1:1 ratio (such as approximately 1:0.5).

As depicted in FIG. 18, the motorized stage 1809*d* is coupled with the second lens 1809*c*. In other embodiments, a motorized stage be coupled with the first lens 1809*b*, to effect movement of the first lens 1809*b* relative to the second lens 1809*c*. In some cases, first lens 1809*b* and second lens 1809*c* may each be coupled with their own respective motorized stages. Movement of any one or more of these motorized stages can operate to change distance D1 and/or D2, and thus change the position of focused spot 1824. According to some embodiments, one or more aspects of a laser beam expansion assembly 1809 can be incorporated into the system 1700 of FIG. 17.

While the above provides a full and complete disclosure of exemplary embodiments of the present invention, various modifications, alternate constructions and equivalents may be employed as desired. Consequently, although the embodiments have been described in some detail, by way of example and for clarity of understanding, a variety of modifications, changes, and adaptations will be obvious to those of skill in the art. Accordingly, the above description and illustrations should not be construed as limiting the invention, which can be defined by the claims.

The invention claimed is:

1. A system for generating an elastic stiffness map for a volume of an ophthalmic tissue of an eye of a patient, the system comprising:
    a laser assembly that generates a collimated illumination laser beam;
    a beam expansion assembly comprising a first lens, a second lens, and a translation stage coupled with the second lens, the beam expansion assembly expanding a portion of the collimated illumination laser beam to produce an expanded beam;
    an objective lens assembly that focuses the expanded beam to produce a focused illumination laser beam having a focused spot;
    a dichroic filter disposed between the second lens of the beam expansion assembly and the objective lens assembly;
    an eye camera assembly that receives imaging light from the eye and generates electrical signals in response to the received imaging light; and
    a Brillouin spectrometer assembly having a Brillouin spectrometer and a spatial filter that is parfocal with the focused spot, wherein the Brillouin spectrometer generates Brillouin signals as the focused spot is scanned to discrete locations throughout the volume of the ophthalmic tissue and Brillouin scattered light from the focused spot at the discrete locations is returned to the spatial filter,
    wherein movement of the second lens of the beam expansion assembly relative to the first lens adjusts a scan position of the focused spot,
    wherein the objective lens assembly remains stationary throughout the movement of the second lens,
    wherein the imaging light travels from the eye through the objective lens assembly to the dichroic filter, reflects from the dichroic filter, and travels from the dichroic filter to the eye camera assembly,
    wherein the expanded beam produced by the beam expansion assembly travels through the dichroic filter, through the objective lens assembly, and toward the eye,
    wherein the imaging light and the expanded beam between the dichroic filter and the objective lens assembly are optically coaxial, and
    wherein the system further comprises a processing assembly in operative association with the beam expansion assembly, the eye camera assembly, and the Brillouin spectrometer assembly, the processing assembly having a processor, an electronic storage location operatively coupled with the processor, and processor executable code stored on the electronic storage location and embodied in a tangible non-transitory computer readable medium, the processor executable code comprising machine-readable instructions that, when executed by the processor, cause the processor to:
    transmit z coordinate scan control signals to the translation stage of the beam expansion assembly, and
    generate the elastic stiffness map for the volume of the ophthalmic tissue of the eye based on the Brillouin signals.

2. The system according to claim 1, further comprising a polarizing beam splitter that produces the portion of the collimated illumination laser beam.

3. The system according to claim 1, wherein the machine-readable instructions, when executed by the processor, cause the processor to generate the elastic stiffness map for the volume of the ophthalmic tissue of the eye based on the electrical signals generated by the eye camera assembly.

4. The system according to claim 3, wherein the electrical signals generated by the eye camera assembly comprise information regarding a location of a reference coordinate of the eye.

5. The system according to claim 1, wherein the machine-readable instructions, when executed by the processor, cause the processor to generate x,y coordinate scan control signals based on the electrical signals generated by the eye camera assembly.

6. The system according to claim 1, wherein the machine-readable instructions, when executed by the processor, cause the processor to generate the z coordinate scan control signals based on the electrical signals generated by the eye camera assembly.

7. The system according to claim 1, further comprising a quarter-wave plate assembly that converts the focused illumination laser beam from a first polarization orientation to a second polarization orientation.

8. The system according to claim 1, further comprising an infrared light source for illuminating the eye.

* * * * *